US012343379B2

(12) United States Patent
Ring et al.

(10) Patent No.: US 12,343,379 B2
(45) **Date of Patent: *Jul. 1, 2025**

(54) INTERLEUKIN-18 VARIANTS AND METHODS OF USE

(71) Applicant: YALE UNIVERSITY, New Haven, CT (US)

(72) Inventors: Aaron Ring, New Haven, CT (US); Ting Zhou, New Haven, CT (US); Suzanne Fischer, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/055,581

(22) Filed: Nov. 15, 2022

(65) Prior Publication Data

US 2023/0241172 A1 Aug. 3, 2023

Related U.S. Application Data

(62) Division of application No. 16/123,063, filed on Sep. 6, 2018, now abandoned.

(Continued)

(51) Int. Cl.

| | |
|---|---|
| ***A61K 38/20*** | (2006.01) |
| ***C07K 14/54*** | (2006.01) |
| *A61K 35/17* | (2025.01) |
| *A61K 35/768* | (2015.01) |
| *A61K 38/17* | (2006.01) |

(Continued)

(52) U.S. Cl.

CPC .............. *A61K 38/20* (2013.01); *C07K 14/54* (2013.01); *A61K 35/17* (2013.01); *A61K 35/768* (2013.01); *A61K 38/1774* (2013.01); *A61K 47/642* (2017.08); *A61K 2300/00* (2013.01); *A61P 35/00* (2018.01); *C07K 14/70596* (2013.01); *C07K 2319/02* (2013.01);

(Continued)

(58) Field of Classification Search

None

See application file for complete search history.

(56) References Cited

U.S. PATENT DOCUMENTS

| | | | |
|---|---|---|---|
| 5,595,756 | A | 1/1997 | Bally |
| 6,479,258 | B1 | 11/2002 | Short |

(Continued)

FOREIGN PATENT DOCUMENTS

| | | |
|---|---|---|
| CN | 1367686 | 9/2002 |
| CN | 1457258 | 11/2003 |

(Continued)

OTHER PUBLICATIONS

Skolnick et al (Trends Biotechnol. Jan. 2000;18(1):34-9) (Year: 2000).*

(Continued)

*Primary Examiner* — Brian Gangle
*Assistant Examiner* — Andrea K McCollum
(74) *Attorney, Agent, or Firm* — Riverside Law LLP

(57) ABSTRACT

The present invention provides compositions and methods comprising an activator of interleukin-18 (IL-18) activity for use in therapeutic and non-therapeutic applications. The activator provides IL-18 signaling activity even in the presence of an inhibitory molecule 5 such as IL-18 binding protein (IL-18BP).

5 Claims, 43 Drawing Sheets

Specification includes a Sequence Listing.

Related U.S. Application Data

(60) Provisional application No. 62/554,605, filed on Sep. 6, 2017, provisional application No. 62/652,279, filed on Apr. 3, 2018.

(51) Int. Cl.

| | |
|---|---|
| *A61K 47/64* | (2017.01) |
| *A61P 35/00* | (2006.01) |
| *C07K 14/705* | (2006.01) |
| *C12N 15/85* | (2006.01) |

(52) U.S. Cl.
CPC ...... *C07K 2319/21* (2013.01); *C07K 2319/35* (2013.01); *C07K 2319/50* (2013.01); *C12N 15/85* (2013.01)

(56) References Cited

U.S. PATENT DOCUMENTS

| | | | |
|---|---|---|---|
| 6,713,279 | B1 | 3/2004 | Short |
| 6,800,479 | B2 | 10/2004 | Im |
| 6,872,551 | B2 | 3/2005 | Lima |
| 7,037,685 | B2 | 5/2006 | Yamamoto |
| 7,060,461 | B2 | 6/2006 | Butt |
| 7,186,528 | B2 | 3/2007 | Kirkpatrick |
| 7,220,576 | B2 | 5/2007 | Butt |
| 7,253,260 | B2 | 8/2007 | Janson |
| 7,279,155 | B2 | 10/2007 | Dinarello |
| 7,311,902 | B2 | 12/2007 | Bam |
| 7,442,526 | B2 | 10/2008 | Johanson |
| 7,498,165 | B2 | 3/2009 | Lima |
| 7,524,488 | B2 | 4/2009 | Dinarello |
| 7,595,039 | B2 | 9/2009 | Dede |
| 7,608,267 | B2 | 10/2009 | Paul |
| 7,655,413 | B2 | 2/2010 | Butt |
| 7,736,639 | B2 | 6/2010 | Bam |
| 7,875,709 | B2 | 1/2011 | Dinarello |
| 7,910,364 | B2 | 3/2011 | Lima |
| 7,928,197 | B2 | 4/2011 | Wonderling |
| 8,034,910 | B2 | 10/2011 | Wang |
| 8,119,369 | B2 | 2/2012 | Zuo |
| 8,609,373 | B2 | 12/2013 | Liu |
| 8,679,471 | B2 | 3/2014 | Carroll |
| 8,691,958 | B2 | 4/2014 | Butt |
| 10,150,803 | B2 | 12/2018 | Chen |
| 10,570,188 | B2 | 2/2020 | Auer |
| 10,882,905 | B2 | 1/2021 | Del Val |
| 10,918,740 | B2 | 2/2021 | Fotin-Mleczek |
| 11,053,293 | B2 | 7/2021 | Krupnick |
| 11,129,883 | B2 | 9/2021 | Marcus |
| 11,291,721 | B2 | 4/2022 | Loew |
| 11,401,324 | B2 | 8/2022 | Wong |
| 11,518,792 | B2 | 12/2022 | Wong |
| 2004/0023336 | A1 | 2/2004 | Heavner |
| 2005/0000086 | A1 | 1/2005 | Bam |
| 2005/0153880 | A1 | 7/2005 | Goto |
| 2005/0261213 | A1 | 11/2005 | Branigan |
| 2008/0076708 | A1 | 3/2008 | Altarocca |
| 2009/0202475 | A1 | 8/2009 | Abbas |
| 2011/0001891 | A1 | 8/2011 | Altarocca |
| 2014/0001129 | A1 | 4/2014 | Bardoff |
| 2019/0151363 | A1 | 5/2019 | Brentjens |
| 2019/0225673 | A1 | 7/2019 | Kruse |
| 2020/0306301 | A1 | 10/2020 | Andresen |
| 2021/0070825 | A1 | 3/2021 | Wong |
| 2021/0100840 | A1 | 4/2021 | Wong |
| 2021/0188968 | A1 | 6/2021 | Del Val |
| 2021/0238222 | A1 | 8/2021 | Borgschulte |
| 2022/0047677 | A1 | 2/2022 | Emtage |
| 2022/0056091 | A1 | 2/2022 | Pattabiraman |
| 2022/0073908 | A1 | 3/2022 | Swain |
| 2022/0226464 | A1 | 7/2022 | Kazer |
| 2022/0363766 | A1 | 11/2022 | Wucherpfennig |

FOREIGN PATENT DOCUMENTS

| | | | | |
|---|---|---|---|---|
| CN | 1764723 A | | 4/2006 | |
| EA | 005769 | | 6/2005 | |
| EP | 0861663 A2 | | 9/1998 | |
| EP | 1392717 | | 3/2004 | |
| EP | 1392830 | | 3/2004 | |
| EP | 1470236 | | 10/2004 | |
| EP | 1669454 A2 | | 6/2006 | |
| EP | 2109673 | | 10/2009 | |
| EP | 2161032 | | 3/2010 | |
| EP | 3054978 | | 8/2016 | |
| EP | 3432909 A1 | | 1/2019 | |
| EP | 3493827 A4 | | 2/2020 | |
| EP | 3649147 A2 | | 5/2020 | |
| EP | 3969035 A1 | | 3/2022 | |
| EP | 4013857 A1 | | 6/2022 | |
| JP | 2004530432 | | 10/2004 | |
| JP | 2011105737 | | 6/2011 | |
| WO | 2002101049 | | 12/2002 | |
| WO | WO-02101049 A2 | * | 12/2002 | .............. A61P 31/00 |
| WO | WO-2004091517 A2 | * | 10/2004 | ....... A61K 47/48215 |
| WO | WO-2005014642 A2 | * | 2/2005 | ................ A61P 1/04 |
| WO | 2005075648 | | 8/2005 | |
| WO | 2017103088 | | 6/2017 | |
| WO | 2018027155 A1 | | 2/2018 | |
| WO | 2020243729 A1 | | 12/2020 | |
| WO | 2022094473 A1 | | 5/2022 | |
| WO | 2022229412 A1 | | 11/2022 | |
| WO | 2022260968 A1 | | 12/2022 | |

OTHER PUBLICATIONS

Burgess et al. (J. Cell Biol. 111:2129-2138, 1990) (Year: 1990).*
Lazar et al. (Mol. Cell. Biol., 8:1247-1252, 1988) (Year: 1988).*
Bork (Genome Research, 2000,10:398-400) (Year: 2000).*
Guido et al (Curr Med Chem. 2008;15(1):37-46) (Year: 2008).*
Clark et al (J. Med. Chem., 2014, 57 (12), pp. 5023-5038) (Year: 2014).*
Vajdos et al. (J Mol Biol. Jul. 5, 2002;320(2):415-28 (Year: 2002).*
Brown et al. (J Immunol. May 1996; 156(9):3285-91 (Year: 1996).*
Aagaard et al (Advanced Drug Delivery Reviews 59 (2007) 75-86) (Year: 2007).*
Warzocha et al (Leukemia and Lymphoma (1997) vol. 24. pp. 267-281) (Year: 1997).*
McKeague et al (J Nucleic Acids. 2012;2012:748913. Epub Oct. 24, 2012) (Year: 2012).*
Ma et al (Clin Cancer Res; 22(12) Jun. 15, 2016) (Year: 2016).*
Garrido et al (Current Opinion in Immunology 2016, 39:44-51). (Year: 2016).*
Choi et al (Gene Therapy (2011) 18, 898-909) (Year: 2011).*
Miosge (Proc Natl Acad Sci U S A. Sep. 15, 2015;112(37):E5189-98) (Year: 2015).*
Aagaard et al ("RNAi therapeutics: Principles, prospects and challenges." Advanced Drug Delivery Reviews 59 (2007) 75-86) (Year: 2007).
Argiris, A. et al., 2017, "Evidence-Based Treatment Options in Recurrent and/or Metastatic Squamous Cell Carcinoma of the Head and Neck.", Frontiers in Oncology 7:72, 14 pages.
Azkur et al, 2020, "Immune response to SARS-CoV-2 and mechanisms of immunopathological changes in COVID-19." Allergy, 75(7): 1564-1581.
Boland, P.M. et al., 2017, "Immunotherapy for Colorectal Cancer." Cancers 9(5): 50, 12 pages.
Bork ("Powers and Pitfalls in Sequence Analysis: the 70% Hurdle." Genome Research, 2000,10:398-400) (Year: 2000).
Bowie et al. "Deciphering the Message in Protein Sequences: Tolerance to Amino Acid Substitutions." Science, 1990, 247:1306-1310.
Brown et al. . ("Tolerance to Single, but not Multiple, Amino Acid Replacements in antibody VH CDR2." J Immunol. 996 May;156(9):3285-91) (Year: 1996).
Burgess et al. "Possible Dissociation of the Heparin-binding and Mitogenic Activities of Heparin-binding (Acidic Fibroblast) Growth Factor-1 from Its Receptor-binding Activities by Site-directed

(56) References Cited

OTHER PUBLICATIONS

Mutagenesis of a Single Lysine Residue." J of Cell Bio. 1990, 111:2129-2138.
Butt et al., 2005, "SUMO fusion technology for difficult-to express proteins." Protein Expression and Purfication, 43, 1-19.
Clark et al ("Discovery and Development of Janus Kinase (JAK) Inhibitors for Inflammatory Diseases." J. Med. Chem., 2014, 57 (12), pp. 5023-5038) (Year: 2014).
Colman P.M. et al.: "Effects of amino acid sequence changes on antibody-antigen interactions", Research in Immunology, 1994, vol. 145, Issue 1, pp. 33-36.
Dine, J. et al., 2017, "Immune Checkpoint Inhibitors: An Innovation in Immunotherapy for the Treatment and Management of Patients with Cancer." Asia-Pacific journal of oncology nursing 4(2): 127, 9 pages.
Fuereder, T., 2016, "Immunotherapy for head and neck squamous cell carcinoma." memo-Magazine of European Medical Oncology 9(2):66-69, 4 pages.
Guido et al ("Virtual Screening and its Integration with Modern Drug Design Technologies." Curr Med Chem. 2008;15(1):37-46) (Year: 2008).
Guldbrandsen, K.F. et al., 2017, "Nuclear Molecular Imaging Strategies in Immune Checkpoint Inhibitor Therapy." Diagnostics, 7(2):23, 12 pages.
Huang et al., 2020, "Clinical features of patients infected with 2019 novel coronavirus in Wuhan, China." Lancet, 395:497-506.
Johnson, D.B. et al., 2017, "Immune Checkpoint Inhibitors in Challenging Populations." Cancer, 123(11):1904-1911, 8 pages.
Kewan et al, 2020, "Tocilizumab for treatment of patients with severe COVID-19: A retrospective cohort study." EClinicalMedicine, 24: 100418.
Kim, J.H. et al., 2017, "Prognostic value of KRAS mutation in advanced non-small-cell lung cancer treated with immune checkpoint inhibitors: A meta-analysis and review." Oncotarget 8(29):48248-48252, 5 pages.
Kim, Soo-Hyun M., et al., "Site-specific mutations in the mature form of human IL-18 with enhanced biological activity and decreased neutralization by IL-18 binding protein", Proc Natl Acad Sci, (2001), vol. 98(6):3304-9, ISSN 0004818512.
Kim, Soo-Hyun M., et al., "Structural requirements of six naturally occurring isoforms of the IL-18 binding protein to Inhibit IL-18", Proc Natl Acad Sci, (2000), vol. 97(3):1190-5, ISSN 0004818513.
Lazar et al. "Transforming Growth Factor alpha: Mutation of Aspartic Acid 47 and Leucine 48 Results in Different Biological Activities." Molecular and Cellular Biology 8:1247-1252, 1988.
Ma Z et al: "Augmentation of immune checkpoint cancer immunotherapy with IL18", Clinical Cancer Research Jun. 15, 2016 American Association for Cancer Research Inc. USA, vol. 22, No. 12, Jun. 15, 2016 (Jun. 15, 2016) , pp. 2969-2980, XP055392162, ISSN: 1078-0432.
Malhotra, J. et al., 2017, "Current state of immunotherapy for non-small cell lung cancer." Translational lung cancer research 6(2):196, 16 pages.
McKeague et al ("Challenges and Opportunities for Small Moleucle Aptamer Development." J Nucleic Acids. 2012;2012:748913. Epub Oct. 24, 2012) (Year: 2012).
Michot et al., 2020, "Tocilizumab, an anti-IL-6 receptor antibody, to treat COVID-19-related respiratory failure: a case report." Annals of Oncology, 31(7):961-964.
Miller et al., 2014, "NP001 regulation of macrophage activation markers in ALS: A phase I clinical and biomarker study." Amyotroph Lateral Scler Frontotemporal Degener. Dec. 2014; 15(7-8): 601-609.
Miller et al., 2015, "Randomized phase 2 trial of NP001-a novel immune regulator: Safety and early efficacy in ALS." Neurol Neuroimmunol Neuroinflamm 2015;2:e100.
NCBI reference for IL-18; downloaded from https://www.ncbi.nlnn.nih.gov/gene?ternn=(i118[gene])%20AND%20(Horno%20sapiens[orgn])%20AND%20alive[prop]%20NOT%2Onewentry[gene]&sort=weight on Feb. 2, 2020 (Year: 2020).
Petrelli, F. et al., 2016, "Early analysis of surrogate endpoints for metastatic melanoma in immune checkpoint inhibitor trials." Medicine 95(26):e3997, 7 pages.
Ruan et al., 2020, "Clinical predictors of mortality due to COVID-19 based on an analysis of data of 150 patients from Wuhan, China." Intensive Care Med, 46(5):846-848.
Sabrina Richards, 2022 "New approach could make bone marrow transplantation safer, stronger." Fred Hutch News Service, https://www.fredhutch.org/en/news/center-news/2022/10/agonist-immunotherapy-bone-marrow-transplant.html, accessed Nov. 4, 2022.
Sarzi-Puttini et al., 2020, "COVID-19, cytokines and immunosuppression: what can we learn from severe acute respiratory syndrome?" Clinical and Experimental Rheumatology, 38: 337-342.
Silva et al., 2019, "De novo design of potent and selective mimics of IL-2 and IL-15", Nature, vol. 565, 29 pages.
Singer et al., 2016, "A Distinct Gene Module for Dysfunction Uncoupled from Activation in Tumor-Infiltrating T Cells." Cell, 166:1500-1511, e1509.
Song et al., 2020, "Cytokine storm induced by SARS-CoV-2." Clinica Chimica Acta, 509: 280-287.
Tinhofer, I. et al., 2016, "The rationale for including immune checkpoint inhibition into multimodal primary treatment concepts of head and neck cancer." Cancers of the Head & Neck 1:8, 11 pages.
Tortajada et al., 2020, "Corticosteroids for COVID-19 patients requiring oxygen support? Yes, but not for everyone: Effect of corticosteroids on mortality and intensive care unit admission in patients with COVID-19 according to patients' oxygen requirements." J Med Virol. 2020;1-7.
Tsutsumi et al., 2014, "The structural basis for receptor recognition of human interleukin-18", Nature Communications, pp. 1-13.
Tsutsumi et al., 2014, "The structural basis for receptor recognition of human interleukin-18", Supplementary Information, pp. 1-11.
Vajdos et al. ("Comprehensive Functional Maps of the Antigen-binding Site of an Anti-ErbB2 Antibody Obtained with Shotgun Scanning Mutagenesis." J Mol Biol. Jul. 5, 2002;320(2):415-28) (Year: 2002).
Wang et al. "Cytokine storm and leukocyte changes in mild versus severe SARS-CoV-2 infection: Review of 3939 COVID-19 patients in China and emerging pathogenesis and therapy concepts." J Leukoc Biol. 2020;1-25.
Warzocha et al ("Antisense Strategy: Biological Utility and Prospects in the Treatment of Hematological Malignancies." Leukemia and Lymphoma (1997) vol. 24. pp. 267-281) (Year: 1997).
Auerbach et al ("Angiogenesis assays: problems and pitfalls" Cancer and Metastasis Reviews, 2000, 19: 167-172) (Year: 2000).
Gura T ("System for identifying new drugs are often faulty." Science, 1997, 278(5340): 1041-1042) (Year: 1997).
HogEnesch et al ("Challenges in pre-clinical testing of anti-cancer drugs in cell culture and in animal models." J Control Release. Dec. 10, 2012; 164(2): 183-186.) (Year: 2012).
Jain RK ("Barriers to drug delivery in solid tumors." Scientific American, Jul. 1994,58-65) (Year: 1994).
Sporn et al, "Chemoprevention of Cancer," Carcinogenesis, vol. 21 (2000), 525-530 (Year: 2000).

* cited by examiner

Human DR-IL-18 variants sequence summary

| | | 1 | 5 | 8 | 51 | 53 | 55 | 59 | 60 | 77 | 103 | 105 | 110 | 111 | 153 | 155 | SEQ ID NO: |
|---|---|---|---|---|---|---|---|---|---|---|---|---|---|---|---|---|---|
| | WT hIL-18 | Y | L | K | M | K | S | G | M | E | Q | S | D | N | V | N | 30 |
| Selected Variants | hC4 | | | Q | T | | K | T | K | | | R | H | | | K | 38 |
| | hA8 | | | R | K | | K | A | Q | | | D | K | H | I | | 39 |
| | hD6 | | | R | D | | K | A | K | | | D | K | H | I | | 40 |
| | hH12 | | H | | T | R | | | K | | | D | N | | T | | 41 |
| | hB11 | | I | | K | | K | A | Q | | | K | Q | H | | K | 42 |
| | hC3 | | I | | T | | R | | K | | E | D | H | H | I | | 43 |
| | hC2 | | I | | T | | K | | K | | | D | K | H | T | H | 44 |
| | hG10 | | I | | T | | K | A | K | | | R | H | H | I | K | 45 |
| | hG1 | | I | R | T | | K | | K | | | D | | Y | I | K | 46 |
| | hF1 | | Y | R | T | R | | | K | | | D | E | H | | K | 47 |
| | hD2 | H | Y | | T | R | | | K | | | D | H | | | K | 48 |
| | hA1 | R | | | T | R | | A | K | | | D | Q | H | A | K | 49 |
| | hB3 | R | | R | D | R | | | R | | K | N | K | Y | | H | 50 |
| | hB4 | R | | R | N | R | | | Q | | K | R | N | H | | K | 51 |
| | hH3 | R | | R | T | | | | K | | | D | K | H | | | 52 |
| | hC5 | R | | R | T | R | | T | K | | | K | N | H | | K | 53 |
| | hH4 | R | | R | T | R | | A | K | | E | D | Q | H | I | K | 54 |
| | hE1 | R | | R | T | R | | T | K | | | N | H | D | | H | 55 |
| | hG2 | R | | R | T | | | A | K | | E | D | Q | H | I | K | 56 |
| | hB9 | R | H | | T | R | | | K | | E | N | K | Y | | | 57 |
| | hE12 | R | Y | | T | | | T | K | D | | D | K | H | | | 58 |
| Consensus Variants | hCS1 | | | | T | | | | K | | | D | K | H | | | 34 |
| | hCS2 | | | | T | | K | A | K | | | D | K | H | I | | 35 |
| | hCS3 | R | | | T | | | | K | | | D | K | H | | | 36 |
| | hCS4 | R | | | T | R | | | K | | | N | K | Y | | | 37 |

FIG. 4

| Residue | Codon | AA |
|---|---|---|
| 1Y | NWT | FYLHINVD |
| 51M | RNG | MTKRVAEG |
| 53K | VNS | LPHQRIMTNKSRVADEG |
| 56Q | VNA | LPQRITKRVAEG |
| 57P | VNA | LPQRITKRVAEG |
| 60M | MDG | MKRLQR |
| 103Q | VVR | QKERRGPTA |
| 105S | DMT | SYTNAD |
| 110D | RRW | DEKNSRGG |
| 111N | VRW | HQNKDERRSRGG |
| 113M | RNG | MTKRVAEG |

| | | 51 | 53 | 56 | 57 | 60 | 103 | 105 | 110 | 111 | 113 | SEQ ID NO: |
|---|---|---|---|---|---|---|---|---|---|---|---|---|
| | WT hIL-18 | M | K | Q | P | M | Q | S | D | N | M | 30 |
| Round 5 variants | 5-18 | E | | E | L | R | P | A | N | R | V | 73 |
| | 5-29 | K | | A | G | L | E | D | S | S | R | 74 |
| | 5-8 | K | G | A | A | L | | | K | R | | 75 |
| | 5-6 | K | G | R | G | L | E | D | N | S | R | 76 |
| | 5-26 | K | G | V | | L | A | A | S | R | T | 77 |
| | 5-20 | K | S | G | A | L | A | A | G | R | T | 78 |
| | 5-2 | K | S | K | A | | A | D | S | S | R | 79 |
| | 5-9 | K | S | L | A | L | | D | S | R | | 80 |
| | 5-42 | K | S | R | A | L | | N | G | R | | 81 |
| | 5-17 | K | S | R | A | L | A | | G | R | T | 192 |
| | 5-41 | K | S | R | A | L | A | D | S | G | R | 193 |
| | 5-1 | K | T | R | | L | E | D | S | S | K | 84 |
| | 5-33 | K | T | R | A | | E | D | N | D | R | 85 |
| | 5-21 | R | | G | K | L | R | | S | R | V | 86 |
| Round 6 variants | 6-31 | K | G | G | A | L | E | D | S | G | V | 87 |
| | 6-20 | K | G | R | | | | A | N | R | | 88 |
| | 6-12 | K | S | L | A | L | | D | S | R | | 89 |
| | 6-27 | K | S | R | A | L | A | | G | R | T | 90 |
| | 6-29 | K | S | R | A | L | | N | G | R | | 91 |

FIG. 8

FIG. 9A
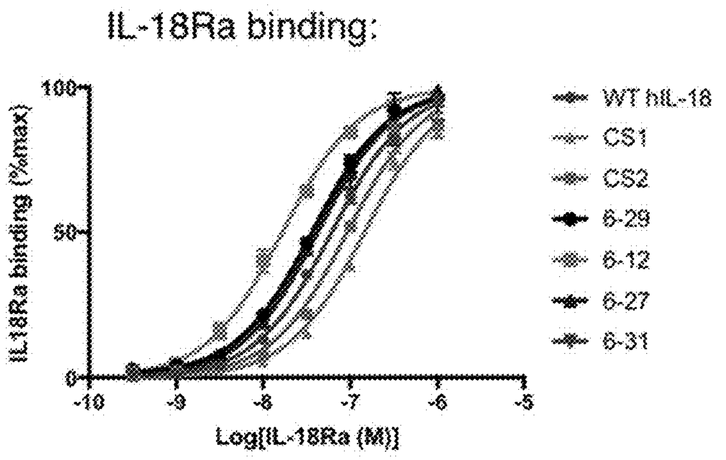
FIG. 9B
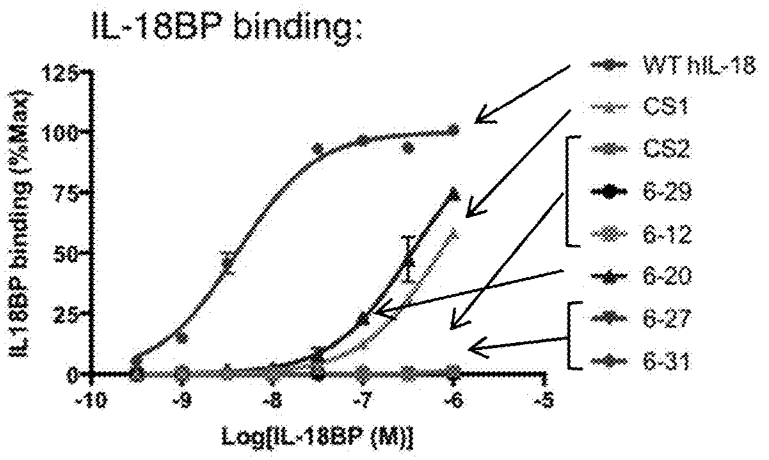
FIG. 9C
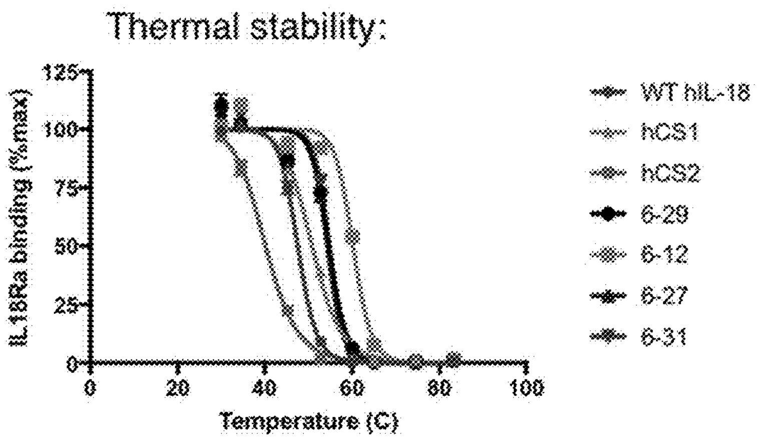
FIG. 9D
| Variant | IL18Rα (KD) | IL18BP (KD) | Rα:BP ratio (norm. to WT) | Tm (°C) |
|---|---|---|---|---|
| WT IL18 | 62 nM | 2.1 nM | 1.0 | 47.6 |
| hCS1 | 146 nM | 710 nM | 140 | 50.9 |
| hCS2 | 92 nM | NBD | >3,200 | 40.2 |
| 6-31 | 41 nM | NBD | >7,200 | 54.9 |
| 6-20 | N.D. | 340 nM | N.D | N.D. |
| 6-12 | 17 nM | NBD | >17,000 | 60.2 |
| 6-27 | 42 nM | NBD | >7,000 | 54.3 |
| 6-29 | 37 nM | NBD | >8,000 | 54.7 |

FIG. 10C

Murine DR-IL-18 variants sequence summary

| | | 1 | 50 | 51 | 52 | 54 | 55 | 56 | 57 | 58 | 59 | 104 | 109 | 151 | SEQ ID NO: |
|---|---|---|---|---|---|---|---|---|---|---|---|---|---|---|---|
| | **mIL-18** | N | M | Y | K | S | E | V | R | G | L | R | N | L | 31 |
| Selected Variants | mC1 | | A | | V | R | R | L | | | K | K | | | 62 |
| | mA12 | | S | | S | K | H | M | | | K | L | | | 63 |
| | mE8 | | V | | T | G | R | R | | | K | K | D | | 64 |
| | mC10 | H | A | | G | | H | M | | | K | Q | | V | 65 |
| | mB7 | H | A | | G | | N | A | G | | R | K | | | 66 |
| | mB1 | H | G | | A | | D | A | | A | K | S | | V | 67 |
| | mD1 | H | G | | S | R | G | S | K | | K | Q | | | 68 |
| | mH7 | Y | | | A | R | R | A | | | K | K | D | V | 69 |
| | mA7 | Y | A | | G | N | R | | | | K | | | | 70 |
| | mE1 | Y | G | | G | | | R | G | | R | | D | | 71 |
| | mH3 | Y | T | R | T | G | G | Q | K | | V | | D | | 72 |
| Consensus Variants | **mCS1** | | G | | A | | R | | | | K | | | | 60 |
| | **mCS2** | H | A | | G | | R | A | | | K | | | | 61 |

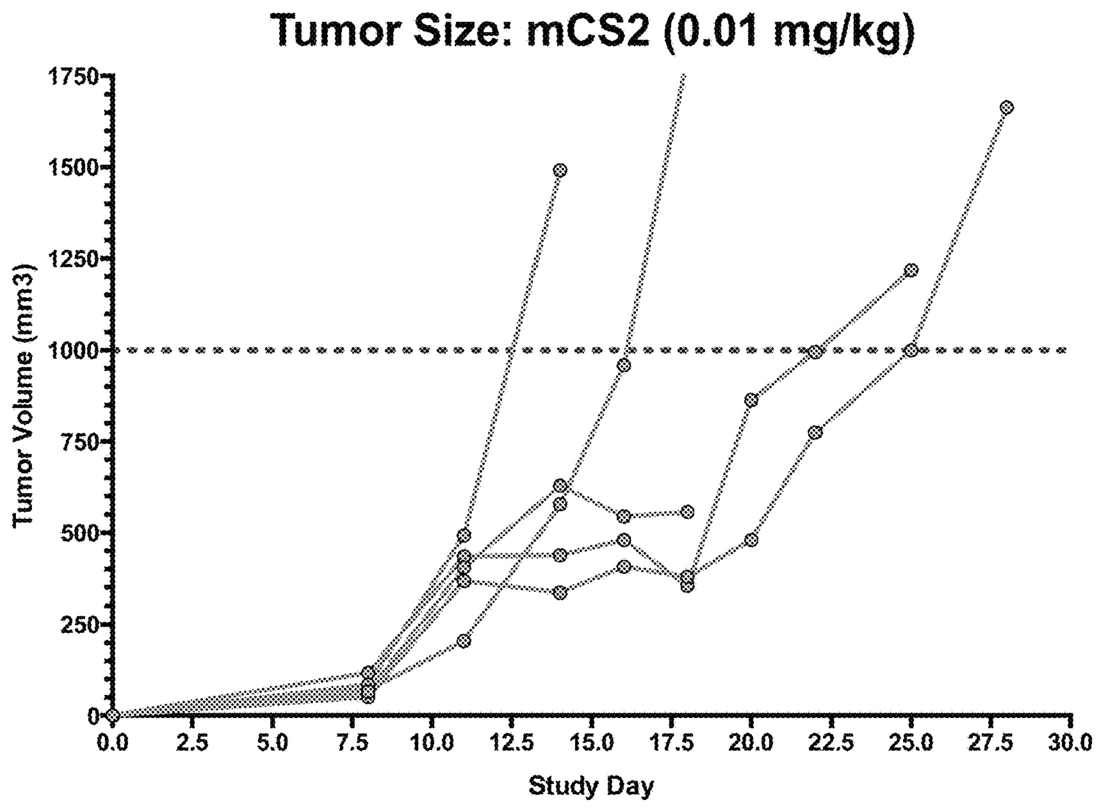
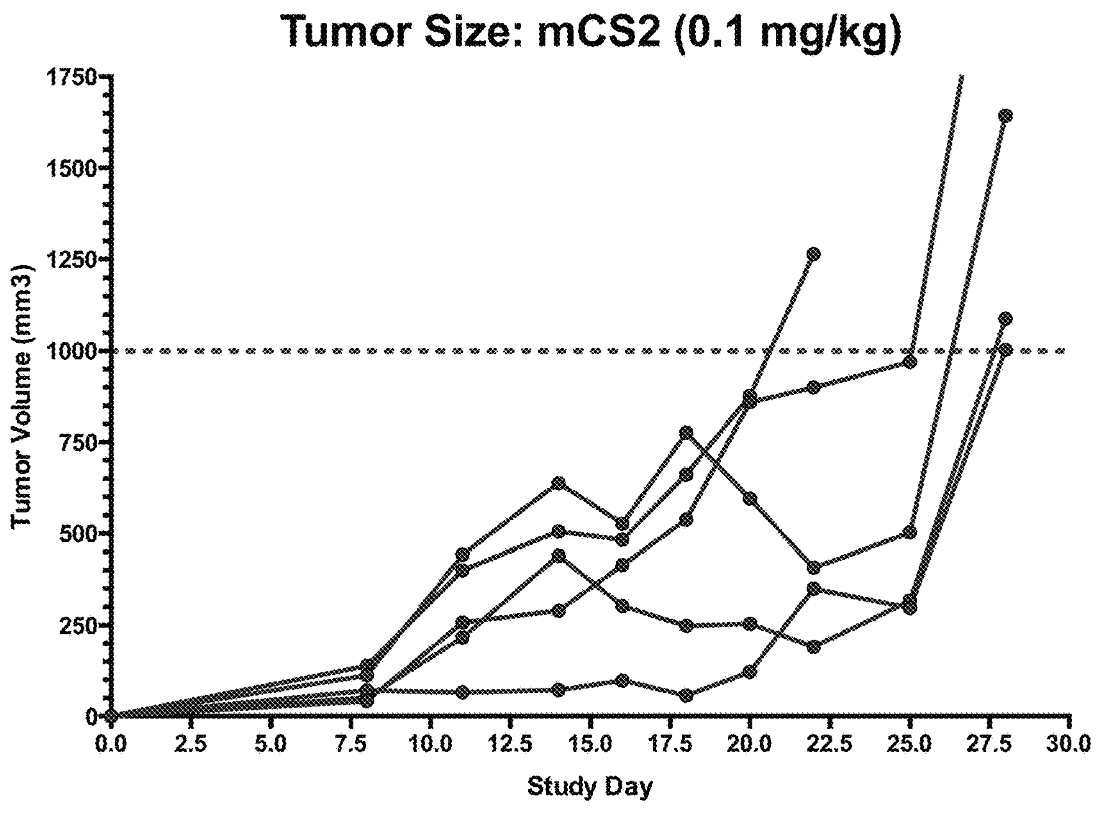
FIG. 16 Cont.

β2m-/- YUMMER1.7 melanoma model

FIG. 20A
| Residue | Amino Acids | Codon |
|---|---|---|
| Y1 | YFLHVD | BWT |
| L5 | L,F,Y,H,R,C | YDT |
| D17 | D,A,G,R,H,P | SVT |
| E31 | E,A,G,T,K,R | RVA |
| T34 | T,A,E,K | RMA |
| D35 | D,A,S,Y | KMT |
| S36 | S,N,K,R | ARW |
| D37 | D,A,Y,S | SNT |
| D40 | D,A,Y,S | KMT |
| N41 | N,K,S,R | ARW |
| M51 | M,I,L,F | WTS |
| M60 | M,I,L,F | WTS |
| Q103 | Q,L,I,K | MWA |
| H109 | H,D,A,P | SMT |
| M113 | M,I,L,F | WTS |
| D132 | D,A,Y,S,V,F | KHY |
FIG. 20B
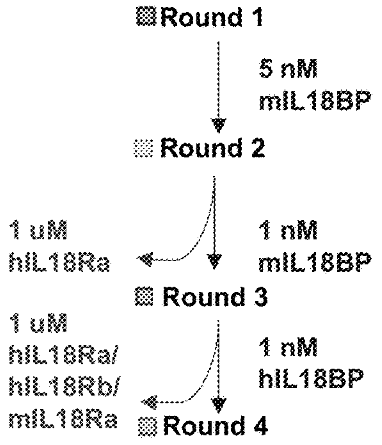
FIG. 20C
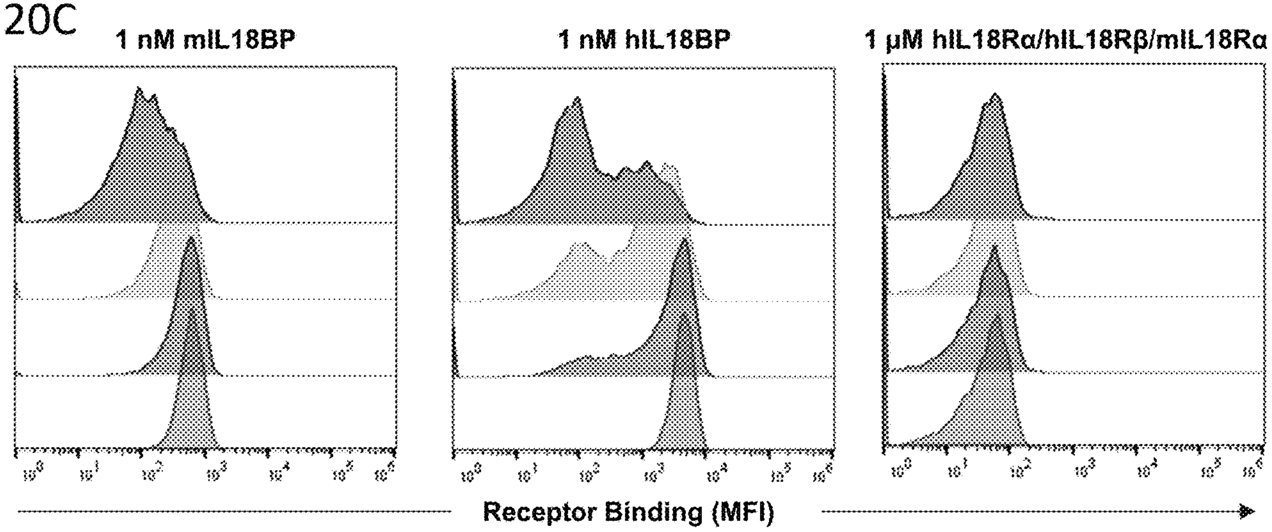

| | 1 | 5 | 17 | 31 | 34 | 35 | 36 | 37 | 40 | 41 | 51 | 56 | 60 | 103 | 109 | 113 | 131 | SEQ ID NO: |
|---|---|---|---|---|---|---|---|---|---|---|---|---|---|---|---|---|---|---|
| WT hIL-18 | Y | L | D | E | T | D | S | D | D | N | M | Q | M | Q | H | M | R | 30 |
| hD2D-5D02 | | | | A | A | S | N | P | Y | K | | | L | L | A | L | | 109 |
| hD2D-5D08 | | | | A | K | A | K | A | S | | F | | F | L | A | I | | 105 |
| hD2D-5A02 | | | A | T | | A | | P | S | S | L | | L | L | P | I | | 122 |
| hD2D-5B02 | | | G | A | | S | K | R | | | L | | F | I | | I | | 120 |
| hD2D-5B10 | | | G | G | | A | K | H | A | R | F | | | I | A | F | | 117 |
| hD2D-5C03 | | | G | K | E | A | N | | S | S | I | | L | I | A | | | 115 |
| hD2D-5C08 | | | G | T | | A | | H | S | S | L | | | L | | F | | 112 |
| hD2D-5E08 | | | G | T | | A | | P | | | F | | L | L | | I | S | 101 |
| hD2D-5C04 | | | G | T | E | S | | L | | | L | | | L | A | F | S | 114 |
| hD2D-5C05 | | | G | T | E | Y | R | L | A | | F | H | L | L | D | L | | 113 |
| hD2D-5D05 | | | G | T | K | S | N | L | S | | F | | I | I | D | I | | 107 |
| hD2D-5F04 | | | R | T | | Y | K | | | | F | | F | I | A | I | | 97 |
| hD2D-5F11 | D | | | A | | | N | P | S | | F | | I | L | P | | | 93 |
| hD2D-5B11 | D | | | A | K | A | | A | A | | | | L | L | | F | | 116 |
| hD2D-5E03 | D | | | A | K | S | N | V | A | | | | | I | P | L | | 102 |
| hD2D-5B05 | F | | G | A | A | S | N | H | A | | L | | L | I | | | | 119 |
| hD2D-5B06 | F | F | G | T | E | S | K | | | R | F | | L | L | | L | | 118 |
| hD2D-5F06 | H | | | T | E | S | K | P | | S | | | I | I | | F | | 96 |
| hD2D-5C09 | H | | G | A | | | N | P | S | R | F | | | I | | F | | 111 |
| hD2D-5D10 | H | | G | A | A | S | N | R | A | | | | F | I | P | F | | 104 |
| hD2D-5F10 | H | | G | A | E | A | | P | | | F | | L | L | | | | 94 |
| hD2D-5E10 | H | | G | A | E | S | N | R | | S | | | F | L | | I | | 100 |
| hD2D-5F02 | H | | G | G | E | A | | P | | | F | | | I | A | L | | 98 |
| hD2D-5E02 | H | | G | G | E | A | | P | A | K | I | | F | L | | F | S | 103 |
| hD2D-5F12 | H | | G | K | | A | | | A | | F | | | I | A | F | | 92 |
| hD2D-5D03 | H | | G | R | A | A | | H | | S | I | | F | L | | I | | 108 |
| hD2D-5F01 | H | | G | T | | S | | | | K | F | | L | L | P | F | | 99 |
| hD2D-5C10 | H | | G | T | A | S | N | H | Y | | | | L | L | A | I | | 110 |
| hD2D-5D06 | H | | H | T | A | | N | A | | | F | | L | I | D | | | 106 |
| hD2D-5F08 | L | | G | A | | S | | P | S | R | F | | F | I | | I | | 95 |
| hD2D-5A09 | L | H | G | G | E | S | | P | Y | | F | | L | I | | | | 121 |
| hD2D-CS1 | | | G | A | | | | | | | | | | L | | | | 123 |
| hD2D-CS2 | | | G | A | | S | | | | | F | | | L | | | | 124 |
| hD2D-CS3 | | | G | A | E | S | | | | | F | | L | L | | | | 125 |

FIG. 21

FIG. 22A
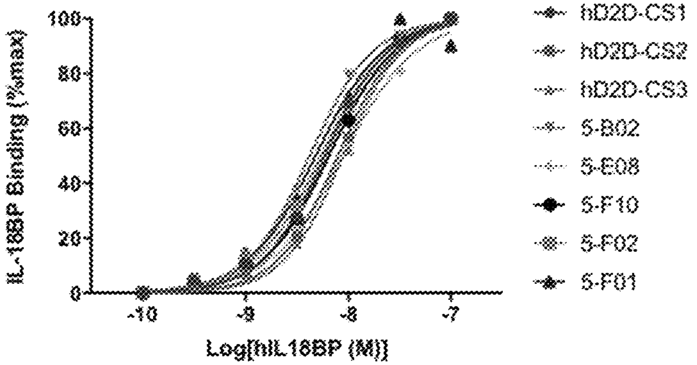
FIG. 22B
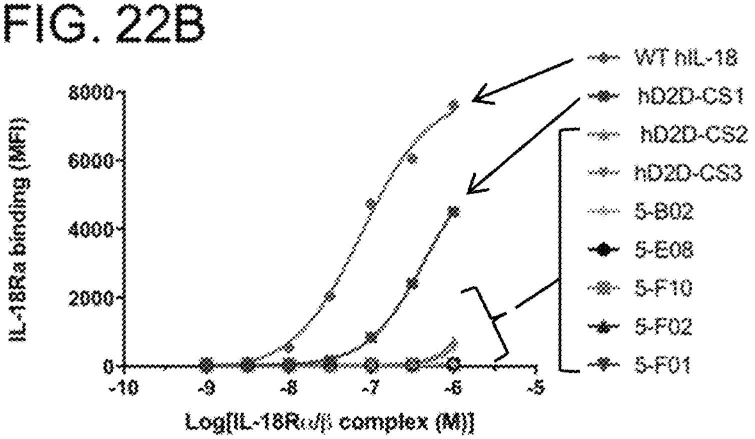
FIG. 22C
| Variant | IL18Rα (KD) | IL18BP (KD) | BP:Rα ratio (norm. to WT) |
|---|---|---|---|
| WT IL18 | 62 nM | 2.1 nM | 1 |
| hD2D-CS1 | 430 nM | 5.9 nM | 2.5 |
| hD2D-CS2 | 21 μM | 7.9 nM | 90 |
| hD2D-CS3 | 9.7 μM | 8.9 nM | 37 |
| 5-B02 | NBD | 4.2 nM | >170 |
| 5-E08 | NBD | 8.8 nM | >81 |
| 5-F10 | NBD | 6.4 nM | >110 |
| 5-F02 | NBD | 5.4 nM | >130 |
| 5-F01 | NBD | 4.8 nM | >150 |

| | 1 | 5 | 17 | 30 | 33 | 34 | 35 | 36 | 50 | 102 | 104 | 108 | 109 | 111 | 129 | 130 | SEQ ID NO: |
|---|---|---|---|---|---|---|---|---|---|---|---|---|---|---|---|---|---|
| WT mIL-18 | N | L | D | E | T | D | I | D | M | Q | R | H | N | M | D | D | 31 |
| mD2D-A5 | Y | Y | Q | A | G | Y | T | V | | L | E | | R | L | | E | 126 |
| mD2D-A6 | D | | | A | G | S | | A | F | L | A | D | | I | A | T | 127 |
| mD2D-A7 | Y | | G | R | A | | T | V | F | I | P | A | S | | A | G | 128 |
| mD2D-A8 | H | | | K | E | Y | T | V | | I | A | D | R | I | | N | 129 |
| mD2D-A9 | Y | | A | A | A | | K | G | | L | P | D | T | | F | G | 130 |
| mD2D-A11 | Y | | E | A | G | | R | H | | I | P | A | S | L | | | 131 |
| mD2D-A12 | H | | | R | G | A | | G | F | I | P | D | S | L | V | | 132 |
| mD2D-B4 | H | | S | T | G | S | | V | | I | G | D | | I | | R | 133 |
| mD2D-B7 | Y | | S | R | E | | T | P | F | I | | D | S | L | F | E | 134 |
| mD2D-B11 | H | | A | G | | A | T | V | F | I | P | D | S | L | | N | 135 |
| mD2D-B12 | | | N | K | E | Y | T | L | F | I | P | D | | L | Y | E | 136 |
| mD2D-C1 | Y | | G | A | E | A | T | R | F | I | G | A | | | | G | 137 |
| mD2D-C3 | | | G | A | R | A | | L | F | L | G | D | | L | | R | 138 |
| mD2D-C5 | Y | | A | A | E | A | T | A | F | I | G | A | S | | | G | 139 |
| mD2D-C6 | L | | G | A | G | A | T | L | | L | P | D | T | | A | S | 140 |
| mD2D-C9 | | | G | | A | Y | T | V | F | I | G | D | S | | Y | | 141 |
| mD2D-C10 | D | | | K | E | S | K | P | F | L | A | A | S | L | A | N | 142 |
| mD2D-C11 | L | | G | A | G | | K | V | | I | P | D | | L | | E | 143 |
| mD2D-D1 | Y | H | Q | R | A | A | T | R | | L | G | D | | | | | 144 |
| mD2D-D9 | | | Q | T | E | S | | G | F | L | A | A | | L | | S | 145 |
| mD2D-D12 | F | H | G | G | G | | R | V | | I | A | D | S | I | | G | 146 |
| mD2D-E3 | V | H | G | K | | Y | | | | L | A | D | T | | A | Q | 147 |
| mD2D-E4 | | | G | A | | A | T | R | | I | Q | A | | I | F | R | 148 |
| mD2D-E5 | D | | G | G | A | Y | | G | F | I | A | | S | I | S | G | 149 |
| mD2D-E7 | Y | | | R | G | S | | A | | I | P | A | T | L | | G | 150 |
| mD2D-E8 | Y | | E | T | E | A | | G | F | I | G | D | R | | | G | 151 |
| mD2D-E9 | F | | N | | E | Y | R | L | | L | P | A | S | L | S | | 152 |
| mD2D-E10 | | | N | A | E | | R | L | | L | G | D | | | | H | 153 |
| mD2D-E11 | Y | | A | R | G | Y | | L | L | L | P | D | T | I | | N | 154 |
| mD2D-E12 | Y | | | G | A | | T | A | F | I | P | D | S | | A | | 155 |
| mD2D-F3 | D | | G | | A | Y | | A | F | I | P | D | S | I | A | | 156 |
| mD2D-F4 | | | E | R | K | Y | | L | F | L | G | D | | | Y | G | 157 |
| mD2D-F5 | D | | E | T | A | Y | | L | F | I | A | D | S | L | | T | 158 |
| mD2D-F7 | D | | N | K | E | S | T | A | | L | G | A | S | L | A | G | 159 |
| mD2D-F8 | H | | E | A | E | A | | G | F | I | G | D | T | L | | G | 160 |
| mD2D-F9 | I | | E | K | R | Y | | V | F | I | E | A | S | L | | E | 161 |
| mD2D-G1 | Y | | A | T | G | Y | T | L | L | I | P | | | I | | R | 162 |
| mD2D-G7 | | | N | R | A | S | T | A | | I | G | | | I | | | 163 |
| mD2D-G9 | D | | G | | K | | R | A | F | L | A | | S | | | E | 164 |
| mD2D-H7 | | | E | A | | | | A | | L | P | D | I | | Y | G | 165 |
| mD2D-E1 | Y | | E | A | | | T | L | F | L | G | D | | | | T | 166 |
| mD2D-A10 | H | | G | K | K | Y | | V | | L | A | | S | I | | S | 169 |
| mD2D-F12 | Y | | G | | K | A | K | A | F | I | P | A | S | | | G | 171 |
| mD2D-E2 | L | | G | G | G | S | | P | F | I | H | A | T | | | N | 174 |
| mD2D-C4 | Y | | S | T | A | Y | T | V | F | I | A | D | S | L | | N | 176 |
| mD2D-C2 | Y | | G | T | G | A | R | V | F | L | P | D | | L | S | G | 178 |
| mD2D-A2 | D | | G | G | K | A | T | G | F | I | A | A | | L | A | G | 180 |
| mD2D-A1 | D | | S | R | G | S | | H | F | L | A | A | | L | | G | 182 |
| mD2D-D4 | Y | | E | K | K | | K | L | F | L | G | D | | L | F | G | 184 |
| mD2D-A3 | Y | | G | A | A | S | T | H | F | L | G | A | | I | | | 186 |
| mD2D-B9 | Y | | S | G | K | Y | | V | F | L | G | D | T | | S | G | 190 |

FIG. 23

SEQUENCE LISTING

```
Sequence total quantity: 194
SEQ ID NO: 1           moltype = DNA  length = 58
FEATURE                Location/Qualifiers
source                 1..58
                       mol_type = other DNA
                       organism = synthetic construct
SEQUENCE: 1
cattttcatt aagatgcagt tacttcgctg tttttcaata ttttctgtta ttgctagc    58

SEQ ID NO: 2           moltype = DNA  length = 80
FEATURE                Location/Qualifiers
variation              31
                       note = n is a, c, g, or t
variation              42
                       note = n is a, c, g, or t
source                 1..80
                       mol_type = other DNA
                       organism = synthetic construct
SEQUENCE: 2
aattacggat gaccgaaagt ykggattcaw ncttgccgaa anrtgctaaa acgctagcaa  60
taacagaaaa tattgaaaaa                                              80

SEQ ID NO: 3           moltype = DNA  length = 51
FEATURE                Location/Qualifiers
source                 1..51
                       mol_type = other DNA
                       organism = synthetic construct
SEQUENCE: 3
actttcggtc atccgtaatt tgaacgacca agtccttttt attgaccagg g           51

SEQ ID NO: 4           moltype = DNA  length = 55
FEATURE                Location/Qualifiers
source                 1..55
                       mol_type = other DNA
                       organism = synthetic construct
SEQUENCE: 4
actatccgtc atatcctcga ataagggacg attgccctgg tcaataaaaa ggact       55

SEQ ID NO: 5           moltype = DNA  length = 44
FEATURE                Location/Qualifiers
source                 1..44
                       mol_type = other DNA
                       organism = synthetic construct
SEQUENCE: 5
cttattcgag gatatgacgg atagtgattg ccgtgacaac gccc                   44

SEQ ID NO: 6           moltype = DNA  length = 84
FEATURE                Location/Qualifiers
variation              22
                       note = n is a, c, g, or t
variation              46
                       note = n is a, c, g, or t
source                 1..84
                       mol_type = other DNA
                       organism = synthetic construct
SEQUENCE: 6
actgagattg ttaccgcchb tnyacggggt tgwyyatcty tatasnyaga gatgatgaaa  60
```

```
attgtacgag gggcgttgtc acgg                                          84

SEQ ID NO: 7            moltype = DNA  length = 52
FEATURE                 Location/Qualifiers
source                  1..52
                        mol_type = other DNA
                        organism = synthetic construct
SEQUENCE: 7
ggcggtaaca atctcagtta agtgcgaaaa aatctcgaca ctttcttgtg aa           52

SEQ ID NO: 8            moltype = DNA  length = 53
FEATURE                 Location/Qualifiers
source                  1..53
                        mol_type = other DNA
                        organism = synthetic construct
SEQUENCE: 8
ggttcatttc cttgaacgaa atgatcttgt tttcacaaga aagtgtcgag att          53

SEQ ID NO: 9            moltype = DNA  length = 62
FEATURE                 Location/Qualifiers
source                  1..62
                        mol_type = other DNA
                        organism = synthetic construct
SEQUENCE: 9
catttcgttc aaggaaatga acccgccgga taatatcaag gatacaaaat cagatattat  60
tt                                                                  62

SEQ ID NO: 10           moltype = DNA  length = 88
FEATURE                 Location/Qualifiers
variation               27
                        note = n is a, c, g, or t
source                  1..88
                        mol_type = other DNA
                        organism = synthetic construct
SEQUENCE: 10
tgatgagctc tcgaattgca tcttatnwtb gtgtccaggc acwyyacgwt bgaagaaaat  60
aatatctgat tttgtatcct tgatatta                                      88

SEQ ID NO: 11           moltype = DNA  length = 51
FEATURE                 Location/Qualifiers
source                  1..51
                        mol_type = other DNA
                        organism = synthetic construct
SEQUENCE: 11
ataagatgca attcgagagc tcatcatacg aaggttactt tttagcctgc g            51

SEQ ID NO: 12           moltype = DNA  length = 50
FEATURE                 Location/Qualifiers
source                  1..50
                        mol_type = other DNA
                        organism = synthetic construct
SEQUENCE: 12
aattaactta aacaggtcgc gctccttctc gcaggctaaa aagtaacctt              50

SEQ ID NO: 13           moltype = DNA  length = 49
FEATURE                 Location/Qualifiers
source                  1..49
                        mol_type = other DNA
                        organism = synthetic construct
SEQUENCE: 13
gcgacctgtt taagttaatt cttaagaaag aagatgagtt gggggatcg               49

SEQ ID NO: 14           moltype = DNA  length = 61
FEATURE                 Location/Qualifiers
source                  1..61
                        mol_type = other DNA
                        organism = synthetic construct
SEQUENCE: 14
ccagaaccac cgtcctcwtb ctgadyggta aacatgatgc tacgatcccc caactcatct  60
t                                                                   61

SEQ ID NO: 15           moltype = DNA  length = 52
FEATURE                 Location/Qualifiers
source                  1..52
                        mol_type = other DNA
                        organism = synthetic construct
SEQUENCE: 15
gaggacggtg gttctggatc cgaacaaaag cttatctccg aagaagactt gg           52
```

```
SEQ ID NO: 16          moltype = DNA  length = 41
FEATURE                Location/Qualifiers
source                 1..41
                       mol_type = other DNA
                       organism = synthetic construct
SEQUENCE: 16
ccaccagatc caccaccacc caagtcttct tcggagataa g                     41

SEQ ID NO: 17          moltype = DNA  length = 62
FEATURE                Location/Qualifiers
source                 1..62
                       mol_type = other DNA
                       organism = synthetic construct
SEQUENCE: 17
cattttcatt aagatgcagt tacttcgctg tttttcaata ttttctgtta ttgctagcgt  60
tt                                                                 62

SEQ ID NO: 18          moltype = DNA  length = 55
FEATURE                Location/Qualifiers
variation              25
                       note = n is a, c, g, or t
source                 1..55
                       mol_type = other DNA
                       organism = synthetic construct
SEQUENCE: 18
ttgtacagtg aagtcggcca aaawntgcta aaacgctagc aataacagaa aatat       55

SEQ ID NO: 19          moltype = DNA  length = 59
FEATURE                Location/Qualifiers
source                 1..59
                       mol_type = other DNA
                       organism = synthetic construct
SEQUENCE: 19
gccgacttca ctgtacaacc gcagtaatac ggaatataaa tgaccaagtt ctcttcgtt   59

SEQ ID NO: 20          moltype = DNA  length = 67
FEATURE                Location/Qualifiers
source                 1..67
                       mol_type = other DNA
                       organism = synthetic construct
SEQUENCE: 20
ttgatcaata tcagtcatat cctcgaacac aggctgtctt ttgtcaacga agagaacttg  60
gtcattt                                                            67

SEQ ID NO: 21          moltype = DNA  length = 54
FEATURE                Location/Qualifiers
source                 1..54
                       mol_type = other DNA
                       organism = synthetic construct
SEQUENCE: 21
gtgttcgagg atatgactga tattgatcaa agtgccagtg aaccccagac caga        54

SEQ ID NO: 22          moltype = DNA  length = 78
FEATURE                Location/Qualifiers
variation              24
                       note = n is a, c, g, or t
variation              30
                       note = n is a, c, g, or t
variation              32
                       note = n is a, c, g, or t
variation              42
                       note = n is a, c, g, or t
variation              44
                       note = n is a, c, g, or t
variation              46
                       note = n is a, c, g, or t
variation              48
                       note = n is a, c, g, or t
source                 1..78
                       mol_type = other DNA
                       organism = synthetic construct
SEQUENCE: 22
tcacagagag ggtcacagcy hbtnywbybn bnybwyygtc snbnynsnyg tatattatca  60
gtctggtctg ggttcac                                                 78

SEQ ID NO: 23          moltype = DNA  length = 58
FEATURE                Location/Qualifiers
source                 1..58
                       mol_type = other DNA
```

-continued

```
                          organism = synthetic construct
SEQUENCE: 23
gctgtgaccc tctctgtgaa ggatagtaaa atgtctaccc tctcctgtaa gaacaaga    58

SEQ ID NO: 24             moltype = DNA  length = 69
FEATURE                   Location/Qualifiers
source                    1..69
                          mol_type = other DNA
                          organism = synthetic construct
SEQUENCE: 24
gtatatcatc aatattttca ggtggatcca tttcctcaaa ggaaatgatc ttgttcttac  60
aggagaggg                                                          69

SEQ ID NO: 25             moltype = DNA  length = 99
FEATURE                   Location/Qualifiers
variation                 59
                          note = n is a, c, g, or t
variation                 74
                          note = n is a, c, g, or t
source                    1..99
                          mol_type = other DNA
                          organism = synthetic construct
SEQUENCE: 25
aatggatcca cctgaaaata ttgatgatat acaaagtgat ctcatattct ttcagaaand  60
hgttccagga cacnataaga tggagtttga atcttcact                         99

SEQ ID NO: 26             moltype = DNA  length = 57
FEATURE                   Location/Qualifiers
source                    1..57
                          mol_type = other DNA
                          organism = synthetic construct
SEQUENCE: 26
ccttttggca agcaagaaag tgtccttcat acagtgaaga ttcaaactcc atcttat     57

SEQ ID NO: 27             moltype = DNA  length = 60
FEATURE                   Location/Qualifiers
source                    1..60
                          mol_type = other DNA
                          organism = synthetic construct
SEQUENCE: 27
ctttcttgct tgccaaaagg aagatgatgc tttcaaactc attctgaaaa aaaaggatga  60

SEQ ID NO: 28             moltype = DNA  length = 77
FEATURE                   Location/Qualifiers
source                    1..77
                          mol_type = other DNA
                          organism = synthetic construct
SEQUENCE: 28
ccaccacttt gatgtaagtt agtrdbagtg aacattacag atttatcccc attttcatcc  60
tttttttca gaatgag                                                  77

SEQ ID NO: 29             moltype = DNA  length = 59
FEATURE                   Location/Qualifiers
source                    1..59
                          mol_type = other DNA
                          organism = synthetic construct
SEQUENCE: 29
actaacttac atcaaagtgg tggttctgga tccgaacaaa agcttatctc cgaagaaga   59

SEQ ID NO: 30             moltype = AA  length = 157
FEATURE                   Location/Qualifiers
source                    1..157
                          mol_type = protein
                          organism = Homo sapiens
SEQUENCE: 30
YFGKLESKLS VIRNLNDQVL FIDQGNRPLF EDMTDSDCRD NAPRTIFIIS MYKDSQPRGM  60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                           157

SEQ ID NO: 31             moltype = AA  length = 157
FEATURE                   Location/Qualifiers
source                    1..157
                          mol_type = protein
                          organism = Mus musculus
SEQUENCE: 31
NFGRLHCTTA VIRNINDQVL FVDKRQPVFE DMTDIDQSAS EPQTRLIIYM YKDSEVRGLA  60
VTLSVKDSKM STLSCKNKII SFEEMDPPEN IDDIQSDLIF FQKRVPGHNK MEFESSLYEG  120
HFLACQKEDD AFKLILKKKD ENGDKSVMFT LTNLHQS                           157
```

-continued

```
SEQ ID NO: 32          moltype = AA  length = 193
FEATURE                Location/Qualifiers
source                 1..193
                       mol_type = protein
                       organism = Homo sapiens
SEQUENCE: 32
MAAEPVEDNC INFVAMKFID NTLYFIAEDD ENLESDYFGK LESKLSVIRN LNDQVLFIDQ  60
GNRPLFEDMT DSDCRDNAPR TIFIISMYKD SQPRGMAVTI SVKCEKISTL SCENKIISFK  120
EMNPPDNIKD TKSDIIFFQR SVPGHDNKMQ FESSSYEGYF LACEKERDLF KLILKKEDEL  180
GDRSIMFTVQ NED                                                    193

SEQ ID NO: 33          moltype = AA  length = 192
FEATURE                Location/Qualifiers
source                 1..192
                       mol_type = protein
                       organism = Mus musculus
SEQUENCE: 33
MAAMSEDSCV NFKEMMFIDN TLYFIPEENG DLESDNFGRL HCTTAVIRNI NDQVLFVDKR  60
QPVFEDMTDI DQSASEPQTR LIIYMYKDSE VRGLAVTLSV KDSKMSTLSC KNKIISFEEM  120
DPPENIDDIQ SDLIFFQKRV PGHNKMEFES SLYEGHFLAC QKEDDAFKLI LKKKDENGDK  180
SVMFTLTNLH QS                                                     192

SEQ ID NO: 34          moltype = AA  length = 157
FEATURE                Location/Qualifiers
source                 1..157
                       mol_type = protein
                       organism = synthetic construct
SEQUENCE: 34
YFGKLESKLS VIRNLNDQVL FIDQGNRPLF EDMTDSDCRD NAPRTIFIIS TYKDSQPRGK  60
AVTISVKCEK ISTLSCENKI ISFKEMNPPD NIKDTKSDII FFQRDVPGHK HKMQFESSSY  120
EGYFLACEKE RDLFKLILKK EDELGDRSIM FTVQNED                          157

SEQ ID NO: 35          moltype = AA  length = 157
FEATURE                Location/Qualifiers
source                 1..157
                       mol_type = protein
                       organism = synthetic construct
SEQUENCE: 35
YFGKLESKLS VIRNLNDQVL FIDQGNRPLF EDMTDSDCRD NAPRTIFIIS TYKDKQPRAK  60
AVTISVKCEK ISTLSCENKI ISFKEMNPPD NIKDTKSDII FFQRDVPGHK HKMQFESSSY  120
EGYFLACEKE RDLFKLILKK EDELGDRSIM FTIQNED                          157

SEQ ID NO: 36          moltype = AA  length = 157
FEATURE                Location/Qualifiers
source                 1..157
                       mol_type = protein
                       organism = synthetic construct
SEQUENCE: 36
RFGKLESKLS VIRNLNDQVL FIDQGNRPLF EDMTDSDCRD NAPRTIFIIS TYKDSQPRGK  60
AVTISVKCEK ISTLSCENKI ISFKEMNPPD NIKDTKSDII FFQRDVPGHK HKMQFESSSY  120
EGYFLACEKE RDLFKLILKK EDELGDRSIM FTVQNED                          157

SEQ ID NO: 37          moltype = AA  length = 157
FEATURE                Location/Qualifiers
source                 1..157
                       mol_type = protein
                       organism = synthetic construct
SEQUENCE: 37
RFGKLESKLS VIRNLNDQVL FIDQGNRPLF EDMTDSDCRD NAPRTIFIIS TYRDSQPRGK  60
AVTISVKCEK ISTLSCENKI ISFKEMNPPD NIKDTKSDII FFQRNVPGHK YKMQFESSSY  120
EGYFLACEKE RDLFKLILKK EDELGDRSIM FTVQNED                          157

SEQ ID NO: 38          moltype = AA  length = 157
FEATURE                Location/Qualifiers
source                 1..157
                       mol_type = protein
                       organism = synthetic construct
SEQUENCE: 38
YFGKLESQLS VIRNLNDQVL FIDQGNRPLF EDMTDSDCRD NAPRTIFIIS TYKDKQPRTK  60
AVTISVKCEK ISTLSCENKI ISFKEMNPPD NIKDTKSDII FFQRRVPGHH NKMQFESSSY  120
EGYFLACEKE RDLFKLILKK EDELGDRSIM FTVQKED                          157

SEQ ID NO: 39          moltype = AA  length = 157
FEATURE                Location/Qualifiers
source                 1..157
                       mol_type = protein
                       organism = synthetic construct
SEQUENCE: 39
YFGKLESRLS VIRNLNDQVL FIDQGNRPLF EDMTDSDCRD NAPRTIFIIS KYKDKQPRAQ  60
```

-continued

```
AVTISVKCEK ISTLSCENKI ISFKEMNPPD NIKDTKSDII FFQRDVPGHK HKMQFESSSY  120
EGYFLACEKE RDLFKLILKK EDELGDRSIM FTIQNED                           157

SEQ ID NO: 40          moltype = AA  length = 157
FEATURE                Location/Qualifiers
source                 1..157
                       mol_type = protein
                       organism = synthetic construct
SEQUENCE: 40
YFGKLESRLS VIRNLNDQVL FIDQGNRPLF EDMTDSDCRD NAPRTIFIIS DYKDKQPRAX  60
AVTISVKCEK ISTLSCENKI ISFKEMNPPD NIKDTKSDII FFQRDVPGHK HKMQFESSSY  120
EGYFLACEKE RDLFKLILKK EDELGDRSIM FTIQNED                           157

SEQ ID NO: 41          moltype = AA  length = 157
FEATURE                Location/Qualifiers
source                 1..157
                       mol_type = protein
                       organism = synthetic construct
SEQUENCE: 41
YFGKHESKLS VIRNLNDQVL FIDQGNRPLF EDMTDSDCRD NAPRTIFIIS TYRDSQPRGK  60
AVTISVKCEK ISTLSCENKI ISFKEMNPPD NIKDTKSDII FFQRDVPGHN NKMQFESSSY  120
EGYFLACEKE RDLFKLILKK EDELGDRSIM FTTQNED                           157

SEQ ID NO: 42          moltype = AA  length = 157
FEATURE                Location/Qualifiers
source                 1..157
                       mol_type = protein
                       organism = synthetic construct
SEQUENCE: 42
YFGKIESKLS VIRNLNDQVL FIDQGNRPLF EDMTDSDCRD NAPRTIFIIS KYKDKQPRAQ  60
AVTISVKCEK ISTLSCENKI ISFKEMNPPD NIKDTKSDII FFQRKVPGHQ HKMQFESSSY  120
EGYFLACEKE RDLFKLILKK EDELGDRSIM FTVQKED                           157

SEQ ID NO: 43          moltype = AA  length = 157
FEATURE                Location/Qualifiers
source                 1..157
                       mol_type = protein
                       organism = synthetic construct
SEQUENCE: 43
YFGKIESKLS VIRNLNDQVL FIDQGNRPLF EDMTDSDCRD NAPRTIFIIS TYKDRQPRGK  60
AVTISVKCEK ISTLSCENKI ISFKEMNPPD NIKDTKSDII FFERDVPGHH HKMQFESSSY  120
EGYFLACEKE RDLFKLILKK EDELGDRSIM FTIQNED                           157

SEQ ID NO: 44          moltype = AA  length = 157
FEATURE                Location/Qualifiers
source                 1..157
                       mol_type = protein
                       organism = synthetic construct
SEQUENCE: 44
YFGKIESKLS VIRNLNDQVL FIDQGNRPLF EDMTDSDCRD NAPRTIFIIS TYKDKQPRGK  60
AVTISVKCEK ISTLSCENKI ISFKEMNPPD NIKDTKSDII FFQRDVPGHK HKMQFESSSY  120
EGYFLACEKE RDLFKLILKK EDELGDRSIM FTTQHED                           157

SEQ ID NO: 45          moltype = AA  length = 157
FEATURE                Location/Qualifiers
source                 1..157
                       mol_type = protein
                       organism = synthetic construct
SEQUENCE: 45
YFGKIESKLS VIRNLNDQVL FIDQGNRPLF EDMTDSDCRD NAPRTIFIIS TYKDKQPRAK  60
AVTISVKCEK ISTLSCENKI ISFKEMNPPD NIKDTKSDII FFQRRVPGHH HKMQFESSSY  120
EGYFLACEKE RDLFKLILKK EDELGDRSIM FTIQKED                           157

SEQ ID NO: 46          moltype = AA  length = 157
FEATURE                Location/Qualifiers
source                 1..157
                       mol_type = protein
                       organism = synthetic construct
SEQUENCE: 46
YFGKIESRLS VIRNLNDQVL FIDQGNRPLF EDMTDSDCRD NAPRTIFIIS TYKDKQPRGK  60
AVTISVKCEK ISTLSCENKI ISFKEMNPPD NIKDTKSDII FFQRDVPGHD YKMQFESSSY  120
EGYFLACEKE RDLFKLILKK EDELGDRSIM FTIQKED                           157

SEQ ID NO: 47          moltype = AA  length = 157
FEATURE                Location/Qualifiers
source                 1..157
                       mol_type = protein
                       organism = synthetic construct
SEQUENCE: 47
```

-continued

```
YFGKYESRLS VIRNLNDQVL FIDQGNRPLF EDMTDSDCRD NAPRTIFIIS TYRDSQPRGK  60
AVTISVKCEK ISTLSCENKI ISFKEMNPPD NIKDTKSDII FFQRDVPGHE HKMQFESSSY  120
EGYFLACEKE RDLFKLILKK EDELGDRSIM FTVQKED                           157

SEQ ID NO: 48          moltype = AA  length = 157
FEATURE                Location/Qualifiers
source                 1..157
                       mol_type = protein
                       organism = synthetic construct
SEQUENCE: 48
HFGKYESKLS VIRNLNDQVL FIDQGNRPLF EDMTDSDCRD NAPRTIFIIS TYRDSQPRGK  60
AVTISVKCEK ISTLSCENKI ISFKEMNPPD NIKDTKSDII FFQRDVPGHH NKMQFESSSY  120
EGYFLACEKE RDLFKLILKK EDELGDRSIM FTVQKED                           157

SEQ ID NO: 49          moltype = AA  length = 157
FEATURE                Location/Qualifiers
source                 1..157
                       mol_type = protein
                       organism = synthetic construct
SEQUENCE: 49
RFGKLESKLS VIRNLNDQVL FIDQGNRPLF EDMTDSDCRD NAPRTIFIIS TYRDSQPRAK  60
AVTISVKCEK ISTLSCENKI ISFKEMNPPD NIKDTKSDII FFQRDVPGHQ HKMQFESSSY  120
EGYFLACEKE RDLFKLILKK EDELGDRSIM FTAQKED                           157

SEQ ID NO: 50          moltype = AA  length = 157
FEATURE                Location/Qualifiers
source                 1..157
                       mol_type = protein
                       organism = synthetic construct
SEQUENCE: 50
RFGKLESRLS VIRNLNDQVL FIDQGNRPLF EDMTDSDCRD NAPRTIFIIS DYRDSQPRGR  60
AVTISVKCEK ISTLSCENKI ISFKEMNPPD NIKDTKSDII FFKRNVPGHK YKMQFESSSY  120
EGYFLACEKE RDLFKLILKK EDELGDRSIM FTVQHED                           157

SEQ ID NO: 51          moltype = AA  length = 157
FEATURE                Location/Qualifiers
source                 1..157
                       mol_type = protein
                       organism = synthetic construct
SEQUENCE: 51
RFGKLESRLS VIRNLNDQVL FIDQGNRPLF EDMTDSDCRD NAPRTIFIIS NYRDSQPRGQ  60
AVTISVKCEK ISTLSCENKI ISFKEMNPPD NIKDTKSDII FFKRRVPGHN HKMQFESSSY  120
EGYFLACEKE RDLFKLILKK EDELGDRSIM FTVQKED                           157

SEQ ID NO: 52          moltype = AA  length = 157
FEATURE                Location/Qualifiers
source                 1..157
                       mol_type = protein
                       organism = synthetic construct
SEQUENCE: 52
RFGKLESRLS VIRNLNDQVL FIDQGNRPLF EDMTDSDCRD NAPRTIFIIS TYKDSQPRGK  60
AVTISVKCEK ISTLSCENKI ISFKEMNPPD NIKDTKSDII FFQRDVPGHK HKMQFESSSY  120
EGYFLACEKE RDLFKLILKK EDELGDRSIM FTVQNED                           157

SEQ ID NO: 53          moltype = AA  length = 157
FEATURE                Location/Qualifiers
source                 1..157
                       mol_type = protein
                       organism = synthetic construct
SEQUENCE: 53
RFGKHESKLS VIRNLNDQVL FIDQGNRPLF EDMTDSDCRD NAPRTIFIIS TYRDSQPRGK  60
AVTISVKCEK ISTLSCENKI ISFKEMNPPD NIKDTKSDII FFERNVPGHK YKMQFESSSY  120
EGYFLACEKE RDLFKLILKK EDELGDRSIM FTVQNED                           157

SEQ ID NO: 54          moltype = AA  length = 157
FEATURE                Location/Qualifiers
source                 1..157
                       mol_type = protein
                       organism = synthetic construct
SEQUENCE: 54
RFGKLESRLS VIRNLNDQVL FIDQGNRPLF EDMTDSDCRD NAPRTIFIIS TYRDSQPRAK  60
AVTISVKCEK ISTLSCENKI ISFKEMNPPD NIKDTKSDII FFERDVPGHQ HKMQFESSSY  120
EGYFLACEKE RDLFKLILKK EDELGDRSIM FTIQXED                           157

SEQ ID NO: 55          moltype = AA  length = 157
FEATURE                Location/Qualifiers
source                 1..157
                       mol_type = protein
                       organism = synthetic construct
```

```
SEQUENCE: 55
RFGKLESRLS VIRNLNDQVL FIDQGNRPLF EDMTDSDCRD NAPRTIFIIS TYRDSQPRTK  60
AVTISVKCEK ISTLSCENKI ISFKEMNPPD NIKDTKSDII FFQRNVPGHH DKMQFESSSY  120
EGYFLACEKE RDLFKLILKK EDELGDRSIM FTVQHED                           157

SEQ ID NO: 56          moltype = AA  length = 157
FEATURE                Location/Qualifiers
source                 1..157
                       mol_type = protein
                       organism = synthetic construct
SEQUENCE: 56
RFGKLESRLS VIRNLNDQVL FIDQGNRPLF EDMTDSDCRD NAPRTIFIIS TYKDSQPRAK  60
AVTISVKCEK ISTLSCENKI ISFKEMNPPD NIKDTKSDII FFERDVPGHQ HKMQFESSSY  120
EGYFLACEKE RDLFKLILKK EDELGDRSIM FTIQKED                           157

SEQ ID NO: 57          moltype = AA  length = 157
FEATURE                Location/Qualifiers
source                 1..157
                       mol_type = protein
                       organism = synthetic construct
SEQUENCE: 57
RFGKHESKLS VIRNLNDQVL FIDQGNRPLF EDMTDSDCRD NAPRTIFIIS TYRDSQPRGK  60
AVTISVKCEK ISTLSCENKI ISFKEMNPPD NIKDTKSDII FFERNVPGHK YKMQFESSSY  120
EGYFLACEKE RDLFKLILKK EDELGDRSIM FTVQNED                           157

SEQ ID NO: 58          moltype = AA  length = 157
FEATURE                Location/Qualifiers
source                 1..157
                       mol_type = protein
                       organism = synthetic construct
SEQUENCE: 58
RFGKYESKLS VIRNLNDQVL FIDQGNRPLF EDMTDSDCRD NAPRTIFIIS TYKDSQPRTK  60
AVTISVKCEK ISTLSCDNKI ISFKEMNPPD NIKDTKSDII FFQRDVPGHK HKMQFESSSY  120
EGYFLACEKE RDLFKLILKK EDELGDRSIM FTVQNED                           157

SEQ ID NO: 59          moltype = AA  length = 157
FEATURE                Location/Qualifiers
source                 1..157
                       mol_type = protein
                       organism = synthetic construct
SEQUENCE: 59
RFGKLESRLS VIRNLNDQVL FIDQGNRPLF EDMTDSDCRD NAPRTIFIIS TYRDSQPRTK  60
AVTISVKCEK ISTLSCENKI ISFKEMNPPD NIKDTKSDII FFQRKVPGHN HKMQFESSSY  120
EGYFLACEKE RDLFKLILKK EDELGDRSIM FTVQKED                           157

SEQ ID NO: 60          moltype = AA  length = 157
FEATURE                Location/Qualifiers
source                 1..157
                       mol_type = protein
                       organism = synthetic construct
SEQUENCE: 60
NFGRLHCTTA VIRNINDQVL FVDKRQPVFE DMTDIDQSAS EPQTRLIIYG YADSRVRGKA  60
VTLSVKDSKM STLSCKNKII SFEEMDPPEN IDDIQSDLIF FQKRVPGHNK MEFESSLYEG  120
HFLACQKEDD AFKLILKKKD ENGDKSVMFT LTNLHQS                           157

SEQ ID NO: 61          moltype = AA  length = 157
FEATURE                Location/Qualifiers
source                 1..157
                       mol_type = protein
                       organism = synthetic construct
SEQUENCE: 61
HFGRLHCTTA VIRNINDQVL FVDKRQPVFE DMTDIDQSAS EPQTRLIIYA YGDSRARGKA  60
VTLSVKDSKM STLSCKNKII SFEEMDPPEN IDDIQSDLIF FQKRVPGHNK MEFESSLYEG  120
HFLACQKEDD AFKLILKKKD ENGDKSVMFT LTNLHQS                           157

SEQ ID NO: 62          moltype = AA  length = 157
FEATURE                Location/Qualifiers
source                 1..157
                       mol_type = protein
                       organism = synthetic construct
SEQUENCE: 62
NFGRLHCTTA VIRNINDQVL FVDKRQPVFE DMTDIDQSAS EPQTRLIIYA YVDRRLRGKA  60
VTLSVKDSKM STLSCKNKII SFEEMDPPEN IDDIQSDLIF FQKKVPGHNK MEFESSLYEG  120
HFLACQKEDD AFKLILKKKD ENGDKSVMFT LTNLHQS                           157

SEQ ID NO: 63          moltype = AA  length = 157
FEATURE                Location/Qualifiers
source                 1..157
                       mol_type = protein
```

```
                         organism = synthetic construct
SEQUENCE: 63
NFGRLHCTTA VIRNINDQVL FVDKRQPVFE DMTDIDQSAS EPQTRLIIYS YSDKHMRGKA  60
VTLSVKDSKM STLSCKNKII SFEEMDPPEN IDDIQSDLIF FQKLVPGHNK MEFESSLYEG  120
HFLACQKEDD AFKLILKKKD ENGDKSVMFT LTNLHQS                          157

SEQ ID NO: 64            moltype = AA  length = 157
FEATURE                  Location/Qualifiers
source                   1..157
                         mol_type = protein
                         organism = synthetic construct
SEQUENCE: 64
NFGRLHCTTA VIRNINDQVL FVDKRQPVFE DMTDIDQSAS EPQTRLIIYV YTDGRRRGKA  60
VTLSVKDSKM STLSCKNKII SFEEMDPPEN IDDIQSDLIF FQKKVPGHDK MEFESSLYEG  120
HFLACQKEDD AFKLILKKKD ENGDKSVMFT LTNLHQS                          157

SEQ ID NO: 65            moltype = AA  length = 157
FEATURE                  Location/Qualifiers
source                   1..157
                         mol_type = protein
                         organism = synthetic construct
SEQUENCE: 65
HFGRLHCTTA VIRNINDQVL FVDKRQPVFE DMTDIDQSAS EPQTRLIIYA YGDSHMRGKA  60
VTLSVKDSKM STLSCKNKII SFEEMDPPEN IDDIQSDLIF FQKQVPGHNK MEFESSLYEG  120
HFLACQKEDD AFKLILKKKD ENGDKSVMFT VTNLHQS                          157

SEQ ID NO: 66            moltype = AA  length = 157
FEATURE                  Location/Qualifiers
source                   1..157
                         mol_type = protein
                         organism = synthetic construct
SEQUENCE: 66
HFGRLHCTTA VIRNINDQVL FVDKRQPVFE DMTDIDQSAS EPQTRLIIYA YGDSNAGGRA  60
VTLSVKDSKM STLSCKNKII SFEEMDPPEN IDDIQSDLIF FQKKVPGHNK MEFESSLYEG  120
HFLACQKEDD AFKLILKKKD ENGDKSVMFT LTNLHQS                          157

SEQ ID NO: 67            moltype = AA  length = 157
FEATURE                  Location/Qualifiers
source                   1..157
                         mol_type = protein
                         organism = synthetic construct
SEQUENCE: 67
HFGRLHCTTA VIRNINDQVL FVDKRQPVFE DMTDIDQSAS EPQTRLIIYG YADSDARAKA  60
VTLSVKDSKM STLSCKNKII SFEEMDPPEN IDDIQSDLIF FQKSVPGHNK MEFESSLYEG  120
HFLACQKEDD AFKLILKKKD ENGDKSVMFT VTNLHQS                          157

SEQ ID NO: 68            moltype = AA  length = 157
FEATURE                  Location/Qualifiers
source                   1..157
                         mol_type = protein
                         organism = synthetic construct
SEQUENCE: 68
HFGRLHCTTA VIRNINDQVL FVDKRQPVFE DMTDIDQSAS EPQTRLIIYG YSDRGSKGKA  60
VTLSVKDSKM STLSCKNKII SFEEMDPPEN IDDIQSDLIF FQKQVPGHNK MEFESSLYEG  120
HFLACQKEDD AFKLILKKKD ENGDKSVMFT LTNLHQS                          157

SEQ ID NO: 69            moltype = AA  length = 157
FEATURE                  Location/Qualifiers
source                   1..157
                         mol_type = protein
                         organism = synthetic construct
SEQUENCE: 69
YFGRLHCTTA VIRNINDQVL FVDKRQPVFE DMTDIDQSAS EPQTRLIIYM YADRRARGKA  60
VTLSVKDSKM STLSCKNKII SFEEMDPPEN IDDIQSDLIF FQKKVPGHDK MEFESSLYEG  120
HFLACQKEDD AFKLILKKKD ENGDKSVMFT VTNLHQS                          157

SEQ ID NO: 70            moltype = AA  length = 157
FEATURE                  Location/Qualifiers
source                   1..157
                         mol_type = protein
                         organism = synthetic construct
SEQUENCE: 70
YFGRLHCTTA VIRNINDQVL FVDKRQPVFE DMTDIDQSAS EPQTRLIIYA YGDNRVRGKA  60
VTLSVKDSKM STLSCKNKII SFEEMDPPEN IDDIQSDLIF FQKRVPGHNK MEFESSLYEG  120
HFLACQKEDD AFKLILKKKD ENGDKSVMFT LTNLHQS                          157

SEQ ID NO: 71            moltype = AA  length = 157
FEATURE                  Location/Qualifiers
source                   1..157
```

```
                        mol_type = protein
                        organism = synthetic construct
SEQUENCE: 71
YFGRLHCTTA VIRNINDQVL FVDKRQPVFE DMTDIDQSAS EPQTRLIIYG YGDSERGGRA  60
VTLSVKDSKM STLSCKNKII SFEEMDPPEN IDDIQSDLIF FQKRVPGHDK MEFESSLYEG  120
HFLACQKEDD AFKLILKKKD ENGDKSVMFT LTNLHQS                           157

SEQ ID NO: 72           moltype = AA  length = 157
FEATURE                 Location/Qualifiers
source                  1..157
                        mol_type = protein
                        organism = synthetic construct
SEQUENCE: 72
YFGRLHCTTA VIRNINDQVL FVDKRQPVFE DMTDIDQSAS EPQTRLIIYT RTDGGQKGVA  60
VTLSVKDSKM STLSCKNKII SFEEMDPPEN IDDIQSDLIF FQKRVPGHDK MEFESSLYEG  120
HFLACQKEDD AFKLILKKKD ENGDKSVMFT LTNLHQS                           157

SEQ ID NO: 73           moltype = AA  length = 157
FEATURE                 Location/Qualifiers
source                  1..157
                        mol_type = protein
                        organism = synthetic construct
SEQUENCE: 73
YFGKLESKLS VIRNLNDQVL FIDQGNRPLF EDMTDSDCRD NAPRTIFIIS EYKDSELRGR  60
AVTISVKCEK ISTLSCENKI ISFKEMNPPD NIKDTKSDII FFPRAVPGHN RKVQFESSSY  120
EGYFLACEKE RDLFKLILKK EDELGDRSIM FTVQNED                           157

SEQ ID NO: 74           moltype = AA  length = 157
FEATURE                 Location/Qualifiers
source                  1..157
                        mol_type = protein
                        organism = synthetic construct
SEQUENCE: 74
YFGKLESKLS VIRNLNDQVL FIDQGNRPLF EDMTDSDCRD NAPRTIFIIS KYKDSAGRGL  60
AVTISVKCEK ISTLSCENKI ISFKEMNPPD NIKDTKSDII FFERDVPGHS NKVQFESSSY  120
EGYFLACEKE RDLFKLILKK EDELGDRSIM FTVQNED                           157

SEQ ID NO: 75           moltype = AA  length = 157
FEATURE                 Location/Qualifiers
source                  1..157
                        mol_type = protein
                        organism = synthetic construct
SEQUENCE: 75
YFGKLESKLS VIRNLNDQVL FIDQGNRPLF EDMTDSDCRD NAPRTIFIIS KYGDSAARGL  60
AVTISVKCEK ISTLSCENKI ISFKEMNPPD NIKDTKSDII FFQRSVPGHK RKMQFESSSY  120
EGYFLACEKE RDLFKLILKK EDELGDRSIM FTVQNED                           157

SEQ ID NO: 76           moltype = AA  length = 157
FEATURE                 Location/Qualifiers
source                  1..157
                        mol_type = protein
                        organism = synthetic construct
SEQUENCE: 76
YFGKLESKLS VIRNLNDQVL FIDQGNRPLF EDMTDSDCRD NAPRTIFIIS KYGDSRGRGL  60
AVTISVKCEK ISTLSCENKI ISFKEMNPPD NIKDTKSDII FFERDVPGHN SKRQFESSSY  120
EGYFLACEKE RDLFKLILKK EDELGDRSIM FTVQNED                           157

SEQ ID NO: 77           moltype = AA  length = 157
FEATURE                 Location/Qualifiers
source                  1..157
                        mol_type = protein
                        organism = synthetic construct
SEQUENCE: 77
YFGKLESKLS VIRNLNDQVL FIDQGNRPLF EDMTDSDCRD NAPRTIFIIS KYGDSVPRGL  60
AVTISVKCEK ISTLSCENKI ISFKEMNPPD NIKDTKSDII FFARAVPGHS RKTQFESSSY  120
EGYFLACEKE RDLFKLILKK EDELGDRSIM FTVQNED                           157

SEQ ID NO: 78           moltype = AA  length = 157
FEATURE                 Location/Qualifiers
source                  1..157
                        mol_type = protein
                        organism = synthetic construct
SEQUENCE: 78
YFGKLESKLS VIRNLNDQVL FIDQGNRPLF EDMTDSDCRD NAPRTIFIIS KYSDSGARGL  60
AVTISVKCEK ISTLSCENKI ISFKEMNPPD NIKDTKSDII FFARAVPGHG RKTQFESSSY  120
EGYFLACEKE RDLFKLILKK EDELGDRSIM FTVQNED                           157

SEQ ID NO: 79           moltype = AA  length = 157
FEATURE                 Location/Qualifiers
```

```
source                 1..157
                       mol_type = protein
                       organism = synthetic construct
SEQUENCE: 79
YFGKLESKLS VIRNLNDQVL FIDQGNRPLF EDMTDSDCRD NAPRTIFIIS KYSDSKARGM  60
AVTISVKCEK ISTLSCENKI ISFKEMNPPD NIKDTKSDII FFARDVPGHS SKRQFESSSY  120
EGYFLACEKE RDLFKLILKK EDELGDRSIM FTVQNED                          157

SEQ ID NO: 80          moltype = AA  length = 157
FEATURE                Location/Qualifiers
source                 1..157
                       mol_type = protein
                       organism = synthetic construct
SEQUENCE: 80
YFGKLESKLS VIRNLNDQVL FIDQGNRPLF EDMTDSDCRD NAPRTIFIIS KYSDSLARGL  60
AVTISVKCEK ISTLSCENKI ISFKEMNPPD NIKDTKSDII FFQRDVPGHS RKMQFESSSY  120
EGYFLACEKE RDLFKLILKK EDELGDRSIM FTVQNED                          157

SEQ ID NO: 81          moltype = AA  length = 157
FEATURE                Location/Qualifiers
source                 1..157
                       mol_type = protein
                       organism = synthetic construct
SEQUENCE: 81
YFGKLESKLS VIRNLNDQVL FIDQGNRPLF EDMTDSDCRD NAPRTIFIIS KYSDSRARGL  60
AVTISVKCEK ISTLSCENKI ISFKEMNPPD NIKDTKSDII FFQRNVPGHG RKMQFESSSY  120
EGYFLACEKE RDLFKLILKK EDELGDRSIM FTVQNED                          157

SEQ ID NO: 82          moltype = AA  length = 157
FEATURE                Location/Qualifiers
source                 1..157
                       mol_type = protein
                       organism = synthetic construct
SEQUENCE: 82
YFGKLESKLS VIRNLNDQVL FIDQGNRPLF EDMTDSDCRD NAPRTIFIIS KYSDSRARGL  60
AVTISVKCEK ISTLSCENKI ISFKEMNPPD NIKDTKSDII FFARSVPGHG RKTQFESSSY  120
EGYFLACEKE RDLFKLILKK EDELGDRSIM FTVQNED                          157

SEQ ID NO: 83          moltype = AA  length = 157
FEATURE                Location/Qualifiers
source                 1..157
                       mol_type = protein
                       organism = synthetic construct
SEQUENCE: 83
YFGKLESKLS VIRNLNDQVL FIDQGNRPLF EDMTDSDCRD NAPRTIFIIS KYSDSRARGL  60
AVTISVKCEK ISTLSCENKI ISFKEMNPPD NIKDTKSDII FFARDVPGHS GKRQFESSSY  120
EGYFLACEKE RDLFKLILKK EDELGDRSIM FTVQNED                          157

SEQ ID NO: 84          moltype = AA  length = 157
FEATURE                Location/Qualifiers
source                 1..157
                       mol_type = protein
                       organism = synthetic construct
SEQUENCE: 84
YFGKLESKLS VIRNLNDQVL FIDQGNRPLF EDMTDSDCRD NAPRTIFIIS KYTDSRPRGL  60
AVTISVKCEK ISTLSCENKI ISFKEMNPPD NIKDTKSDII FFERDVPGHS SKKQFESSSY  120
EGYFLACEKE RDLFKLILKK EDELGDRSIM FTVQNED                          157

SEQ ID NO: 85          moltype = AA  length = 157
FEATURE                Location/Qualifiers
source                 1..157
                       mol_type = protein
                       organism = synthetic construct
SEQUENCE: 85
YFGKLESKLS VIRNLNDQVL FIDQGNRPLF EDMTDSDCRD NAPRTIFIIS KYTDSRARGM  60
AVTISVKCEK ISTLSCENKI ISFKEMNPPD NIKDTKSDII FFERDVPGHN DKRQFESSSY  120
EGYFLACEKE RDLFKLILKK EDELGDRSIM FTVQNED                          157

SEQ ID NO: 86          moltype = AA  length = 157
FEATURE                Location/Qualifiers
source                 1..157
                       mol_type = protein
                       organism = synthetic construct
SEQUENCE: 86
YFGKLESKLS VIRNLNDQVL FIDQGNRPLF EDMTDSDCRD NAPRTIFIIS RYKDSGKRGL  60
AVTISVKCEK ISTLSCENKI ISFKEMNPPD NIKDTKSDII FFRRSVPGHS RKVQFESSSY  120
EGYFLACEKE RDLFKLILKK EDELGDRSIM FTVQNED                          157

SEQ ID NO: 87          moltype = AA  length = 157
```

-continued

```
FEATURE                 Location/Qualifiers
source                  1..157
                        mol_type = protein
                        organism = synthetic construct
SEQUENCE: 87
YFGKLESKLS VIRNLNDQVL FIDQGNRPLF EDMTDSDCRD NAPRTIFIIS KYGDSGARGL  60
AVTISVKCEK ISTLSCENKI ISFKEMNPPD NIKDTKSDII FFERDVPGHS GKVQFESSSY  120
EGYFLACEKE RDLFKLILKK EDELGDRSIM FTVQNED                            157

SEQ ID NO: 88           moltype = AA  length = 157
FEATURE                 Location/Qualifiers
source                  1..157
                        mol_type = protein
                        organism = synthetic construct
SEQUENCE: 88
YFGKLESKLS VIRNLNDQVL FIDQGNRPLF EDMTDSDCRD NAPRTIFIIS KYGDSRPRGM  60
AVTISVKCEK ISTLSCENKI ISFKEMNPPD NIKDTKSDII FFQRAVPGHN RKMQFESSSY  120
EGYFLACEKE RDLFKLILKK EDELGDRSIM FTVQNED                            157

SEQ ID NO: 89           moltype = AA  length = 157
FEATURE                 Location/Qualifiers
source                  1..157
                        mol_type = protein
                        organism = synthetic construct
SEQUENCE: 89
YFGKLESKLS VIRNLNDQVL FIDQGNRPLF EDMTDSDCRD NAPRTIFIIS KYSDSLARGL  60
AVTISVKCEK ISTLSCENKI ISFKEMNPPD NIKDTKSDII FFQRDVPGHS RKMQFESSSY  120
EGYFLACEKE RDLFKLILKK EDELGDRSIM FTVQNED                            157

SEQ ID NO: 90           moltype = AA  length = 157
FEATURE                 Location/Qualifiers
source                  1..157
                        mol_type = protein
                        organism = synthetic construct
SEQUENCE: 90
YFGKLESKLS VIRNLNDQVL FIDQGNRPLF EDMTDSDCRD NAPRTIFIIS KYSDSRARGL  60
AVTISVKCEK ISTLSCENKI ISFKEMNPPD NIKDTKSDII FFARSVPGHG RKTQFESSSY  120
EGYFLACEKE RDLFKLILKK EDELGDRSIM FTVQNED                            157

SEQ ID NO: 91           moltype = AA  length = 157
FEATURE                 Location/Qualifiers
source                  1..157
                        mol_type = protein
                        organism = synthetic construct
SEQUENCE: 91
YFGKLESKLS VIRNLNDQVL FIDQGNRPLF EDMTDSDCRD NAPRTIFIIS KYSDSRARGL  60
AVTISVKCEK ISTLSCENKI ISFKEMNPPD NIKDTKSDII FFQRNVPGHG RKMQFESSSY  120
EGYFLACEKE RDLFKLILKK EDELGDRSIM FTVQNED                            157

SEQ ID NO: 92           moltype = AA  length = 157
FEATURE                 Location/Qualifiers
source                  1..157
                        mol_type = protein
                        organism = synthetic construct
SEQUENCE: 92
HFGKLESKLS VIRNLNGQVL FIDQGNRPLF KDMTASDCRA NAPRTIFIIS FYKDSQPRGM  60
AVTISVKCEK ISTLSCENKI ISFKEMNPPD NIKDTKSDII FFIRSVPGAD NKFQFESSSY  120
EGYFLACEKE RDLFKLILKK EDELGDRSIM FTVQNED                            157

SEQ ID NO: 93           moltype = AA  length = 157
FEATURE                 Location/Qualifiers
source                  1..157
                        mol_type = protein
                        organism = synthetic construct
SEQUENCE: 93
DFGKLESKLS VIRNLNDQVL FIDQGNRPLF ADMTDNPCRS NAPRTIFIIS FYKDSQPRGI  60
AVTISVKCEK ISTLSCENKI ISFKEMNPPD NIKDTKSDII FFLRSVPGPD NKMQFESSSY  120
EGYFLACEKE RDLFKLILKK EDELGDRSIM FTVQNED                            157

SEQ ID NO: 94           moltype = AA  length = 157
FEATURE                 Location/Qualifiers
source                  1..157
                        mol_type = protein
                        organism = synthetic construct
SEQUENCE: 94
HFGKLESKLS VIRNLNGQVL FIDQGNRPLF ADMEASPCRD NAPRTIFIIS FYKDSQPRGL  60
AVTISVKCEK ISTLSCENKI ISFKEMNPPD NIKDTKSDII FFLRSVPGHD NKMQFESSSY  120
EGYFLACEKE RDLFKLILKK EDELGDRSIM FTVQNED                            157
```

```
SEQ ID NO: 95           moltype = AA  length = 157
FEATURE                 Location/Qualifiers
source                  1..157
                        mol_type = protein
                        organism = synthetic construct
SEQUENCE: 95
LFGKLESKLS VIRNLNGQVL FIDQGNRPLF ADMTSSPCRS RAPRTIFIIS FYKDSQPRGF  60
AVTISVKCEK ISTLSCENKI ISFKEMNPPD NIKDTKSDII FFIRSVPGHD NKIQFESSSY  120
EGYFLACEKE RDLFKLILKK EDELGDRSIM FTVQNED                           157

SEQ ID NO: 96           moltype = AA  length = 157
FEATURE                 Location/Qualifiers
source                  1..157
                        mol_type = protein
                        organism = synthetic construct
SEQUENCE: 96
HFGKLESKLS VIRNLNDQVL FIDQGNRPLF TDMESKPCRD SAPRTIFIIS MYKDSQPRGI  60
AVTISVKCEK ISTLSCENKI ISFKEMNPPD NIKDTKSDII FFIRSVPGHD NKFQFESSSY  120
EGYFLACEKE RDLFKLILKK EDELGDRSIM FTVQNED                           157

SEQ ID NO: 97           moltype = AA  length = 157
FEATURE                 Location/Qualifiers
source                  1..157
                        mol_type = protein
                        organism = synthetic construct
SEQUENCE: 97
YFGKLESKLS VIRNLNRQVL FIDQGNRPLF TDMTYKDCRD NAPRTIFIIS FYKDSQPRGF  60
AVTISVKCEK ISTLSCENKI ISFKEMNPPD NIKDTKSDII FFIRSVPGAD NKIQFESSSY  120
EGYFLACEKE RDLFKLILKK EDELGDRSIM FTVQNED                           157

SEQ ID NO: 98           moltype = AA  length = 157
FEATURE                 Location/Qualifiers
source                  1..157
                        mol_type = protein
                        organism = synthetic construct
SEQUENCE: 98
HFGKLESKLS VIRNLNGQVL FIDQGNRPLF GDMEASPCRD NAPRTIFIIS FYKDSQPRGM  60
AVTISVKCEK ISTLSCENKI ISFKEMNPPD NIKDTKSDII FFIRSVPGAD NKLQFESSSY  120
EGYFLACEKE RDLFKLILKK EDELGDRSIM FTVQNED                           157

SEQ ID NO: 99           moltype = AA  length = 157
FEATURE                 Location/Qualifiers
source                  1..157
                        mol_type = protein
                        organism = synthetic construct
SEQUENCE: 99
HFGKLESKLS VIRNLNGQVL FIDQGNRPLF TDMTSSDCRD KAPRTIFIIS FYKDSQPRGL  60
AVTISVKCEK ISTLSCENKI ISFKEMNPPD NIKDTKSDII FFLRSVPGPD NKFQFESSSY  120
EGYFLACEKE RDLFKLILKK EDELGDRSIM FTVQNED                           157

SEQ ID NO: 100          moltype = AA  length = 157
FEATURE                 Location/Qualifiers
source                  1..157
                        mol_type = protein
                        organism = synthetic construct
SEQUENCE: 100
HFGKLESKLS VIRNLNGQVL FIDQGNRPLF ADMESNRCRD SAPRTIFIIS MYKDSQPRGF  60
AVTISVKCEK ISTLSCENKI ISFKEMNPPD NIKDTKSDII FFLRSVPGHD NKIQFESSSY  120
EGYFLACEKE RDLFKLILKK EDELGDRSIM FTVQNED                           157

SEQ ID NO: 101          moltype = AA  length = 157
FEATURE                 Location/Qualifiers
source                  1..157
                        mol_type = protein
                        organism = synthetic construct
SEQUENCE: 101
YFGKLESKLS VIRNLNGQVL FIDQGNRPLF TDMTASPCRD NAPRTIFIIS FYKDSQPRGL  60
AVTISVKCEK ISTLSCENKI ISFKEMNPPD NIKDTKSDII FFLRSVPGHD NKIQFESSSY  120
EGYFLACEKE RSLFKLILKK EDELGDRSIM FTVQNED                           157

SEQ ID NO: 102          moltype = AA  length = 157
FEATURE                 Location/Qualifiers
source                  1..157
                        mol_type = protein
                        organism = synthetic construct
SEQUENCE: 102
DFGKLESKLS VIRNLNDQVL FIDQGNRPLF ADMKSNVCRA NAPRTIFIIS MYKDSQPRGM  60
AVTISVKCEK ISTLSCENKI ISFKEMNPPD NIKDTKSDII FFIRSVPGPD NKLQFESSSY  120
EGYFLACEKE RDLFKLILKK EDELGDRSIM FTVQNED                           157
```

```
SEQ ID NO: 103         moltype = AA  length = 157
FEATURE                Location/Qualifiers
source                 1..157
                       mol_type = protein
                       organism = synthetic construct
SEQUENCE: 103
HFGKLESKLS VIRNLNGQVL FIDQGNRPLF GDMEASPCRA KAPRTIFIIS IYKDSQPRGF  60
AVTISVKCEK ISTLSCENKI ISFKEMNPPD NIKDTKSDII FFLRSVPGHD NKFQFESSSY  120
EGYFLACEKE RSLFKLILKK EDELGDRSIM FTVQNED                           157

SEQ ID NO: 104         moltype = AA  length = 157
FEATURE                Location/Qualifiers
source                 1..157
                       mol_type = protein
                       organism = synthetic construct
SEQUENCE: 104
HFGKLESKLS VIRNLNGQVL FIDQGNRPLF ADMASNRCRA NAPRTIFIIS MYKDSQPRGF  60
AVTISVKCEK ISTLSCENKI ISFKEMNPPD NIKDTKSDII FFIRSVPGPD NKFQFESSSY  120
EGYFLACEKE RDLFKLILKK EDELGDRSIM FTVQNED                           157

SEQ ID NO: 105         moltype = AA  length = 157
FEATURE                Location/Qualifiers
source                 1..157
                       mol_type = protein
                       organism = synthetic construct
SEQUENCE: 105
YFGKLESKLS VIRNLNDQVL FIDQGNRPLF ADMKAKACRS NAPRTIFIIS FYKDSQPRGF  60
AVTISVKCEK ISTLSCENKI ISFKEMNPPD NIKDTKSDII FFLRSVPGAD NKIQFESSSY  120
EGYFLACEKE RDLFKLILKK EDELGDRSIM FTVQNED                           157

SEQ ID NO: 106         moltype = AA  length = 157
FEATURE                Location/Qualifiers
source                 1..157
                       mol_type = protein
                       organism = synthetic construct
SEQUENCE: 106
HFGKLESKLS VIRNLNHQVL FIDQGNRPLF TDMADNACRD NAPRTIFIIS FYKDSQPRGL  60
AVTISVKCEK ISTLSCENKI ISFKEMNPPD NIKDTKSDII FFIRSVPGDD NKMQFESSSY  120
EGYFLACEKE RDLFKLILKK EDELGDRSIM FTVQNED                           157

SEQ ID NO: 107         moltype = AA  length = 157
FEATURE                Location/Qualifiers
source                 1..157
                       mol_type = protein
                       organism = synthetic construct
SEQUENCE: 107
YFGKLESKLS VIRNLNGQVL FIDQGNRPLF TDMKSNLCRS NAPRTIFIIS FYKDSQPRGI  60
AVTISVKCEK ISTLSCENKI ISFKEMNPPD NIKDTKSDII FFIRSVPGDD NKIQFESSSY  120
EGYFLACEKE RDLFKLILKK EDELGDRSIM FTVQNED                           157

SEQ ID NO: 108         moltype = AA  length = 157
FEATURE                Location/Qualifiers
source                 1..157
                       mol_type = protein
                       organism = synthetic construct
SEQUENCE: 108
HFGKLESKLS VIRNLNGQVL FIDQGNRPLF RDMAASHCRD SAPRTIFIIS IYKDSQPRGF  60
AVTISVKCEK ISTLSCENKI ISFKEMNPPD NIKDTKSDII FFLRSVPGHD NKIQFESSSY  120
EGYFLACEKE RDLFKLILKK EDELGDRSIM FTVQNED                           157

SEQ ID NO: 109         moltype = AA  length = 157
FEATURE                Location/Qualifiers
source                 1..157
                       mol_type = protein
                       organism = synthetic construct
SEQUENCE: 109
YFGKLESKLS VIRNLNDQVL FIDQGNRPLF ADMASNPCRY KAPRTIFIIS MYKDSQPRGL  60
AVTISVKCEK ISTLSCENKI ISFKEMNPPD NIKDTKSDII FFLRSVPGAD NKLQFESSSY  120
EGYFLACEKE RDLFKLILKK EDELGDRSIM FTVQNED                           157

SEQ ID NO: 110         moltype = AA  length = 157
FEATURE                Location/Qualifiers
source                 1..157
                       mol_type = protein
                       organism = synthetic construct
SEQUENCE: 110
HFGKLESKLS VIRNLNGQVL FIDQGNRPLF TDMASNHCRY NAPRTIFIIS MYKDSQPRGL  60
AVTISVKCEK ISTLSCENKI ISFKEMNPPD NIKDTKSDII FFLRSVPGAD NKIQFESSSY  120
```

-continued

```
EGYFLACEKE RDLFKLILKK EDELGDRSIM FTVQNED                      157

SEQ ID NO: 111         moltype = AA  length = 157
FEATURE                Location/Qualifiers
source                 1..157
                       mol_type = protein
                       organism = synthetic construct
SEQUENCE: 111
HFGKLESKLS VIRNLNGQVL FIDQGNRPLF ADMTDNPCRS RAPRTIFIIS FYKDSQPRGM  60
AVTISVKCEK ISTLSCENKI ISFKEMNPPD NIKDTKSDII FFIRSVPGHD NKFQFESSSY  120
EGYFLACEKE RDLFKLILKK EDELGDRSIM FTVQNED                      157

SEQ ID NO: 112         moltype = AA  length = 157
FEATURE                Location/Qualifiers
source                 1..157
                       mol_type = protein
                       organism = synthetic construct
SEQUENCE: 112
YFGKLESKLS VIRNLNGQVL FIDQGNRPLF TDMTASHCRS SAPRTIFIIS LYKDSQPRGM  60
AVTISVKCEK ISTLSCENKI ISFKEMNPPD NIKDTKSDII FFLRSVPGHD NKFQFESSSY  120
EGYFLACEKE RDLFKLILKK EDELGDRSIM FTVQNED                      157

SEQ ID NO: 113         moltype = AA  length = 157
FEATURE                Location/Qualifiers
source                 1..157
                       mol_type = protein
                       organism = synthetic construct
SEQUENCE: 113
YFGKLESKLS VIRNLNGQVL FIDQGNRPLF TDMEYRLCRA NAPRTIFIIS FYKDSHPRGL  60
AVTISVKCEK ISTLSCENKI ISFKEMNPPD NIKDTKSDII FFLRSVPGDD NKLQFESSSY  120
EGYFLACEKE RDLFKLILKK EDELGDRSIM FTVQNED                      157

SEQ ID NO: 114         moltype = AA  length = 157
FEATURE                Location/Qualifiers
source                 1..157
                       mol_type = protein
                       organism = synthetic construct
SEQUENCE: 114
YFGKLESKLS VIRNLNGQVL FIDQGNRPLF TDMESSLCRD NAPRTIFIIS LYKDSQPRGM  60
AVTISVKCEK ISTLSCENKI ISFKEMNPPD NIKDTKSDII FFLRSVPGAD NKFQFESSSY  120
EGYFLACEKE RSLFKLILKK EDELGDRSIM FTVQNED                      157

SEQ ID NO: 115         moltype = AA  length = 157
FEATURE                Location/Qualifiers
source                 1..157
                       mol_type = protein
                       organism = synthetic construct
SEQUENCE: 115
YFGKLESKLS VIRNLNGQVL FIDQGNRPLF KDMEANDCRS SAPRTIFIIS IYKDSQPRGL  60
AVTISVKCEK ISTLSCENKI ISFKEMNPPD NIKDTKSDII FFIRSVPGAD NKMQFESSSY  120
EGYFLACEKE RDLFKLILKK EDELGDRSIM FTVQNED                      157

SEQ ID NO: 116         moltype = AA  length = 157
FEATURE                Location/Qualifiers
source                 1..157
                       mol_type = protein
                       organism = synthetic construct
SEQUENCE: 116
DFGKLESKLS VIRNLNDQVL FIDQGNRPLF ADMKASACRA NAPRTIFIIS MYKDSQPRGL  60
AVTISVKCEK ISTLSCENKI ISFKEMNPPD NIKDTKSDII FFLRSVPGHD NKFQFESSSY  120
EGYFLACEKE RDLFKLILKK EDELGDRSIM FTVQNED                      157

SEQ ID NO: 117         moltype = AA  length = 157
FEATURE                Location/Qualifiers
source                 1..157
                       mol_type = protein
                       organism = synthetic construct
SEQUENCE: 117
YFGKLESKLS VIRNLNGQVL FIDQGNRPLF GDMTAKHCRA RAPRTIFIIS FYKDSQPRGM  60
AVTISVKCEK ISTLSCENKI ISFKEMNPPD NIKDTKSDII FFIRSVPGAD NKFQFESSSY  120
EGYFLACEKE RDLFKLILKK EDELGDRSIM FTVQNED                      157

SEQ ID NO: 118         moltype = AA  length = 157
FEATURE                Location/Qualifiers
source                 1..157
                       mol_type = protein
                       organism = synthetic construct
SEQUENCE: 118
FFGKFESKLS VIRNLNGQVL FIDQGNRPLF TDMESKDCRD RAPRTIFIIS FYKDSQPRGL  60
```

```
AVTISVKCEK ISTLSCENKI ISFKEMNPPD NIKDTKSDII FFLRSVPGHD NKLQFESSSY  120
EGYFLACEKE RDLFKLILKK EDELGDRSIM FTVQNED                           157

SEQ ID NO: 119         moltype = AA  length = 157
FEATURE                Location/Qualifiers
source                 1..157
                       mol_type = protein
                       organism = synthetic construct
SEQUENCE: 119
FFGKLESKLS VIRNLNGQVL FIDQGNRPLF ADMASNHCRA NAPRTIFIIS LYKDSQPRGL  60
AVTISVKCEK ISTLSCENKI ISFKEMNPPD NIKDTKSDII FFIRSVPGHD NKMQFESSSY  120
EGYFLACEKE RDLFKLILKK EDELGDRSIM FTVQNED                           157

SEQ ID NO: 120         moltype = AA  length = 157
FEATURE                Location/Qualifiers
source                 1..157
                       mol_type = protein
                       organism = synthetic construct
SEQUENCE: 120
YFGKLESKLS VIRNLNGQVL FIDQGNRPLF ADMTSKRCRD NAPRTIFIIS LYKDSQPRGF  60
AVTISVKCEK ISTLSCENKI ISFKEMNPPD NIKDTKSDII FFIRSVPGHD NKIQFESSSY  120
EGYFLACEKE RDLFKLILKK EDELGDRSIM FTVQNED                           157

SEQ ID NO: 121         moltype = AA  length = 157
FEATURE                Location/Qualifiers
source                 1..157
                       mol_type = protein
                       organism = synthetic construct
SEQUENCE: 121
LFGKHESKLS VIRNLNGQVL FIDQGNRPLF GDMESSPCRY NAPRTIFIIS FYKDSQPRGL  60
AVTISVKCEK ISTLSCENKI ISFKEMNPPD NIKDTKSDII FFIRSVPGHD NKMQFESSSY  120
EGYFLACEKE RDLFKLILKK EDELGDRSIM FTVQNED                           157

SEQ ID NO: 122         moltype = AA  length = 157
FEATURE                Location/Qualifiers
source                 1..157
                       mol_type = protein
                       organism = synthetic construct
SEQUENCE: 122
YFGKLESKLS VIRNLNAQVL FIDQGNRPLF TDMTASPCRS SAPRTIFIIS LYKDSQPRGL  60
AVTISVKCEK ISTLSCENKI ISFKEMNPPD NIKDTKSDII FFLRSVPGPD NKIQFESSSY  120
EGYFLACEKE RDLFKLILKK EDELGDRSIM FTVQNED                           157

SEQ ID NO: 123         moltype = AA  length = 157
FEATURE                Location/Qualifiers
source                 1..157
                       mol_type = protein
                       organism = synthetic construct
SEQUENCE: 123
YFGKLESKLS VIRNLNGQVL FIDQGNRPLF ADMTDSDCRD NAPRTIFIIS MYKDSQPRGM  60
AVTISVKCEK ISTLSCENKI ISFKEMNPPD NIKDTKSDII FFLRSVPGHD NKMQFESSSY  120
EGYFLACEKE RDLFKLILKK EDELGDRSIM FTVQNED                           157

SEQ ID NO: 124         moltype = AA  length = 157
FEATURE                Location/Qualifiers
source                 1..157
                       mol_type = protein
                       organism = synthetic construct
SEQUENCE: 124
YFGKLESKLS VIRNLNGQVL FIDQGNRPLF ADMTSSDCRD NAPRTIFIIS FYKDSQPRGM  60
AVTISVKCEK ISTLSCENKI ISFKEMNPPD NIKDTKSDII FFLRSVPGHD NKMQFESSSY  120
EGYFLACEKE RDLFKLILKK EDELGDRSIM FTVQNED                           157

SEQ ID NO: 125         moltype = AA  length = 157
FEATURE                Location/Qualifiers
source                 1..157
                       mol_type = protein
                       organism = synthetic construct
SEQUENCE: 125
YFGKLESKLS VIRNLNGQVL FIDQGNRPLF ADMESSDCRD NAPRTIFIIS FYKDSQPRGL  60
AVTISVKCEK ISTLSCENKI ISFKEMNPPD NIKDTKSDII FFLRSVPGHD NKMQFESSSY  120
EGYFLACEKE RDLFKLILKK EDELGDRSIM FTVQNED                           157

SEQ ID NO: 126         moltype = AA  length = 157
FEATURE                Location/Qualifiers
source                 1..157
                       mol_type = protein
                       organism = synthetic construct
SEQUENCE: 126
```

-continued

```
YFGRYHCTTA VIRNINQQVL FVDKRQPVFA DMGYTVQSAS EPQTRLIIYM YKDSEVRGLA  60
VTLSVKDSKM STLSCKNKII SFEEMDPPEN IDDIQSDLIF FLKEVPGHRK LEFESSLYEG  120
HFLACQKEDE AFKLILKKKD ENGDKSVMFT LTNLHQS                           157

SEQ ID NO: 127         moltype = AA  length = 157
FEATURE                Location/Qualifiers
source                 1..157
                       mol_type = protein
                       organism = synthetic construct
SEQUENCE: 127
DFGRLHCTTA VIRNINDQVL FVDKRQPVFA DMGSIAQSAS EPQTRLIIYF YKDSEVRGLA  60
VTLSVKDSKM YTLSCKNKII SFEEMDPPEN IDDIQSDLIF FLKAVPGDNK IEFESSLYEG  120
HFLACQKEAT AFKLILKKKD ENGDKSVMFT LTNLHQS                           157

SEQ ID NO: 128         moltype = AA  length = 157
FEATURE                Location/Qualifiers
source                 1..157
                       mol_type = protein
                       organism = synthetic construct
SEQUENCE: 128
YFGRLHCTTA VIRNINGQVL FVDKRQPVFR DMADTVQSAS EPQTRLIIYF YKDSEVRGLA  60
VTLSVKDSKM STLSCKNKII SFEEMDPPEN IDDIQSDLIF FIKPVPGASK MEFESSLYEG  120
HFLACQKEAG AFKLILKKKD ENGDKSVMFT LTNLHQS                           157

SEQ ID NO: 129         moltype = AA  length = 157
FEATURE                Location/Qualifiers
source                 1..157
                       mol_type = protein
                       organism = synthetic construct
SEQUENCE: 129
HFGRLHCTTA VIRNINDQVL FVDKRQPVFK DMEYTVQSAS EPQTRLIIYM YKDSEVRGLA  60
VTLSVKDSKM STLSCKNKII SFEEMDPPEN IDDIQSDLIF FIKAVPGDRK IEFESSLYEG  120
HFLACQKEDN AFKLILKKKD ENGDKSVMFT LTNLHQS                           157

SEQ ID NO: 130         moltype = AA  length = 157
FEATURE                Location/Qualifiers
source                 1..157
                       mol_type = protein
                       organism = synthetic construct
SEQUENCE: 130
YFGRLHCTTA VIRNINAQVL FVDKRQPVFA DMADKGQSAS EPQTRLIIYM YKDSEVRGLA  60
VTLSVKDSKM STLSCKNKII SFEEMDPPEN IDDIQSDLIF FLKPVPGDTK MEFESSLYEG  120
HFLACQKEFG AFKLILKKKD ENGDKSVMFT LTNLHQS                           157

SEQ ID NO: 131         moltype = AA  length = 157
FEATURE                Location/Qualifiers
source                 1..157
                       mol_type = protein
                       organism = synthetic construct
SEQUENCE: 131
YFGRLHCTTA VIRNINEQVL FVDKRQPVFA DMGDRHQSAS EPQTRLIIYM YKDSEVRGLA  60
VTLSVKDSKM STLSCKNKII SFEEMDPPEN IDDIQSDLIF FIKPVPGASK LEFESSLYEG  120
HFLACQKEDD AFKLILKKKD ENGDKSVMFT LTNLHQS                           157

SEQ ID NO: 132         moltype = AA  length = 157
FEATURE                Location/Qualifiers
source                 1..157
                       mol_type = protein
                       organism = synthetic construct
SEQUENCE: 132
HFGRLHCTTA VIRNINDQVL FVDKRQPVFR DMGAIGQSAS EPQTRLIIYF YKDSEVRGLA  60
VTLSVKDSKM STLSCKNKII SFEEMDPPEN IDDIQSDLIF FIKPVPGDSK LEFESSLYEG  120
HFLACQKEVD AFKLILKKKD ENGDKSVMFT LTNLHQS                           157

SEQ ID NO: 133         moltype = AA  length = 157
FEATURE                Location/Qualifiers
source                 1..157
                       mol_type = protein
                       organism = synthetic construct
SEQUENCE: 133
HFGRLHCTTA VIRNINSQVL FVDKRQPVFT DMGSIVQSAS EPQTRLIIYM YKDSEVRGLA  60
VTLSVKDSKM STLSCKNKII SFEEMDPPEN IDDIQSDLIF FIKGVPGDNK IEFESSLYEG  120
HFLACQKEDR AFKLILKKKD ENGDKSVMFT LTNLHQS                           157

SEQ ID NO: 134         moltype = AA  length = 157
FEATURE                Location/Qualifiers
source                 1..157
                       mol_type = protein
                       organism = synthetic construct
```

```
SEQUENCE: 134
YFGRLHCTTA VIRNINSQVL FVDKRQPVFR DMEDTPQSAS EPQTRLIIYF YKDSEVRGLA  60
VTLSVKDSKM STLSCKNKII SFEEMDPPEN IDDIQSDLIF FIKRVPGDSK LEFESSLYEG  120
HFLACQKEFE AFKLILKKKD ENGDKSVMFT LTNLHQS                          157

SEQ ID NO: 135          moltype = AA  length = 157
FEATURE                 Location/Qualifiers
source                  1..157
                        mol_type = protein
                        organism = synthetic construct
SEQUENCE: 135
HFGRLHCTTA VIRNINAQVL FVDKRQPVFG DMTATVQSAS EPQTRLIIYF YKDSEVRGLA  60
VTLSVKDSKM STLSCKNKII SFEEMDPPEN IDDIQSDLIF FIKPVPGDSK LEFESSLYEG  120
HFLACQKEDN AFKLILKKKD ENGDKSVMFT LTNLHQS                          157

SEQ ID NO: 136          moltype = AA  length = 157
FEATURE                 Location/Qualifiers
source                  1..157
                        mol_type = protein
                        organism = synthetic construct
SEQUENCE: 136
NFGRLHCTTA VIRNINNQVL FVDKRQPVFK DMEYTLQSAS EPQTRLIIYF YKDSEVRGLA  60
VTLSVKDSKM STLSCKNKII SFEEMDPPEN IDDIQSDLIF FIKPVPGDNK LEFESSLYEG  120
HFLACQKEYE AFKLILKKKD ENGDKSVMFT LTNLHQS                          157

SEQ ID NO: 137          moltype = AA  length = 157
FEATURE                 Location/Qualifiers
source                  1..157
                        mol_type = protein
                        organism = synthetic construct
SEQUENCE: 137
YFGRLHCTTA VIRNINGQVL FVDKRQPVFA DMEATRQSAS EPQTRLIIYF YKDSEVRGLA  60
VTLSVKDSKM STLSCKNKII SFEEMDPPEN IDDIQSDLIF FIKGVPGANK MEFESSLYEG  120
HFLACQKEDG AFKLILKKKD ENGDNSVMFT LTNLHQS                          157

SEQ ID NO: 138          moltype = AA  length = 157
FEATURE                 Location/Qualifiers
source                  1..157
                        mol_type = protein
                        organism = synthetic construct
SEQUENCE: 138
NFGRLHCTTA VIRNINGQVL FVDKRQPVFA DMRAILQSAS EPQTRLIIYF YKDSEVRGLA  60
VTLSVKDSKM STLSCKNKII SFEEMDPPEN IDDIQSDLIF FLKGVPGDNK LEFESSLYEG  120
HFLACQKEDR AFKLILKKKD ENGDKSVMFT LTNLHQS                          157

SEQ ID NO: 139          moltype = AA  length = 157
FEATURE                 Location/Qualifiers
source                  1..157
                        mol_type = protein
                        organism = synthetic construct
SEQUENCE: 139
YFGRLHCTTA VIRNINAQVL FVDKRQPVFA DMEATAQSAS EPQTRLIIYF YKDSEVRGLA  60
VTLSVKDSKM STLSCKNKII SFEEMDPPEN IDDIQSDLIF FIKGVPGASK MEFESSLYEG  120
HFLACQKEDG AFKLILKKKD ENGDKSVMFT LTNLHQS                          157

SEQ ID NO: 140          moltype = AA  length = 157
FEATURE                 Location/Qualifiers
source                  1..157
                        mol_type = protein
                        organism = synthetic construct
SEQUENCE: 140
LFGRLHCTTA VIRNINGQVL FVDKRQPVFA DMGATLQSAS EPQTRLIIYM YKDSEVRGLA  60
VTLSVKDSKM STLSCKNKII SFEEMDPPEN IDDIQSDLIF FLKPVPGDTK MEFESSLYEG  120
HFLACQKEAS AFKLILKKKD ENGDKSVMFT LTNLHQS                          157

SEQ ID NO: 141          moltype = AA  length = 157
FEATURE                 Location/Qualifiers
source                  1..157
                        mol_type = protein
                        organism = synthetic construct
SEQUENCE: 141
NFGRLHCTTA VIRNINGQVL FVDKRQPVFE DMAYTVQSAS EPQTRLIIYF YKDSEVRGLA  60
VTLSVKDSKM STLSCKNKII SFEEMDPPEN IDDIQSDLIF FIKGVPGDSK MEFESSLYEG  120
HFLACQKEYD AFKLILKKKD ENGDKSVMFT LTNLHQS                          157

SEQ ID NO: 142          moltype = AA  length = 157
FEATURE                 Location/Qualifiers
source                  1..157
                        mol_type = protein
```

```
                        organism = synthetic construct
SEQUENCE: 142
DFGRLHCTTA VIRNINDQVL FVDKRQPVFK DMESKPQSAS EPQTRLIIYF YKDSEVRGLA  60
VTLSVKDSKM STLSCKNKII SFEEMDPPEN IDDIQSDLIF FLKAVPGASK LEFESSLYEG  120
HFLACQKEAN AFKLILKKKD ENGDKSVMFT LTNLHQS                           157

SEQ ID NO: 143          moltype = AA  length = 157
FEATURE                 Location/Qualifiers
source                  1..157
                        mol_type = protein
                        organism = synthetic construct
SEQUENCE: 143
LFGRLHCTTA VIRNINGQVL FVDKRQPVFA DMGDKVQSAS EPQTRLIIYM YKDSEVRGLA  60
VTLSVKDSKM STLSCKNKII SFEEMDPPEN IDDIQSDLIF FIKPVPGDNK LEFESSLYEG  120
HFLACQKEDE AFKLILKTKD ENGDKSVMFT LTNLHQS                           157

SEQ ID NO: 144          moltype = AA  length = 157
FEATURE                 Location/Qualifiers
source                  1..157
                        mol_type = protein
                        organism = synthetic construct
SEQUENCE: 144
YFGRHHCTTA VIRNINQQVL FVDKRQPVFR DMAATRQSAS EPQTRLIIYM YKDSEVRGLA  60
VTLSVKDSKM STLSCKNKII SFEEMDPPEN IDDIQSDLIF FLKGVPGDNK MEFESSLYEG  120
HFLACQKEDD AFKLILKKKD ENGDKSVMFT LTNLHQS                           157

SEQ ID NO: 145          moltype = AA  length = 157
FEATURE                 Location/Qualifiers
source                  1..157
                        mol_type = protein
                        organism = synthetic construct
SEQUENCE: 145
NFGRLHCTTA VIRNINQQVL FVDKRQPVFT DMESIGQSAS EPQTRLIIYF YKDSEVRGLA  60
VTLSVKDSKM STLSCKNKII SFEEMDPPEN IDDIQSDLIF FLKAVPGANK LEFESSLYEG  120
HFLACQKEDS AFKLILKKKD ENGDKSVMFT LTNLHQS                           157

SEQ ID NO: 146          moltype = AA  length = 157
FEATURE                 Location/Qualifiers
source                  1..157
                        mol_type = protein
                        organism = synthetic construct
SEQUENCE: 146
FFGRHHCTTA VIRNINGQVL FVDKRQPVFG DMGDRVQSAS EPQTRLIIYM YKDSEVRGLA  60
VTLSVKDSKM STLSCKNKII SFEEMDPPEN IDDIQSDLIF FIKAVPGDSK IEFESSLYEG  120
HFLACQKEDG AFKLILKKKD ENGDKSVMFT LTNLHQS                           157

SEQ ID NO: 147          moltype = AA  length = 157
FEATURE                 Location/Qualifiers
source                  1..157
                        mol_type = protein
                        organism = synthetic construct
SEQUENCE: 147
VFGRHHCTTA VIRNINGQVL FVDKRQPVFK DMTYIDQSAS EPQTRLIIYM YKDSEVRGLA  60
VTLSVKDSKM STLSCKNKII SFEEMDPPEN IDDIQSDLIF FLKAVPGDTK MEFESSLYEG  120
HFLACQKEAQ AFKLILKKKD EIGDKSVMFT LTNLHQS                           157

SEQ ID NO: 148          moltype = AA  length = 157
FEATURE                 Location/Qualifiers
source                  1..157
                        mol_type = protein
                        organism = synthetic construct
SEQUENCE: 148
NFGRLHCTTA VIRNINGQVL FVDKRQPVFA DMTATRQSAS EPQTRLIIYM YKDSEVRGLA  60
VTLSVKDSKM STLSCKNKII SFEEMDPPEN IDDIQSDLIF FIKQVPGANK IEFESSLYEG  120
HFLACQKEFR AFKLILKKKD ENGDKSVMFT LTNLHQS                           157

SEQ ID NO: 149          moltype = AA  length = 157
FEATURE                 Location/Qualifiers
source                  1..157
                        mol_type = protein
                        organism = synthetic construct
SEQUENCE: 149
DFGRLHCTTA VIRNINGQVL FVDKRQPVFG DMAYIGQSAS EPQTRLIIYF YKDSEVRGLA  60
VTLSVKDSKM STLSCKNKII SFEEMDPPEN IDDIQSDLIF FIKAVPGHSK IEFESSLYEG  120
HFLACQKESG AFKLILKKKD ENGDKSVMFT LTNLHQS                           157

SEQ ID NO: 150          moltype = AA  length = 157
FEATURE                 Location/Qualifiers
source                  1..157
```

```
                         mol_type = protein
                         organism = synthetic construct
SEQUENCE: 150
YFGRLHCTTA VIRNINDQVL FVDKRQPVFR DMGSIAQSAS EPQTRLIIYM YKDSEVRGLA  60
VTLSVKDSKM STLSCKNKII SFEEMDPPEN IDDIQSDLIF FIKPVPGATK LEFESSLYEG  120
HFLACQKEDG AFKLILKKKD ENGDNSVMFT LTNLHQS                          157

SEQ ID NO: 151           moltype = AA  length = 157
FEATURE                  Location/Qualifiers
source                   1..157
                         mol_type = protein
                         organism = synthetic construct
SEQUENCE: 151
YFGRLHCTTA VIRNINEQVL FVDKRQPVFT DMEAIGQSAS EPQTRLIIYF YKDSEVRGLA  60
VTLSVKDSKM STLSCKNKII SFEEMDPPEN IDDIQSDLIF FIKGVPGDRK MEFESSLYEG  120
HFLACQKEDG AFKLILKKKD ENGDKSVMFT LTNLHQS                          157

SEQ ID NO: 152           moltype = AA  length = 157
FEATURE                  Location/Qualifiers
source                   1..157
                         mol_type = protein
                         organism = synthetic construct
SEQUENCE: 152
FFGRLHCTTA VIRNINNQVL FVDKRQPVFE DMEYRLQSAS EPQTRLIIYM YKDSEVRGLA  60
VTLSVKDSKM STLSCKNKII SFEEMDPPEN IDDIQSDLIF FLKPVPGASK LEFESSLYEG  120
HFLACQKESD AFKLILKKKD ENGDKSVMFT LTNLHQS                          157

SEQ ID NO: 153           moltype = AA  length = 157
FEATURE                  Location/Qualifiers
source                   1..157
                         mol_type = protein
                         organism = synthetic construct
SEQUENCE: 153
NFGRLHCTTA VIRNINNQVL FVDKRQPVFA DMEDRLQSAS EPQTRLIIYM YKDSEVRGLA  60
VTLSVKDSKM STLSCKNKII SFEEMDPPEN IDDIQSDLIF FLKGVPGDNK MEFESSLYEG  120
HFLACQKEDH AFKLILKKKD ENGDKSVMFT LTNLHQS                          157

SEQ ID NO: 154           moltype = AA  length = 157
FEATURE                  Location/Qualifiers
source                   1..157
                         mol_type = protein
                         organism = synthetic construct
SEQUENCE: 154
YFGRLHCTTA VIRNINAQVL FVDKRQPVFR DMGYILQSAS EPQTRLIIYL YKDSEVRGLA  60
VTLSVKESKM STLSCKNKII SFEEMDPPEN IDDIQSDLIF FLKPVPGDTK IEFESSLYEG  120
HFLACQKEDN AFKLILKKKD ENGDKSVMFT LTNLHQS                          157

SEQ ID NO: 155           moltype = AA  length = 157
FEATURE                  Location/Qualifiers
source                   1..157
                         mol_type = protein
                         organism = synthetic construct
SEQUENCE: 155
YFGRLHCTTA VIRNINDQVL FVDKRQPVFG DMADTAQSAS EPQTRLIIYF YKDSEVRGLA  60
VTLSVKDSKM STLSCKNKII SFEEMDPPEN IDDIQSDLIF FIKPVPGDSK MEFESSLYEG  120
HFLACQKEAD AFKLILKKKD ENGDKSVMFT LTNLHQS                          157

SEQ ID NO: 156           moltype = AA  length = 157
FEATURE                  Location/Qualifiers
source                   1..157
                         mol_type = protein
                         organism = synthetic construct
SEQUENCE: 156
DFGRLHCTTA VIRNINGQVL FVDKRQPVFE DMAYIAQSAS EPQTRLIIYF YKDSEVRGLA  60
VTLSVKDSKM STLSCKNKII SFEEMDPPEN IDDIQSDLIF FIKPVPGDSK IEFESSLYEG  120
HFLACQKEAD AFKLILKKKD ENGDKSVMFT LTNLHQS                          157

SEQ ID NO: 157           moltype = AA  length = 157
FEATURE                  Location/Qualifiers
source                   1..157
                         mol_type = protein
                         organism = synthetic construct
SEQUENCE: 157
NFGRLHCTTA VIRNINEQVL SVDKRQPVFR DMKYILQSAS EPQTRLIIYF YKDSEVRGLA  60
VTLSVKDSKM STLSCKNKII SFEEMDPPEN IDDIQSDLIF FLKGVPGDNK MEFESSLYEG  120
HFLACQKEYG AFKLILKKKD ENGDKSVMFT LTNLHQS                          157

SEQ ID NO: 158           moltype = AA  length = 157
FEATURE                  Location/Qualifiers
```

```
source                  1..157
                        mol_type = protein
                        organism = synthetic construct
SEQUENCE: 158
DFGRLHCTTA VIRNINEQVL FVDKRQPVFT DMAYILQSAS EPQTRLIIYF YKDSEVRGLA  60
VTLSVKESKM STLSCKNKII SFEEMDPPEN IDDIQSDLIF FIKAVPGDSK LEFESSLYEG  120
HFLACQKEDT AFKLILKKKD ENGDKSVMFT LTNLHQS                          157

SEQ ID NO: 159          moltype = AA  length = 157
FEATURE                 Location/Qualifiers
source                  1..157
                        mol_type = protein
                        organism = synthetic construct
SEQUENCE: 159
DFGRLHCTTA VIRNINNQVL FVDKRQPVFK DMESTAQSAS EPQTRLIIYM YKDSEVRGLA  60
VTLSVKDSKM STLSCKNKII SFEEMDPPEN IDDIQSDLIF FLKGVPGASK LEFESSLYEG  120
HFLACQKEAG AFKLILKKKD ENGDKSVMFT LTNLHQS                          157

SEQ ID NO: 160          moltype = AA  length = 157
FEATURE                 Location/Qualifiers
source                  1..157
                        mol_type = protein
                        organism = synthetic construct
SEQUENCE: 160
HFGRLHCTTA VIRNINEQVL FVDKRQPVFA DMEAIGQSAS EPQTRLIIYF YKDSEVRGLA  60
VTLSVKESKM STLSCKNKII SFEEMDPPEN IDDIQSDLIF FIKGVPGDTK LEFESSLYAG  120
HFLACQKEDG AFKLILKKKD ENGDKSVMFT LTNLHQS                          157

SEQ ID NO: 161          moltype = AA  length = 157
FEATURE                 Location/Qualifiers
source                  1..157
                        mol_type = protein
                        organism = synthetic construct
SEQUENCE: 161
IFGRLHCTTA VIRNINEQVL FVDKRQPVFK DMRYIVQSAS EPQTRLIIYF YKDSEVRGLA  60
VTLSVKDSKM STLSCKNKII SFEEMDPPEN IDDIQSDLIF FIKEVPGASK LEFESSLYEG  120
HFLACQKEDE AFKLILKKKD ENGDKSVMFT LTNLHQS                          157

SEQ ID NO: 162          moltype = AA  length = 157
FEATURE                 Location/Qualifiers
source                  1..157
                        mol_type = protein
                        organism = synthetic construct
SEQUENCE: 162
YFGRLHCTTA VIRNINAQVL FVDKRQPVFT DMGYTLQSAS EPQTRLIIYL YKDSEVRGLA  60
VTLSVKDSKM STLSCKNKII SFEEMDPPEN IDDIQSDLIF FIKPVPGHNK IEFESSLYEG  120
HFLACQKEDR AFKLILKKKD ENGDKSVMFT LTNLHQS                          157

SEQ ID NO: 163          moltype = AA  length = 157
FEATURE                 Location/Qualifiers
source                  1..157
                        mol_type = protein
                        organism = synthetic construct
SEQUENCE: 163
NFGRLHCTTA VIRNINNQVL FVDKRQPVFR DMASTAQSAS EPQTRLIIYM YKDSEVRGLA  60
VTLSVKDSKM STLSCKNKII SFEEMDPPEN IDDIQSDLIF FIKGVPGANK IEFESSLYEG  120
HFLACQKEDD AFKLILKKKD ENGDKSVMFT LTNLHQS                          157

SEQ ID NO: 164          moltype = AA  length = 157
FEATURE                 Location/Qualifiers
source                  1..157
                        mol_type = protein
                        organism = synthetic construct
SEQUENCE: 164
DFGRLHCTTA VIRNINGQVL FVDKRQPVFE DMKDRAQSAS EPQTRLIIYF YKDSEVRGLA  60
VTLSVKDSKM STLSCKNKII SFEEMDPPEN IDDIQSDLIF FLKAVPGHSK MEFESSLYEG  120
HFLACQKEDE AFKLILKKKD ENGDKSVMFT LTNLHQS                          157

SEQ ID NO: 165          moltype = AA  length = 157
FEATURE                 Location/Qualifiers
source                  1..157
                        mol_type = protein
                        organism = synthetic construct
SEQUENCE: 165
NFGRLHCTTA VIRNINEQVL FVDKRQPVFA DMTDIAQSAS EPQTRLIIYM YKDSEVRGLA  60
VTLSVKESKM STLSCKNKII SFEEMDPPEN IDDIQSDLIF FLKPVPGDIK MEFESSLYEG  120
HFLACQKEYG AFKLILKKKD ENGDNSVMFT LTNLHQS                          157

SEQ ID NO: 166          moltype = AA  length = 157
```

```
FEATURE                Location/Qualifiers
source                 1..157
                       mol_type = protein
                       organism = synthetic construct
SEQUENCE: 166
YFGRLHCTTA VIRNINEQVL FVDKRQPVFA DMTDTLQSAS EPQTRLIIYF YKDSEVRGLA  60
VTLSVKDSKM STLSCKNKII SFEEMDPPEN IDDIQSDLIF FLKGVPGDNK MEFESSLYEG  120
HFLACQKEDT AFKLILKKKD ENGDKSVMFT LTNLHQS                           157

SEQ ID NO: 167         moltype = AA  length = 157
FEATURE                Location/Qualifiers
source                 1..157
                       mol_type = protein
                       organism = synthetic construct
SEQUENCE: 167
YFGRLHCTTA VIRNINEQVL FVDKRQPVFA DMTDTLQSAS EPQTRLIIYF YKDSEVRGLA  60
VTLSVKDSKM STLSCKNKII SFEEMDPPEN IDDIQSDLIF FLKGVPGDNK MEFESSLYEG  120
HFLACQKEDT AFKLILKKKD ENGDKSVMFT LTNLHQS                           157

SEQ ID NO: 168         moltype = AA  length = 157
FEATURE                Location/Qualifiers
source                 1..157
                       mol_type = protein
                       organism = synthetic construct
SEQUENCE: 168
YFGRLHCTTA VIRNINEQVL FVDKRQPVFA DMTDTLQSAS EPQTRLIIYF YKDSEVRGLA  60
VTLSVKDSKM STLSCKNKII SFEEMDPPEN IDDIQSDLIF FLKGVPGDNK MEFESSLYEG  120
HFLACQKEDT AFKLILKKKD ENGDKSVMFT LTNLHQS                           157

SEQ ID NO: 169         moltype = AA  length = 157
FEATURE                Location/Qualifiers
source                 1..157
                       mol_type = protein
                       organism = synthetic construct
SEQUENCE: 169
HFGRLHCTTA VIRNINGQVL FVDKRQPVFK DMKYIVQSAS EPQTRLIIYM YKDSEVRGLA  60
VTLSVKDSKM STLSCKNKII SFEEMDPPEN IDDIQSDLIF FLKAVPGHSK IEFESSLYEG  120
HFLACQKEDS AFKLILKKKD ENGDKSVMFT LTNLHQS                           157

SEQ ID NO: 170         moltype = AA  length = 157
FEATURE                Location/Qualifiers
source                 1..157
                       mol_type = protein
                       organism = synthetic construct
SEQUENCE: 170
HFGRLHCTTA VIRNINGQVL FVDKRQPVFK DMKYIVQSAS EPQTRLIIYM YKDSEVRGLA  60
VTLSVKDSKM STLSCKNKII SFEEMDPPEN IDDIQSDLIF FLKAVPGHSK IEFESSLYEG  120
HFLACQKEDS AFKLILKKKD ENGDKSVMFT LTNLHQS                           157

SEQ ID NO: 171         moltype = AA  length = 157
FEATURE                Location/Qualifiers
source                 1..157
                       mol_type = protein
                       organism = synthetic construct
SEQUENCE: 171
YFGRLHCTTA VIRNINGQVL FVDKRQPVFE DMKAKAQSAS EPQTRLIIYF YKDSEVRGLA  60
VTLSVKDSKM STLSCKNKII SFEEMDPPEN IDDIQSDLIF FIKPVPGASK MEFESSLYEG  120
HFLACQKEDG AFKLILKKKD ENGDKSVMFT LTNLHQS                           157

SEQ ID NO: 172         moltype = AA  length = 157
FEATURE                Location/Qualifiers
source                 1..157
                       mol_type = protein
                       organism = synthetic construct
SEQUENCE: 172
YFGRLHCTTA VIRNINGQVL FVDKRQPVFE DMKAKAQSAS EPQTRLIIYF YKDSEVRGLA  60
VTLSVKDSKM STLSCKNKII SFEEMDPPEN IDDIQSDLIF FIKPVPGASK MEFESSLYEG  120
HFLACQKEDG AFKLILKKKD ENGDKSVMFT LTNLHQS                           157

SEQ ID NO: 173         moltype = AA  length = 157
FEATURE                Location/Qualifiers
source                 1..157
                       mol_type = protein
                       organism = synthetic construct
SEQUENCE: 173
YFGRLHCTTA VIRNINGQVL FVDKRQPVFE DMKAKAQSAS EPQTRLIIYF YKDSEVRGLA  60
VTLSVKDSKM STLSCKNKII SFEEMDPPEN IDDIQSDLIF FIKPVPGASK MEFESSLYEG  120
HFLACQKEDG AFKLILKKKD ENGDKSVMFT LTNLHQS                           157
```

-continued

```
SEQ ID NO: 174         moltype = AA  length = 157
FEATURE                Location/Qualifiers
source                 1..157
                       mol_type = protein
                       organism = synthetic construct
SEQUENCE: 174
LFGRLHCTTA VIRNINGQVL FVDKRQPVFG DMGSIPQSAS EPQTRLIIYF YKDSEVRGLA  60
VTLSVKDSKM STLSCKNKII SFEEMDPPEN IDDIQSDLIF FIKHVPGATK MEFESSLYEG  120
HFLACQKEDN AFKLILKKKD ENGDKSVMFT LTNLHQS                           157

SEQ ID NO: 175         moltype = AA  length = 157
FEATURE                Location/Qualifiers
source                 1..157
                       mol_type = protein
                       organism = synthetic construct
SEQUENCE: 175
LFGRLHCTTA VIRNINGQVL FVDKRQPVFG DMGSIPQSAS EPQTRLIIYF YKDSEVRGLA  60
VTLSVKDSKM STLSCKNKII SFEEMDPPEN IDDIQSDLIF FIKHVPGATK MEFESSLYEG  120
HFLACQKEDN AFKLILKKKD ENGDKSVMFT LTNLHQS                           157

SEQ ID NO: 176         moltype = AA  length = 157
FEATURE                Location/Qualifiers
source                 1..157
                       mol_type = protein
                       organism = synthetic construct
SEQUENCE: 176
YFGRLHCTTA VIRNINSQVL FVDKRQPVFT DMAYTVQSAS EPQTRLIIYF YKDSEVRGLA  60
VTLSVKDSKM STLSCKNKII SFEEMDPPEN IDDIQSDLIF FIKAVPGDSK LEFESSLYEG  120
HFLACQKEDN AFKLILKKKD ENGDKSVMFT LTNLHQS                           157

SEQ ID NO: 177         moltype = AA  length = 157
FEATURE                Location/Qualifiers
source                 1..157
                       mol_type = protein
                       organism = synthetic construct
SEQUENCE: 177
YFGRLHCTTA VIRNINSQVL FVDKRQPVFT DMAYTVQSAS EPQTRLIIYF YKDSEVRGLA  60
VTLSVKDSKM STLSCKNKII SFEEMDPPEN IDDIQSDLIF FIKAVPGDSK LEFESSLYEG  120
HFLACQKEDN AFKLILKKKD ENGDKSVMFT LTNLHQS                           157

SEQ ID NO: 178         moltype = AA  length = 157
FEATURE                Location/Qualifiers
source                 1..157
                       mol_type = protein
                       organism = synthetic construct
SEQUENCE: 178
YFGRLHCTTA VIRNINGQVL FVDKRQPVFT DMGARVQSAS EPQTRLIIYF YKDSEVRGLA  60
VTLSVKDSKM YTLSCKNKII SFEEMDPPEN IDDIQSDLIF FLKPVPGDNK LEFESSLYEG  120
HFLACQKESG AFKLILKKKD ENGDKSVMFT LTNLHQS                           157

SEQ ID NO: 179         moltype = AA  length = 157
FEATURE                Location/Qualifiers
source                 1..157
                       mol_type = protein
                       organism = synthetic construct
SEQUENCE: 179
YFGRLHCTTA VIRNINGQVL FVDKRQPVFT DMGARVQSAS EPQTRLIIYF YKDSEVRGLA  60
VTLSVKDSKM YTLSCKNKII SFEEMDPPEN IDDIQSDLIF FLKPVPGDNK LEFESSLYEG  120
HFLACQKESG AFKLILKKKD ENGDKSVMFT LTNLHQS                           157

SEQ ID NO: 180         moltype = AA  length = 157
FEATURE                Location/Qualifiers
source                 1..157
                       mol_type = protein
                       organism = synthetic construct
SEQUENCE: 180
DFGRLHCTTA VIRNINGQVL FVDKRQPVFG DMKATGQSAS EPQTRLIIYF YKDSEVRGLA  60
VTLSVKDSKM STLSCKNKII SFEEMDPPEN IDDIQSDLIF FIKAVPGANK LEFESSLYEG  120
HFLACQKEAG AFKLILKKKD ENGDKSVMFT LTNLHQS                           157

SEQ ID NO: 181         moltype = AA  length = 157
FEATURE                Location/Qualifiers
source                 1..157
                       mol_type = protein
                       organism = synthetic construct
SEQUENCE: 181
DFGRLHCTTA VIRNINGQVL FVDKRQPVFG DMKATGQSAS EPQTRLIIYF YKDSEVRGLA  60
VTLSVKDSKM STLSCKNKII SFEEMDPPEN IDDIQSDLIF FIKAVPGANK LEFESSLYEG  120
HFLACQKEAG AFKLILKKKD ENGDKSVMFT LTNLHQS                           157
```

```
SEQ ID NO: 182          moltype = AA  length = 157
FEATURE                 Location/Qualifiers
source                  1..157
                        mol_type = protein
                        organism = synthetic construct
SEQUENCE: 182
DFGRLHCTTA VIRNINSQVL FVDKRQPVFR DMGSIHQSAS EPQTRLIIYF YKDSEVRGLA  60
VTLSVKDSKM STLSCKNKII SFEEMDPPEN IDDIQSDLIF FLKAVPGANK LEFESSLYEG  120
HFLACQKEDG AFKLILKKKD ENGDKSVMFT LTNLHQS                           157

SEQ ID NO: 183          moltype = AA  length = 157
FEATURE                 Location/Qualifiers
source                  1..157
                        mol_type = protein
                        organism = synthetic construct
SEQUENCE: 183
DFGRLHCTTA VIRNINSQVL FVDKRQPVFR DMGSIHQSAS EPQTRLIIYF YKDSEVRGLA  60
VTLSVKDSKM STLSCKNKII SFEEMDPPEN IDDIQSDLIF FLKAVPGANK LEFESSLYEG  120
HFLACQKEDG AFKLILKKKD ENGDKSVMFT LTNLHQS                           157

SEQ ID NO: 184          moltype = AA  length = 157
FEATURE                 Location/Qualifiers
source                  1..157
                        mol_type = protein
                        organism = synthetic construct
SEQUENCE: 184
YFGRLHCTTA VIRNINEQVL FVDKRQPVFK DMKDKLQSAS EPQTRLIIYF YKDSEVRGLA  60
VTLSVKDSKM STLSCKNKII SFEEMDPPEN IDDIQSDLIF FLKGVPGDNK LEFESSLYEG  120
HFLACQKEFG AFKLILKKKD ENGDKSVMFT LTNLHQS                           157

SEQ ID NO: 185          moltype = AA  length = 157
FEATURE                 Location/Qualifiers
source                  1..157
                        mol_type = protein
                        organism = synthetic construct
SEQUENCE: 185
YFGRLHCTTA VIRNINEQVL FVDKRQPVFK DMKDKLQSAS EPQTRLIIYF YKDSEVRGLA  60
VTLSVKDSKM STLSCKNKII SFEEMDPPEN IDDIQSDLIF FLKGVPGDNK LEFESSLYEG  120
HFLACQKEFG AFKLILKKKD ENGDKSVMFT LTNLHQS                           157

SEQ ID NO: 186          moltype = AA  length = 157
FEATURE                 Location/Qualifiers
source                  1..157
                        mol_type = protein
                        organism = synthetic construct
SEQUENCE: 186
YFGRLHCTTA VIRNINGQVL FVDKRQPVFA DMASTHQSAS EPQTRLIIYF YKDSEVRGLA  60
VTLSVKDSKM STLSCKNKII SFEEMDPPEN IDDIQSDLIF FLKGVPGANK IEFESSLYEG  120
HFLACQKEDD AFKLILKKKD ENGDKSVMFT LTNLHQS                           157

SEQ ID NO: 187          moltype = AA  length = 157
FEATURE                 Location/Qualifiers
source                  1..157
                        mol_type = protein
                        organism = synthetic construct
SEQUENCE: 187
YFGRLHCTTA VIRNINGQVL FVDKRQPVFA DMASTHQSAS EPQTRLIIYF YKDSEVRGLA  60
VTLSVKDSKM STLSCKNKII SFEEMDPPEN IDDIQSDLIF FLKGVPGANK IEFESSLYEG  120
HFLACQKEDD AFKLILKKKD ENGDKSVMFT LTNLHQS                           157

SEQ ID NO: 188          moltype = AA  length = 157
FEATURE                 Location/Qualifiers
source                  1..157
                        mol_type = protein
                        organism = synthetic construct
SEQUENCE: 188
YFGRLHCTTA VIRNINGQVL FVDKRQPVFA DMASTHQSAS EPQTRLIIYF YKDSEVRGLA  60
VTLSVKDSKM STLSCKNKII SFEEMDPPEN IDDIQSDLIF FLKGVPGANK IEFESSLYEG  120
HFLACQKEDD AFKLILKKKD ENGDKSVMFT LTNLHQS                           157

SEQ ID NO: 189          moltype = AA  length = 157
FEATURE                 Location/Qualifiers
source                  1..157
                        mol_type = protein
                        organism = synthetic construct
SEQUENCE: 189
YFGRLHCTTA VIRNINSQVL FVDKRQPVFG DMKYIVQSAS EPQTRLIIYF YKDSEVRGLA  60
VTLSVKDSKM STLSCKNKII SFEEMDPPEN IDDIQSDLIF FLKGVPGDTK MEFESSLYEG  120
```

-continued

```
HFLACQKESG AFKLILKKKD ENGDKSVMFT LTNLHQS                        157

SEQ ID NO: 190          moltype = AA  length = 157
FEATURE                 Location/Qualifiers
source                  1..157
                        mol_type = protein
                        organism = synthetic construct
SEQUENCE: 190
YFGRLHCTTA VIRNINSQVL FVDKRQPVFG DMKYIVQSAS EPQTRLIIYF YKDSEVRGLA  60
VTLSVKDSKM STLSCKNKII SFEEMDPPEN IDDIQSDLIF FLKGVPGDTK MEFESSLYEG  120
HFLACQKESG AFKLILKKKD ENGDKSVMFT LTNLHQS                        157

SEQ ID NO: 191          moltype = AA  length = 157
FEATURE                 Location/Qualifiers
source                  1..157
                        mol_type = protein
                        organism = synthetic construct
SEQUENCE: 191
YFGKLESKLS VIRNLNDQVL FIDQGNRPLF EDMTDSDCRD NAPRTIFIIS KYGDSVPRGL  60
AVTISVKCEK ISTLSCENKI ISFKEMNPPD NIKDTKSDII FFARAVPGHS RKTQFESSSY  120
EGYFLACEKE RDLFKLILKK EDELGDRSIM FTVQNED                        157

SEQ ID NO: 192          moltype = AA  length = 157
FEATURE                 Location/Qualifiers
source                  1..157
                        mol_type = protein
                        organism = synthetic construct
SEQUENCE: 192
YFGKLESKLS VIRNLNDQVL FIDQGNRPLF EDMTDSDCRD NAPRTIFIIS KYSDSRARGL  60
AVTISVKCEK ISTLSCENKI ISFKEMNPPD NIKDTKSDII FFARSVPGHG RKTQFESSSY  120
EGYFLACEKE RDLFKLILKK EDELGDRSIM FTVQNED                        157

SEQ ID NO: 193          moltype = AA  length = 157
FEATURE                 Location/Qualifiers
source                  1..157
                        mol_type = protein
                        organism = synthetic construct
SEQUENCE: 193
YFGKLESKLS VIRNLNDQVL FIDQGNRPLF EDMTDSDCRD NAPRTIFIIS KYSDSRARGL  60
AVTISVKCEK ISTLSCENKI ISFKEMNPPD NIKDTKSDII FFARDVPGHS GKRQFESSSY  120
EGYFLACEKE RDLFKLILKK EDELGDRSIM FTVQNED                        157

SEQ ID NO: 194          moltype = AA  length = 15
FEATURE                 Location/Qualifiers
source                  1..15
                        mol_type = protein
                        organism = synthetic construct
SEQUENCE: 194
GLNDIFEAQK IEWHE                                                15
```

INTERLEUKIN-18 VARIANTS AND METHODS OF USE

CROSS-REFERENCE TO RELATED APPLICATIONS

This application is a divisional of Ser. No. 16/123,063, filed Sep. 6, 2018, which claims the benefit of U.S. Provisional Patent Application Nos. 62/554,605 filed Sep. 6, 2017, and 62/652,279 filed Apr. 3, 2018, each of which application is incorporated herein by reference in its entirety.

REFERENCE TO A "SEQUENCE LISTING", A TABLE, OR A COMPUTER PROGRAM LISTING APPENDIX SUBMITTED AS AN XML FILE

The present application hereby incorporates by reference the entire contents of the XML file named "047162-5249-01US_SequenceListing3.xml" in XML format, which was created on Sep. 8, 2023, and is 201,093 bytes in size.

INTRODUCTION

Interleukin 18 (IL-18) is a pro-inflammatory cytokine that can stimulate T cells, NK cells, and myeloid cells. IL-18 has been proposed as an immunotherapeutic agent for the treatment of cancer, given its ability to stimulate anti-tumor immune cells. However, the clinical efficacy of IL-18 has been limited.

Thus, there is a need for compositions and methods that provide effective IL-18 signaling activity to treat and prevent cancer and other diseases and disorders. The present invention addresses this unmet need.

SUMMARY

In one aspect, the disclosure relates to a composition comprising an IL-18 variant polypeptide. In some embodiments, the IL-18 variant polypeptide specifically binds to IL-18 receptor (IL-18R) and wherein the IL-18 variant polypeptide exhibits substantially reduced binding to IL-18 binding protein (IL-18BP).

In some embodiments, the IL-18 variant polypeptide comprises at least one mutation relative to wild-type (WT) IL-18. In some embodiments, the WT IL-18 is human IL-18 comprising the amino acid sequence of SEQ ID NO: 30. In some embodiments, the WT IL-18 is murine IL-18 comprising the amino acid sequence of SEQ ID NO: 31.

In some embodiments, the IL-18 variant polypeptide comprises at least one mutation selected from the group consisting of Y1X, L5X, K8X, M51X, K53X, S55X, Q56X, P57X, G59X, M60X, E77X, Q103X, S105X, D10X, N111X, M113X, V153X, and N155X, relative to SEQ ID NO: 30.

In some embodiments, the IL-18 variant polypeptide comprises at least one mutation selected from the group consisting of Y1H, Y1R, L5H, L5I, L5Y, K8Q, K8R, M51T, M51K, M51D, M51N, M51E, M51R, K53R, K53G, K53S, K53T, S55K, S55R, Q56E, Q56A, Q56R, Q56V, Q56G, Q56K, Q56L, P57L, P57G, P57A, P57K, G59T, G59A, M60K, M60Q, M60R, M60L, E77D, Q103E, Q103K, Q103P, Q103A, Q103R, S105R, S105D, S105K, S105N, S105A, D110H, D110K, D1 ION, D110Q, D110E, D110S, D110G, N111H, N111Y, N111D, N111R, N111S, N111G, M113V, M113R, M113T, M113K, V1531, V153T, V153A, N155K, and N155H, relative to SEQ ID NO: 30.

In some embodiments, the IL-18 variant polypeptide comprises the mutations M51X, M60X, S105X, D110X, and N111X, relative to SEQ ID NO: 30.

In some embodiments, the IL-18 variant polypeptide comprises the mutations M51X, K53X, Q56X, S105X, and N111X, relative to SEQ ID NO: 30.

In some embodiments, the IL-18 variant polypeptide comprises the amino acid sequence set forth in any one of SEQ ID NOs.: 34-59, 73-91, 191-193, or a fragment thereof.

In some embodiments, the IL-18 variant polypeptide comprises at least one mutation selected from the group consisting of NIX, M50X, Y51X, K52X, S54X, E55X, V56X, R57X, G58X, L59X, R104X, N109X, and L151X, relative to SEQ ID NO: 31.

In some embodiments, the IL-18 variant polypeptide comprises at least one mutation selected from the group consisting of N1H, N1Y, M50A, M50S, M50V, M50G, M50T, Y51R, K52V, K52S, K52T, K52G, K52A, S54R, S54K, S54G, S54N, E55R, E55H, E55N, E55D, E55G, V56L, V56M, V56R, V56A, V56S, V56Q, R57G, R57K, G58A, L59K, L59R, L59V, R104K, R104L, R104Q, R104S, N109D, and L151V, relative to SEQ ID NO: 31.

In some embodiments, the IL-18 variant polypeptide comprises the amino acid sequence set forth in any one of SEQ ID NOs.: 60-72, or a fragment thereof.

In one aspect, the disclosure relates to a composition comprising a nucleic acid encoding the IL-18 variant polypeptide.

In some embodiments, the composition further comprises one or more agents selected from: (i) an immune checkpoint inhibitor; (ii) an agent that inhibits one or more proteins selected from PD-L1, PD1, CTLA4, TIM3, TIGIT, LAG3, B7H3, B7H4, VISTA, ICOS, GITR, 41BB, OX40, and CD40; (iii) a cancer cell opsonizing agent; and (iv) an agent that targets one or more antigens selected from: CD19, CD20, CD22, CD24, CD25, CD30, CD33, CD37, CD38, CD44, CD45, CD47, CD51, CD52, CD56, CD62L, CD70, CD74, CD79, CD80, CD96, CD97, CD99, CD123, CD134, CD138, CD152 (CTLA-4), CD200, CD213A2, CD221, CD248, CD276 (B7-H3), B7-H4, CD279 (PD-1), CD274 (PD-L1), CD319, EGFR, EPCAM, 17-1A, HER1, HER2, HER3, CD117, C-Met, HGFR, PDGFRA, AXL, TWEAKR, PTHR2, HAVCR2 (TIM3), GD2 ganglioside, MUC1, mucin CanAg, mesothelin, endoglin, Lewis-Y antigen, CEA, CEACAM1, CEACAM5, CA-125, PSMA, BAFF, FGFR2, TAG-72, gelatinase B, glypican 3, nectin-4, BCMA, CSF1R, SLAMF7, integrin $\alpha_v\beta_3$, TYRP1, GPNMB, CLDN18.2, FOLR1, CCR4, CXCR4, MICA, C242 antigen, D113, D114, EGFL7, vimentin, fibronectin extra domain-B, TROP-2, LRRC15, FAP, SLITRK6, NOTCH2, NOTCH3, Tenascin-3, STEAP1, and NRP1.

In one aspect, the disclosure relates to a method of treating or preventing a disease or disorder in a subject in need thereof, comprising administering to the subject a composition comprising the IL-18 variant polypeptide or the nucleic acid encoding the IL-18 variant polypeptide.

In some embodiments, the disease or disorder is cancer. In some embodiments, the cancer is a cancer that is resistant to immune checkpoint inhibitors (ICIs). In some embodiments, the cancer is associated with a tumor that has lost expression of MHC class I.

In some embodiments, the disease or disorder is a metabolic disease or disorder. In some embodiments, the disease or disorder is an infectious disease.

In some embodiments, the method comprises administering to the subject the IL-18 variant polypeptide and at least one other agent. In some embodiments, the at least one other agent comprises an immune checkpoint inhibitor. In some embodiments, the immune checkpoint inhibitor is an agent that inhibits PD-L1, PD1, CTLA4, TIM3, TIGIT, LAG3, B7H3, B7H4, VISTA, ICOS, GITR, 41BB, OX40, or CD40, or any combination thereof.

In some embodiments, the at least one other agent comprises a cancer cell opsonizing agent. In some embodiments, the at least one other agent targets one or more antigens selected from: CD19, CD20, CD22, CD24, CD25, CD30, CD33, CD37, CD38, CD44, CD45, CD47, CD51, CD52, CD56, CD62L, CD70, CD74, CD79, CD80, CD96, CD97, CD99, CD123, CD134, CD138, CD152 (CTLA-4), CD200, CD213A2, CD221, CD248, CD276 (B7-H3), B7-H4, CD279 (PD-1), CD274 (PD-L1), CD319, EGFR, EPCAM, 17-1A, HER1, HER2, HER3, CD117, C-Met, HGFR, PDGFRA, AXL, TWEAKR, PTHR2, HAVCR2 (TIM3), GD2 ganglioside, MUC1, mucin CanAg, mesothelin, endoglin, Lewis-Y antigen, CEA, CEACAM1, CEACAM5, CA-125, PSMA, BAFF, FGFR2, TAG-72, gelatinase B, glypican 3, nectin-4, BCMA, CSF1R, SLAMF7, integrin $\alpha_v\beta_3$, TYRP1, GPNMB, CLDN18.2, FOLR1, CCR4, CXCR4, MICA, C242 antigen, D113, D114, EGFL7, vimentin, fibronectin extra domain-B, TROP-2, LRRC15, FAP, SLITRK6, NOTCH2, NOTCH3, Tenascin-3, STEAP1, and NRP1. In some embodiments, the at least one other agent is conjugated to the IL-18 variant polypeptide. In some embodiments, the at least one other agent is an altered T-cell or NK cell. In some embodiments, the at least one other agent is an oncolytic virus.

In one aspect, the disclosure relates to a composition comprising an IL-18 binding protein (IL-18BP) inhibitor or IL-18BP antagonist, wherein the inhibitor or antagonist inhibits the ability of IL-18BP to neutralize endogenous IL-18. In some embodiments, the inhibitor or antagonist comprises at least one selected from the group consisting of: a chemical compound, a polypeptide, a peptide, a peptidomimetic, an antibody, a ribozyme, a small molecule chemical compound, and an antisense nucleic acid molecule.

In some embodiments, the composition comprises an IL-18 variant polypeptide, wherein the IL-18 variant polypeptide specifically binds to IL-18BP and wherein the IL-18 variant polypeptide exhibits substantially reduced binding to IL-18 receptor (IL-18R).

In some embodiments, the IL-18 variant polypeptide comprises at least one mutation relative to wild-type (WT) IL-18. In some embodiments, the WT IL-18 is human IL-18 comprising the amino acid sequence of SEQ ID NO: 30. In some embodiments, the WT IL-18 is murine IL-18 comprising the amino acid sequence of SEQ ID NO: 31.

In some embodiments, the IL-18 variant polypeptide comprises at least one mutation selected from the group consisting of Y1X, L5X, D17X, E31X, T34X, D35X, S36X, D37X, D40X, N41X, M51X, Q56X, M60X, Q103X, H109X, M113X, and R131X, relative to SEQ ID NO: 30.

In some embodiments, the IL-18 variant polypeptide comprises at least one mutation selected from the group consisting of Y1D, Y1F, Y1H, Y1L, L5F, L5H, D17A, D17G, D17R, D17H, E31A, E31T, E31G, E31K, E31R, T34A, T34K T34E, D35S, D35A, D35Y, S36N, S36K, S36R, D37P, D37A, D37R, D37H, D37L, D37V, D40Y D40S, D40A, N41K, N41S, N41R, M51F, M51L, M51I, Q56H, M60L, M60F, M60I, Q103L, Q103I, H109A, H109P, H109D, M113L, M1131, M113F, and R131 S, relative to SEQ ID NO: 30.

In some embodiments, the IL-18 variant polypeptide comprises the amino acid sequence set forth in any one of SEQ ID NOs.: 92-125, or a fragment thereof.

In some embodiments, the IL-18 variant polypeptide comprises the mutations D17X, E30X, and Q103X, relative to SEQ ID NO: 30.

In some embodiments, the IL-18 variant polypeptide comprises the mutations D17X, E30X, D35X, M51X, and Q103X, relative to SEQ ID NO: 30.

In some embodiments, the IL-18 variant polypeptide comprises at least one mutation selected from the group consisting of NIX, L5X, D17X, E30X, T33X, D34X, 135X, D36X, M50X, Q102X, R104, H108X, N109X, M111X, D129X, and D130X, relative to SEQ ID NO: 31.

In some embodiments, the IL-18 variant polypeptide comprises at least one mutation selected from the group consisting of N1Y, N1D, N1H, N1L, N1F, N1V, N1I, L5Y, L5H, D17Q, D17G, D17A, D17E, D17S, D17N, E30A, E30R, E30K, E30T, E30G, T33G, T33A, T33E, T33R, T33K, D34Y, D34S, D34A, 135T, I35K, I35R, D36V, D36A, D36G, D36H, D36P, D36R, D36L, M50F, M50L, Q102L, Q102I, R104E, R104A, R104P, R104G, R104Q, R104H, H108D, H108A, N109R, N109S, N109T, N109I, M111L, M111I, D129A, D129F, D129V, D129Y, D129S, D130E, D130T, D130G, D130N, D130R, D130S, D130Q, and D130H, relative to SEQ ID NO: 31.

In some embodiments, the IL-18 variant polypeptide comprises the amino acid sequence set forth in any one of SEQ ID NOs.: 126-190, or a fragment thereof.

In one aspect, the disclosure relates to a composition comprising a nucleic acid encoding the IL-18 variant polypeptide.

In one aspect, the composition further comprises one or more agents selected from: (i) an immune checkpoint inhibitor; (ii) an agent that inhibits one or more proteins selected from PD-L1, PD1, CTLA4, TIM3, TIGIT, LAG3, B7H3, B7H4, VISTA, ICOS, GITR, 41BB, OX40, and CD40; (iii) a cancer cell opsonizing agent; and (iv) an agent that targets one or more antigens selected from: CD19, CD20, CD22, CD24, CD25, CD30, CD33, CD37, CD38, CD44, CD45, CD47, CD51, CD52, CD56, CD62L, CD70, CD74, CD79, CD80, CD96, CD97, CD99, CD123, CD134, CD138, CD152 (CTLA-4), CD200, CD213A2, CD221, CD248, CD276 (B7-H3), B7-H4, CD279 (PD-1), CD274 (PD-L1), CD319, EGFR, EPCAM, 17-1A, HER1, HER2, HER3, CD117, C-Met, HGFR, PDGFRA, AXL, TWEAKR, PTHR2, HAVCR2 (TIM3), GD2 ganglioside, MUC1, mucin CanAg, mesothelin, endoglin, Lewis-Y antigen, CEA, CEACAM1, CEACAM5, CA-125, PSMA, BAFF, FGFR2, TAG-72, gelatinase B, glypican 3, nectin-4, BCMA, CSF1R, SLAMF7, integrin $\alpha_v\beta_3$, TYRP1, GPNMB, CLDN18.2, FOLR1, CCR4, CXCR4, MICA, C242 antigen, D113, D114, EGFL7, vimentin, fibronectin extra domain-B, TROP-2, LRRC15, FAP, SLITRK6, NOTCH2, NOTCH3, Tenascin-3, STEAP1, and NRP1.

In one aspect, the disclosure relates to a method of treating or preventing a disease or disorder in a subject in need thereof, comprising administering to the subject a composition comprising the IL-18 binding protein (IL-18BP) inhibitor or IL-18BP antagonist.

In some embodiments, the disease or disorder is cancer. In some embodiments, the cancer is a cancer that is resistant to immune checkpoint inhibitors (ICIs). In some embodiments, the cancer is associated with a tumor that has lost expression of MHC class I.

In some embodiments, the disease or disorder is a metabolic disease or disorder. In some embodiments, the disease or disorder is an infectious disease.

In some embodiments, the method comprises administering to the subject at least one other agent in addition to the IL-18BP inhibitor or IL-18BP antagonist. In some embodiments, the at least one other agent comprises an immune checkpoint inhibitor. In some embodiments, the immune checkpoint inhibitor is an agent that inhibits PD-L1, PD1, CTLA4, TIM3, TIGIT, LAG3, B7H3, B7H4, VISTA, ICOS, GITR, 41BB, OX40, or CD40, or any combination thereof. In some embodiments, the at least one other agent comprises a cancer cell opsonizing agent. In some embodiments, the at least one other agent targets one or more antigens selected from: CD19, CD20, CD22, CD24, CD25, CD30, CD33, CD37, CD38, CD44, CD45, CD47, CD51, CD52, CD56, CD62L, CD70, CD74, CD79, CD80, CD96, CD97, CD99, CD123, CD134, CD138, CD152 (CTLA-4), CD200, CD213A2, CD221, CD248, CD276 (B7-H3), B7-H4, CD279 (PD-1), CD274 (PD-L1), CD319, EGFR, EPCAM, 17-1A, HER1, HER2, HER3, CD117, C-Met, HGFR, PDGFRA, AXL, TWEAKR, PTHR2, HAVCR2 (TIM3), GD2 ganglioside, MUC1, mucin CanAg, mesothelin, endoglin, Lewis-Y antigen, CEA, CEACAM1, CEACAM5, CA-125, PSMA, BAFF, FGFR2, TAG-72, gelatinase B, glypican 3, nectin-4, BCMA, CSF1R, SLAMF7, integrin $\alpha_v\beta_3$, TYRP1, GPNMB, CLDN18.2, FOLR1, CCR4, CXCR4, MICA, C242 antigen, D113, D114, EGFL7, vimentin, fibronectin extra domain-B, TROP-2, LRRC15, FAP, SLITRK6, NOTCH2, NOTCH3, Tenascin-3, STEAP1, and NRP1. In some embodiments, the inhibitor or antagonist is an IL-18 variant polypeptide, and the at least one other agent is conjugated to the IL-18 variant polypeptide. In some embodiments, the at least one other agent is an altered T-cell or NK cell. In some embodiments, the at least one other agent is an oncolytic virus.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

(FIG. 1A) The IL-18 pathway (including IL-18 and its receptor subunits) is upregulated in both activated and dysfunctional tumor T cell programs, as seen in RNAseq expression analysis for cytokines and receptors in CD8+TILs. Genes are assigned "activation" and "dysfunction" scores in comparison to naïve T cells. Yellow highlights indicate IL-18 cytokine, IL-18R1 (Rα), and IL-18RAP (Rβ). Data are adapted from Singer et al. (Singer, M. et al., 2016, Cell, 166:1500-1511, e1509). (FIG. 1B) The IL-18 receptor subunits IL-18Rα and IL-18RP are part of a gene expression program associated with chronic antigen exposure, as seen after infection with LCMV (left; CD4) or VSV-OVA (right; CD8). Data are from the ImmGen database.

(FIG. 2A) IL-18BP mediates Interferon-γ (IFN-γ) driven negative feedback of IL-18, reminiscent of the immune checkpoint PD-L1. A schematic of the IL-18/IFN-γ/IL-18BP feedback loop is depicted. Black arrows indicate stimulation, red circuits indicate inhibition. (FIG. 2B) IL-18BP is upregulated in gastric and breast cancer, as seen in data from the TCGA (The Cancer Genome Atlas) and Oncomine® databases. (FIG. 2C) PD-1 and IL-18BP expression is strongly correlated in bulk breast and gastric cancer samples (from TCGA database). R=0.78 and 0.65, respectively.

(FIG. 3A) A structure-guided library to randomize residues on the IL-18:IL-18BP interface was designed and introduced into a yeast-display system. Yeast clones were selected using magnetic and fluorescence cell sorting for binding to IL-18Rα and counter-selected against IL-18BP. (FIG. 3B) Summary of directed evolution to generate IL-18BP resistant IL-18 variants. Blue text indicates positive selection conditions, red text shows counterselection. (FIG. 3C) Flow cytometric analysis of yeast-displayed WT IL-18 (left) or variants after directed evolution (right). Y-axes show IL-18BP binding, x-axes show IL-18Ra binding. After 5 rounds of directed evolution, the remaining clones greatly preferred IL-18Rα to IL-18BP.

FIG. 4 depicts results from example experiments, demonstrating a summary of the sequences of decoy-resistant human IL-18 ("DR-IL-18", also called "DR-18") variants. The position of each mutated position and the corresponding residue in the mature form of wild-type human IL-18 (SEQ ID NO: 30) is indicated at the top of the table. hC4 through hE12 represent sequences obtained after selection with directed evolution. hCS1-hCS4 are consensus sequences derived from the selected sequences. Shaded residues represent the five most conserved mutations observed.

(FIG. 5A) Yeast-displayed DR-IL-18 variants hCS1-hCS4 and A8 are capable of binding hIL-18Rα with comparable binding isotherms as WT human IL-18 (left). By contrast, very little binding is observed with the same variants and hIL-18BP (right). (FIG. 5B) Representative surface plasmon resonance sensorgrams between immobilized biotinylated hIL-18BP and the DR-IL-18 variants. Recombinant hIL-18 (left) binds IL-18BP with exquisitely high affinity, $K_D$=2.0 pM, whereas hCS1 (right) shows greatly attenuated binding, with a much faster off-rate and $K_D$=15.2 nM. This data is summarized in Tables 6 and 7.

(FIG. 6A) Recombinant IL-18BP inhibits biotinylated IL-18Rα from binding yeast-displayed WT IL-18, but does not affect the DR-IL-18 variants hCS1-4 and A8 (left). By contrast, IL-18BP effectively neutralizes the IL-18 E42A, K89A and E42A/K89A previously described (Kim et al., 2001, Proc. Natl. Acad. Sci., 98(6): 3304-3309) (right) [E42 and K89 of Kim et al. are E6 and K53 of SEQ ID NO: 30, respectively]. Biotinylated IL-18Rα was kept at a fixed concentration of 100 nM for all samples. (FIG. 6B) WT IL-18 and hCS1, hCS3, and hCS4 stimulate IL-18 HEK-Blue reporter cells with comparable potency and efficacy (left). Wild-type IL-18 is highly sensitive to application of recombinant IL-18BP in this assay (IC50=3 nM), whereas hCS1 and hCS3 are not inhibited by recombinant IL-18BP, even at IL-18BP concentrations of 1 μM (Right). hIL-18 was kept at a fixed concentration of 5 nM and hCS1 and hCS3 at 2.5 nM.

(FIG. 7A) Summary of the positions in human IL-18 randomized in the version 2.0 library. Degenerate codons and the set of encoded amino acids are given for each position. (FIG. 7B) Summary of directed evolution to generate version 2.0 IL-18BP resistant IL-18 variants. Blue text indicates positive selection conditions, red text shows counterselection. (FIG. 7C) Flow cytometric analysis of progress in creating version 2.0 DR-IL-18 variants. Yeast obtained after rounds 1, 4, and 6 were stained simultaneously with 250 nM IL-18BP streptavidin-PE tetramers or 100 nM IL-18Rα directly labeled with AlexaFluor® 647. Y-axes show IL-18BP binding, x-axes show IL-18Rα binding. After 6 rounds of directed evolution, the remaining clones greatly preferred IL-18Rα to IL-18BP.

FIG. 8 depicts results from example experiments, demonstrating a summary of the sequences of version 2.0 decoy-resistant human IL-18 (DR-IL-18) variants. The position of each mutated position and the corresponding residue in the mature form of wild-type human IL-18 (SEQ ID NO: 30) is indicated at the top of the table. Shaded rows indicate recurrent sequence variants obtained in both round 5 and round 6.

FIG. 9A through FIG. 9D depict results from example experiments, demonstrating biophysical characterization of version 2.0 human DR-IL-18 variants. (FIG. 9A) Yeast-displayed version 2.0 DR-IL-18 variants are capable of binding hIL-18Rα with comparable binding isotherms as WT human IL-18. (FIG. 9B) By contrast, very little binding is observed with the same variants and hIL-18BP. (FIG. 9C) Thermal stability of the version 2.0 DR-IL-18 variants was assessed by heating the yeast-displayed variants across a range of temperatures for 15 minutes, followed by staining with hIL-18Rα. The version 2.0 DR-IL-18 variants were more thermostable than WT IL-18 (Tm=47.6° C.) and the first-generation consensus sequences (Tm=50.9 and 40.2 for hCS1 and hCS2, respectively). (FIG. 9D) Summary of the receptor binding properties and thermal stability of the second-generation DR-IL-18 variants. NBD=no binding detected. N.D.=value not determined.

FIG. 10A through FIG. 10C depict results from example experiments, demonstrating engineering murine IL-18 variants for independence to IL-18BP using yeast display. (FIG. 10A) Summary of directed evolution to generate IL-18BP resistant murine IL-18 variants. Blue text indicates positive selection conditions, red text shows counterselection. (FIG. 10B) Flow cytometric analysis of yeast-displayed murine IL-18 variants after 5 rounds of directed evolution. Y-axes show IL-18BP binding, x-axes show IL-18Rα binding. (FIG. 10C) Summary of the sequences of decoy-resistant murine IL-18 (DR-IL-18) variants. The position of each mutated position and the corresponding residue in the mature form of wild-type murine IL-18 (SEQ ID NO: 31) is indicated at the top of the table. mC1 through mH3 represent sequences obtained after selection with directed evolution. mCS1 and mCS2 are consensus sequences derived from the selected sequences. Shaded residues represent the five most conserved mutations observed.

(FIG. 11A) Yeast-displayed DR-IL-18 variants mA7, mB1, mC1, mE8, mCS1, and mCS2 are capable of binding mIL-18Rα with comparable binding isotherms as WT murine IL-18 (left). By contrast, very little binding is observed with the same variants and mIL-18BP (right). (FIG. 11B) Representative surface plasmon resonance sensorgrams between immobilized biotinylated mIL-18BP and the murine DR-IL-18 variants. Recombinant mIL-18 (left) binds mIL-18BP with high affinity, $K_D$=0.8 pM, whereas mCS2 (right) shows greatly decreased binding with a $K_D$ value greater than 10 μM. This data is summarized in Tables 8 and 9.

(FIG. 12A) Schematic of study design. Mice were administered vehicle (PBS), mIL-18 (1 mg/kg), or the DR-IL-18 variant mCS2 (1 mg/kg) once daily for seven total doses (depicted as syringes). Blood samples were taken five hours post-injection two days prior to the experiment, and on days 0, 3, and 6. (FIG. 12B) Peripheral blood cell counts for CD4, CD8, NK cells, and monocytes at day 0, day 3, and day 6. Both IL-18 and mCS2 expanded NK cells and monocytes to a similar degree by day 3. For each time point (day), left bar is PBS, middle bar is IL-18, and right bar is mCS2. (FIG. 12C) CD69 expression on peripheral CD4, CD8, and NK cells. mCS2, but not IL-18 stimulated CD69 expression on CD4 and CD8 cells. Both IL-18 and mCS2 increased CD69 on NK cells, but mCS2 treatment caused sustained CD69 expression evident at day 6, in comparison to IL-18, which reverted to baseline CD69 levels. For each time point (day), left bar is PBS, middle bar is IL-18, and right bar is mCS2. (FIG. 12D) Serum cytokine levels for interferon-γ (IFN-γ), MIP-1b, and G-CSF. mCS2 treatment yielded higher levels of IFN-γ, MIP-1b, and G-CSF than mIL-18 treatment.

(FIG. 14A) Tumor growth spider plots for mice bearing Yummer1.7 melanoma tumors treated with saline (control), WT IL-18 (0.32 mg/kg), the DR-IL-18 variant mCS2 (0.32 mg/kg), anti-PD1 (8 mg/kg), IL-18+anti-PD1, or mCS2+anti-PD-1 twice per week. (FIG. 14B) Survival curves from the same groups as in (FIG. 11A). mCS2 was effective as a monotherapy and synergized in combination with anti-PD1 in this model.

(FIG. 15A) Tumor growth spider plots for mice bearing Yummer1.7 melanoma tumors treated with saline (control), or the DR-IL-18 variant mCS2 (0.32 mg/kg) alone, or in combination with depleting antibodies against CD8, CD4, interferon gamma, or NK1.1. (FIG. 15B) Survival curves from the same groups as in (FIG. 15A).

(FIG. 18A) Tumor immunophenotyping experiments from mice treated twice weekly for four doses with saline, WT IL-18, or the DR-IL-18 variant mCS2. DR-IL-18 treatment resulted in increased numbers of CD8 and NK cells per mg of tumor (upper left two panels) and increased expression of activation markers granzyme B and KLRG1 on CD8 and NK cells (upper right two panels). DR-IL-18 treatment did not improve the CD8:Treg ratio compared to saline treatment, whereas WT IL-18 made the ratio less favorable. However, DR-IL-18 treatment increased the ratio of CD8 cells to inhibitory myeloid populations including tumor associated macrophages (TAM), and monocytic and granulocytic myeloid derived suppressor cells (mMDSCs and gMDSCs). (FIG. 18B) Serum Luminex® cytokine measurements from the same mice as (FIG. 18A) taken 24 hours after the $4^{th}$ treatment dose. DR-IL-18 shows a dramatically altered secondary cytokine release profile from treatment with WT IL-18, notably increasing Interferon-gamma, IL-7, and IL-15 levels by more than 100-fold.

(FIG. 19A) Tumor growth spider plots from mice bearing B2m-deficient Yummer1.7 tumors treated with saline, anti-PD1+anti-CTLA4, the DR-IL-18 variant mCS2, or mCS2 with depletion of NK cells with anti-NK1.1 antibodies. DR-IL-18 demonstrated strong efficacy in terms of tumor growth and survival (FIG. 19B), curing 60% of treated mice in this model that is completely resistant to even combination treatment with anti-CTLA4+anti-PD1. This efficacy is NK cell dependent since administration of anti-NK1.1 abrogates the mCS2 treatment effect. (FIG. 19C) NK cells isolated from B2m-deficient Yummer1.7 are dysfunctional and show diminished proliferation (Ki67 staining) and function (Interferon-gamma secretion). However, treatment with DR-IL-18 reverses this phenotype to enable robust proliferation and cytokine secretion.

FIG. 20A through FIG. 20C depicts example experiments demonstrating engineering of human IL-18 variants as IL-18BP antagonists (or "decoys-to-the-decoy", D2D) using yeast display. These variants bind IL-18BP but do not signal, thereby antagonizing the effect of IL-18BP on endogenous IL-18 (FIG. 20A) Summary of the positions in human IL-18 randomized in the D2D library. Degenerate codons and the set of encoded amino acids are given for each position. (FIG. 20B) Summary of directed evolution to generate D2D IL-18 variants that bind and neutralize IL-18BP, but do not signal through the IL-18R. Blue text indicates positive selection conditions, red text shows counter-selection. (FIG. 20C) Flow cytometric analysis of progress in creating D2D hIL-18 variants. Yeast obtained after rounds 1-4 were stained with 1 nM of mouse IL-18BP (left panel), 1 nM human IL-18BP (middle panel), or 1 μM IL18Rα plus 1 μM IL18Rβ. Selected variants show enhanced IL-18BP binding across rounds of selection without increases in IL18Rα or IL18Rβ binding.

FIG. 21 depicts results from example experiments demonstrating a summary of the sequences of D2D human IL-18 variants. The position of each mutated position and the corresponding residue in the mature form of wild-type human IL-18 (SEQ ID NO: 30) is indicated at the top of the table.

FIG. 22A through FIG. 22C depict results from example experiments demonstrating biophysical characterization of the human decoy-to-the-decoy (D2D) IL-28 variants. (FIG. 22A) Yeast-displayed D2D IL-8 variants 5-B02, 5-E08, 5-F10, 5-F02, 5-F01, hD2D-CS1, hD2D-CS2, and hD2D-CS3 are capable of binding hIL-18RBP with comparable binding isotherms as WT human IL-18. (FIG. 22*b*) By contrast, very little binding is observed with the same variants and hIL-18Rα. (FIG. 11C) Summary of the receptor binding properties of the D2D IL-18 variants. NBD=no binding detected.

FIG. 23 depicts results from example experiments demonstrating a summary of the sequences of D2D murine IL-18 variants. The position of each mutated position and the corresponding residue in the mature form of wild-type murine IL-18 (SEQ ID NO: 31) is indicated at the top of the table.

(FIG. 30A) WT IL-18 and h6-12, h6-27, h6-29, and h6-31 stimulate IL-18 HEK-Blue reporter cells. h6-12, h6-27, and h6-29 show enhanced potency compared to WT hIL-18, whereas h6-31 has equivalent potency as WT hIL-18. The data demonstrate, therefore, that all tested second generation human DR-IL-18 variants actively signal through IL-18R.

DETAILED DESCRIPTION

Figure 1A:
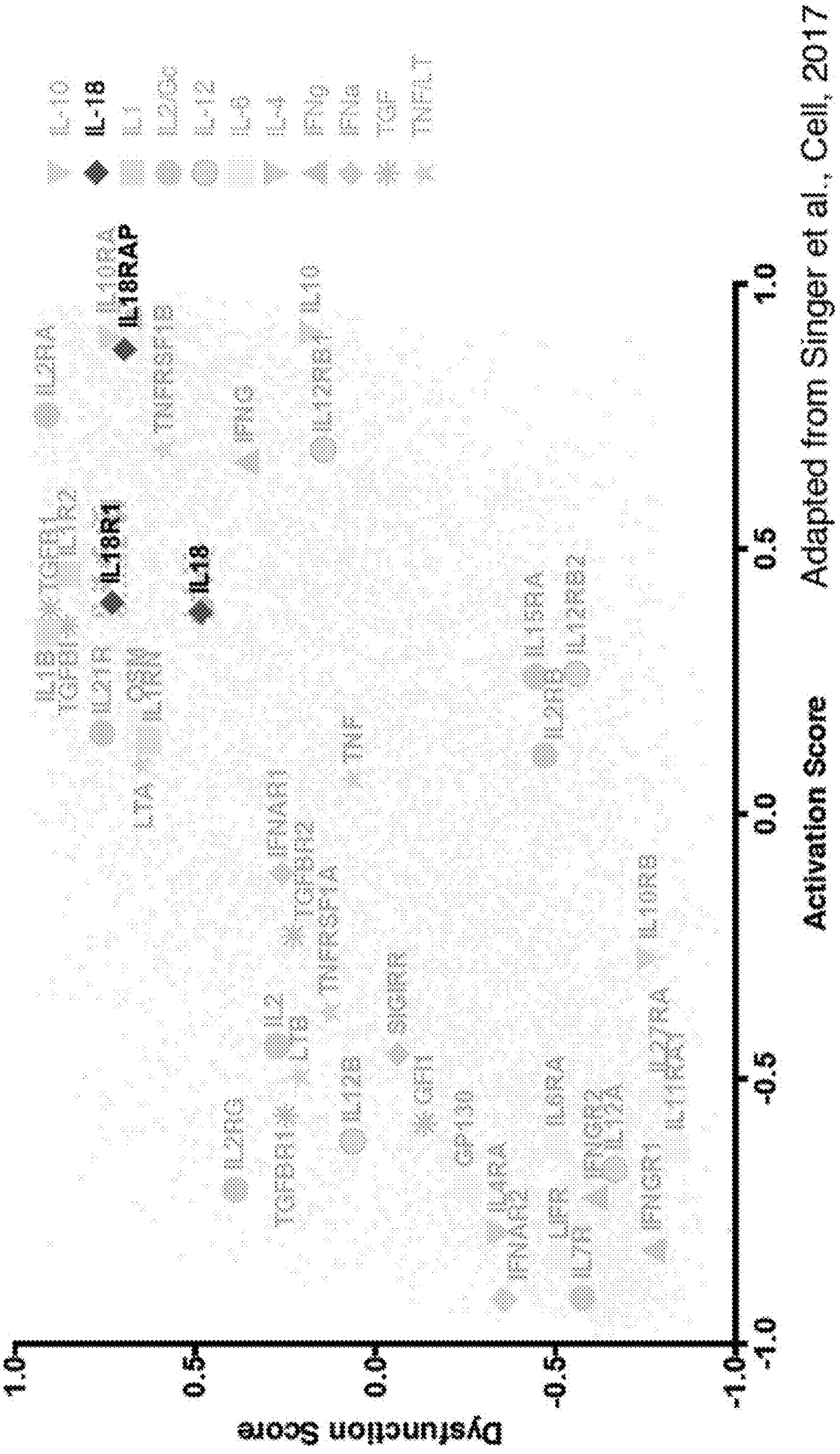
FIG. 1A and FIG. 1B depict results from example experiments, demonstrating the IL-18 pathway is a target for tumor immunotherapy.

The present invention relates to the variants of IL-18 to induce or enhance IL-18 signaling. In one aspect, the invention relates to variants of IL-18 that can bind to IL-18 receptor (IL-18R) but do not bind to IL-18 binding protein (IL-18BP), thereby providing IL-18 signaling activity while not capable of being inhibited by IL-18BP. In one aspect, the invention relates to variants of IL-18 that binds to IL-18BP, thereby reducing or preventing IL-18BP from binding to and inhibiting endogenous IL-18 and thereby providing IL-18 signaling activity. Thus, the invention provides compositions and methods for providing IL-18 signaling activity even in the presence of IL-18BP.

In various embodiments, the invention is an IL-18 variant polypeptide, or a fragment thereof, that specifically binds to IL-18R, and exhibits substantially reduced binding to IL-18BP. In some embodiments, an IL-18 variant polypeptide, or a fragment thereof, that binds to IL-18R, but does not bind substantially to IL-18BP, is useful for providing IL-18 signaling activity that is uninhibited by the presence and activity of IL-18BP. In various embodiments, the invention relates to IL-18 variant polypeptide, or fragment thereof, that specifically binds to IL-18BP and reducing or preventing IL-18BP from inhibiting endogenous IL-18. In some embodiments, an IL-18 variant polypeptide, or a fragment thereof, that binds to IL-18BP, is useful for inhibiting IL-18BP activity thereby inducing, enhancing, or promoting IL-18 signaling activity.

In some embodiments, the IL-18 variant polypeptides are useful for the treatment and prevention of a disease or disorder. In various embodiments, the disease or disorder is cancer or an infectious disease, such as poxviruses that encode an IL-18BP ortholog, a metabolic disease or disorder (including obesity and diabetes), or macular degeneration (e.g., wet macular degeneration, e.g., wet age-related macular degeneration, e.g., the IL-18 variant can be used as an anti-angiogenic—as an illustrative example in some cases a subject IL-18 variant polypeptide can attenuate Choroidal neovascularization). Thus, in some embodiments, the invention is a composition comprising at least one IL-18 variant polypeptide, or a fragment thereof. In other embodiments, the invention is a method of administering at least one IL-18 variant polypeptide, or a fragment thereof, to treat or prevent a disease or disorder, such as, but not limited to, cancer, or infectious disease, a metabolic disease or disorder, or macular degeneration (e.g., wet macular degeneration such as wet age-related macular degeneration).

In various embodiments, the IL-18 variant polypeptide comprises a mutation relative to a wild-type (WT) IL-18 polypeptide. In some embodiments, the WT IL-18 polypeptide comprises the amino acid sequence of SEQ ID NO: 30. In other embodiments, the WT IL-18 polypeptide comprises the amino acid sequence of SEQ ID NO: 31.

In some embodiments, the IL-18 variant polypeptides of the invention exhibit decreased binding affinity to IL-18BP, as compared with the WT IL-18 polypeptide. In some embodiments, the IL-18 variant polypeptides of the invention exhibit increased binding affinity to IL-18BP, as compared with the WT IL-18 polypeptide. In some embodiments, the IL-18 variant polypeptides of the invention exhibit similar binding affinity to IL-18BP, as compared with the WT IL-18 polypeptide.

In some embodiments, the IL-18 variant polypeptide exhibits increased binding affinity to IL-18R, as compared with the WT IL-18 polypeptide. In some embodiments, the IL-18 variant polypeptide exhibits similar binding affinity to IL-18R, as compared with the WT IL-18 polypeptide. In some embodiments, the IL-18 variant polypeptide exhibits decreased binding affinity to IL-18R, as compared with the WT IL-18 polypeptide.

In some embodiments, the IL-18 variant polypeptide is a mammalian IL-18 variant polypeptide. In some embodiments, the IL-18 variant polypeptide is a human IL-18 variant polypeptide. In some embodiments, the IL-18 variant polypeptide is a murine IL-18 variant polypeptide.

In various embodiments, the compositions and methods of the invention include compositions and methods for treating and preventing disease and disorders, such as cancer, infectious disease, and metabolic diseases and disorders. In some embodiments, a method comprises administering to a subject in need thereof a composition comprising at least one IL-18 variant polypeptide. In some embodiments, a method comprises administering to a subject in need thereof a composition comprising at least one IL-18 variant polypeptide, and administering to the subject a composition comprising an additional agent.

In one such embodiment, the additional agent comprises an immunotherapeutic agent comprising at least one selected from the group including, but not limited to an altered T-cell, a chimeric antigen receptor T-cell (CAR-T), an armored CAR-T cell, a virus, an antigen, a vaccine, an antibody, an immune checkpoint inhibitor, a small molecule, a chemotherapeutic agent, and a stem cell. In some embodiments, a composition comprising at least one IL-18 variant polypeptide is used in a method to increase immune system activity before, during, or after infection by a bacterium, virus, or other pathogen. In some embodiments, a composition comprising at least one IL-18 variant polypeptide is used in a method to increase the number and/or activity of immune cells in vitro, in vivo or ex vivo, such as the number and/or activity of T cells, NK cells, and/or myeloid cells.

Definitions

Unless defined otherwise, all technical and scientific terms used herein have the same meaning as commonly understood by one of ordinary skill in the art to which the invention pertains. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass non-limiting variations of ±40% or ±20% or ±10%, ±5%, ±1%, or ±0.1% from the specified value, as such variations are appropriate.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, synthetic antibodies, chimeric antibodies, and a humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, New York; Houston et al., 1988, Proc. Natl. Acad. Sci. USA 85:5879-5883; Bird et al., 1988, Science 242:423-426).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. K and X light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, an "immunoassay" refers to any binding assay that uses an antibody capable of binding specifically to a target molecule to detect and quantify the target molecule.

By the term "specifically binds," as used herein with respect to an IL-18 variant polypeptide, is meant an IL-18 variant polypeptide that recognizes and binds to a specific receptor, such as IL-18R, or to IL-18BP. In some instances, the IL-18 variant polypeptide substantially reduced binding to IL-18BP. For example, an IL-18 variant polypeptide that specifically binds to a receptor from one species may also bind to that receptor from one or more species. But, such cross-species reactivity does not itself alter the classification of an IL-18 variant polypeptide as specific. In another example, an IL-18 variant polypeptide that specifically binds to a receptor may also bind to different allelic forms of the receptor. However, such cross reactivity does not itself alter the classification of an IL-18 variant polypeptide as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an IL-18 variant polypeptide recognizes and binds to a specific protein structure rather than to proteins generally.

By the term "applicator," as the term is used herein, is meant any device including, but not limited to, a hypodermic syringe, a pipette, an iontophoresis device, a patch, and the like, for administering the compositions of the invention to a subject.

"Cancer," as used herein, refers to the abnormal growth or division of cells. Generally, the growth and/or life span of a cancer cell exceeds, and is not coordinated with, that of the normal cells and tissues around it. Cancers may be benign, pre-malignant or malignant. Cancer occurs in a variety of cells and tissues, including the oral cavity (e.g., mouth, tongue, pharynx, etc.), digestive system (e.g., esophagus, stomach, small intestine, colon, rectum, liver, bile duct, gall bladder, pancreas, etc.), respiratory system (e.g., larynx, lung, bronchus, etc.), bones, joints, skin (e.g., basal cell, squamous cell, meningioma, etc.), breast, genital system, (e.g., uterus, ovary, prostate, testis, etc.), urinary system (e.g., bladder, kidney, ureter, etc.), eye, nervous system (e.g., brain, etc.), endocrine system (e.g., thyroid, etc.), and hematopoietic system (e.g., lymphoma, myeloma, leukemia, acute lymphocytic leukemia, chronic lymphocytic leukemia, acute myeloid leukemia, chronic myeloid leukemia, etc.).

The term "coding sequence," as used herein, means a sequence of a nucleic acid or its complement, or a part, thereof, that can be transcribed and/or translated to produce the mRNA and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the coding sequence can be deduced therefrom. In contrast, the term "non-coding sequence," as used herein, means a sequence of a nucleic acid or its complement, or a part thereof, that is not translated into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, and the like.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic, prophylactic, or other desired benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "fragment," as applied to a nucleic acid, refers to a subsequence of a larger nucleic acid. A "fragment" of a nucleic acid can be at least about nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein, polypeptide or peptide, refers to a subsequence of a larger protein, polypeptide or peptide. A "fragment" of a protein, polypeptide, or peptide can be at least about 5 amino acids in length; for example, at least about 10 amino acids in length; at least about 20 amino acids in length; at least about 50 amino acids in length; at least about 100 amino acids in length; at least about 200 amino acids in length; or at least about 300 amino acids in length (and any integer value in between).

The term "gene" refers to a nucleic acid (e.g., DNA) sequence that includes coding sequences necessary for the production of a polypeptide, precursor, or RNA (e.g., mRNA). The polypeptide may be encoded by a full-length coding sequence or by any portion of the coding sequence so long as the desired activity or functional property (e.g., enzymatic activity, receptor binding, signal transduction, immunogenicity, etc.) of the full-length or fragment is retained. The term also encompasses the coding region of a structural gene and the sequences located adjacent to the coding region on both the 5' and 3' ends for a distance of about 2 kb or more on either end such that the gene corresponds to the length of the full-length mRNA and 5' regulatory sequences which influence the transcriptional properties of the gene. Sequences located 5' of the coding region and present on the mRNA are referred to as 5'-untranslated sequences. The 5'-untranslated sequences usually contain the regulatory sequences. Sequences located 3' or downstream of the coding region and present on the mRNA are referred to as 3'-untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

"Homologous", "identical," or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Instructional material," as that term is used herein, includes a publication, a recording, a diagram, or any other medium of expression which can be used to communicate the usefulness of the nucleic acid, peptide, polypeptide, and/or compound of the invention in the kit for identifying or alleviating or treating the various diseases or disorders recited herein. Optionally, or alternately, the instructional material may describe one or more methods of identifying or alleviating the diseases or disorders in a cell or a tissue of a subject. The instructional material of the kit may, for example, be affixed to a container that contains the nucleic acid, polypeptide, and/or compound of the invention or be shipped together with a container that contains the nucleic acid, polypeptide, and/or compound. Alternatively, the instructional material may be shipped separately from the container with the intention that the recipient uses the instructional material and the compound cooperatively.

"Isolated" means altered or removed from the natural state. For example, a nucleic acid or a polypeptide naturally present in a living animal is not "isolated," but the same nucleic acid or polypeptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The term "label" when used herein refers to a detectable compound or composition that is conjugated directly or indirectly to a probe to generate a "labeled" probe. The label may be detectable by itself (e.g., radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

By the term "modulating," as used herein, is meant mediating a detectable increase or decrease in the activity and/or level of a mRNA, polypeptide, or a response in a subject compared with the activity and/or level of a mRNA, polypeptide or a response in the subject in the absence of a treatment or compound, and/or compared with the activity and/or level of a mRNA, polypeptide, or a response in an otherwise identical but untreated subject. The term encompasses activating, inhibiting and/or otherwise affecting a native signal or response thereby mediating a beneficial therapeutic, prophylactic, or other desired response in a subject, for example, a human.

A "mutation," "mutant," or "variant," as used herein, refers to a change in nucleic acid or polypeptide sequence relative to a reference sequence (which may be a naturally-occurring normal or the "wild-type" sequence), and includes translocations, deletions, insertions, and substitutions/point mutations. A "mutant" or "variant" as used herein, refers to either a nucleic acid or protein comprising a mutation.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix.

"Polynucleotide" and "oligonucleotide" are used interchangeably in this disclosure. It will be understood that when a nucleotide sequence is represented herein by a DNA sequence (e.g., A, T, G, and C), this also includes the corresponding RNA sequence (e.g., A, U, G, C) in which "U" replaces "T".

The terms "patient," "subject," "individual," and the like are used interchangeably herein, and refer to any animal, or cells thereof whether in vivo, in vitro or in situ, amenable to the methods described herein. In certain non-limiting embodiments, the patient, subject or individual is a human.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, mutant polypeptides, variant polypeptides, or a combination thereof.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to exhibit non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

To "prevent" a disease or disorder as the term is used herein, means to reduce the severity or frequency of at least one sign or symptom of a disease or disorder that is to be experienced by a subject.

"Sample" or "biological sample" as used herein means a biological material isolated from a subject. The biological sample may contain any biological material suitable for detecting a mRNA, polypeptide or other marker of a physiologic or pathologic process in a subject, and may comprise fluid, tissue, cellular and/or non-cellular material obtained from the individual.

As used herein, "substantially purified" refers to being essentially free of other components. For example, a substantially purified polypeptide is a polypeptide which has been separated from other components with which it is normally associated in its naturally occurring state.

As used herein, the terms "therapy" or "therapeutic regimen" refer to those activities taken to prevent, treat or alter a disease or disorder, e.g., a course of treatment intended to reduce or eliminate at least one sign or symptom of a disease or disorder using pharmacological, surgical, dietary and/or other techniques. A therapeutic regimen may include a prescribed dosage of one or more compounds or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

The term "therapeutically effective amount" refers to the amount of the subject compound or composition that will elicit the biological, physiologic, clinical or medical response of a cell, tissue, organ, system, or subject that is being sought by the researcher, veterinarian, medical doctor or other clinician. The term "therapeutically effective amount" includes that amount of a compound or composition that, when administered, is sufficient to prevent development of, or treat to some extent, one or more of the signs or symptoms of the disorder or disease being treated. The therapeutically effective amount will vary depending on the compound or composition, the disease and its severity and the age, weight, etc., of the subject to be treated.

To "treat" a disease or disorder as the term is used herein, means to reduce the frequency or severity of at least one sign or symptom of a disease or disorder experienced by a subject. The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), e.g., slowing or arresting their development (e.g., halting the growth of tumors, slowing the rate of tumor growth, halting the rate of cancer cell proliferation, and the like); or (c) relieving the disease symptom(s), i.e., causing regression of the disease and/or symptom(s) (e.g., causing decrease in tumor size, reducing the number of cancer cells present, and the like). Those in need of treatment include those already inflicted (e.g., those with cancer, those with an infection, those with a metabolic disorder, those with macular degeneration, etc.) as well as those in which prevention is desired (e.g., those with increased susceptibility to cancer, those with an increased likelihood of infection, those suspected of having cancer, those suspected of harboring an infection, those with increased susceptibility for metabolic disease, those with increased susceptibility for macular degeneration, etc.).

As used herein, the term "wild-type" refers to a gene or gene product isolated from a naturally occurring source. A wild-type gene is that which is most frequently observed in a population and is thus arbitrarily designated the "normal" or "wild-type" form of the gene. In contrast, the term "modified," "variant," or "mutant" refers to a gene or gene product that possesses modifications in sequence and/or functional properties (i.e., altered characteristics) when compared to the wild-type gene or gene product.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

In some embodiments, the compositions and methods of the invention comprise an activator of IL-18 activity, such as signaling activity through IL-18R. In some embodiments, the activator is an IL-18 variant polypeptide. In some embodiments, the activator is a molecule that is able to bind and to signal through the IL-18R. In some embodiments, the activator is a molecule that inhibits IL-18BP, thereby promoting IL-18 signaling.

In some embodiments, the invention is an IL-18 variant polypeptide, or a fragment thereof, that specifically binds to IL-18R, and exhibits substantially reduced binding IL-18BP. In some embodiments, an IL-18 variant polypeptide, or a fragment thereof, that binds to IL-18R, but does not bind substantially to IL-18BP, is useful for providing IL-18 signaling activity that is uninhibited by the presence and activity of IL-18BP.

In some embodiments, the IL-18 variant polypeptide is resistant to or independent of negative regulation by IL-18BP polypeptide. In some embodiments, IL-18BP polypeptide is unable to substantially bind to the IL-18 variant polypeptide. The IL-18 variant polypeptides of the invention exhibit decreased binding affinity to IL-18BP, as compared with the WT IL-18 polypeptide. In some embodiments, the IL-18 variant polypeptide exhibits increased binding affinity to IL-18R, as compared with the WT IL-18 polypeptide. In some embodiments, the IL-18 variant polypeptide exhibits similar binding affinity to IL-18R, as compared with the WT IL-18 polypeptide. In some embodiments, the IL-18 variant polypeptide exhibits decreased binding affinity to IL-18R, as compared with the WT IL-18 polypeptide.

In some embodiments, the invention provides a composition comprising an inhibitor of IL-18BP, wherein the inhibitor inhibits or reduces IL-18BP expression, activity, or both. Exemplary inhibitors of IL-18BP include, but are not limited to, a chemical compound, a protein, a peptidomimetic, an antibody, a ribozyme, and an antisense nucleic acid molecule. In certain embodiments, the inhibitor of IL-18BP comprises a IL-18 variant that binds IL-18BP, thereby reducing or preventing IL-18BP from inhibiting IL-18 and IL-18 signaling.

In some embodiments, the IL-18 variant polypeptides are useful for the treatment or prevention of a disease or disorder. In various embodiments, the disease or disorder is cancer or a metabolic disease or disorder, including obesity and diabetes (e.g., a subject method can cause a decrease in body fat). Thus, in some embodiments, the invention is a composition comprising at least one IL-18 variant polypeptide, or a fragment thereof. In other embodiments, the invention is a method of administering at least one IL-18 variant polypeptide, or a fragment thereof, to treat or prevent a disease or disorder, such as, but not limited to, cancer or a metabolic disease or disorder.

In some embodiments, the IL-18 variant polypeptide binds to IL-18R and exhibits substantially reduced binding to IL-18BP. In some embodiments, the IL-18 variant polypeptide that binds to IL-18R and exhibits substantially reduced binding to IL-18BP binds to IL-18BP with a binding affinity that is about 0.000000000001% to about 95% of the binding affinity of wild-type IL-18 to IL-18BP.

In some embodiments, the IL-18 variant polypeptide that binds to IL-18R and exhibits substantially reduced binding to IL-18BP binds to IL-18BP with a binding affinity that is about 95% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 90% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 85% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 80% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 75% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 70% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 65% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 60% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 55% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 50% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 45% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 40% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 35% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 30% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 25% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 20% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 15% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 10% of the binding affinity of wild-type IL-18 to IL-18BP.

In some embodiments, the IL-18 variant polypeptide that binds to IL-18R and exhibits substantially reduced binding to IL-18BP binds to IL-18BP with a binding affinity that is about 5% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 4% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 3% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 2% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 1% of the binding affinity of wild-type IL-18 to IL-18BP.

In some embodiments, the IL-18 variant polypeptide that binds to IL-18R and exhibits substantially reduced binding to IL-18BP binds to IL-18BP with a binding affinity that is about 0.1% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.01% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.001% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.0001% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.00001% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.000001% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.0000001% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.00000001% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.000000001% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.0000000001% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.00000000001% of the binding affinity of wild-type IL-18 to IL-18BP. In some embodiments, the IL-18 variant polypeptide that binds to IL-18R and exhibits substantially reduced binding to IL-18BP binds to IL-18BP with a binding affinity that is about 0.000000000001% of the binding affinity of wild-type IL-18 to IL-18BP.

In some embodiments, a subject IL-18 variant polypeptide (a DR-IL-18) that binds to IL-18R and exhibits substantially reduced binding to IL-18BP has a $K_D$ for IL-18BP that is 10 nM or greater (higher $K_D$ means lower binding affinity). In some embodiments, a subject DR-IL-18 variant polypeptide has a $K_D$ for IL-18BP that is 20 nM or greater (e.g., 50 nM or greater, 100 nM or greater, 500 nM or greater, or 1 μM or greater).

In some embodiments, the IL-18 variant polypeptide binds to IL-18R and exhibits substantially reduced binding to IL-18BP. In some embodiments, the variant polypeptide that binds to IL-18R and exhibits substantially reduced binding to IL-18BP has an IL-18BP/IL-18R dissociation constant ratio that is about at least 2-fold higher than the IL-18BP/IL-18R dissociation constant ratio of wild-type IL-18 (note that an increased dissociation constant ratio implies a relative decrease in IL-18BP binding relative to IL-18R binding). In some embodiments, the variant polypeptide that binds to IL-18R and exhibits substantially reduced binding to IL-18BP has an IL-18BP/IL-18R dissociation constant ratio that is about at least 20-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 200-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 2,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 20,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 200,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 2,000,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 20,000,000-fold higher than the IL-18BP/IL-18R dissociation constant ratio of wild-type IL-18.

In some embodiments, the IL-18 variant polypeptide binds to IL-18R and exhibits substantially reduced binding to IL-18BP. In some embodiments, the variant polypeptide that binds to IL-18R and exhibits substantially reduced binding to IL-18BP has an IL-18BP/IL-18R dissociation constant ratio that is about at least 3-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 30-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 300-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 3,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 30,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 300,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 3,000,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 30,000,000-fold higher than the IL-18BP/IL-18R dissociation constant ratio of wild-type IL-18.

In some embodiments, the IL-18 variant polypeptide binds to IL-18R and exhibits substantially reduced binding to IL-18BP. In some embodiments, the variant polypeptide that binds to IL-18R and exhibits substantially reduced binding to IL-18BP has an IL-18BP/IL-18R dissociation constant ratio that is about at least 5-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 50-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 500-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 5,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 50,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 500,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 5,000,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 50,000,000-fold higher than the IL-18BP/IL-18R dissociation constant ratio of wild-type IL-18.

In some embodiments, the IL-18 variant polypeptide binds to IL-18R and exhibits substantially reduced binding to IL-18BP. In some embodiments, the variant polypeptide that binds to IL-18R and exhibits substantially reduced binding to IL-18BP has an IL-18BP/IL-18R dissociation constant ratio that is about at least 10-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 100-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 1000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 10,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 100,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 1,000,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 10,000,000-fold higher than the IL-18BP/IL-18R dissociation constant ratio of wild-type IL-18. In some embodiments, the variant polypeptide that binds to IL-18R and exhibits substantially reduced binding to IL-18BP has an IL-18BP/IL-18R dissociation constant ratio that is about at least 100,000,000-fold higher than the IL-18BP/IL-18R dissociation constant ratio of wild-type IL-18.

In some embodiments, a subject IL-18 variant polypeptide (a DR-IL-18) that binds to IL-18R and exhibits substantially reduced binding to IL-18BP has an inhibitor constant (Ki) for IL-18BP that is greater than 3 nM (e.g., 5 nM or more, 10 nM or more, 50 nM or more, 100 nM or more, 500 nM or more, 750 nM or more, or 1 μM or more). In some embodiments, a subject DR-IL-18 variant polypeptide has a Ki for IL-18BP that is 500 nM or more. In some embodiments, a subject DR-IL-18 variant polypeptide has a Ki for IL-18BP that is 1 μM or more.

In some embodiments, a subject IL-18 variant polypeptide (a DR-IL-18) that binds to IL-18R and exhibits substantially reduced binding to IL-18BP has a Ki for IL-18BP that is greater than 200 nM (e.g., 500 nM or more, 750 nM or more, or 1 μM or more). In some embodiments, a subject DR-IL-18 variant polypeptide has a Ki for IL-18BP that is 1 μM or more.

In some embodiments, a subject IL-18 variant polypeptide (a DR-IL-18) that binds to IL-18R and exhibits substantially reduced binding to IL-18BP has an inhibitor constant (Ki) for IL-18BP that is at least 2-fold higher than the Ki of wild type IL-18 for IL-18BP (i.e., the Ki of the subject IL-18 variant polypeptide for IL-18BP is at least 2-fold relative to the Ki of WT IL-18 for IL-18BP). For example, in some cases a subject DR-IL-18 variant polypeptide has a Ki for IL-18BP that is at least 5-fold higher (e.g., at least 10-fold, at least 50-fold, at least 100-fold, at least 200-fold, at least 500-fold, or at least 1000-folder higher) than the Ki of wild type IL-18 for IL-18BP.

In some embodiments, a subject IL-18 variant polypeptide (a DR-IL-18) that binds to IL-18R and exhibits substantially reduced binding to IL-18BP has an $EC_{50}$ for IL-18BP that is at least 2-fold higher than the $EC_{50}$ of wild type IL-18 for IL-18BP (i.e., the $EC_{50}$ of the subject IL-18 variant polypeptide for IL-18BP is at least 2-fold relative to the $EC_{50}$ of WT IL-18 for IL-18BP). For example, in some cases a subject DR-IL-18 variant polypeptide has a $EC_{50}$ for IL-18BP that is at least 5-fold higher (e.g., at least 10-fold, at least 50-fold, at least 100-fold, at least 200-fold, at least 500-fold, or at least 1000-folder higher) than the $EC_{50}$ of wild type IL-18 for IL-18BP.

In various embodiments, the IL-18 variant polypeptide comprises a mutation relative to a wild-type (WT) IL-18 polypeptide. In some embodiments, the WT IL-18 polypeptide comprises the amino acid sequence of SEQ ID NO: 30. In other embodiments, the WT IL-18 polypeptide comprises the amino acid sequence of SEQ ID NO: 31. Unless otherwise specified, the term "X" is used below to represent any amino acid.

In various embodiments, the human IL-18 variant polypeptide, or fragment thereof, comprises at least one mutation (e.g., at least 2, at least 3, at least 4, at least 5, or at least 6 mutations) selected from the group consisting of Y1X, L5X, K8X, M51X, K53X, S55X, Q56X, P57X, G59X, M60X, E77X, Q103X, S105X, D110X, N111X, M113X, V153X, and N155X, wherein X denotes any amino acid. In various embodiments, the human IL-18 variant polypeptide, or fragment thereof, comprises at least 4 mutations selected from the group consisting of Y1X, L5X, K8X, M51X, K53X, S55X, Q56X, P57X, G59X, M60X, E77X, Q103X, S105X, D110X, N111X, M113X, V153X, and N155X. In various embodiments, the human IL-18 variant polypeptide, or fragment thereof, comprises at least 6 mutations selected from the group consisting of Y1X, L5X, K8X, M51X, K53X, S55X, Q56X, P57X, G59X, M60X, E77X, Q103X, S105X, D110X, N111X, M113X, V153X, and N155X. In various embodiments, the human IL-18 variant polypeptide, or fragment thereof, comprises at least one mutation (e.g., at least 2, at least 3, at least 4, at least 5, or at least 6 mutations) selected from the group consisting of Y1X, L5X, K8X, S55X, Q56X, P57X, G59X, E77X, Q103X, S105X, D110X, N111X, M113X, V153X, and N155X In some embodiments, a human IL-18 variant polypeptide, or fragment thereof, comprises at least one mutation (e.g., at least 2, at least 3, at least 4, at least 5, or at least 6 mutations) selected from the group consisting of Y1H, Y1R, L5H, L51, L5Y, K8Q, K8R, M51T, M51K, M51D, M51N, M51E, M51R, K53R, K53G, K53S, K53T, S55K, S55R, Q56E, Q56A, Q56R, Q56V, Q56G, Q56K, Q56L, P57L, P57G, P57A, P57K, G59T, G59A, M60K, M60Q, M60R, M60L, E77D, Q103E, Q103K, Q103P, Q103A, Q103R, S105R, S105D, S105K, S105N, S105A, D110H, D110K, D110N, D110Q, D111E, DIOS, D110G, N111H, N111Y, N111D, N111R, N111S, N111G, M113V, M113R, M113T, M113K, V1531, V153T, V153A, N155K, and N155H. In some embodiments, a human IL-18 variant polypeptide comprises at least one IL-18 variant polypeptide, or fragment thereof, selected from the group consisting of hCS1 (SEQ ID NO: 34), hCS2 (SEQ ID NO: 35), hCS3 (SEQ ID NO: 36), hCS4 (SEQ ID NO: 37), hC4 (SEQ ID NO: 38), hA8 (SEQ ID NO: 39), hD6 (SEQ ID NO: 40), hH12 (SEQ ID NO: 41), hB11 (SEQ ID NO: 42), hC3 (SEQ ID NO: 43), hC2 (SEQ ID NO: 44), hG10 (SEQ ID NO: 45), hG1 (SEQ ID NO: 46), hF1 (SEQ ID NO: 47), hD2 (SEQ ID NO: 48), hA1 (SEQ ID NO: 49), hB3 (SEQ ID NO: 50), hB4 (SEQ ID NO: 51), hH3 (SEQ ID NO: 52), hH5 (SEQ ID NO: 53), hH4 (SEQ ID NO: 54), hE1 (SEQ ID NO: 55), hG2 (SEQ ID NO: 56), hB9 (SEQ ID NO: 57), hE12 (SEQ ID NO: 58), hC5 (SEQ ID NO: 59), 5-18 (SEQ ID NO: 73), 5-29 (SEQ ID NO: 74), 5-8 (SEQ ID NO: 75), 5-6 (SEQ ID NO: 76), 5-27 (SEQ ID NO: 77), 5-20 (SEQ ID NO: 78), 5-2 (SEQ ID NO: 79), 5-9 (SEQ ID NO: 80), 5-42 (SEQ ID NO: 81), 5-13 (SEQ ID NO: 82), 5-12 (SEQ ID NO: 83), 5-1 (SEQ ID NO: 84), 5-33 (SEQ ID NO: 85), 5-21 (SEQ ID NO: 86), 6-31 (SEQ ID NO: 87), 6-20 (SEQ ID NO: 88), 6-12 (SEQ ID NO: 89), 6-27 (SEQ ID NO: 90), 6-29 (SEQ ID NO: 91), 5-26 (SEQ ID NO: 191), 5-17 (SEQ ID NO: 192), 5-41 (SEQ ID NO: 193), or a fragment thereof.

In some cases a subject DR-IL-18 variant, or fragment thereof, includes at least one mutation (e.g., at least 2, at least 3, or at least 4 mutations) selected from the group consisting of M51X, M60X, S105X, D110X, and N111X, relative to SEQ ID NO: 30. In some cases a subject DR-IL-18 variant, or fragment thereof, includes at least 3 mutations selected from the group consisting of M51X, M60X, S105X, D110X, and N111X, relative to SEQ ID NO: 30. In some cases a subject DR-IL-18 variant, or fragment thereof, includes at least one mutation (e.g., at least 2, at least 3, or at least 4 mutations) selected from the group consisting of M51$X_1$, M60$X_2$, S105$X_3$, D110$X_4$, and N111$X_5$, relative to SEQ ID NO: 30, where $X_1$ is T, K, D, E, R, or N; $X_2$ is K, Q, L, or R; $X_3$ is R, D, K, A, or N; $X_4$ is H, K, N, Q, E, N, S, or G; and $X_5$ is H, D, Y, R, S, or G. In some cases a subject DR-IL-18 variant, or fragment thereof, includes at least 3 mutations (e.g., at least 2, at least 3, or at least 4 mutations) selected from the group consisting of M51$X_1$, M60$X_2$, S105$X_3$, D110$X_4$, and N111s $X_5$, relative to SEQ ID NO: 30, where $X_1$ is T, K, D, E, R, or N; $X_2$ is K, Q, L, or R; $X_3$ is R, D, K, A, or N; $X_4$ is H, K, N, Q, E, N, S, or G; and $X_5$ is H, D, Y, R, S, or G. In some cases a subject DR-IL-18 variant, or fragment thereof, includes at least one mutation (e.g., at least 2, at least 3, or at least 4 mutations) selected from the group consisting of M51$X_1$, M60$X_2$, S105$X_3$, D110$X_4$, and N111$X_5$, relative to SEQ ID NO: 30, where $X_1$ is T or K; $X_2$ is K or L; $X_3$ is D, N, or A; $X_4$ is K, N, S, or G; and $X_5$ is H, Y, G, or R.

In some cases a subject DR-IL-18 variant, or fragment thereof, includes the mutations M51X, M60X, S105X, D110X, and N111X, relative to SEQ ID NO: 30. For example, in some cases a subject DR-IL-18 variant, or fragment thereof, includes the mutations M51$X_1$, M60$X_2$, S105$X_3$, D110$X_4$, and N111$X_5$, relative to SEQ ID NO: 30, where $X_1$ is T, K, D, E, R, or N; $X_2$ is K, Q, L, or R; $X_3$ is R, D, K, A, or N; $X_4$ is H, K, N, Q, E, N, S, or G; and $X_5$ is H, D, Y, R, S, or G. In some cases a subject DR-IL-18 variant, or fragment thereof, includes the mutations M51$X_1$, M60$X_2$, S105$X_3$, D110$X_4$, and N111$X_5$, relative to SEQ ID NO: 30, where $X_1$ is T or K; $X_2$ is K or L; $X_3$ is D, N, or A; $X_4$ is K, N, S, or G; and $X_5$ is H, Y, G, or R. In other words, in some cases a subject DR-IL-18 variant, or fragment thereof, includes the mutations {M51T or M51K}; {M60K or M60L}; {S105D, S105N, S105A}; {D110K, D110N, D110S, or D110G}; and {N111H, N111Y, N111R, or N111G}, relative to SEQ ID NO: 30.

In some cases a subject DR-IL-18 variant, or fragment thereof, includes at least one mutation (e.g., at least 2, at least 3, or at least 4 mutations) selected from the group consisting of M51X, K53X, Q56X, S105X, and N111X, relative to SEQ ID NO: 30. In some cases a subject DR-IL-18 variant, or fragment thereof, includes at least 3 mutations selected from the group consisting of M51X, K53X, Q56X, S105X, and N111X, relative to SEQ ID NO: 30. In some cases a subject DR-IL-18 variant, or fragment thereof, includes at least one mutation (e.g., at least 2, at least 3, or at least 4 mutations) selected from the group consisting of $M51X_1$, $K53X_2$, $Q56X_3$, $S105X_4$, and $N111X_5$, relative to SEQ ID NO: 30, where $X_1$ is E, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, includes at least 3 mutations selected from the group consisting of $M51X_1$, $K53X_2$, $Q56X_3$, $S105X_4$, and $N111X_5$, relative to SEQ ID NO: 30, where $X_1$ is E, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, includes at least one mutation (e.g., at least 2, at least 3, or at least 4 mutations) selected from the group consisting of $M51X_1$, $K53X_2$, $Q56X_3$, $S105X_4$, and N111 $X_5$, relative to SEQ ID NO: 30, where $X_1$ is K; $X_2$ is G or S; $X_3$ is G, R, or L; $X_4$ is S, N, or G; and $X_5$ is G or R.

In some cases a subject DR-IL-18 variant, or fragment thereof, includes the mutations M51X, K53X, Q56X, S105X, and N111X, relative to SEQ ID NO: 30. For example, in some cases a subject DR-IL-18 variant, or fragment thereof, includes the mutations $M51X_1$, $K53X_2$, $Q56X_3$, $S105X_4$, and $N111X_5$, relative to SEQ ID NO: 30, where $X_1$ is E, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, includes the mutations $M51X_1$, $K53X_2$, $Q56X_3$, $S105X_4$, and $N111X_5$, relative to SEQ ID NO: 30, where $X_1$ is K; $X_2$ is G or S; $X_3$ is G, R, or L; $X_4$ is S, N, or G; and $X_5$ is G or R. In other words, in some cases a subject DR-IL-18 variant, or fragment thereof, includes the mutations {M51K}; {K53G or K53S}; {Q56G, Q56R, or Q56L}; {D110S, D110N, or D110G}; and {N111R, or N111G}, relative to SEQ ID NO: 30.

In some cases a subject DR-IL-18 variant, or fragment thereof, comprises an amino acid sequence having 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30. As such in some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) relative to wild type IL-18 (e.g., human IL-18).

In some cases a subject DR-IL-18 variant, or fragment thereof, comprises an amino acid sequence having 85% or more sequence identity (e.g., 90% or more, 92% or more, 93% or more, 94% or more, 95% or more, 96% or more, 97% or more, 98% or more, or 99% or more sequence identity) with the amino acid sequence set forth in any one of SEQ ID NOs: 34-59, 73-91, and 191-193. As such in some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the amino acid sequence set forth in any one of SEQ ID NOs: 34-59, 73-91, and 191-193; and (ii) includes at least one mutation (e.g., at least 2, at least 3, at least 4, at least 5, or at least 6 mutations) relative to wild type IL-18 (e.g., human IL-18).

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of Y1X, L5X, K8X, M51X, K53X, S55X, Q56X, P57X, G59X, M60X, E77X, Q103X, S105X, D110X, N11X, M113X, V153X, and N155X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 4 mutations selected from the group consisting of Y1X, L5X, K8X, M51X, K53X, S55X, Q56X, P57X, G59X, M60X, E77X, Q103X, S105X, D110X, N111X, M113X, V153X, and N155X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 6 mutations selected from the group consisting of Y1X, L5X, K8X, M51X, K53X, S55X, Q56X, P57X, G59X, M60X, E77X, Q103X, S105X, D110X, N111X, M113X, V153X, and N155X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of Y1X, L5X, K8X, S55X, Q56X, P57X, G59X, E77X, Q103X, S105X, D110X, N111X, M113X, V153X, and N155X, relative to SEQ ID NO: 30.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51X, M60X, S105X, D110X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 3 mutations selected from the group consisting of M51X, M60X, S105X, D110X, and N111 X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51$X_1$, M60$X_2$, S105$X_3$, D110$X_4$, and N111$X_5$, relative to SEQ ID NO: 30, where $X_1$ is T, K, D, E, R, or N; $X_2$ is K, Q, L, or R; $X_3$ is R, D, K, A, or N; $X_4$ is H, K, N, Q, E, N, S, or G; and $X_5$ is H, D, Y, R, S, or G. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 3 mutations selected from the group consisting of M51$X_1$, M60$X_2$, S105$X_3$, D110$X_4$, and N111$X_5$, relative to SEQ ID NO: 30, where $X_1$ is T, K, D, E, R, or N; $X_2$ is K, Q, L, or R; $X_3$ is R, D, K, A, or N; $X_4$ is H, K, N, Q, E, N, S, or G; and $X_5$ is H, D, Y, R, S, or G. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51$X_1$, M60$X_2$, S105$X_3$, D110$X_4$, and N111$X_5$, relative to SEQ ID NO: 30, where $X_1$ is T or K; $X_2$ is K or L; $X_3$ is D, N, or A; $X_4$ is K, N, S, or G; and $X_5$ is H, Y, G, or R.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51X, M60X, S105X, D110X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51$X_1$, M60$X_2$, S105$X_3$, D110$X_4$, and N111$X_5$, relative to SEQ ID NO: 30, where $X_1$ is T, K, D, E, R, or N; $X_2$ is K, Q, L, or R; $X_3$ is R, D, K, A, or N; $X_4$ is H, K, N, Q, E, N, S, or G; and $X_5$ is H, D, Y, R, S, or G. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51$X_1$, M60$X_2$, S105$X_3$, D110$X_4$, and N111$X_5$, relative to SEQ ID NO: 30, where $X_1$ is T or K; $X_2$ is K or L; $X_3$ is D, N, or A; $X_4$ is K, N, S, or G; and $X_5$ is H, Y, G, or R.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51X, K53X, Q56X, S105X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 3 mutations selected from the group consisting of M51X, K53X, Q56X, S105X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51$X_1$, K53$X_2$, Q56$X_3$, S105$X_4$, and N111$X_5$, relative to SEQ ID NO: 30, where $X_1$ is E, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 3 mutations selected from the group consisting of M51$X_1$, K53$X_2$, Q56$X_3$, S105$X_4$, and N111$X_5$, relative to SEQ ID NO: 30, where $X_1$ is E, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51$X_1$, K53$X_2$, Q56$X_3$, S105$X_4$, and N111$X_5$, relative to SEQ ID NO: 30, where $X_1$ is K; $X_2$ is G or S; $X_3$ is G, R, or L; $X_4$ is S, N, or G; and $X_5$ is G or R.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51X, K53X, Q56X, S105X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51$X_1$, K53$X_2$, Q56$X_3$, S105$X_4$, and N111 $X_5$, relative to SEQ ID NO: 30, where $X_1$ is E, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51$X_1$, K53$X_2$, Q56$X_3$, S105$X_4$, and N111$X_5$, relative to SEQ ID NO: 30, where $X_1$ is K; $X_2$ is G or S; $X_3$ is G, R, or L; $X_4$ is S, N, or G; and $X_5$ is G or R.

In some embodiments, the murine IL-18 variant polypeptide comprises at least one mutation (e.g., at least 2, at least 3, at least 4, at least 5, or at least 6 mutations) selected from the group consisting of NIX, M50X, Y51X, K52X, S54X, E55X, V56X, R57X, G58X, L59X, R104X, N109X, and L151X, wherein X denotes any amino acid. In some embodiments, a murine IL-18 variant polypeptide, or fragment thereof, comprises at least one mutation (e.g., at least 2, at least 3, at least 4, at least 5, or at least 6 mutations) selected from the group consisting of N1H, N1Y, M50A, M50S, M50V, M50G, M50T, Y51R, K52V, K52S, K52T, K52G, K52A, S54R, S54K, S54G, S54N, E55R, E55H, E55N, E55D, E55G, V56L, V56M, V56R, V56A, V56S, V56Q, R57G, R57K, G58A, L59K, L59R, L59V, R104K, R104L, R104Q, R104S, N109D, and L151V. In some embodiments, a murine IL-18 variant polypeptide comprises at least one variant selected from the group consisting of mCS1 (SEQ ID NO: 60), mCS2 (SEQ ID NO: 61), mC1 (SEQ ID NO: 62), mA12 (SEQ ID NO: 63), mE8 (SEQ ID NO: 64), mC10 (SEQ ID NO: 65), mB7 (SEQ ID NO: 66), mB1 (SEQ ID NO: 67), mD1 (SEQ ID NO: 68), mH7 (SEQ ID NO: 69), mA7 (SEQ ID NO: 70), mE1 (SEQ ID NO: 71), and mH3 (SEQ ID NO: 72), or a fragment thereof.

In some embodiments, the invention is a nucleic acid (e.g., DNA, cDNA, mRNA, etc.) that encodes at least one IL-18 variant polypeptide.

Therapeutic Inhibitor Compositions and Methods

In various embodiments, the present invention includes IL-18BP inhibitor compositions and methods of treating or preventing a disease or disorder where a diminished activity or level of IL-18BP is desired. The indications for such an agent are encompassed by the indications elaborated for a DR-IL-18 variant above. Non-limiting examples of diseases or disorders where a diminished activity or level of IL-18BP is desired which can be treated or prevented with the compositions and methods of the invention include cancer, infectious disease, metabolic diseases or disorders, and macular degeneration. In various embodiments, the IL-18BP inhibitor compositions and methods of treatment or prevention of the invention diminish the amount of IL-18BP polypeptide, the amount of IL-18BP mRNA, the amount of IL-18BP enzymatic activity, the amount of IL-18BP substrate binding activity, or a combination thereof.

It will be understood by one skilled in the art, based upon the disclosure provided herein, that a decrease in the level of IL-18BP encompasses a decrease in IL-18BP expression, including transcription, translation, or both. The skilled artisan will also appreciate, once armed with the teachings of the present invention, that a decrease in the level of IL-18BP includes a decrease in IL-18BP activity (e.g., enzymatic activity, substrate binding activity, etc.). Thus, decreasing the level or activity of IL-18BP includes, but is not limited to, decreasing transcription, translation, or both, of a nucleic acid encoding IL-18BP; and it also includes decreasing any activity of an IL-18BP polypeptide as well. The IL-18BP inhibitor compositions and methods of the invention can selectively inhibit IL-18BP, or can inhibit both IL-18BP and another molecule.

Inhibition of IL-18BP can be assessed using a wide variety of methods, including those disclosed herein, as well as methods known in the art or to be developed in the future. That is, the routineer would appreciate, based upon the disclosure provided herein, that decreasing the level or activity of IL-18BP can be readily assessed using methods that assess the level of a nucleic acid encoding IL-18BP (e.g., mRNA), the level of an IL-18BP polypeptide present in a biological sample, the level of IL-18BP activity (e.g., enzymatic activity, substrate binding activity, etc.), or combinations thereof.

One skilled in the art, based upon the disclosure provided herein, would understand that the invention is useful in treating or preventing a disease or disorder in a subject in need thereof, whether or not the subject is also being treated with another medication or therapy. Further, the skilled artisan would appreciate, based upon the teachings provided herein, that the disease or disorder treatable by the compositions and methods described herein encompass any disease or disorder where IL-18BP plays a role and where diminished IL-18BP level or activity promotes a positive therapeutic outcome.

The IL-18BP inhibitor compositions and methods of the invention that decrease the level or activity (e.g., enzymatic activity, ligand binding activity, etc.) of IL-18BP include, but should not be construed as being limited to, a chemical compound, a polypeptide, a peptide, a peptidomimetic, an antibody, a ribozyme, a small molecule chemical compound, an antisense nucleic acid molecule (e.g., siRNA, miRNA, etc.), or combinations thereof. One of skill in the art would readily appreciate, based on the disclosure provided herein, that an IL-18BP inhibitor composition encompasses a chemical compound that decreases the level or activity of IL-18BP. Additionally, an IL-18BP inhibitor composition encompasses a chemically modified compound, and derivatives, as is well known to one of skill in the chemical arts.

The IL-18BP inhibitor compositions and methods of the invention that decrease the level or activity (e.g., enzymatic activity, ligand binding activity, etc.) of IL-18BP include antibodies. The antibodies of the invention include a variety of forms of antibodies including, for example, polyclonal antibodies, monoclonal antibodies, intracellular antibodies ("intrabodies"), Fv, Fab and F(ab)2, single chain antibodies (scFv), heavy chain antibodies (such as camelid antibodies), synthetic antibodies, chimeric antibodies, and humanized antibodies. In some embodiments, the antibody of the invention is an antibody that specifically binds to IL-1813P.

In some embodiments, the IL-18BP inhibitor comprises an engineered IL-18 variant that is designed to bind to IL-18BP, but does not substantially bind to or interact with the IL-18R (e.g., IL-18Rα and IL-18Rβ). This variant, a "decoy-to-the-decoy" (D2D), serves to bind to IL-18BP and thus prevent IL-18BP from inhibiting endogenously-produced or therapeutically-introduced IL-18. The "decoy-to-the-decoy' could be engineered using nearly the same yeast display selection strategies described elsewhere herein, but instead positively selecting for IL-18BP binding, and counter-selected against substantially binding to IL-18Rα.

In various embodiments, the IL-18 variant polypeptide that binds to and inhibits IL-18BP, comprises a mutation relative to a wild-type (WT) IL-18 polypeptide. In some embodiments, the WT IL-18 polypeptide comprises the amino acid sequence of SEQ ID NO: 30. In other embodiments, the WT IL-18 polypeptide comprises the amino acid sequence of SEQ ID NO: 31.

In various embodiments, the IL-18 variant polypeptide that binds to and inhibits IL-18BP comprises a human IL-18 variant polypeptide, or fragment thereof, comprising at least one mutation (e.g., at least 2, at least 3, at least 4, at least 5, or at least 6 mutations) selected from the group consisting of Y1X, L5X, D17X, E31X, T34X, D35X, S36X, D37X, D40X, N41X, M51X, Q56X, M60X, Q103X, H109X, M113X, and R131X, wherein X denotes any amino acid. In some embodiments, the IL-18 variant polypeptide that binds to and inhibits IL-18BP comprises a human IL-18 variant polypeptide, or fragment thereof, comprising at least one mutation (e.g., at least 2, at least 3, at least 4, at least 5, or at least 6 mutations) selected from the group consisting of Y1D, Y1F, Y1H, Y1L, L5F, L5H, D17A, D17G, D17R, D17H, E31A, E31T, E31G, E31K, E31R, T34A, T34K T34E, D35S, D35A, D35Y, S36N, S36K, S36R, D37P, D37A, D37R, D37H, D37L, D37V, D40Y D40S, D40A, N41K, N41S, N41R, M51F, M51L, M511, Q56H, M60L, M60F, M60I, Q103L, Q103I, H109A, H109P, H109D, M113L, M1131, M113F, and R131S. In some embodiments, the IL-18 variant polypeptide that binds to and inhibits IL-18BP comprises a human IL-18 variant polypeptide, or fragment thereof, selected from the group consisting of hD2D-5F12 (SEQ ID NO: 92), hD2D-5F11 (SEQ ID NO: 93), hD2D-5F10 (SEQ ID NO: 94), hD2D-5F08 (SEQ ID NO: 95), hD2D-5F06 (SEQ ID NO: 96), hD2D-5F04 (SEQ ID NO: 97), hD2D-5F02 (SEQ ID NO: 98), hD2D-5F01 (SEQ ID NO: 99), hD2D-5E10 (SEQ ID NO: 100), hD2D-5E08 (SEQ ID NO: 101), hD2D-5E03 (SEQ ID NO: 102), hD2D-5E02 (SEQ ID NO: 103), hD2D-5D10 (SEQ ID NO: 104), hD2D-5D08 (SEQ ID NO: 105), hD2D-5D06 (SEQ ID NO: 106), hD2D-5D05 (SEQ ID NO: 107), hD2D-5D03 (SEQ ID NO: 108), hD2D-5D02 (SEQ ID NO: 109), hD2D-5C10 (SEQ ID NO: 110), hD2D-5C09 (SEQ ID NO: 111), hD2D-5C08 (SEQ ID NO: 112), hD2D-5C05 (SEQ ID NO: 113), hD2D-5C04 (SEQ ID NO: 114), hD2D-5C03 (SEQ ID NO: 115), hD2D-5B11 (SEQ ID NO: 116), hD2D-5B10 (SEQ ID NO: 117), hD2D-5B06 (SEQ ID NO: 118), hD2D-5B05 (SEQ ID NO: 119), hD2D-5B02 (SEQ ID NO: 120), hD2D-5A09 (SEQ ID NO: 121), hD2D-5A02 (SEQ ID NO: 122), hD2D-CS1 (SEQ ID NO: 123), hD2D-CS2 (SEQ ID NO: 124), hD2D-CS3 (SEQ ID NO: 125), or a fragment thereof.

In some cases a subject D2D-IL-18 variant, or fragment thereof, includes at least one mutation (e.g., at least 2, at least 3, or at least 4 mutations) selected from the group consisting of D17X, E30X, and Q103X, relative to SEQ ID NO: 30. In some cases a subject D2D-IL-18 variant, or fragment thereof, includes at least one mutation (e.g., at least 2, at least 3, or at least 4 mutations) selected from the group consisting of D17$X_1$, E30$X_2$, and Q103$X_3$, relative to SEQ ID NO: 30, where $X_1$ is G, H, R, or A; $X_2$ is A, T, G, K, or R; and $X_3$ is I or L. In some cases a subject D2D-IL-18 variant, or fragment thereof, includes at least one mutation (e.g., at least 2, at least 3, or at least 4 mutations) selected from the group consisting of D17G, E30A, and (Q103L or Q103I).

In some cases a subject D2D-IL-18 variant, or fragment thereof, includes the mutations D17X, E30X, and Q103X, relative to SEQ ID NO: 30. For example, in some cases a subject D2D-IL-18 variant, or fragment thereof, includes the mutations D17$X_1$, E30$X_2$, and Q103$X_3$, relative to SEQ ID NO: 30, where $X_1$ is G, H, R, or A; $X_2$ is A, T, G, K, or R; and $X_3$ is I or L. In some cases a subject D2D-IL-18 variant, or fragment thereof, includes the mutations D17G, E30A, and (Q103L or Q103I).

In some cases a subject D2D-IL-18 variant, or fragment thereof, includes at least one mutation (e.g., at least 2, at least 3, or at least 4 mutations) selected from the group consisting of D17X, E30X, D35X, M51X, and Q103X, relative to SEQ ID NO: 30. In some cases a subject D2D-IL-18 variant, or fragment thereof, includes at least one mutation (e.g., at least 2, at least 3, or at least 4 mutations) selected from the group consisting of D17$X_1$, E30$X_2$, D35$X_3$, M51$X_4$, and Q103$X_3$, relative to SEQ ID NO: 30, where $X_1$ is G, H, R, or A; $X_2$ is A, T, G, K, or R; $X_3$ is S, A, or Y; $X_4$ is F, I, or L; and $X_5$ is I or L. In some cases a subject D2D-IL-18 variant, or fragment thereof, includes at least one mutation (e.g., at least 2, at least 3, or at least 4 mutations) selected from the group consisting of D17G, E30A, D35S, M51F, and (Q103L or Q103I), relative to SEQ ID NO: 30.

In some cases a subject D2D-IL-18 variant, or fragment thereof, includes the mutations D17X, E30X, D35X, M51X, and Q103X, relative to SEQ ID NO: 30. For example, in some cases a subject D2D-IL-18 variant, or fragment thereof, includes the mutations D17$X_1$, E30$X_2$, D35$X_3$, M51$X_4$, and Q103$X_3$, relative to SEQ ID NO: 30, where $X_1$ is G, H, R, or A; $X_2$ is A, T, G, K, or R; $X_3$ is S, A, or Y; $X_4$ is F, I, or L; and $X_5$ is I or L. In some cases a subject D2D-IL-18 variant, or fragment thereof, includes the mutations D17G, E30A, D35S, M51F, and (Q103L or Q103I), relative to SEQ ID NO: 30.

In some cases a subject D2D-IL-18 variant, or fragment thereof, comprises an amino acid sequence having 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30. As such in some cases a subject D2D-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) relative to wild type IL-18 (e.g., human IL-18).

In some cases a subject D2D-IL-18 variant, or fragment thereof, comprises an amino acid sequence having 85% or more sequence identity (e.g., 90% or more, 92% or more, 93% or more, 94% or more, 95% or more, 96% or more, 97% or more, 98% or more, or 99% or more sequence identity) with the amino acid sequence set forth in any one of SEQ ID NOs: 126-190. As such in some cases a subject D2D-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the amino acid sequence set forth in any one of SEQ ID NOs: 126-190; and (ii) includes at least one mutation (e.g., at least 2, at least 3, at least 4, at least 5, or at least 6 mutations) relative to wild type IL-18 (e.g., human IL-18).

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of Y1X, L5X, D17X, E31X, T34X, D35X, S36X, D37X, D40X, N41X, M51X, Q56X, M60X, Q103X, H109X, M113X, and R131X.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of D17X, E30X, and Q103X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of $D17X_1$, $E30X_2$, and $Q103X_3$, relative to SEQ ID NO: 30, where $X_1$ is G, H, R, or A; $X_2$ is A, T. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of D17G, E30A, and (Q103L or Q103I).

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations D17X, E30X, and Q103X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations $D17X_1$, $E30X_2$, and $Q103X_3$, relative to SEQ ID NO: 30, where $X_1$ is G, H, R, or A; $X_2$ is A, T. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations D17G, E30A, and (Q103L or Q103I).

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of D17X, E30X, D35X, M51X, and Q103X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of $D17X_1$, $E30X_2$, $D35X_3$, $M51X_4$, and $Q103X_3$, relative to SEQ ID NO: 30, where $X_1$ is G, H, R, or A; $X_2$ is A, T, G, K, or R; $X_3$ is S, A, or Y; $X_4$ is F, I, or L; and $X_5$ is I or L. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of D17G, E30A, D35S, M51F, and (Q103L or Q1031), relative to SEQ ID NO: 30.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations D17X, E30X, D35X, M51X, and Q103X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations $D17X_1$, $E30X_2$, $D35X_3$, $M51X_4$, and $Q103X_3$, relative to SEQ ID NO: 30, where $X_1$ is G, H, R, or A; $X_2$ is A, T, G, K, or R; $X_3$ is S, A, or Y; $X_4$ is F, I, or L; and $X_5$ is I or L. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations D17G, E30A, D35S, M51F, and (Q103L or Q1031), relative to SEQ ID NO: 30.

In some embodiments, the IL-18 variant polypeptide that binds to and inhibits IL-18BP comprises a murine IL-18 variant polypeptide comprising at least one mutation (e.g., at least 2, at least 3, at least 4, at least 5, or at least 6 mutations) selected from the group consisting of NIX, L5X, D17X, E30X, T33X, D34X, 135X, D36X, M50X, Q102X, R104, H108X, N109X, M111X, D129X, and D130X, wherein X denotes any amino acid. In some embodiments, the IL-18 variant polypeptide that binds to and inhibits IL-18BP comprises a murine IL-18 variant polypeptide, or fragment thereof, comprising at least one mutation (e.g., at least 2, at least 3, at least 4, at least 5, or at least 6 mutations) selected from the group consisting of N1Y, N1D, N1H, NIL, N1F, N1V, N1I, L5Y, L5H, D17Q, D17G, D17A, D17E, D17S, D17N, E30A, E30R, E30K, E30T, E30G, T33G, T33A, T33E, T33R, T33K, D34Y, D34S, D34A, I35T, I35K, I35R, D36V, D36A, D36G, D36H, D36P, D36R, D36L, M50F, M50L, Q102L, Q102I, R104E, R104A, R104P, R104G, R104Q, R104H, H108D, H108A, N109R, N109S, N109T, N1091, M111L, M111, D129A, D129F, D129V, D129Y, D129S, D130E, D130T, D130G, D130N, D130R, D130S, D130Q, and D130H. In some embodiments, the IL-18 variant polypeptide that binds to and inhibits IL-18BP comprises a murine IL-18 variant polypeptide, or fragment thereof, selected from the group consisting of mD2D-A5 (SEQ ID NO: 126), mD2D-A6 (SEQ ID NO: 127), mD2D-A7 (SEQ ID NO: 128), mD2D-A8 (SEQ ID NO: 129), mD2D-A9 (SEQ ID NO: 130), mD2D-A11 (SEQ ID NO: 131), mD2D-A12 (SEQ ID NO: 132), mD2D-B4 (SEQ ID NO: 133), mD2D-B7 (SEQ ID NO: 134), mD2D-B11 (SEQ ID NO: 135), mD2D-B12 (SEQ ID NO: 136), mD2D-C1 (SEQ ID NO: 137), mD2D-C3 (SEQ ID NO: 138), mD2D-C5 (SEQ ID NO: 139), mD2D-C6 (SEQ ID NO: 140), mD2D-C9 (SEQ ID NO: 141), mD2D-C10 (SEQ ID NO: 142), mD2D-C11 (SEQ ID NO: 143), mD2D-D1 (SEQ ID NO: 144), mD2D-D9 (SEQ ID NO: 145), mD2D-D12 (SEQ ID NO: 146), mD2D-E3 (SEQ ID NO: 147), mD2D-E4 (SEQ ID NO: 148), mD2D-E5 (SEQ ID NO: 149), mD2D-E7 (SEQ ID NO: 150), mD2D-E8 (SEQ ID NO: 151), mD2D-E9 (SEQ ID NO: 152), mD2D-E10 (SEQ ID NO: 153), mD2D-E11 (SEQ ID NO: 154), mD2D-E12 (SEQ ID NO: 155), mD2D-F3 (SEQ ID NO: 156), mD2D-F4 (SEQ ID NO: 157), mD2D-F5 (SEQ ID NO: 158), mD2D-F7 (SEQ ID NO: 159), mD2D-F8 (SEQ ID NO: 160), mD2D-F9 (SEQ ID NO: 161), mD2D-G1 (SEQ ID NO: 162), mD2D-G7 (SEQ ID NO: 163), mD2D-G9 (SEQ ID NO: 164), mD2D-H7 (SEQ ID NO: 165), mD2D-E1 (SEQ ID NO: 166), mD2D-G8 (SEQ ID NO: 167), mD2D-H3 (SEQ ID NO: 168), mD2D-A10 (SEQ ID NO: 169), mD2D-H1 (SEQ ID NO: 170), mD2D-F12 (SEQ ID NO: 171), mD2D-G10 (SEQ ID NO: 172), mD2D-G12 (SEQ ID NO: 173), mD2D-E2 (SEQ ID NO: 174), mD2D-G11 (SEQ ID NO: 175), mD2D-C4 (SEQ ID NO: 176), mD2D-F11 (SEQ ID NO: 177), mD2D-C2 (SEQ ID NO: 178), mD2D-F10 (SEQ ID NO: 179), mD2D-A2 (SEQ ID NO: 180), mD2D-F6 (SEQ ID NO: 181), mD2D-A1 (SEQ ID NO: 182), mD2D-E6 (SEQ ID NO: 183), mD2D-D4 (SEQ ID NO: 184), mD2D-D6 (SEQ ID NO: 185), mD2D-A3 (SEQ ID NO: 186), mD2D-A4 (SEQ ID NO: 187), mD2D-B10 (SEQ ID NO: 188), mD2D-B8 (SEQ ID NO: 189), mD2D-B9 (SEQ ID NO: 190), or a fragment thereof.

In some embodiments, the invention is a nucleic acid (e.g., DNA, cDNA, mRNA, etc.) that encodes at least one IL-18 variant polypeptide.

In some embodiments, the IL-18BP inhibitor is an IL-18 variant polypeptide that binds to IL-18BP and exhibits substantially reduced binding to IL-18R. In some embodiments, IL-18BP inhibitor that binds to IL-18BP and exhibits substantially reduced binding to IL-18R binds to IL-18R with a binding affinity that is about 0.000000000001% to about 95% of the binding affinity of wild-type IL-18 to IL-18R.

In some embodiments, the IL-18 variant polypeptide that binds to IL-18BP and exhibits substantially reduced binding to IL-18R binds to IL-18R with a binding affinity that is about 95% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 90% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 85% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 80% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 75% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 70% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 65% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 60% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 55% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 50% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 45% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 40% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 35% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 30% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 25% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 20% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 15% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 10% of the binding affinity of wild-type IL-18 to IL-18R.

In some embodiments, the IL-18 variant polypeptide that binds to IL-18BP and exhibits substantially reduced binding to IL-18R binds to IL-18R with a binding affinity that is about 5% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 4% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 3% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 2% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 1% of the binding affinity of wild-type IL-18 to IL-18R.

In some embodiments, the IL-18 variant polypeptide that binds to IL-18BP and exhibits substantially reduced binding to IL-18R binds to IL-18R with a binding affinity that is about 0.1% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.01% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.001% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.0001% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.00001% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.000001% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.0000001% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.00000001% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.000000001% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.0000000001% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.00000000001% of the binding affinity of wild-type IL-18 to IL-18R. In some embodiments, the IL-18 variant polypeptide that binds to IL-18BP and exhibits substantially reduced binding to IL-18R binds to IL-18R with a binding affinity that is about 0.000000000001% of the binding affinity of wild-type IL-18 to IL-18R.

Further, one of skill in the art, when equipped with this disclosure and the methods exemplified herein, would appreciate that an IL-18BP inhibitor composition includes such inhibitors as discovered in the future, as can be identified by well-known criteria in the art of pharmacology, such as the physiological results of inhibition of IL-18BP as described in detail herein and/or as known in the art. Therefore, the present invention is not limited in any way to any particular IL-18BP inhibitor composition as exemplified or disclosed herein; rather, the invention encompasses those inhibitor compositions that would be understood by the routineer to be useful as are known in the art and as are discovered in the future.

Further methods of identifying and producing IL-18BP inhibitor compositions are well known to those of ordinary skill in the art, including, but not limited to, obtaining an inhibitor from a naturally occurring source (e.g., *Streptomyces* sp., *Pseudomonas* sp., *Stylotella aurantium*, etc.). Alternatively, an IL-18BP inhibitor can be synthesized chemically. Further, the routineer would appreciate, based upon the teachings provided herein, that an IL-18BP inhibitor composition can be obtained from a recombinant organism. Compositions and methods for chemically synthesizing IL-18BP inhibitors and for obtaining them from natural sources are well known in the art and are described in the art.

One of skill in the art will appreciate that an inhibitor can be administered as a small molecule chemical, a protein, an antibody, a nucleic acid construct encoding a protein, an antisense nucleic acid, a nucleic acid construct encoding an antisense nucleic acid, or combinations thereof. Numerous vectors and other compositions and methods are well known for administering a protein or a nucleic acid construct encoding a protein to cells or tissues. Therefore, the invention includes a method of administering a protein or a nucleic acid encoding a protein that is an inhibitor of IL-18BP. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself increases the amount or activity of IL-18BP can serve in the compositions and methods of the present invention to decrease the amount or activity of IL-18BP.

Antisense oligonucleotides are DNA or RNA molecules that are complementary to some portion of an RNA molecule. When present in a cell, antisense oligonucleotides hybridize to an existing RNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of an antisense oligonucleotide to diminish the amount of IL-18BP, or to diminish the amount of a molecule that causes an increase in the amount or activity of IL-18BP, thereby decreasing the amount or activity of IL-18BP.

Contemplated in the present invention are antisense oligonucleotides that are synthesized and provided to the cell by way of methods well known to those of ordinary skill in the art. As an example, an antisense oligonucleotide can be synthesized to be between about 10 and about 100, more exemplary between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing IL-18BP, or of a gene expressing a protein that increases the level or activity of IL-18BP, can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168, 053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One of skill in the art will appreciate that inhibitors of IL-18BP can be administered acutely (e.g., over a short period of time, such as a day, a week or a month) or chronically (e.g., over a long period of time, such as several months or a year or more). One of skill in the art will appreciate that inhibitors of IL-18BP can be administered singly or in any combination with other agents. Further, IL-18BP inhibitors can be administered singly or in any combination in a temporal sense, in that they may be administered concurrently, and/or before, and/or after each other. One of ordinary skill in the art will appreciate, based on the disclosure provided herein, that IL-18BP inhibitor compositions can be used to treat or prevent a disease or disorder in a subject in need thereof, and that an inhibitor composition can be used alone or in any combination with another agent to affect a therapeutic result.

In various embodiments, any of the inhibitors of IL-18BP of the invention described herein can be administered alone or in combination with other inhibitors of other molecules associated with a disease or disorder disclosed herein or known in the art.

It will be appreciated by one of skill in the art, when armed with the present disclosure including the methods detailed herein, that the invention is not limited to treatment of a disease or disorder that is already established. Particularly, the disease or disorder need not have manifested to the point of detriment to the subject; indeed, the disease or disorder need not be detected in a subject before treatment is administered. That is, significant disease or disorder does not have to occur before the present invention may provide benefit. Therefore, the present invention includes a method for preventing a disease or disorder in a subject, in that an IL-18BP inhibitor composition, as discussed previously elsewhere herein, can be administered to a subject prior to the onset of the disease or disorder, thereby preventing the disease or disorder from developing. The preventive methods described herein also include the treatment of a subject that is in remission for the prevention of a recurrence of a disease or disorder.

One of skill in the art, when armed with the disclosure herein, would appreciate that the prevention of a disease or disorder encompasses administering to a subject an IL-18BP inhibitor composition as a preventative measure against the disease or disorder. As more fully discussed elsewhere herein, methods of decreasing the level or activity of IL-18BP encompass a wide plethora of techniques for decreasing not only IL-18BP activity, but also for decreasing expression of a nucleic acid encoding IL-18BP, including either a decrease in transcription, a decrease in translation, or both.

Additionally, as disclosed elsewhere herein, one skilled in the art would understand, once armed with the teaching provided herein, that the present invention encompasses a method of preventing a wide variety of diseases, disorders and pathologies where a decrease in expression and/or activity of IL-18BP mediates, treats or prevents the disease, disorder or pathology. Methods for assessing whether a disease relates to the levels or activity of IL-18BP are known in the art. Further, the invention encompasses treatment or prevention of such diseases discovered in the future.

The invention encompasses administration of an inhibitor of IL-18BP to practice the methods of the invention; the skilled artisan would understand, based on the disclosure provided herein, how to formulate and administer the appropriate IL-18BP inhibitor to a subject. However, the present invention is not limited to any particular method of administration or treatment regimen.

Cytokine Inhibitors

In some embodiments, the composition of the present invention comprises an inhibitor of one or more cytokines. In some embodiments, the inhibitor of one or more cytokines comprises a chemical compound, a protein, a peptide, a peptidomimetic, an antibody, a ribozyme, a small molecule chemical compound, or an antisense nucleic acid molecule (e.g., siRNA, miRNA, etc.) that inhibits the expression, activity, or both of one or more cytokines. In some embodiments, the inhibitor inhibits the expression, activity, or both of IL-17, IL-5, or IL-3. In some embodiments, the cytokine inhibitor decreases toxicity. In some embodiments, the cytokine inhibitor increases efficacy of an administered IL-18 variant polypeptide or IL-18BP inhibitor.

Compositions and Methods of Treatment and Prevention

In various embodiments, the present invention includes compositions comprising an activator of IL-18 activity, such as signaling activity through at least one IL-18R, and methods of increasing IL-18 activity, such as signaling through at least one IL-18R, in a cell, tissue, organ, system, or subject in need thereof. In various embodiments, the activator of IL-18 activity compositions, and methods of treatment of the invention, increase the amount of IL-18R signaling, the amount of immune cell activity, or both. In various embodiments, the diseases and disorders in which an increase in IL-18R signaling may improve therapeutic outcomes include, but are not limited to cancer, infectious diseases, macular degeneration, and metabolic diseases or disorders.

The following are non-limiting examples of cancers that can be treated or prevented by the methods and compositions of the invention: acute lymphoblastic leukemia, acute myeloid leukemia, adrenocortical carcinoma, appendix cancer, basal cell carcinoma, bile duct cancer, bladder cancer, bone cancer, brain and spinal cord tumors, brain stem glioma, brain tumor, breast cancer, bronchial tumors, burkitt lymphoma, carcinoid tumor, central nervous system atypical teratoid/rhabdoid tumor, central nervous system embryonal tumors, central nervous system lymphoma, cerebellar astrocytoma, cerebral astrocytoma/malignant glioma, cerebral astrocytotna/malignant glioma, cervical cancer, childhood visual pathway tumor, chordoma, chronic lymphocytic leukemia, chronic myelogenous leukemia, chronic myeloproliferative disorders, colon cancer, colorectal cancer, craniopharyngioma, cutaneous cancer, cutaneous t-cell lymphoma, endometrial cancer, ependymoblastoma, ependymoma, esophageal cancer, ewing family of tumors, extracranial cancer, extragonadal germ cell tumor, extrahepatic bile duct cancer, extrahepatic cancer, eye cancer, fungoides, gallbladder cancer, gastric (stomach) cancer, gastrointestinal cancer, gastrointestinal carcinoid tumor, gastrointestinal stromal tumor (gist), germ cell tumor, gestational cancer, gestational trophoblastic tumor, glioblastoma, glioma, hairy cell leukemia, head and neck cancer, hepatocellular (liver) cancer, histiocytosis, hodgkin lymphoma, hypopharyngeal cancer, hypothalamic and visual pathway glioma, hypothalamic tumor, intraocular (eye) cancer, intraocular melanoma, islet cell tumors, kaposi sarcoma, kidney (renal cell) cancer, langerhans cell cancer, langerhans cell histiocytosis, laryngeal cancer, leukemia, lip and oral cavity cancer, liver cancer, lung cancer, lymphoma, macroglobulinemia, malignant fibrous histiocytoma of bone and osteosarcoma, medulloblastoma, medulloepithelioma, melanoma, merkel cell carcinoma, mesothelioma, metastatic squamous neck cancer with occult primary, mouth cancer, multiple endocrine neoplasia syndrome, multiple myeloma, mycosis, myelodysplastic syndromes, myelodysplastic/myeloproliferative diseases, myelogenous leukemia, myeloid leukemia, myeloma, myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma, osteosarcoma and malignant fibrous histiocytoma of bone, ovarian, ovarian cancer, ovarian epithelial cancer, ovarian germ cell tumor, ovarian low malignant potential tumor, pancreatic cancer, papillomatosis, paraganglioma, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm, plasma cell neoplasm/multiple myeloma, pleuropulmonary blastoma, primary central nervous system cancer, primary central nervous system lymphoma, prostate cancer, rectal cancer, renal cell (kidney) cancer, renal pelvis and ureter cancer, respiratory tract carcinoma involving the nut gene on chromosome 15, retinoblastoma, rhabdomyosarcoma, salivary gland cancer, sarcoma, sezary syndrome, skin cancer (melanoma), skin cancer (nonmelanoma), skin carcinoma, small cell lung cancer, small intestine cancer, soft tissue cancer, soft tissue sarcoma, squamous cell carcinoma, squamous neck cancer, stomach (gastric) cancer, supratentorial primitive neuroectodermal tumors, supratentorial primitive neuroectodermal tumors and pineoblastoma, T-cell lymphoma, testicular cancer, throat cancer, thymoma and thymic carcinoma, thyroid cancer, transitional cell cancer, transitional cell cancer of the renal pelvis and ureter, trophoblastic tumor, urethral cancer, uterine cancer, uterine sarcoma, vaginal cancer, visual pathway and hypothalamic glioma, vulvar cancer, waldenstrom macroglobulinemia, and Wilms Tumor.

Thus, non-limiting examples of cancers that can be treated or prevented by the methods and compositions of the disclosure include solid tumor cancers, liquid cancers, blood cancers, teratomas, sarcomas, and carcinomas.

In some embodiments, the method of the present invention is useful for treating or preventing a tumor or cancer that is resistant to immune checkpoint inhibitors (ICIs). Exemplary immune checkpoint inhibitors include, but is not limited to, anti-PD1 (e.g., nivolumab), anti-CTLA4 (e.g., ipilimumab), anti-TIM3, anti-TIGIT, anti-LAG3, anti-B7H3, anti-B7H4, anti-VISTA, anti-ICOS, anti-GITR, anti-41BB, anti-OX40, and anti-CD40. Examples of targets of immune checkpoint inhibitors include but are not limited to: PD-L1, PD1, CTLA4, TIM3, TIGIT, LAG3, B7H3, B7H4, VISTA, ICOS, GITR, 41BB, OX40, and CD40. Thus, examples of immune checkpoint inhibitors include agents that inhibit proteins such as: PD-L1, PD1, CTLA4, TIM3, TIGIT, LAG3, B7H3, B7H4, VISTA, ICOS, GITR, 41BB, OX40, or CD40. In some cases, a subject IL-18 variant polypeptide (e.g., a DR-IL-18 variant, a D2D-IL-18 variant) is co-administered with an immune checkpoint inhibitor (e.g., an agent that inhibits PD-L1, PD1, CTLA4, TIM3, TIGIT, LAG3, B7H3, B7H4, VISTA, ICOS, GITR, 41BB, OX40, or CD40, or any combination thereof).

Fusions/Conjugations

In some embodiments, an IL-18 variant polypeptide of the present disclosure is fused to another protein, i.e., an IL-18 variant polypeptide or a fragment thereof can be fused in frame with a second polypeptide (a fusion partner). In some embodiments, the second polypeptide (the fusion partner) is capable of increasing the overall size of the fusion protein, e.g., so that the fusion protein will not be cleared from the circulation rapidly. In some cases, a IL-18 variant polypeptide or a fragment thereof is not fused to a second polypeptide.

In some embodiments, the second polypeptide (the fusion partner for a IL-18 variant polypeptide or a fragment thereof) is part or whole of an immunoglobulin Fe region (i.e., an antibody Fc sequence). In other embodiments, the second polypeptide is any suitable polypeptide that is substantially similar to Fe, e.g., providing increased size, multimerization domains, and/or additional binding or interaction with Ig molecules. In some embodiments, the second polypeptide is part or whole of Human Serum Albumin (HSA). In some embodiments, the second polypeptide is part or whole of an antibody, antibody fragment, camelid antibody or "nanobody" or other affinity reagent that binds to or interacts with HSA. These fusion proteins can facilitate purification, multimerization, and show an increased half-life in vivo. Fusion proteins having disulfide-linked multimeric structures can also, in some cases, be more efficient in binding and neutralizing other molecules.

When fused to a heterologous polypeptide, the portion corresponding to the IL-18 variant polypeptide or a fragment thereof can be referred to as the "IL-18 variant polypeptide portion" of a subject IL-18 variant polypeptide. In some cases, the "IL-18 variant polypeptide portion" can be 100 amino acids or more in length (e.g., 110 amino acids or more, 125 amino acids or more, 150 amino acids or more, 90 amino acids or more, 95 amino acids or more, 100 amino acids or more, 105 amino acids or more, 110 amino acids or more, 115 amino acids or more, 120 amino acids or more, 125 amino acids or more, 130 amino acids or more, 140 amino acids or more, or 150 amino acids or more), up to full-length IL-18, and can further be fused to a heterologous polypeptide.

In some cases, IL-18 variant polypeptide portion of a IL-18 variant polypeptide has a length in a range of from 100 amino acids to 157 amino acids (e.g., from 100 amino acids to 150 amino acids, from 100 amino acids to 140 amino acids, from 140 amino acids to 157 amino acids, from 140 amino acids to 150 amino acids, from 145 amino acids to 157 amino acids, or from 150 amino acids to 157 amino acids).

In some cases, the second polypeptide is a marker sequence (e.g., an affinity tag), such as a peptide that facilitates purification of the fused polypeptide. For example, the marker amino acid sequence can be a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86: 821-824, 1989, for instance, hexa-histidine provides for convenient purification of the fusion protein. Another peptide tag useful for purification, the "HA" tag, corresponds to an epitope derived from the influenza hemagglutinin protein. Wilson et al., Cell 37: 767, 1984. The addition of peptide moieties to facilitate handling of polypeptides are familiar and routine techniques in the art.

A subject IL-18 variant polypeptide can be modified, e.g., joined/conjugated to a wide variety of other oligopeptides, proteins, and/or non-protein moieties for a variety of purposes. For example, post-translationally modified, for example by prenylation, acetylation, amidation, carboxylation, glycosylation, PEGylation (covalent attachment of polyethylene glycol (PEG) polymer chains), etc. Such modifications can also include modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. In some embodiments, a subject IL-18 variant polypeptide has one or more phosphorylated amino acid residues, e.g. phosphotyrosine, phosphoserine, or phosphothreonine.

In some other embodiments, IL-18 variant polypeptides of the disclosure include reagents further modified to improve their resistance to proteolytic degradation or to optimize solubility properties or to render them more suitable as a therapeutic agent. For example, variants of the present disclosure further include analogs containing residues other than naturally occurring L-amino acids, e.g. D-amino acids or non-naturally occurring synthetic amino acids. D-amino acids may be substituted for some or all of the amino acid residues.

Co-Administration and Multispecific IL-18 Variant Polypeptides

As noted elsewhere in this disclosure, in some cases a subject IL-18 variant polypeptide is administered with an additional agent. The terms "co-administration", "co-administer", and "in combination with" include the administration of two or more therapeutic agents (e.g., a subject IL-18 variant such as DR-IL-18 or D2D in combination with an additional agent) either simultaneously, concurrently or sequentially within no specific time limits. In some embodiments, the agents are present in the cell or in the subject's body at the same time or exert their biological or therapeutic effect at the same time. In some embodiments, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

In some cases, a subject IL-18 variant (e.g., a DR-IL-18 variant or a D2D variant) (e.g., formulated as a pharmaceutical composition) is co-administered with a cancer therapeutic drug, therapeutic drug to treat an infection, or cancer-directed antibody. Such administration may involve concurrent (i.e. at the same time), prior, or subsequent administration of the drug/antibody with respect to the administration of an agent or agents of the disclosure. A person of ordinary skill in the art would have no difficulty determining the appropriate timing, sequence and dosages of administration for particular drugs and compositions of the present disclosure.

In some embodiments, treatment is accomplished by administering a combination (co-administration) of a subject IL-18 variant (e.g., a DR-IL-18 variant or a D2D variant) with another agent (e.g., an immune stimulant, an agent to treat chronic infection, a cytotoxic agent, an anti-cancer agent, etc.). One example class of cytotoxic agents that can be used are chemotherapeutic agents. Exemplary chemotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, duocarmycin, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol™), pilocarpine, prochloroperazine, rituximab, saproin, tamoxifen, taxol, topotecan hydrochloride, trastuzumab, vinblastine, vincristine and vinorelbine tartrate.

A subject IL-18 variant (e.g., a DR-IL-18 variant or a D2D variant) need not be, but is optionally formulated with one or more agents that potentiate activity, or that otherwise increase the therapeutic effect. In some embodiments, treatment is accomplished by administering a combination (co-administration) of a subject IL-18 variant (e.g., a DR-IL-18 variant) and an agent that opsonizes a target cell. Thus, also envisioned herein are compositions (and methods that use the compositions) that include: (a) a subject IL-18 variant (e.g., a DR-IL-18 variant); and (b) an agent that opsonizes the target cell. In some cases, that agent that opsonizes the target cell is Rituximab. In some cases, that agent that opsonizes the target cell is Cetuximab.

An "agent that opsonizes a target cell" (an "opsonizing agent") is any agent that can bind to a target cell (e.g., a cancer cell, a cell harboring an intracellular pathogen, etc.) and opsonize the target cell (e.g., mark the target cell for phagocytosis and/or for antibody-dependent cell mediated cytotoxicity (ADCC)). For example, any antibody that can bind to a target cell (e.g., a cancer cell such as a tumor cell), where the antibody has an FC region, is considered to be an agent that opsonizes a target cell. In some cases, the agent that opsonizes a target cell is an antibody that binds to a target cell (e.g., an anti-tumor antibody, an anti-cancer antibody, an anti-infection antibody, and the like).

For example antibodies selective for tumor cell markers, radiation, surgery, and/or hormone deprivation, see Kwon et al., Proc. Natl. Acad. Sci U.S.A., 96: 15074-9, 1999. Angiogenesis inhibitors can also be combined with the methods of the invention. A number of antibodies are currently in clinical use for the treatment of cancer, and others are in varying stages of clinical development. For example, there are a number of antigens and corresponding monoclonal antibodies for the treatment of B cell malignancies. One target antigen is CD20. Rituximab is a chimeric unconjugated monoclonal antibody directed at the CD20 antigen. CD20 has an important functional role in B cell activation, proliferation, and differentiation. The CD52 antigen is targeted by the monoclonal antibody alemtuzumab, which is indicated for treatment of chronic lymphocytic leukemia. CD22 is targeted by a number of antibodies, and has recently demonstrated efficacy combined with toxin in chemotherapy-resistant hairy cell leukemia. Two new monoclonal antibodies targeting CD20, tositumomab and ibritumomab, have been submitted to the Food and Drug Administration (FDA). These antibodies are conjugated with radioisotopes. CAMPATH® (Alemtuzumab) is used in the treatment of chronic lymphocytic leukemia; MYLOTARG® (Gemtuzumab) finds use in the treatment of acute myelogenous leukemia; ZEVALIN©(Ibritumomab) finds use in the treatment of non-Hodgkin's lymphoma; VECTIBIX© (Panitumumab) finds use in the treatment of colon cancer.

Monoclonal antibodies useful in the methods of the disclosure that have been used in solid tumors include, without limitation, edrecolomab and HERCEPTIN© (trastuzumab). Edrecolomab targets the 17-1A antigen seen in colon and rectal cancer, and has been approved for use in Europe for these indications. Trastuzumab targets the HER-2/neu antigen. ERBITUX® (Cetuximab) is also of interest for use in the methods of the disclosure. The antibody binds to the EGF receptor (EGFR), and has been used in the treatment of solid tumors including colon cancer and squamous cell carcinoma of the head and neck (SCCHN).

A subject IL-18 variant polypeptide (e.g., a DR-IL-18 variant, a D2D-IL-18 variant) can be combined with any of the above mentioned agents (e.g., agents such as antibodies that opsonize a target cell). Thus, in some cases, a subject IL-18 variant polypeptide (e.g., a DR-IL-18 variant, a D2D-IL-18 variant) is used in a combination therapy (is co-administered) with one or more opsonizing agents selective for cancer cells, e.g., tumor cells. In some cases, a subject IL-18 variant polypeptide (e.g., a DR-IL-18 variant, a D2D-IL-18 variant) is used in a combination therapy (is co-administered) with one or more of: cetuximab (binds EGFR), panitumumab (binds EGFR), rituximab (binds CD20), trastuzumab (binds HER2), pertuzumab (binds HER2), alemtuzumab (binds CD52), brentuximab (binds CD30), tositumomab, ibritumomab, gemtuzumab, ibritumomab, and edrecolomab (binds 17-1A), or a combination thereof.

In some cases, a subject IL-18 variant polypeptide (e.g., a DR-IL-18 variant, a D2D-IL-18 variant) is co-administered with a cancer cell opsonizing agent (e.g., one that comprises an antigen binding region that targets CD19, CD20, CD22, CD24, CD25, CD30, CD33, CD37, CD38, CD44, CD45, CD47, CD51, CD52, CD56, CD62L, CD70, CD74, CD79, CD80, CD96, CD97, CD99, CD123, CD134, CD138, CD152 (CTLA-4), CD200, CD213A2, CD221, CD248, CD276 (B7-H3), B7-H4, CD279 (PD-1), CD274 (PD-L1), CD319, EGFR, EPCAM, 17-1A, HER1, HER2, HER3, CD117, C-Met, HGFR, PDGFRA, AXL, TWEAKR, PTHR2, HAVCR2 (TIM3), GD2 ganglioside, MUC1, mucin CanAg, mesothelin, endoglin, Lewis-Y antigen, CEA, CEACAM1, CEACAM5, CA-125, PSMA, BAFF, FGFR2, TAG-72, gelatinase B, glypican 3, nectin-4, BCMA, CSF1R, SLAMF7, integrin $\alpha_v\beta_3$, TYRP1, GPNMB, CLDN18.2, FOLR1, CCR4, CXCR4, MICA, C242 antigen, D113, D114, EGFL7, vimentin, fibronectin extra domain-B, TROP-2, LRRC15, FAP, SLITRK6, NOTCH2, NOTCH3, Tenascin-3, STEAP1, or NRP1, or any combination thereof).

In some cases, a subject IL-18 variant polypeptide (e.g., a DR-IL-18 variant, a D2D-IL-18 variant) is co-administered with and agent that targets one or more antigens selected from: CD19, CD20, CD22, CD24, CD25, CD30, CD33, CD38, CD44, CD47, SIRPA, CD52, CD56, CD70, CD96, CD97, CD99, CD123, CD279 (PD-1), CD274 (PD-L1), EGFR, 17-1A, HER2, CD117, C-Met, PTHR2, and HAVCR2 (TIM3).

In some cases, a subject IL-18 variant polypeptide (e.g., a DR-IL-18 variant, a D2D-IL-18 variant) is used in a combination therapy (is co-administered) with any convenient immunomodulatory agent (e.g., an anti-CTLA4 antibody, an anti-PD-1 antibody, an anti-PD-L1 antibody, a TIGIT antibody, a TIM3 antibody, a LAG3 antibody, a VISTA antibody, a B7H3 antibody, a B7H4 antibody, a CD40 agonist, a 4-1BB modulator (e.g., a 41BB-agonist), an OX-40 modulator (e.g., an OX-40 agonist), a GITR modulator (e.g., a GITR agonist), a CD47 binding agent such as an anti-CD47 antibody or a high affinity CD47 binding agent, a SIRPA binding agent such as an anti-SIRPA antibody or high affinity SIRPA binding agent, and the like), a TGFbeta antagonist such as an anti-TGFbeta antibody, a cytokine or a cytokine variant including IL-1, IL-2, IL-10, IL-12, IL-15, IL-18, IL-21, IL-33, Interferon alpha, Interferon beta, Interferon gamma, TNF, TRAIL, lymphotoxin, LIGHT/TNSF14, or an agonist of a Toll Like Receptor including TLR2, TLR4, TLR5, TLR7, TLR9, an agonist of an inflammasome, an agonist of the STING/cGAS pathway, or an agonist of the RIG-I pathway, an antagonist of the adenosine receptors A2aR/A2bR, an antagonist of the Aryl hydrocarbon receptor, an antagonist of IDO and/or TDO, or an oncolytic virus.

In some cases, a subject IL-18 variant polypeptide (e.g., a DR-IL-18 variant, a D2D-IL-18 variant) is used in a combination therapy (is co-administered) with an inhibitor of BTLA and/or CD160. In some cases, a subject IL-18 variant polypeptide (e.g., a DR-IL-18 variant, a D2D-IL-18 variant) is used in a combination therapy (is co-administered) with an anti-CD47/SIRPA agent (e.g., anti-CD47, anti-SIRPA, a high affinity CD47 binding agent, a high affinity SIRPA binding agent, and the like). In some cases, a subject IL-18 variant polypeptide (e.g., a DR-IL-18 variant, a D2D-IL-18 variant) is used in a combination therapy (is co-administered) with an inhibitor of TIM3 and/or CEACAM1.

As noted above, in some cases a subject IL-18 variant polypeptide is fused to another protein (i.e., a "fusion partner", a "second polypeptide"). In some embodiments, the second polypeptide (the fusion partner for a subject IL-18 variant polypeptide) specifically binds to a target molecule other than the target molecule bound by the IL-18 variant polypeptide portion of the fusion protein (e.g., other than IL-18R for variants that bind IL-18R; or other than IL-18BP for variants that bind to IL-18BP).

Thus, in some embodiments, a subject IL-18 variant polypeptide is multispecific (e.g., bispecific). The terms "multispecific" or "bispecific" are commonly used when referring to agents (e.g., ligands or antibodies) that recognize two or more different antigens by virtue of possessing at least one region (e.g., a ligand or a Fab of a first antibody) that is specific for a first target, and at least a second region (e.g., a ligand or a Fab of a second antibody) that is specific for a second target. A bispecific agent specifically binds to two targets and is thus one type of multispecific agent.

In some embodiments, a subject IL-18 variant polypeptide is multispecific (e.g., bispecific), such that a first region of the polypeptide includes a subject IL-18 variant polypeptide sequence (i.e., the first region includes a IL-18 variant polypeptide), and a second region that specifically binds to another target molecule (e.g., an antigen). For example, in some cases, a IL-18 variant polypeptide is fused to a second polypeptide that binds specifically to a target molecule other than the target molecule bound by the IL-18 variant polypeptide.

Any one of the agents discussed above in the context of co-administration can be conjugated to a subject IL-18 variant polypeptide. The term "co-administration" as used herein is meant to encompass such conjugated compounds. For example, when agent 1 is co-administered with agent 2, the term is meant to encompass embodiments where agent 1 and agent 2 are not conjugated to one another, and is also meant to encompass embodiments where agent 1 and agent 2 are conjugated to one another (e.g., where agent 1 and agent 2 are both proteins and agent 1 is fused to agent 2).

In some cases, the second region of a multispecific IL-18 variant polypeptide is a checkpoint inhibitor. In some cases, the second region of a multispecific IL-18 variant polypeptide inhibits one or more proteins selected from: PD-L1, PD1, CTLA4, TIM3, TIGIT, LAG3, B7H3, B7H4, VISTA, ICOS, GITR, 41BB, OX40, and CD40.

In some cases, the second region of a multispecific IL-18 variant polypeptide is a cancer cell opsonizing agent. In some cases, the second region of a multispecific IL-18 variant polypeptide targets one or more proteins selected from: CD19, CD20, CD22, CD24, CD25, CD30, CD33, CD38, CD44, CD47, SIRPA, CD52, CD56, CD70, CD96, CD97, CD99, CD123, CD279 (PD-1), CD274 (PD-L1), EGFR, 17-1A, HER2, CD117, C-Met, PTHR2, and HAVCR2 (TIM3). In some cases, the second region of a multispecific IL-18 variant polypeptide is an opsonizing agent that targets one or more proteins selected from: CD19, CD20, CD22, CD24, CD25, CD30, CD33, CD38, CD44, CD47, SIRPA, CD52, CD56, CD70, CD96, CD97, CD99, CD123, CD279 (PD-1), CD274 (PD-L1), EGFR, 17-1A, HER2, CD117, C-Met, PTHR2, and HAVCR2 (TIM3).

For example, in some cases, the second region of a multispecific IL-18 variant polypeptide includes an ectodomain, e.g., an ectodomain from PD-1, PD-L1, CD47 (e.g., a high affinity CD47 variant/polypeptide), or SIRPA. (e.g., a high affinity SIRPA variant/polypeptide). In some cases, the second region of a multispecific IL-18 variant polypeptide specifically binds an antigen selected from: CTLA-4, Lag-3, BTLA, Tim-3, CD244, CD40, CD40L, CD47, SIRPA, PD-1, and PD-L1.

In some embodiments, a subject IL-18 variant polypeptide includes a linker (e.g., a linker polypeptide). For example, in some embodiments, a subject IL-18 variant polypeptide and a fusion partner are separated by a linker (e.g., a linker polypeptide). A linker polypeptide may have any of a variety of amino acid sequences. Proteins can be joined by a linker polypeptide can be of a flexible nature (e.g., a flexible linker polypeptide), although other chemical linkages are not excluded. Suitable linkers include polypeptides of between about 6 amino acids and about 40 amino acids in length, or between about 6 amino acids and about 25 amino acids in length. These linkers can be produced by using synthetic, linker-encoding oligonucleotides to couple the proteins. Peptide linkers with a degree of flexibility can be used. The linking peptides may have virtually any amino acid sequence, bearing in mind that the in some case, linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

In some embodiments the IL-18 variant polypeptide is co-administered with an engineered immune cell such as a CAR-T or CAR-NK cell or T or NK cell transduced with an engineered T cell receptor. In other embodiments, the IL-18 variant polypeptide is co-adminstered with an oncolytic virus.

In some embodiments, a nucleic acid encoding an IL-18 variant polypeptide is included within an engineered ("altered") immune cell such as a CAR-T or CAR-NK cell or T or NK cell transduced with an engineered T cell receptor. In this instance, the engineered cell (e.g., altered T cell, altered NK cell) would secrete the IL-18 variant polypeptide. The ability to secrete the IL-18 variant peptide can be regulated in a contextual manner (e.g., turned on within the tumor microenvironment), for instance, by a synthetic NOTCH receptor.

In some embodiments, a nucleic acid encoding an IL-18 variant polypeptide is included within an oncolytic virus. In this instance, cells infected by the oncolytic virus would secrete the IL-18 variant polypeptide.

In some embodiments, the method of the present invention is useful for treating or preventing a tumor or cancer tumors that have lost surface expression of MHC class I; such as a tumor that has lost B2m, the MHC locus, or has mutations in other members of the antigen presentation and/or antigen loading complex, such as tapasin.

Metabolic diseases and disorders include various metabolic and endocrine-related diseases and disorders. The following are non-limiting examples of metabolic and endocrine-related diseases and disorders that can be treated or prevented by the methods and compositions of the invention: obesity, diabetes, prediabetes, type II diabetes, mature onset diabetes of the young (MODY), hyperglycemia, metabolic syndrome, dyslipidemia, hypertriglyceridemia, and hypercholesterolemia.

Non-limiting examples of other diseases and disorders that can be treated or prevented using the compositions and methods of the invention include viral infections, bacterial infections, parasitic infections, and low immune activity. In some embodiments, the viral infection is at least one of a pox virus, a smallpox virus, molluscum contagiosum, HPV infection, and warts caused by a virus. In some embodiments, the infection is a systemic infection. In some embodiments, the viral infection is a vaccinia virus infection. In some embodiments, the viral infection is a systemic vaccinia virus infection. In some embodiments, the bacterial infection is sepsis. In some embodiments, the low immune activity is neutropenia, for example, as may occur with chemotherapy.

Non-limiting examples of other diseases and disorders that can be treated or prevented using the compositions and methods of the invention include macular degeneration. For example, in some cases the disease or disorder is wet macular degeneration, and in some cases the disease or disorder is wet age-related macular degeneration. In some such cases, the IL-18 variant can be used as an anti-angiogenic. For example, a subject IL-18 variant polypeptide can in some cases attenuate choroidal neovascularization.

Thus, the present invention relates to the prevention and treatment of a disease or disorder by administration of a therapeutically effective amount of an IL-18 variant polypeptide, a recombinant IL-18 variant polypeptide, an active IL-18 variant polypeptide fragment (e.g., IL-18 variant peptide, etc.), an activator of IL-18 variant expression or activity, or a nucleic acid (e.g., DNA, cDNA, mRNA, etc.) that encodes at least one IL-18 variant polypeptide, to a cell, tissue, organ, or subject in need thereof, for the treatment or prevention of a disease or disorder, or its associated signs, symptoms or pathologies.

In some embodiments, a composition of the invention is administered to a cell, tissue, organ, system, or subject to treat or prevent a disease or disorder. In some embodiments, a human IL-18 variant polypeptide is administered to a cell, tissue, organ, system, or subject. In some embodiments, a nucleic acid (e.g., DNA, cDNA, mRNA, etc.) encoding at least one human IL-18 variant polypeptide is administered to a cell, tissue, organ, system, or subject.

In various embodiments, the human IL-18 variant polypeptide, or fragment thereof, comprises at least one mutation (e.g., at least 2, at least 3, at least 4, at least 5, or at least 6 mutations) selected from the group consisting of Y1X, L5X, K8X, M51X, K53X, S55X, Q56X, P57X, G59X, M60X, E77X, Q103X, S105X, D110X, N111X, M113X, V153X, and N155X, wherein X denotes any amino acid. In various embodiments, the human IL-18 variant polypeptide, or fragment thereof, comprises at least 4 mutations selected from the group consisting of Y1X, L5X, K8X, M51X, K53X, S55X, Q56X, P57X, G59X, M60X, E77X, Q103X, S105X, D110X, N111X, M113X, V153X, and N155X, wherein X denotes any amino acid. In various embodiments, the human IL-18 variant polypeptide, or fragment thereof, comprises at least 6 mutations selected from the group consisting of Y1X, L5X, K8X, M51X, K53X, S55X, Q56X, P57X, G59X, M60X, E77X, Q103X, S105X, D110X, N111X, M113X, V153X, and N155X. In various embodiments, the human IL-18 variant polypeptide, or fragment thereof, comprises at least one mutation (e.g., at least 2, at least 3, at least 4, at least 5, or at least 6 mutations) selected from the group consisting of Y1X, L5X, K8X, S55X, Q56X, P57X, G59X, E77X, Q103X, S105X, D110X, N111X, M113X, V153X, and N155X.

In some embodiments, a human IL-18 variant polypeptide, or fragment thereof, comprises at least one mutation (e.g., at least 2, at least 3, at least 4, at least 5, or at least 6 mutations) selected from the group consisting of Y1H, Y1R, L5H, L5I, L5Y, K8Q, K8R, M51T, M51K, M51D, M51N, M51E, M51R, K53R, K53G, K53S, K53T, S55K, S55R, Q56E, Q56A, Q56R, Q56V, Q56G, Q56K, Q56L, P57L, P57G, P57A, P57K, G59T, G59A, M60K, M60Q, M60R, M60L, E77D, Q103E, Q103K, Q103P, Q103A, Q103R, S105R, S105D, S105K, S105N, S105A, D110H, D110K, D110N, D110Q, D110E, D110S, D110G, N111H, N111Y, N111D, N111R, N111S, N111G, M113V, M113R, M113T, M113K, V153I, V153T, V153A, N155K, and N155H. In some embodiments, a human IL-18 variant polypeptide comprises at least one IL-18 variant polypeptide, or fragment thereof, selected from the group consisting of hCS1 (SEQ ID NO: 34), hCS2 (SEQ ID NO: 35), hCS3 (SEQ ID NO: 36), hCS4 (SEQ ID NO: 37), hC4 (SEQ ID NO: 38), hA8 (SEQ ID NO: 39), hD6 (SEQ ID NO: 40), hH12 (SEQ ID NO: 41), hB11 (SEQ ID NO: 42), hC3 (SEQ ID NO: 43), hC2 (SEQ ID NO: 44), hG10 (SEQ ID NO: 45), hG1 (SEQ ID NO: 46), hF1 (SEQ ID NO: 47), hD2 (SEQ ID NO: 48), hA1 (SEQ ID NO: 49), hB3 (SEQ ID NO: 50), hB4 (SEQ ID NO: 51), hH3 (SEQ ID NO: 52), hH5 (SEQ ID NO: 53), hH4 (SEQ ID NO: 54), hE1 (SEQ ID NO: 55), hG2 (SEQ ID NO: 56), hB9 (SEQ ID NO: 57), hE12 (SEQ ID NO: 58), hC5 (SEQ ID NO: 59), 5-18 (SEQ ID NO: 73), 5-29 (SEQ ID NO: 74), 5-8 (SEQ ID NO: 75), 5-6 (SEQ ID NO: 76), 5-27 (SEQ ID NO: 77), 5-20 (SEQ ID NO: 78), 5-2 (SEQ ID NO: 79), 5-9 (SEQ ID NO: 80), 5-42 (SEQ ID NO: 81), 5-13 (SEQ ID NO: 82), 5-12 (SEQ ID NO: 83), 5-1 (SEQ ID NO: 84), 5-33 (SEQ ID NO: 85), 5-21 (SEQ ID NO: 86), 6-31 (SEQ ID NO: 87), 6-20 (SEQ ID NO: 88), 6-12 (SEQ ID NO: 89), 6-27 (SEQ ID NO: 90), 6-29 (SEQ ID NO: 91), 5-26 (SEQ ID NO: 191), 5-17 (SEQ ID NO: 192), 5-41 (SEQ ID NO: 193), or a fragment thereof.

In some cases a subject DR-IL-18 variant, or fragment thereof, includes at least one mutation (e.g., at least 2, at least 3, or at least 4 mutations) selected from the group consisting of M51X, M60X, S105X, D110X, and N111X, relative to SEQ ID NO: 30. In some cases a subject DR-IL-18 variant, or fragment thereof, includes at least 3 mutations selected from the group consisting of M51X, M60X, S105X, D110X, and N111X, relative to SEQ ID NO: 30. In some cases a subject DR-IL-18 variant, or fragment thereof, includes at least one mutation (e.g., at least 2, at least 3, or at least 4 mutations) selected from the group consisting of M51$X_1$, M60$X_2$, S105$X_3$, D110$X_4$, and N111$X_5$, relative to SEQ ID NO: 30, where $X_1$ is T, K, D, E, R, or N; $X_2$ is K, Q, L, or R; $X_3$ is R, D, K, A, or N; $X_4$ is H, K, N, Q, E, N, S, or G; and $X_5$ is H, D, Y, R, S, or G. In some cases a subject DR-IL-18 variant, or fragment thereof, includes at least 3 mutations selected from the group consisting of M51$X_1$, M60$X_2$, S105$X_3$, D110$X_4$, and N111$X_5$, relative to SEQ ID NO: 30, where $X_1$ is T, K, D, E, R, or N; $X_2$ is K, Q, L, or R; $X_3$ is R, D, K, A, or N; $X_4$ is H, K, N, Q, E, N, S, or G; and $X_5$ is H, D, Y, R, S, or G. In some cases a subject DR-IL-18 variant, or fragment thereof, includes at least one mutation (e.g., at least 2, at least 3, or at least 4 mutations) selected from the group consisting of M51$X_1$, M60$X_2$, S105$X_3$, D10 $X_4$, and N111$X_5$, relative to SEQ ID NO: 30, where $X_1$ is T or K; $X_2$ is K or L; $X_3$ is D, N, or A; $X_4$ is K, N, S, or G; and $X_5$ is H, Y, G, or R.

In some cases a subject DR-IL-18 variant, or fragment thereof, includes the mutations M51X, M60X, S105X, D110X, and N111X, relative to SEQ ID NO: 30. For example, in some cases a subject DR-IL-18 variant, or fragment thereof, includes the mutations M51$X_1$, M60$X_2$, S105$X_3$, D110$X_4$, and N111$X_5$, relative to SEQ ID NO: 30, where $X_1$ is T, K, D, E, R, or N; $X_2$ is K, Q, L, or R; $X_3$ is R, D, K, A, or N; $X_4$ is H, K, N, Q, E, N, S, or G; and $X_5$ is H, D, Y, R, S, or G. In some cases a subject DR-IL-18 variant, or fragment thereof, includes the mutations M51$X_1$, M60$X_2$, S105$X_3$, D110$X_4$, and N111$X_5$, relative to SEQ ID NO: 30, where $X_1$ is T or K; $X_2$ is K or L; $X_3$ is D, N, or A; $X_4$ is K, N, S, or G; and $X_5$ is H, Y, G, or R. In other words, in some cases a subject DR-IL-18 variant, or fragment thereof, includes the mutations {M51T or M51K}; {M60K or M60L}; {S105D, S105N, S105A}; {D110K, D110N, D110S, or D110G}; and {N111H, N111Y, N111R, or N111G}, relative to SEQ ID NO: 30.

In some cases a subject DR-IL-18 variant, or fragment thereof, includes at least one mutation (e.g., at least 2, at least 3, or at least 4 mutations) selected from the group consisting of M51X, K53X, Q56X, S105X, and N111X, relative to SEQ ID NO: 30. In some cases a subject DR-IL-18 variant, or fragment thereof, includes at least 3 mutations selected from the group consisting of M51X, K53X, Q56X, S105X, and N111X, relative to SEQ ID NO: 30. In some cases a subject DR-IL-18 variant, or fragment thereof, includes at least one mutation (e.g., at least 2, at least 3, or at least 4 mutations) selected from the group consisting of M51$X_1$, K53$X_2$, Q56$X_3$, S105$X_4$, and N111$X_5$, relative to SEQ ID NO: 30, where $X_1$ is E, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, includes at least 3 mutations selected from the group consisting of M51$X_1$, K53$X_2$, Q56$X_3$, S105$X_4$, and N111$X_5$, relative to SEQ ID NO: 30, where $X_1$ is E, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, includes at least one mutation (e.g., at least 2, at least 3, or at least 4 mutations) selected from the group consisting of M51$X_1$, K53$X_2$, Q56$X_3$, S105$X_4$, and N111$X_5$, relative to SEQ ID NO: 30, where $X_1$ is K; $X_2$ is G or S; $X_3$ is G, R, or L; $X_4$ is S, N, or G; and $X_5$ is G or R.

In some cases a subject DR-IL-18 variant, or fragment thereof, includes the mutations M51X, K53X, Q56X, S105X, and N111X, relative to SEQ ID NO: 30. For example, in some cases a subject DR-IL-18 variant, or fragment thereof, includes the mutations M51$X_1$, K53$X_2$, Q56$X_3$, S105$X_4$, and N111$X_5$, relative to SEQ ID NO: 30, where $X_1$ is E, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, includes the mutations M51$X_1$, K53$X_2$, Q56$X_3$, S105$X_4$, and N111$X_5$, relative to SEQ ID NO: 30, where $X_1$ is K; $X_2$ is G or S; $X_3$ is G, R, or L; $X_4$ is S, N, or G; and $X_5$ is G or R. In other words, in some cases a subject DR-IL-18 variant, or fragment thereof, includes the mutations {M51K}; {K53G or K53S}; {Q56G, Q56R, or Q56L}; {D110S, D110N, or D110G}; and {N111R, or N111G}, relative to SEQ ID NO: 30.

In some cases a subject DR-IL-18 variant, or fragment thereof, comprises an amino acid sequence having 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30. As such in some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) relative to wild type IL-18 (e.g., human IL-18).

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of Y1X, L5X, K8X, M51X, K53X, S55X, Q56X, P57X, G59X, M60X, E77X, Q103X, S105X, D110X, N111X, M113X, V153X, and N155X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 4 mutations selected from the group consisting of Y1X, L5X, K8X, M51X, K53X, S55X, Q56X, P57X, G59X, M60X, E77X, Q103X, S105X, D110X, N111X, M113X, V153X, and N155X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 6 mutations selected from the group consisting of Y1X, L5X, K8X, M51X, K53X, S55X, Q56X, P57X, G59X, M60X, E77X, Q103X, S105X, D110X, N111X, M113X, V153X, and N155X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of Y1X, L5X, K8X, S55X, Q56X, P57X, G59X, E77X, Q103X, S105X, D110X, N111X, M113X, V153X, and N155X, relative to SEQ ID NO: 30.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51X, M60X, S105X, D110X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 3 mutations (e.g., at least 2, at least 3, or at least 4 mutations) selected from the group consisting of M51X, M60X, S105X, D110X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51$X_1$, M60$X_2$, S105$X_3$, D10$X_4$, and N111$X_5$, relative to SEQ ID NO: 30, where $X_1$ is T, K, D, E, R, or N; $X_2$ is K, Q, L, or R; $X_3$ is R, D, K, A, or N; $X_4$ is H, K, N, Q, E, N, S, or G;

and $X_5$ is H, D, Y, R, S, or G. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 3 mutations selected from the group consisting of M51$X_1$, M60$X_2$, S105$X_3$, D110$X_4$, and N111$X_5$, relative to SEQ ID NO: 30, where $X_1$ is T, K, D, E, R, or N; $X_2$ is K, Q, L, or R; $X_3$ is R, D, K, A, or N; $X_4$ is H, K, N, Q, E, N, S, or G; and $X_5$ is H, D, Y, R, S, or G. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51$X_1$, M60$X_2$, S105$X_3$, D110$X_4$, and N111$X_5$, relative to SEQ ID NO: 30, where $X_1$ is T or K; $X_2$ is K or L; $X_3$ is D, N, or A; $X_4$ is K, N, S, or G; and $X_5$ is H, Y, G, or R.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51X, M60X, S105X, D110X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51$X_1$, M60$X_2$, S105$X_3$, D110$X_4$, and N111$X_5$, relative to SEQ ID NO: 30, where $X_1$ is T, K, D, E, R, or N; $X_2$ is K, Q, L, or R; $X_3$ is R, D, K, A, or N; $X_4$ is H, K, N, Q, E, N, S, or G; and $X_5$ is H, D, Y, R, S, or G. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51$X_1$, M60$X_2$, S105$X_3$, D110$X_4$, and N111$X_5$, relative to SEQ ID NO: 30, where $X_1$ is T or K; $X_2$ is K or L; $X_3$ is D, N, or A; $X_4$ is K, N, S, or G; and $X_5$ is H, Y, G, or R.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51X, K53X, Q56X, S105X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 3 mutations selected from the group consisting of M51X, K53X, Q56X, S105X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51$X_1$, K53$X_2$, Q56$X_3$, S105$X_4$, and N111$X_5$, relative to SEQ ID NO: 30, where $X_1$ is E, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 3 mutations selected from the group consisting of M51$X_1$, K53$X_2$, Q56$X_3$, S105$X_4$, and N111$X_5$, relative to SEQ ID NO: 30, where $X_1$ is E, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51$X_1$, K53$X_2$, Q56$X_3$, S105$X_4$, and N111$X_5$, relative to SEQ ID NO: 30, where $X_1$ is K; $X_2$ is G or S; $X_3$ is G, R, or L; $X_4$ is S, N, or G; and $X_5$ is G or R.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51X, K53X, Q56X, S105X, and N111X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51$X_1$, K53$X_2$, Q56$X_3$, S105$X_4$, and N111$X_5$, relative to SEQ ID NO: 30, where $X_1$ is E, R, or K; $X_2$ is G, S, or T; $X_3$ is E, A, R, V, G, K, or L; $X_4$ is N, S, K, or G; and $X_5$ is R, S, G, or D. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51$X_1$, K53$X_2$, Q56$X_3$, S105$X_4$, and N111$X_5$, relative to SEQ ID NO: 30, where $X_1$ is K; $X_2$ is G or S; $X_3$ is G, R, or L; $X_4$ is S, N, or G; and $X_5$ is G or R.

In various embodiments, the IL-18 variant polypeptide that binds to and inhibits IL-18BP comprises a human IL-18 variant polypeptide, or fragment thereof, comprising at least one mutation (e.g., at least 2, at least 3, at least 4, at least 5, or at least 6 mutations) selected from the group consisting of Y1X, L5X, D17X, E31X, T34X, D35X, S36X, D37X, D40X, N41X, M51X, Q56X, M60X, Q103X, H109X, M113X, and R131X, wherein X denotes any amino acid. In some embodiments, the IL-18 variant polypeptide that binds to and inhibits IL-18BP comprises a human IL-18 variant polypeptide, or fragment thereof, comprising at least one mutation (e.g., at least 2, at least 3, at least 4, at least 5, or at least 6 mutations) selected from the group consisting of Y1D, Y1F, Y1H, Y1L, L5F, L5H, D17A, D17G, D17R, D17H, E31A, E31T, E31G, E31K, E31R, T34A, T34K T34E, D35S, D35A, D35Y, S36N, S36K, S36R, D37P, D37A, D37R, D37H, D37L, D37V, D40Y D40S, D40A, N41K, N41S, N41R, M51F, M51L, M511, Q56H, M60L, M60F, M601, Q103L, Q1031, H109A, H1109P, H109D, M113L, M1131, M113F, and R131S. In some embodiments, the IL-18 variant polypeptide that binds to and inhibits IL-18BP comprises a human IL-18 variant polypeptide, or fragment thereof, selected from the group consisting of hD2D-5F12 (SEQ ID NO: 92), hD2D-5F11 (SEQ ID NO: 93), hD2D-5F10 (SEQ ID NO: 94), hD2D-5F08 (SEQ ID NO: 95), hD2D-5F06 (SEQ ID NO: 96), hD2D-5F04 (SEQ ID NO: 97), hD2D-5F02 (SEQ ID NO: 98), hD2D-5F01 (SEQ ID NO: 99), hD2D-5E10 (SEQ ID NO: 100), hD2D-5E08 (SEQ ID NO: 101), hD2D-5E03 (SEQ ID NO: 102), hD2D-5E02 (SEQ ID NO: 103), hD2D-5D10 (SEQ ID NO: 104), hD2D-5D08 (SEQ ID NO: 105), hD2D-5D06 (SEQ ID NO: 106), hD2D-5D05 (SEQ ID NO: 107), hD2D-5D03 (SEQ ID NO: 108), hD2D-5D02 (SEQ ID NO: 109), hD2D-5C10 (SEQ ID NO: 110), hD2D-5C09 (SEQ ID NO: 111), hD2D-5C08 (SEQ ID NO: 112), hD2D-5C05 (SEQ ID NO: 113), hD2D-5C04 (SEQ ID NO: 114), hD2D-5C03 (SEQ ID NO: 115), hD2D-5B11 (SEQ ID NO: 116), hD2D-5B10 (SEQ ID NO: 117), hD2D-5B06 (SEQ ID NO: 118), hD2D-5B05 (SEQ ID NO: 119), hD2D-5B02 (SEQ ID NO: 120), hD2D-5A09 (SEQ ID NO: 121), hD2D-5A02 (SEQ ID NO: 122), hD2D-CS1 (SEQ ID NO: 123), hD2D-CS2 (SEQ ID NO: 124), hD2D-CS3 (SEQ ID NO: 125), or a fragment thereof.

In some cases a subject D2D-IL-18 variant, or fragment thereof, includes at least one mutation (e.g., at least 2, at least 3, or at least 4 mutations) selected from the group consisting of D17X, E30X, and Q103X, relative to SEQ ID NO: 30. In some cases a subject D2D-IL-18 variant, or fragment thereof, includes at least one mutation (e.g., at least 2, at least 3, or at least 4 mutations) selected from the group consisting of D17$X_1$, E30$X_2$, and Q103$X_3$, relative to SEQ ID NO: 30, where $X_1$ is G, H, R, or A; $X_2$ is A, T, G, K, or R; and $X_3$ is I or L. In some cases a subject D2D-IL-18 variant, or fragment thereof, includes at least one mutation (e.g., at least 2, at least 3, or at least 4 mutations) selected from the group consisting of D17G, E30A, and (Q103L or Q1031).

In some cases a subject D2D-IL-18 variant, or fragment thereof, includes the mutations D17X, E30X, and Q103X, relative to SEQ ID NO: 30. For example, in some cases a subject D2D-IL-18 variant, or fragment thereof, includes the mutations D17$X_1$, E30$X_2$, and Q103$X_3$, relative to SEQ ID NO: 30, where $X_1$ is G, H, R, or A; $X_2$ is A, T, G, K, or R; and $X_3$ is I or L. In some cases a subject D2D-IL-18 variant, or fragment thereof, includes the mutations D17G, E30A, and (Q103L or Q103I).

In some cases a subject D2D-IL-18 variant, or fragment thereof, includes at least one mutation (e.g., at least 2, at least 3, or at least 4 mutations) selected from the group consisting of D17X, E30X, D35X, M51X, and Q103X, relative to SEQ ID NO: 30. In some cases a subject D2D-IL-18 variant, or fragment thereof, includes at least one mutation (e.g., at least 2, at least 3, or at least 4 mutations) selected from the group consisting of D17$X_1$, E30$X_2$, D35$X_3$, M51$X_4$, and Q103$X_3$, relative to SEQ ID NO: 30, where $X_1$ is G, H, R, or A; $X_2$ is A, T, G, K, or R; $X_3$ is S, A, or Y; $X_4$ is F, I, or L; and $X_5$ is I or L. In some cases a subject D2D-IL-18 variant, or fragment thereof, includes at least one mutation (e.g., at least 2, at least 3, or at least 4 mutations) selected from the group consisting of D17G, E30A, D35S, M51F, and (Q103L or Q1031), relative to SEQ ID NO: 30.

In some cases a subject D2D-IL-18 variant, or fragment thereof, includes the mutations D17X, E30X, D35X, M51X, and Q103X, relative to SEQ ID NO: 30. For example, in some cases a subject D2D-IL-18 variant, or fragment thereof, includes the mutations D17$X_1$, E30$X_2$, D35$X_3$, M51$X_4$, and Q103$X_3$, relative to SEQ ID NO: 30, where $X_1$ is G, H, R, or A; $X_2$ is A, T, G, K, or R; $X_3$ is S, A, or Y; $X_4$ is F, I, or L; and $X_5$ is I or L. In some cases a subject D2D-IL-18 variant, or fragment thereof, includes the mutations D17G, E30A, D35S, M51F, and (Q103L or Q103I), relative to SEQ ID NO: 30.

In some cases a subject D2D-IL-18 variant, or fragment thereof, comprises an amino acid sequence having 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30. As such in some cases a subject D2D-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) relative to wild type IL-18 (e.g., human IL-18).

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of Y1X, L5X, D17X, E31X, T34X, D35X, S36X, D37X, D40X, N41X, M51X, Q56X, M60X, Q103X, H109X, M113X, and R131X.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of D17X, E30X, and Q103X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of D17$X_1$, E30$X_2$, and Q103$X_3$, relative to SEQ ID NO: 30, where $X_1$ is G, H, R, or A; $X_2$ is A, T. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of D17G, E30A, and (Q103L or Q103I).

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations D17X, E30X, and Q103X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations D17$X_1$, E30$X_2$, and Q103$X_3$, relative to SEQ ID NO: 30, where $X_1$ is G, H, R, or A; $X_2$ is A, T. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations D17G, E30A, and (Q103L or Q1031).

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of D17X, E30X, D35X, M51X, and Q103X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of D17$X_1$, E30$X_2$, D35$X_3$, M51$X_4$, and Q103$X_3$, relative to SEQ ID NO: 30, where $X_1$ is G, H, R, or A; $X_2$ is A, T, G, K, or R; $X_3$ is S, A, or Y; $X_4$ is F, I, or L; and $X_5$ is I or L. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) selected from the group consisting of D17G, E30A, D35S, M51F, and (Q103L or Q1031), relative to SEQ ID NO: 30.

In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations D17X, E30X, D35X, M51X, and Q103X, relative to SEQ ID NO: 30. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations D17$X_1$, E30$X_2$, D35$X_3$, M51$X_4$, and Q103$X_3$, relative to SEQ ID NO: 30, where $X_1$ is G, H, R, or A; $X_2$ is A, T, G, K, or R; $X_3$ is S, A, or Y; $X_4$ is F, I, or L; and $X_5$ is I or L. In some cases a subject DR-IL-18 variant, or fragment thereof, comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations D17G, E30A, D35S, M51F, and (Q103L or Q103I), relative to SEQ ID NO: 30.

In some embodiments, a composition of the invention is administered to a murine cell, tissue, organ, system, or subject to treat or prevent a disease or disorder. In some embodiments, a murine IL-18 variant polypeptide, or a fragment thereof, is administered to a cell, tissue, organ, system, or subject (e.g., a human cell, tissue, organ, system, or subject). In some embodiments, a nucleic acid (e.g., DNA, cDNA, mRNA, etc.) encoding at least one murine IL-18 variant polypeptide is administered to a cell, tissue, organ, system, or subject.

In some embodiments, a murine IL-18 variant polypeptide, or a fragment thereof, comprises at least one mutation (e.g., at least 2, at least 3, at least 4, at least 5, or at least 6 mutations) selected from the group consisting of NIX, M50X, Y51X, K52X, S54X, E55X, V56X, R57X, G58X, L59X, R104X, N109X, and L151X, wherein X denotes any amino acid. In some embodiments, a murine IL-18 variant polypeptide, or fragment thereof, comprises at least one mutation (e.g., at least 2, at least 3, at least 4, at least 5, or at least 6 mutations) selected from the group consisting of N1H, N1Y, M50A, M50S, M50V, M50G, M50T, Y51R, K52V, K52S, K52T, K52G, K52A, S54R, S54K, S54G, S54N, E55R, E55H, E55N, E55D, E55G, V56L, V56M, V56R, V56A, V56S, V56Q, R57G, R57K, G58A, L59K, L59R, L59V, R104K, R104L, R104Q, R104S, N109D, and L151V. In some embodiments, a murine IL-18 variant polypeptide comprises at least one variant selected from the group consisting of mCS1 (SEQ ID NO: 60), mCS2 (SEQ ID NO: 61), mC1 (SEQ ID NO: 62), mA12 (SEQ ID NO: 63), mE8 (SEQ ID NO: 64), mC10 (SEQ ID NO: 65), mB7 (SEQ ID NO: 66), mB1 (SEQ ID NO: 67), mD1 (SEQ ID NO: 68), mH7 (SEQ ID NO: 69), mA7 (SEQ ID NO: 70), mE1 (SEQ ID NO: 71), and mH3 (SEQ ID NO: 72), or a fragment thereof.

In some embodiments, the IL-18 variant polypeptide that binds to and inhibits IL-18BP comprises a murine IL-18 variant polypeptide comprising at least one mutation (e.g., at least 2, at least 3, at least 4, at least 5, or at least 6 mutations) selected from the group consisting of NIX, L5X, D17X, E30X, T33X, D34X, 135X, D36X, M50X, Q102X, R104, H108X, N109X, M111X, D129X, and D130X, wherein X denotes any amino acid. In some embodiments, the IL-18 variant polypeptide that binds to and inhibits IL-18BP comprises a murine IL-18 variant polypeptide, or fragment thereof, comprising at least one mutation (e.g., at least 2, at least 3, at least 4, at least 5, or at least 6 mutations) selected from the group consisting of N1Y, N1D, N1H, NIL, N1F, N1V, N1I, L5Y, L5H, D17Q, D17G, D17A, D17E, D17S, D17N, E30A, E30R, E30K, E30T, E30G, T33G, T33A, T33E, T33R, T33K, D34Y, D34S, D34A, 135T, 135K, 135R, D36V, D36A, D36G, D36H, D36P, D36R, D36L, M50F, M50L, Q102L, Q102I, R104E, R104A, R104P, R104G, R104Q, R104H, H108D, H108A, N109R, N109S, N109T, N1091, M111 L, M111I, D129A, D129F, D129V, D129Y, D129S, D130E, D130T, D130G, D130N, D130R, D130S, D130Q, and D130H. the IL-18 variant polypeptide that binds to and inhibits IL-18BP comprises a murine IL-18 variant polypeptide, or fragment thereof, selected from the group consisting of mD2D-A5 (SEQ ID NO: 126), mD2D-A6 (SEQ ID NO: 127), mD2D-A7 (SEQ ID NO: 128), mD2D-A8 (SEQ ID NO: 129), mD2D-A9 (SEQ ID NO: 130), mD2D-A11 (SEQ ID NO: 131), mD2D-A12 (SEQ ID NO: 132), mD2D-B4 (SEQ ID NO: 133), mD2D-B7 (SEQ ID NO: 134), mD2D-B11 (SEQ ID NO: 135), mD2D-B12 (SEQ ID NO: 136), mD2D-C1 (SEQ ID NO: 137), mD2D-C3 (SEQ ID NO: 138), mD2D-C5 (SEQ ID NO: 139), mD2D-C6 (SEQ ID NO: 140), mD2D-C9 (SEQ ID NO: 141), mD2D-C10 (SEQ ID NO: 142), mD2D-C11 (SEQ ID NO: 143), mD2D-D1 (SEQ ID NO: 144), mD2D-D9 (SEQ ID NO: 145), mD2D-D12 (SEQ ID NO: 146), mD2D-E3 (SEQ ID NO: 147), mD2D-E4 (SEQ ID NO: 148), mD2D-E5 (SEQ ID NO: 149), mD2D-E7 (SEQ ID NO: 150), mD2D-E8 (SEQ ID NO: 151), mD2D-E9 (SEQ ID NO: 152), mD2D-E10 (SEQ ID NO: 153), mD2D-E11 (SEQ ID NO: 154), mD2D-E12 (SEQ ID NO: 155), mD2D-F3 (SEQ ID NO: 156), mD2D-F4 (SEQ ID NO: 157), mD2D-F5 (SEQ ID NO: 158), mD2D-F7 (SEQ ID NO: 159), mD2D-F8 (SEQ ID NO: 160), mD2D-F9 (SEQ ID NO: 161), mD2D-G1 (SEQ ID NO: 162), mD2D-G7 (SEQ ID NO: 163), mD2D-G9 (SEQ ID NO: 164), mD2D-H7 (SEQ ID NO: 165), mD2D-E1 (SEQ ID NO: 166), mD2D-G8 (SEQ ID NO: 167), mD2D-H3 (SEQ ID NO: 168), mD2D-A10 (SEQ ID NO: 169), mD2D-H1 (SEQ ID NO: 170), mD2D-F12 (SEQ ID NO: 171), mD2D-G10 (SEQ ID NO: 172), mD2D-G12 (SEQ ID NO: 173), mD2D-E2 (SEQ ID NO: 174), mD2D-G11 (SEQ ID NO: 175), mD2D-C4 (SEQ ID NO: 176), mD2D-F11 (SEQ ID NO: 177), mD2D-C2 (SEQ ID NO: 178), mD2D-F10 (SEQ ID NO: 179), mD2D-A2 (SEQ ID NO: 180), mD2D-F6 (SEQ ID NO: 181), mD2D-A1 (SEQ ID NO: 182), mD2D-E6 (SEQ ID NO: 183), mD2D-D4 (SEQ ID NO: 184), mD2D-D6 (SEQ ID NO: 185), mD2D-A3 (SEQ ID NO: 186), mD2D-A4 (SEQ ID NO: 187), mD2D-B10 (SEQ ID NO: 188), mD2D-B8 (SEQ ID NO: 189), mD2D-B9 (SEQ ID NO: 190), or a fragment thereof.

In some embodiments, the method comprises administering to a subject, cell, or tissue, an isolated nucleic acid molecule encoding on or more of the IL-18 variant peptides described herein.

It will be understood by one skilled in the art that an increase in the level of IL-18 signaling through the IL-18R encompasses an increase in the amount of IL-18 or IL-18 variant polypeptide available for binding to and activating IL-18R. This can be accomplished by increasing the level or activity of IL-18 which includes, but is not limited to, the direct or indirect administration of IL-18, the direct or indirect administration of an IL-18 variant polypeptide, and the direct or indirect administration of an inhibitor of IL-18BP, as well as increasing transcription, translation, or both, of a nucleic acid encoding IL-18 or an IL-18 variant polypeptide; and it also includes increasing any activity of IL-18 or IL-18 variant polypeptide as well.

The increased level of IL-18 signaling, including by using an IL-18 variant polypeptide, can be assessed using a wide variety of methods, including those disclosed herein, as well as methods known in the art or to be developed in the future. That is, the routineer would appreciate, based upon the disclosure provided herein, that increasing the level or activity of IL-18 signaling can be readily assessed using methods that assess the level of a nucleic acid (e.g., mRNA) encoding IL-18 or an IL-18 variant polypeptide or fragment thereof, the level of IL-18 or an IL-18 variant polypeptide or fragment polypeptide, and/or the level of IL-18 or an IL-18 variant polypeptide or fragment activity in a biological sample obtained from a subject.

One skilled in the art, based upon the disclosure provided herein, would understand that the invention is useful in subjects who, in whole (e.g., systemically) or in part (e.g., locally, cell, tissue, organ), are being or will be, treated for a disease or disorder where an increase in IL-18 signaling activity would be beneficial. The skilled artisan will appreciate, based upon the teachings provided herein, that the diseases and disorders treatable by the compositions and methods described herein encompass any disease or disorder wherein an increase in IL-18 signaling will promote a positive biologic, physiologic, clinical or therapeutic outcome.

One of skill in the art will realize that in addition to increasing IL-18 signaling directly, diminishing the amount or activity of a molecule that itself diminishes the amount or activity of IL-18 signaling can also serve to increase the amount or activity of IL-18 signaling. Thus, an activator of IL-18 activity can include, but should not be construed as being limited to, a chemical compound, a protein, a peptidomimetic, an antibody, a ribozyme, and an antisense nucleic acid molecule. One of skill in the art would readily appreciate, based on the disclosure provided herein, that an activator of IL-18 activity encompasses a compound that increases the level of IL-18 signaling. Additionally, an activator of IL-18 activity encompasses a compound that inhibits the level or activity of a molecule that itself diminishes the amount or activity of IL-18 signaling (i.e., IL-18BP). Contemplated in the present inventions are IL-18BP antagonists that include (but are not limited to) monoclonal antibodies, small molecular therapeutics that neutralize IL-18BP, and an engineered IL-18 variant that binds to IL-18BP but does not substantially bind to or interact with the IL-18R by inhibiting IL-18BP in this manner, the activity of endogenously-produced IL-18 is enhanced through disinhibition.

The skilled artisan will also appreciate, once armed with the teachings of the present invention, that an increase in the level of IL-18 signaling includes an increase in IL-18 level or IL-18 activity (e.g., receptor binding activity, receptor signaling activity, etc.). Thus, increasing the level or activity of IL-18 signaling includes, but is not limited to, increasing the amount of available IL-18 polypeptide or IL-18 variant polypeptide, increasing transcription, translation, or both, of a nucleic acid encoding IL-18 polypeptide or an IL-18 variant polypeptide; and it also includes increasing any activity of an IL-18 polypeptide or IL-18 variant polypeptide as well. The activator of IL-18 activity compositions and methods of the invention can selectively activate IL-18 signaling, or can activate both IL-18 signaling and another molecule or pathway. Thus, the present invention relates to administration of an activator of IL-18 activity, a recombinant activator of IL-18 activity polypeptide, an active activator of IL-18 activity polypeptide fragment, or an activator of IL-18 signaling pathway component expression or activity.

Further, one of skill in the art would, when equipped with this disclosure and the methods exemplified herein, appreciate that an activator of IL-18 activity includes such activators as discovered in the future, as can be identified by well-known criteria in the art of pharmacology, such as the physiological results of activation of IL-18 signaling as described in detail herein and/or as known in the art. Therefore, the present invention is not limited in any way to any particular activator of IL-18 activity as exemplified or disclosed herein; rather, the invention encompasses those activators that would be understood by the routineer to be useful as are known in the art and as are discovered in the future.

Further methods of identifying and producing an activator of IL-18 activity are well known to those of ordinary skill in the art, including, but not limited, obtaining an activator from a naturally occurring source (e.g., *Streptomyces* sp., *Pseudomonas* sp., *Stylotella aurantium*, etc.). Alternatively, an activator of IL-18 activity can be synthesized chemically. Further, the routineer would appreciate, based upon the teachings provided herein, that an activator of IL-18 activity can be obtained from a recombinant organism. Compositions and methods for chemically synthesizing an activator of IL-18 activity, and for obtaining them from natural sources, are well known and are described in the art.

One of skill in the art will appreciate that an activator can be administered as a small molecule chemical, a polypeptide, a nucleic acid construct encoding a polypeptide, or combinations thereof. Numerous vectors and other compositions and methods are well known for administering a polypeptide or a nucleic acid encoding a polypeptide to cells or tissues. Therefore, the invention includes a method of administering a polypeptide or a nucleic acid encoding a polypeptide that is an activator of IL-18 signaling. (Sambrook et al., 2012, Molecular Cloning: A Laboratory Manual, Cold Spring Harbor Laboratory, New York; Ausubel et al., 1997, Current Protocols in Molecular Biology, John Wiley & Sons, New York).

One of skill in the art will realize that diminishing the amount or activity of a molecule that itself diminishes the amount or activity of IL-18 signaling can serve to increase the amount or activity of IL-18 signaling (e.g., IL-18BP). Antisense oligonucleotides are DNA or RNA molecules that are complementary to some portion of a mRNA molecule. When present in a cell, antisense oligonucleotides hybridize to an existing mRNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931). The methods of the invention include the use of an antisense oligonucleotide to diminish the amount of a molecule that causes a decrease in the amount or activity of IL-18 signaling, thereby increasing the amount or activity of IL-18 signaling. Contemplated in the present invention are antisense oligonucleotides that are synthesized and provided to the cell by way of methods well known to those of ordinary skill in the art. As an example, an antisense oligonucleotide can be synthesized to be between about 10 and about 100, more exemplary between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing a protein that diminishes the level or activity of IL-18 signaling can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

One of skill in the art will appreciate that an activator of IL-18 activity, such as an IL-18 variant polypeptide, or fragment thereof, or a nucleic acid (e.g., DNA, cDNA, mRNA, etc.) encoding an IL-18 variant polypeptide, or fragment thereof, can be administered singly or in any combination thereof.

One of skill in the art will also appreciate administration can be acute (e.g., over a short period of time, such as a day, a week or a month) or chronic (e.g., over a long period of time, such as several months or a year or more). Further, an activator of IL-18 activity, such as an IL-18 variant polypeptide or fragment thereof, or a nucleic acid (e.g., DNA, cDNA, mRNA, etc.) encoding an IL-18 variant polypeptide, or fragment thereof, can be administered singly or in any combination thereof, in a temporal sense, in that they may be administered simultaneously, before, and/or after each other. One of ordinary skill in the art will appreciate, based on the disclosure provided herein, that a activator of IL-18 activity, a activator of IL-18 activity polypeptide, a recombinant activator of IL-18 activity polypeptide, or an active activator of IL-18 activity polypeptide fragment can be used alone or in any combination with another activator of IL-18 activity, activator of IL-18 activity polypeptide, recombinant activator of IL-18 activity polypeptide, or active activator of IL-18 activity polypeptide fragment to effect a therapeutic result.

It will be appreciated by one of skill in the art, when armed with the present disclosure including the methods detailed herein, that the invention is not limited to treatment of a disease or disorder once it is established. Particularly, the symptoms of the disease or disorder need not have manifested to the point of detriment to the subject; indeed, the disease or disorder need not be detected in a subject before treatment is administered. That is, significant pathology from disease or disorder does not have to occur before the present invention may provide benefit. Therefore, the present invention, as described more fully herein, includes a method for preventing diseases and disorders in a subject, in that an activator of IL-18 activity molecule (e.g., polypeptide, peptide, etc.), or an activator of IL-18 activity, as discussed elsewhere herein, can be administered to a subject prior to the onset of the disease or disorder, thereby preventing the disease or disorder from developing.

The invention encompasses administration of an activator of IL-18 activity, an activator of IL-18 activity polypeptide, a recombinant IL-18 signaling polypeptide, or an active IL-18 signaling polypeptide fragment to practice the methods of the invention; the skilled artisan would understand, based on the disclosure provided herein, how to formulate and administer the appropriate activator of IL-18 activity, activator of IL-18 activity polypeptide, recombinant IL-18 signaling polypeptide, or active IL-18 signaling polypeptide fragment to a subject. However, the present invention is not limited to any particular method of administration or treatment regimen. This is especially true where it would be appreciated by one skilled in the art, equipped with the disclosure provided herein, including the reduction to practice using an art-recognized model of disease, that methods of administering a activator of IL-18 activity, IL-18 signaling polypeptide, a recombinant IL-18 signaling polypeptide, or an active IL-18 signaling polypeptide fragment can be determined by one of skill in the pharmacological arts.

In some embodiments, a method comprises administering to a subject in need thereof a composition comprising at least one IL-18 variant polypeptide, and administering to the subject a composition comprising an additional agent. In one such embodiment, the additional agent comprises an immunotherapeutic agent comprising at least one selected from the group including, but not limited to an altered T-cell, a chimeric antigen receptor T-cell (CAR-T), an armored CAR-T cell, a virus, an antigen, a vaccine, an antibody, an immune checkpoint inhibitor, a small molecule, a chemotherapeutic agent, and a stem cell. In some embodiments, a composition comprising at least one IL-18 variant polypeptide is used in a method to increase immune system activity before, during, or after infection by a bacterium, virus, or other pathogen. In some embodiments, a composition comprising at least one IL-18 variant polypeptide is used in a method to increase the number and/or activity of immune cells in vitro, in vivo or ex vivo, such as the number and/or activity of T cells, NK cells, and/or myeloid cells.

In some embodiments, the additional agent comprises an inhibitor of one or more cytokines. In some embodiments, the inhibitor of one or more cytokines comprises a chemical compound, a protein, a peptide, a peptidomimetic, an antibody, a ribozyme, a small molecule chemical compound, or an antisense nucleic acid molecule (e.g., siRNA, miRNA, etc.) that inhibits the expression, activity, or both of one or more cytokines. In some embodiments, the inhibitor inhibits the expression, activity, or both of IL-17, IL-5, or IL-3. In some embodiments, the administration of a cytokine inhibitor decreases toxicity. In some embodiments, the administration of a cytokine inhibitor increases efficacy of an administered IL-18 variant polypeptide or IL-18BP inhibitor.

As used herein, the term "pharmaceutically-acceptable carrier" means a chemical composition with which an appropriate IL-18 signaling modulator may be combined and which, following the combination, can be used to administer the appropriate IL-18 signaling modulator thereof, to a subject.

Kits

The present invention also pertains to kits useful in the methods of the invention. Such kits comprise various combinations of components useful in any of the methods described elsewhere herein, including for example, an activator of IL-18 activity, such as an IL-18 variant polypeptide, and/or an IL-18BP inhibitor, and/or materials for quantitatively analyzing IL-18 variant polypeptide or IL-18 variant nucleic acid, and/or materials for assessing the activity of an IL-18 variant polypeptide or an IL-18 variant nucleic acid, and/or instructional material. For example, In some embodiments, the kit comprises components useful for the quantification of IL-18 variant nucleic acid in a biological sample. In another embodiment, the kit comprises components useful for the quantification of IL-18 variant polypeptide in a biological sample. In a further embodiment, the kit comprises components useful for the assessment of the activity (e.g., enzymatic activity, ligand binding activity, etc.) of an IL-18 variant polypeptide in a biological sample.

In a further embodiment, the kit comprises the components of an assay for monitoring the effectiveness of a treatment administered to a subject in need thereof, containing instructional material and the components for determining whether the level of IL-18 signaling in a biological sample obtained from the subject is modulated during or after administration of the treatment. In various embodiments, to determine whether the level of IL-18 signaling is modulated in a biological sample obtained from the subject, the level of IL-18 signaling is compared with the level of at least one comparator control contained in the kit, such as a positive control, a negative control, a historical control, a historical norm, or the level of another reference molecule in the biological sample. In certain embodiments, the ratio of IL-18 signaling and a reference molecule is determined to aid in the monitoring of the treatment.

Pharmaceutical Compositions and Administration

Compositions comprising a polypeptide, a polypeptide fragment, an activator of IL-18 signaling level or activity, or an inhibitor of IL-18BP level or activity, as described elsewhere herein can be formulated and administered to a subject, as now described. By way of non-limiting examples, a composition identified as an activator of IL-18 activity, including IL-18 variant polypeptides, recombinant IL-18 variant polypeptides, and active IL-18 variant polypeptide fragments, for the treatment and/or prevention of a disease or disorder can be formulated and administered to a subject, as now described. By way of more non-limiting examples, a composition identified as a useful IL-18BP inhibitor, including a chemical compound, a protein, a peptide, a peptidomimetic, an antibody, a ribozyme, a small molecule chemical compound, an antisense nucleic acid molecule (e.g., siRNA, miRNA, etc.), for the treatment and/or prevention of a disease or disorder can be formulated and administered to a subject, as now described.

The invention encompasses the preparation and use of pharmaceutical compositions comprising a composition useful for the treatment or prevention of a disease or disorder, disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art. In various embodiments, the active ingredient is a polypeptide, a polypeptide fragment, an activator of IL-18 signaling level or activity, an inhibitor of IL-18BP level or activity, or a combination thereof, as elsewhere described herein.

As used herein, the term "pharmaceutically-acceptable carrier" means a chemical composition with which an appropriate IL-18 signaling modulator thereof, may be combined and which, following the combination, can be used to administer the appropriate modulator (e.g., activator, inhibitor, etc.) thereof, to a subject.

In some embodiments, pharmaceutical compositions can include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

The pharmaceutical compositions useful for practicing the invention may be administered to deliver a dose of between about 0.1 ng/kg/day and 100 mg/kg/day, or more.

In various embodiments, the pharmaceutical compositions useful in the methods of the invention may be administered, by way of example, systemically, parenterally, or topically, such as, in oral formulations, inhaled formulations, including solid or aerosol, and by topical or other similar formulations. In addition to the appropriate therapeutic composition, such pharmaceutical compositions may contain pharmaceutically acceptable carriers and other ingredients known to enhance and facilitate drug administration. Other possible formulations, such as nanoparticles, liposomes, other preparations containing the active ingredient, and immunologically based systems may also be used to administer an appropriate modulator thereof, according to the methods of the invention.

A carrier may bear a subject agent (e.g., IL-18 variant polypeptide) in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. A carrier may also bear a IL-18 variant polypeptide by non-covalent associations, such as non-covalent bonding or by encapsulation. The nature of the carrier can be either soluble or insoluble for purposes of the invention.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Compositions can be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S.

Food and Drug Administration.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Pharmaceutical compositions that are useful in the methods of the invention may be prepared, packaged, or sold in formulations suitable for oral, rectal, vaginal, parenteral, topical, pulmonary, intranasal, buccal, intravenous, transdermal, intralesional, subcutaneous, intramuscular, ophthalmic, intrathecal and other known routes of administration. Other contemplated formulations include projected nanoparticles, liposomal preparations, other preparations containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

Pharmaceutically acceptable excipients used in the manufacture of pharmaceutical compositions include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Liquid formulations of a pharmaceutical composition of the invention may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent.

Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, cutaneous, subcutaneous, intraperitoneal, intravenous, intramuscular, intracisternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In some embodiments of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers. The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers.

Such a formulation is administered in the manner in which snuff is taken i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, contain 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically dosages of the compound of the invention which may be administered to an animal, preferably a human, range in amount from about 0.001 mg to about 1000 mg per kilogram of body weight of the animal. The precise dosage administered will vary depending upon any number of factors, including, but not limited to, the type of animal and type of disease or disorder being treated, the age of the animal and the route of administration. Preferably, the dosage of the compound will vary from about 0.1 mg to about 10 mg per kilogram of body weight of the animal. The compound can be administered to an animal as frequently as several times daily, or it can be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease or disorder being treated, the type and age of the animal, etc.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: IL-18 Variant Polypeptides

IL-18 is a pro-inflammatory cytokine that can stimulate T, NK, and myeloid cells. It has been proposed as an immunotherapeutic agent for cancer given its ability to stimulate anti-tumor immune cells. As demonstrated herein, the therapeutic efficacy of recombinant IL-18 treatment is greatly limited by upregulation of its natural endogenous soluble inhibitor IL-18BP. The present invention is based, in part, on the development of variants of both human and mouse IL-18 that are almost entirely independent of IL-18BP. The cytokine variants exhibit altered relative preference for the receptors (IL-18Rα and IL-18BP) by hundreds of thousands to over a million-fold. These variants have potent anti-tumor activity in preclinical tumor models, both as monotherapies and in combination with immune checkpoint inhibitors such as anti-PD-1. As an additional application, IL-18 also has a well-established anti-obesity role and it is demonstrated herein that administration of the variants greatly reduces body fat composition compared to WT IL-18 treatment. The new variants thus have indications in endocrinology/metabolism/obesity in addition to tumor immunotherapies.

Also described herein are an additional set of IL-18 variants that act as IL-18BP antagonists by exclusively binding IL-18BP with absent or greatly reduced binding IL-18Rα. It is envisaged that these proteins could be used to enhance the activity of endogenous IL-18 by neutralizing IL-18BP.

The materials and methods employed in these experiments are now described.

Protein Expression and Purification

Human IL-18, mouse IL-18 (amino acids 1-157) and variants thereof, were assembled as gBlocks® (Gene fragments) (Integrated DNA Technologies, IDT) and cloned into a pET28a-smt vector for expression of N-terminal sumo-tagged and C-terminal hexahistidine-tagged proteins in E. coli BL21 (DE3) Rosetta strain. Protein expression was induced with 0.5 mM IPTG at 16° C. for 20 hours. The fusion proteins were first purified using Ni-chelating resins, followed by cleavage of the sumo tag with sumo protease. Proteins were then separated from aggregates by successive ammonium sulfate cuts, with aggregates precipitating at 20% ammonium sulfate and the target proteins at 70% ammonium sulfate. Protein pellets were resuspended and applied to Ni-chelating resins again to remove sumo tags, and were subjected to an endotoxin removal wash with 0.1% Triton™ X-114 (polyethylene glycol tert-octylphenyl ether). Finally, eluted protein was buffer exchanged to PBS by PD-10 column (GE Healthcare). Protein sample was tested for monodispersity by size exclusion chromatography using an FPLC (Bio-Rad) and SEC650 column (Bio-Rad).

Human IL-18Rα ectodomain (amino acids 19-329), IL-18Rβ ectodomain (amino acids 15-356), and IL-18BP (amino acids 31-194), were secreted and purified via a baculovirus expression system. In brief, all construct sequences were cloned into the pAcBN-BH3 vector (BD Biosciences) with an N-terminal gp67 signal peptide and a C-terminal AviTag™ (biotinylation tag) and hexahistidine tag. *Spodoptera frugiperda* (Sf9) insect cells cultured at 27° C. in SF900™ II SFM medium (Invitrogen) were transfected with the plasmid constructs to establish high-titer recombinant virus, which was subsequently amplified. Trichopulsia ni (High Five™) insect cells (Invitrogen) grown in Insect-XPRESS™ medium (protein-free insect cell medium, Lonza) at 27° C. were infected with the viruses to express recombinant protein. Three days after infection, proteins were extracted via Ni-NTA (QIAGEN) affinity chromatography, concentrated, and purified to >98% homogeneity with SEC650 sizing column (Bio-Rad) equilibrated in 10 mM HEPES (pH 7.5) and 150 mM NaCl.

Mouse IL-18Rα ectodomain (amino acids 19-329) and IL-18BP (amino acids 31-194) were produced as secreted proteins using the Expi293™ expression system (Thermo Fisher). In brief, all construct sequences were cloned into the BacMam expression vector pEZT_D_Lux with an N-terminal H7 signal peptide and a C-terminal AviTag™ and hexahistidine tag. Expi293™ cells cultured at 37° C. in Expi293™ expression medium (Thermo Fisher) were transfected with plasmids using the ExpiFectamine™ 293 Transfection Kit (Thermo Fisher) according to the manufacturer's instructions. Cells were harvested 3-5 days after transfection. Protein purification procedures were the same as with the human proteins.

For protein biotinylation, AviTag™ GLNDIFEAQKIEWHE (SEQ ID NO:194), a C-terminal biotin acceptor peptide was fused to all IL-18 receptor constructs. Protein biotinylation was carried out with soluble BirA ligase enzyme in 0.1 mM Bicine (pH 8.3), 10 mM ATP, 10 mM magnesium acetate, and 0.5 mM biotin (Sigma). Proteins were purified by size exclusion on a SEC650 column, as described above.

Yeast Display of IL-18

Human and mouse IL-18 gene block (IDT) were synthesized and cloned into the vector pYAL and displayed on the *Saccharomyces cerevisiae* strain EBY100. Individual colonies of IL-18 yeast were grown overnight at 30° C. in SDCAA liquid media and induced in SGCAA liquid media for 1 day at 20° C. IL-18 display levels on yeast were verified by flow cytometry using an anti-cMyc tag antibody (anti-myc-PE; Cell Signaling Technologies). Receptor staining with biotinylated IL-18Rα (with or without IL-18R$) or biotinylated IL-18BP was performed in PBS supplemented with 0.5% BSA and 2 mM EDTA (PBE) on ice. All analysis was performed on a Sony SA3800 flow cytometer.

Human IL-18 Library Construction and Selection

For the first human decoy-resistant IL-18 library, fourteen hIL-18Rα and hIL-18BP contact residues in hIL-18 (Table 1) were identified from homologous positions by aligning the structure of hIL-18/hIL-18Rα/hIL-18Rβ complex (Protein Data Bank (PDB ID) code 3OW4) to the structure of IL-18/IL-18BP (PDB ID 3F62). A library randomizing these residues was constructed using assembly PCR with the degenerate primers listed in Table 2. The library had a theoretical diversity of ~$1.96\times10^{11}$ unique protein sequences. The PCR products were further amplified with primers having homology to the pYAL vector and co-electroporated together with linearized pYAL into EBY100 yeast. The resulting library contained $2.5\times10^{1}$ transformants.

Figures 7A, 7B:
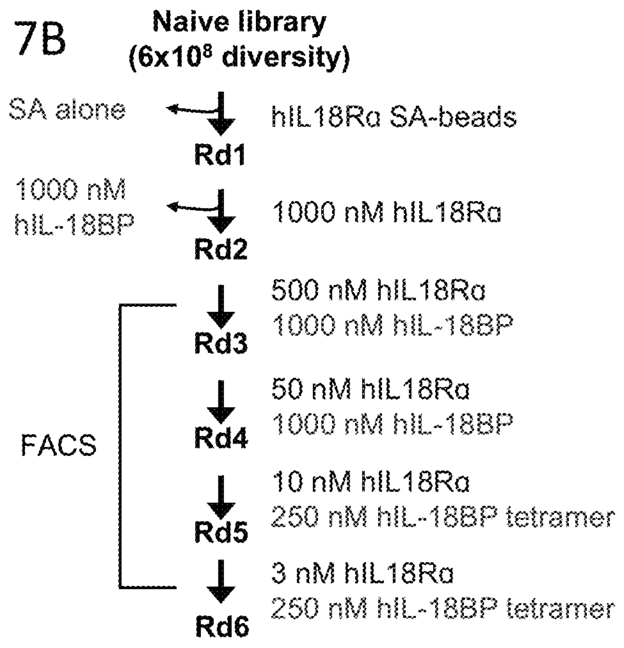
FIG. 7A through FIG. 7C depict results from example experiments demonstrating engineering additional human IL-18 variants for independence to IL-18BP (version 2 variants) using yeast display.

For the second V2.0 human decoy-resistant IL-18 library, eleven hIL-18Rα and hIL-18BP contact residues in hIL-18 were selected to randomize, with a theoretical diversity of $3.44\times10^{9}$ variants (described in FIG. 7A). A library randomizing these residues was constructed using assembly PCR with the degenerate primers and co-electroporated with pYAL into EBY100 yeast. The resulting library had a diversity of $6\times10^{8}$ transformants.

TABLE 1

First Human IL-18 library design

| Residue | Codon | Potential residues |
|---|---|---|
| 1Y | YNT | Y, F, S, C, L, P, H, R |
| L5 | NWT | L, F, I, Y, H, N, V, D |
| 8K | MRA | K, R, R, Q |
| 51M | RNS | M, I, T, N, K, S, R, V, A, D, E, G |
| 53K | ARA | K, R |
| 55S | RRW | S, R, G, G, N, K, D, E |
| 59G | RNA | G, E, A, V, I, T, K, R |
| 60M | VDG | M, K, R, L, Q, R, V, E, G |
| 103Q | VAW | Q, K, E, D, N, H |
| 105S | RRW | S, K, R, N, D, E, G, G |
| 110D | VAW | D, E, K, N, Q, H |
| 111N | NAT | N, D, H, Y |
| 153V | RHT | V, A, D, I, T, N |
| 155N | VAW | N, K, D, E, Q, H |

TABLE 2

First human IL-18 library assembly primers

| Primer | Sequence (5' to 3') |
|---|---|
| hIL18Lib1 | CATTTTCATTAAGATGCAGTTACTTCGCTGTTTTTCAATATTTTCTGTTATTGCTAGC (SEQ ID NO: 1) |
| hIL18Lib2 | AATTACGGATGACCGAAAGTYKGGATTCAWNCTTGCCGAAANRTGCTAAAACGCTAGCAATAACAGAAAATATTGAAAAA (SEQ ID NO: 2) |
| hIL18Lib3 | ACTTTCGGTCATCCGTAATTTGAACGACCAAGTCCTTTTTATTGACCAGGG (SEQ ID NO: 3) |
| hIL18Lib4 | ACTATCCGTCATATCCTCGAATAAGGGACGATTGCCCTGGTCAATAAAAAGGACT (SEQ ID NO: 4) |
| hIL18Lib5 | CTTATTCGAGGATATGACGGATAGTGATTGCCGTGACAACGCCC (SEQ ID NO: 5) |
| hIL18Lib6 | ACTGAGATTGTTACCGCCHBTNYACGGGGTTGWYYATCTYTATASNYAGAGATGATGAAAATTGTACGAGGGGCGTTGTCACGG (SEQ ID NO: 6) |
| hIL18Lib7 | GGCGGTAACAATCTCAGTTAAGTGCGAAAAAATCTCGACACTTTCTTGTGAA (SEQ ID NO: 7) |
| hIL18Lib8 | GGTTCATTTCCTTGAACGAAATGATCTTGTTTTCACAAGAAAGTGTCGAGATT (SEQ ID NO: 8) |
| hIL18Lib9 | CATTTCGTTCAAGGAAATGAACCCGCCGGATAATATCAAGGATACAAAATCAGATATTATTT (SEQ ID NO: 9) |
| hIL18Lib10 | TGATGAGCTCTCGAATTGCATCTTATNWTBGTGTCCAGGCACWYYACGWTBGAAGAAAATAATATCTGATTTTGTATCCTTGATATTA (SEQ ID NONO) |

TABLE 2-continued

| First human IL-18 library assembly primers | |
|---|---|
| Primer | Sequence (5' to 3') |
| hIL18Lib11 | ATAAGATGCAATTCGAGAGCTCATCATACGAAGGTTACTTTTTAGCCTGCG (SEQ ID NO: 11) |
| hIL18Lib12 | AATTAACTTAAACAGGTCGCGCTCCTTCTCGCAGGCTAAAAAGTAACCTT (SEQ ID NO: 12) |
| hIL18Lib13 | GCGACCTGTTTAAGTTAATTCTTAAGAAAGAAGATGAGTTGGGGGATCG (SEQ ID NO: 13) |
| hIL18Lib14 | CCAGAACCACCGTCCTCWTBCTGADYGGTAAACATGATGCTACGATCCCCCAACTCATCTT (SEQ ID NO: 14) |
| hIL18Lib15 | GAGGACGGTGGTTCTGGATCCGAACAAAAGCTTATCTCCGAAGAAGACTTGG (SEQ ID NO: 15) |
| hIL18Lib16 | CCACCAGATCCACCACCACCCAAGTCTTCTTCGGAGATAAG(SEQIDNO: 16) |

For both libraries, transformed yeast were recovered and expanded in liquid synthetic dextrose medium with casamino acids (SDCAA) medium at 30° C. and induced by dilution 1:10 into liquid synthetic galactose medium with casamino acids (SGCAA) medium and cultured at 20° C. for 24 hours. Appropriate numbers of induced yeast were used in each round to ensure at least 10-fold coverage of the expected diversity of the library at each step, and not less than $10^1$ cells. All selection steps were carried out at 4° C. using PBE buffer (PBS with 0.5% BSA and 2 mM EDTA). For the first generation library, each round's selection reagents are listed in Table 3. For round 1, yeast were counter selected with anti-Cy®5 (fluorescent dye)/AlexaFluor® 647 (fluorescent dye) microbeads (Miltenyi) and an LS MACS column (Miltenyi) to remove non-specific bead binders. Positive selection was performed by labeling yeast with 1 μM biotinylated hIL-18Rα for 1 hour at 4° C., followed by magnetic selection with SA/AlexaFluor® 647 microbeads and an LS MACS column. For round 2, counter-selection was performed with 1 μM biotinylated IL-18BP, with positive selection identical to round 1. For rounds 3-5, selection was performed by incubating yeast with 100 nM (rounds 3-4) or 10 nM (round 5) biotinylated IL-18Rα and 250 nM pre-formed, biotin-capped hIL-18BP/SA-PE tetramers. After competition binding, yeast were washed and labeled with SA AlexaFluor® 647 to detect IL-18Rα. Display levels were determined by staining with AlexaFluor® 488-conjugated anti-cMyc (Cell Signaling Technologies), and the top 1% of display-normalized IL-18Rα binders (out of IL-18BP non-binders) were isolated using FACS with a Sony SA3800 cell sorter. After each round of selection, recovered yeast were expanded in SDCAA medium at 30° C. overnight and later induced at 20° C. by a 1:10 dilution into SGCAA medium for 24 hours.

The V2.0 human DR-IL-18 library was selected in a similar fashion, with specific selection steps elaborated in FIG. 7B.

Mouse IL-18 Library Construction and Selection

Construction and selection procedures are similar to human IL-18, with the following changes. Library construction was informed by an in-silico modeled mouse IL-18/receptor complex structure (predicted by Phyer2.0). Thirteen positions were chosen for randomization (Table 3) using primers described in Table 4. Co-electroporation with pYAL yielded a library of $4\times10^8$ transformants. Selection reagents used for each round are listed in Table 5.

TABLE 3

| Mouse IL-18 library design | | |
|---|---|---|
| Residue | Codon | Potential residues |
| 1N | NWT | F, Y, L, H, I, N, V, D |
| 50M | RNS | M, I, T, N, K, S, R, V, A, D, E, G |
| 51Y | NRN | Y, K, R, D, E |
| 52K | VNS | L, P, H, Q, R, I, M, T, N, K, S, V, A, D, E, G |
| 54S | RRW | S, R, G, G, N, K, D, E |
| 55E | VRN | E, K, N, R, S, R, H |
| 56V | VNV | V, S, P, T, A, K, R |
| 57R | RVW | R, D, E, S, T |
| 58G | RNA | G, E, A, V, I, T, K, R |
| 59L | VDR | L, K, R, Q, R, V, E, G |
| 104R | NDH | R, D, E, N, Y, F, I, L, V |
| 109N | NAT | N, D, H, Y |
| 151L | VHY | L, V, A, D, I, T, N |

TABLE 4

| Mouse IL-18 library assembly primers | |
|---|---|
| Primer | Sequence (5' to 3') |
| mIL18lib1 | CATTTTCATTAAGATGCAGTTACTTCGCTGTTTTTCAATATTTTCTGTTATTGCTAGCGTTT (SEQ ID NO: 17) |
| mIL18lib2 | TTGTACAGTGAAGTCGGCCAAAAWNTGCTAAAACGCTAGCAATAACAGAAAATAT (SEQ ID NO: 18) |
| mIL18lib3 | GCCGACTTCACTGTACAACCGCAGTAATACGGAATATAAATGACCAAGTTCTCTTCGTT (SEQ ID NO: 19) |
| mIL18lib4 | TTGATCAATATCAGTCATATCCTCGAACACAGGCTGTCTTTTGTCAACGAAGAGAACTTGGTCATTT (SEQ ID NO: 20) |
| mIL18lib5 | GTGTTCGAGGATATGACTGATATTGATCAAAGTGCCAGTGAACCCCAGACCAGA (SEQ ID NO: 21) |
| mIL18lib6 | TCACAGAGAGGGTCACAGCYHBTNYWBYBNBNYBWYYGTCSNBNYNSNYGTATATTATCAGTCTGGTCTGGGGTTCAC (SEQ ID NO: 22) |
| mIL18lib7 | GCTGTGACCCTCTCTGTGAAGGATAGTAAAATGTCTACCCTCTCCTGTAAGAACAAGA (SEQ ID NO: 23) |
| mIL18lib8 | GTATATCATCAATATTTTCAGGTGGATCCATTTCCTCAAAGGAAATGATCTTGTTCTTACAGGAGAGGG (SEQ ID NO: 24) |
| mIL18lib9 | AATGGATCCACCTGAAAATATTGATGATATACAAAGTGATCTCATATTCTTTCAGAAANDHGTTCCAGGACACNATAAGATGGAGTTTGAATCTTCACT (SEQ ID NO: 25) |
| mIL18lib10 | CCTTTTGGCAAGCAAGAAAGTGTCCTTCATACAGTGAAGATTCAAACTCCATCTTAT (SEQ ID NO: 26) |
| mIL18lib11 | CTTTCTTGCTTGCCAAAAGGAAGATGATGCTTTCAAACTCATTCTGAAAAAAAAGGATGA (SEQ ID NO: 27) |
| mIL18lib12 | CCACCACTTTGATGTAAGTTAGTRDBAGTGAACATTACAGATTTATCCCCATTTTCATCCTTTTTTTTCAGAATGAG (SEQ ID NO: 28) |
| mIL18lib13 | ACTAACTTACATCAAAGTGGTGGTTCTGGATCCGAACAAAAGCTTATCTCCGAAGAAGA (SEQ ID NO: 29) |

TABLE 5

| Summary of library selection reagents | | | | |
|---|---|---|---|---|
| | Human IL-18 library selection | | Mouse IL-18 library selection | |
| | Counter-selection | Positive Selection | Counter-selection | Positive Selection |
| Round1 | SA-beads alone | 1 μM hIL-18Rα-SA-beads | — | 1000 nM IL-18Ra-SA-beads |
| Round2 | 1 μM IL-18BP | 1 μM IL-18Rα-SA-beads | — | 1 μM IL-18Rα |
| Round3 | 1 μM IL-18BP | 100 nM hIL-18Rα | 1 μM IL-18BP | 1 μM IL-18Rα |
| Round4 | 1 μM IL-18BP | 10 nM hIL-18Rα | 1 μM IL-18BP | 100 nM IL-18Rα |
| Round5 | 250 nM IL-18BP tetramer | 10 nM hIL-18Rα | 1 μM IL-18BP | 10 nM IL-18Rα |
| Round6 | — | — | 250 nM IL-18BP tetramer | 200 nM IL-18Rα |

Surface Plasmon Resonance

Experiments were conducted using a Biacore™ T100 (Protein analysis interaction system) and carried out at 25° C. Biotinylated IL-18Rα or IL-18BP were immobilized onto a Biacore™ biotin capture chip (Series S CAP sensor chip, GE Healthcare) to yield an Rmax of ~50 RU (IL-18Rα) or ~10 RU (IL-18BP). Measurements were made with serial dilutions of the IL-18 variants in HEPES buffered Saline-P+ buffer (10 mM HEPES pH 7.4, 150 mM NaCl, 0.005% surfactant P20). The surface was regenerated by three 60-sec injections of regeneration buffer (3/4 (v/v) 8M guanidine hydrochloride with 1/4 (v/v) 1M sodium hydroxide). Experiments were performed in multiple channels simultaneously for increased observations. All data were analyzed with the Biacore T100 evaluation software version 2.0 with a 1:1 Langmuir binding model.

Cell Lines

HEK-Blue™ IL-18 sensor cells (InvivoGen) were maintained in complete media (DMEM containing 10% heat-inactivated FBS, 2 mM L-glutamine, 50 U/mL penicillin, and 50 μg/mL streptomycin) supplemented with 100 μg/mL Normocin™ (antimicrobial reagent), 30 μg/mL Blasticidin, 180 μg/mL Zeocin® (phleomycin D1), and 200 μg/mL Hygromycin. YUMMER1.7 melanoma cells were cultured and prepared as previously described (Wang et al., 2017, Pigment Cell Melanoma Res., 30(4):428-435).

HEK-Blue™ Cytokine Activity Assay

For cytokine activity measurements, 50,000 HEK-Blue™ IL-18 sensor cells per well of a flat-bottom 96-well plate were incubated with recombinant human IL-18 at successively decreasing concentrations in a total volume of 200 μL of complete media. After 20-24 hours of incubation at 37° C. and 5% CO2, 30 μL of cell culture supernatant was mixed with 170 μL QUANTI-Blue™ detection media (Medium for detection and quantification of alkaline phosphatase) (InvivoGen) and incubated at 37° C. and 5% CO2 until a color change from pink to blue was detectable (0.5-4 hours). Levels of alkaline phosphatase were quantified using a spectrophotometer at 655 nm wavelength. Cytokine activity was determined by calculating the relative absorbance value (percentage of the maximal absorbance value measured at 655 nm) for each cytokine in the assay.

For IL-18BP blockade experiments, a fixed concentration of recombinant human IL-18 was pre-incubated with recombinant human IL-18BP at successively decreasing concentrations for 1 hour at 4° C. Subsequently, the protein mixture was added to the HEK-Blue™ IL-18 sensor cells and the assay was performed as described.

Mice

C57BL/6 wild type mice (6-9 weeks old) from Jackson Laboratory were used for in vivo mouse experiments. Experimental groups were matched by weight, sex, and age. All animal experiments were conducted in compliance with approval from the Yale Institutional Animal Care and Use Committee.

In Vivo Pharmacodynamic and Pharmacokinetic Studies

Mice (n=9 per group) received daily intraperitoneal (i.p.) injections of 1 mg/kg recombinant IL-18 (WT or variant mCS2), or PBS as vehicle control. On day 1, day 4, and day 7 of the experiment, 3 mice per group were sacrificed 5 hours post-injection for blood collection via cardiac puncture, and subsequent analysis of blood plasma or white blood cells (see mouse IL-18BP ELISA, Luminex®-based multiplex immunoassay for mouse cytokine analysis, as well as immunophenotyping via flow cytometry) was performed. Throughout the 7 days of the experiment, body temperatures were monitored daily using the Rodent thermometer BIO-TK8851 (Bioseb) and the RET 3 rectal probe for mice (Braintree Scientific Inc.). Body weights were monitored daily.

Plasma Preparation from Whole Blood

Plasma preparation from whole blood was performed using EDTA-coated Microtainer® Plasma Separator Tubes (BD) according to manufacturer's instruction. Plasma samples were frozen once at −20° C. before being used for analytical assays.

IFN-γ and IL-18BP ELISA

To measure levels of human IFN-γ in cell culture supernatant, the Human IFN-γ ELISA MAX™ Deluxe Set (ELISA kit) (BioLegend) with a sensitivity of 4 μg/mL and a detection range of 7.8-500 μg/mL was used according to the manufacturer's instructions. For quantification of human IL-18BP in cell culture supernatant, the Quantikine™ Human IL-18BP Immunoassay (R&D Systems) with a sensitivity of 7.52 pg/mL and a detection range of 26.6-1,700 μg/mL was used. Mouse IL-18BP levels in blood plasma were quantified using the Mouse IL-18BP ELISA Kit (R&D systems) with a sensitivity of 0.156 ng/mL and a detection range of 0.156-10 ng/mL. All assays including sample preparation were performed according to manufacturer's instructions.

Luminex®-Based Multiplex Immunoassay for Mouse Cytokine Analysis

To quantify a variety of mouse cytokine levels in blood plasma including IFN-γ and IL-12, the Luminex®-based Bio-Plex® Pro multiplex immunoassay (Bio-Rad) was performed using the Bio-Plex® 200 System (Bio-Rad). Cytokines of interest were analyzed using the Bio-Plex® Pro Mouse Cytokine Standard 23-Plex (Group I) reconstituted in DMEM, following the manufacturer's instructions.

Immunophenotyping Via Flow Cytometry

For white blood cell analysis, 100 μL of whole blood were collected into an EDTA-coated Microtainer® Plasma Separator Tube (BD) additionally containing 50 μL Heparin-solution, and mixed by inverting several times. Red blood cell lysis was performed by adding ACK Lysing Buffer (VWR) and incubating for 3-5 minutes at room temperature. After adding MACS buffer (2 mM EDTA, 2% FBS, in PBS), white blood cells were collected by centrifugation (5 minutes, 400×g, 4° C.) and aspiration of the supernatant. White blood cells were washed once with cold MACS buffer, and collected again as described. The cell pellet was resuspended in 200 μL MACS buffer containing 10% (v/v) rat serum (STEMCELL Technologies Inc.) and specific fluorescently-labeled antibodies to stain for subsequent flow cytometric analysis. Staining was performed for 30 minutes at 4° C. using the following antibodies: αCD4-AF700 (BioLegend), αCD8-APC (BioLegend), B220-APC-Cy7 (BioLegend), CD11b-PB (BioLegend), NK1.1-PE (BioLegend), NKp46-PE (BioLegend), and CD69-FITC (BioLegend). Thereafter, white blood cells were washed twice with MACS buffer as described before. Finally, the cells were resuspended in 100 μL MACS buffer and samples were acquired using the flow cytometer (Sony SA3800). An aliquot of 10 μL was taken to perform cell counting using the Invitrogen Countess® II Automated Cell Counter (Thermo Fisher Scientific). FlowJo v10.3 software was used for data analysis, and cells were gated for leukocytes and single events using the forward and side scatter.

Tumor Treatment Experiments $0.5\times10^6$ YUMMER1.7 cells were implanted subcutaneously into C57BL/6J mice. 7 days after implantation, when tumors were approximately 50 mg, treatment was initiated. Mice were divided into treatment cohorts which included: 1) vehicle (saline), 2) anti-PD1 (rat clone RMP1-14, Bio X Cell, West Lebanon, New Hampshire, US), 3) wildtype IL-18, 4) mCS2, 5) wild type IL-18+anti-PD-1, and 6) CS2 IL-18+anti-PD1. Anti PD-1, wild type IL-18, and mCS2 IL-18 were administered via intraperitoneal injection twice weekly at 8 mg/kg, 0.32 mg/kg, and 0.32 mg/kg, respectively. Mice were monitored for signs of clinical toxicity, and tumor growth was tracked twice weekly using caliper measurements. Mice were euthanized when the tumor diameter reached or exceeded 1.5 cm in greatest dimension; this was considered the endpoint for survival analyses.

B2m-deficient YUMMER1.7 studies were conducted in a similar fashion, with the minor changes. $1.0\times10^6$ cells were engrafted, as tumors grew slower than the parental strain. Treatments consisted of saline, anti-PD1 plus anti-CTLA4, and mCS2 given at the same schedule and dose as the studies above.

The results of the experiments are now described.

The IL-18 Axis as a Target for Cancer Immunotherapy

Figure 1B:
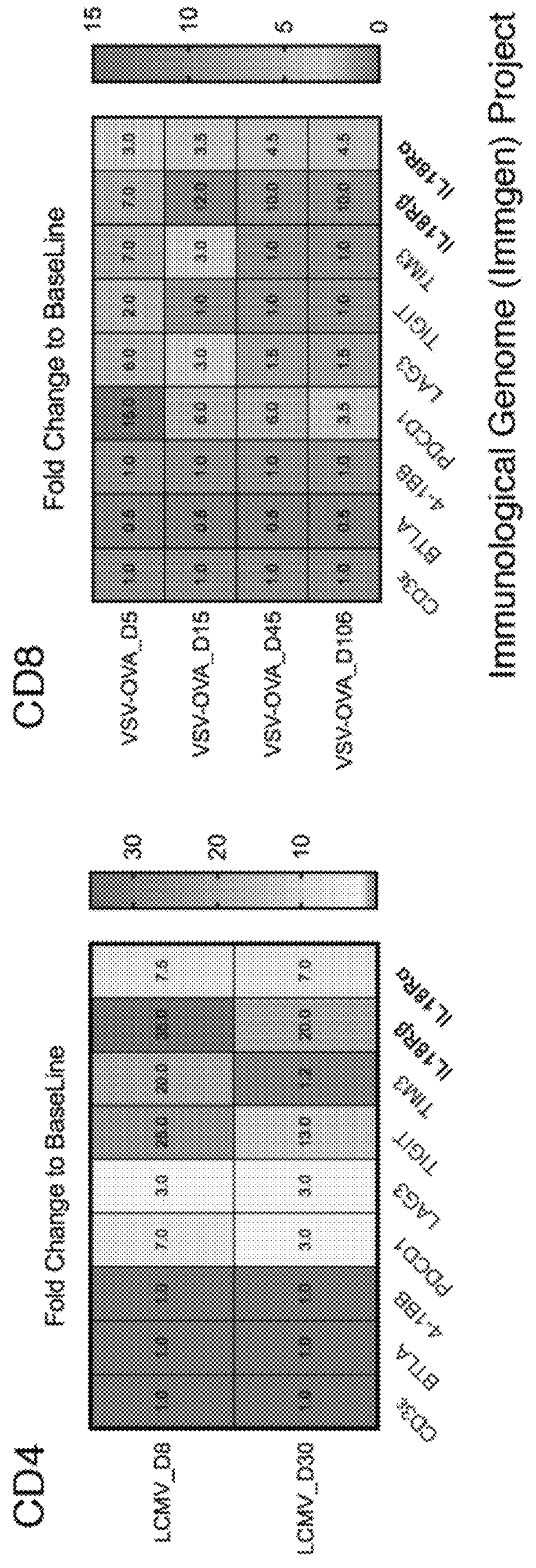

To identify potential signaling nodes for immunotherapeutic intervention, single cell RNAseq data from tumor infiltrating lymphocytes was analyzed for the expression of cytokine pathway components (Singer et al., 2016, Cell, 166:1500-1511, e1509). As seen in FIG. 1A, the receptor subunits for IL-18-IL-18Rα (i.e., IL-18R1) and IL-18Rβ (i.e., IL-18RAP)—as well as IL-18 itself were upregulated in both activated and dysfunctional lymphocyte programs. Further analysis of the Immunological Genome (ImmGen) database revealed that expression of both IL-18 receptor subunits correlated with expression of T cell "exhaustion" markers in CD4 and CD8 cells including PD-1, Tim3, Lag3, and TIGIT following chronic antigen exposure (FIG. 1B). These expression features suggested that the IL-18 pathway could be used to selectively stimulate activated and dysfunctional/exhausted T cells within tumors as an immunotherapeutic paradigm.

Figures 2A, 2B, 2C:
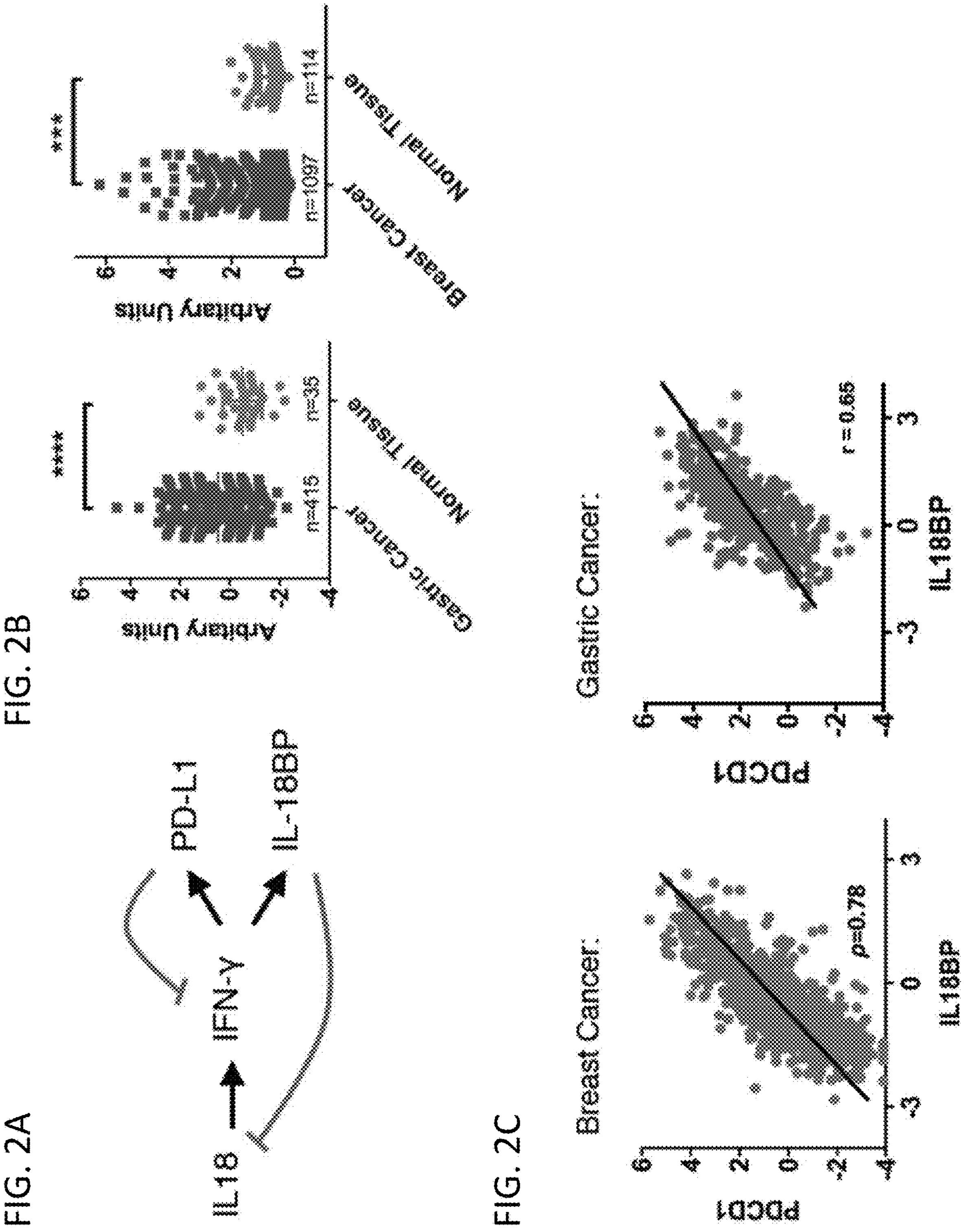
FIG. 2A through FIG. 2C depict results from example experiments, demonstrating IL-18BP has features of a "soluble immune checkpoint".

IL-18 is a Th1 cytokine initially termed "interferon-gamma-inducing-factor" (IGIF) for its ability to robustly stimulate release of interferon gamma (IFN-γ) by T and NK cells. Feedback inhibition of IL-18 is achieved by IFN-γ-driven induction of IL-18BP, a high-affinity secreted decoy receptor for IL-18 that sterically hinders IL-18's ability to bind and activate its receptor (FIG. 2A). Without wishing to be bound by any particular theory, this mechanism is reminiscent of the induction of PD-L1 by IFN-γ, suggesting that IL-18BP may act as a "soluble immune checkpoint." Consistent with this hypothesis, it was found that IL-18BP is upregulated in several types of cancer, most notably breast, gastric, and brain cancer in the TCGA and Oncomine® databases (FIG. 2B). Furthermore, IL-18BP expression strongly correlates with expression of the crucial immune checkpoint PD-1 in tumors (r=0.65 and 0.78 in gastric and breast cancer respectively, FIG. 2C), suggesting that IL-18BP may also contribute to tumor immune evasion and lymphocyte exhaustion.

Recombinant IL-18 has been administered to cancer patients in multiple clinical trials. It was found to be well-tolerated even at high doses of 2 mg/kg, with robust pharmacodynamics outputs including expansion of activated $CD69^+$ natural killer (NK) cells and dramatic increases in serum IFN-γ levels. However, a phase II trial of melanoma patients was discontinued due to lack of efficacy. Examination of the reported pharmacodynamics results from these clinical trials reveals that the effectiveness of rIL-18 wanes with repeated dosing, with tachyphylaxis seen with respect to peripheral NK cell activation/expansion and cytokine release (including IFN-γ and GM-CSF). The waning effectiveness of rIL-18 coincides with a profound increase in the serum levels of IL-18BP, more than two orders of magnitude over pre-treatment levels and often exceeding 100 ng/mL. Without wishing to be bound by any particular theory, it was hypothesized that IL-18BP limits the effectiveness of rIL-18 therapy and that IL-18 variants that are impervious to IL-18BP inhibition could be effective tumor immunotherapies. Additionally, inhibitors of IL-18BP will likely be effective for tumor immunotherapy.

Engineering IL-18 Variants that are Resistant to IL-18BP Inhibition (Human DR-IL-18 Variants)

Figure 3A:
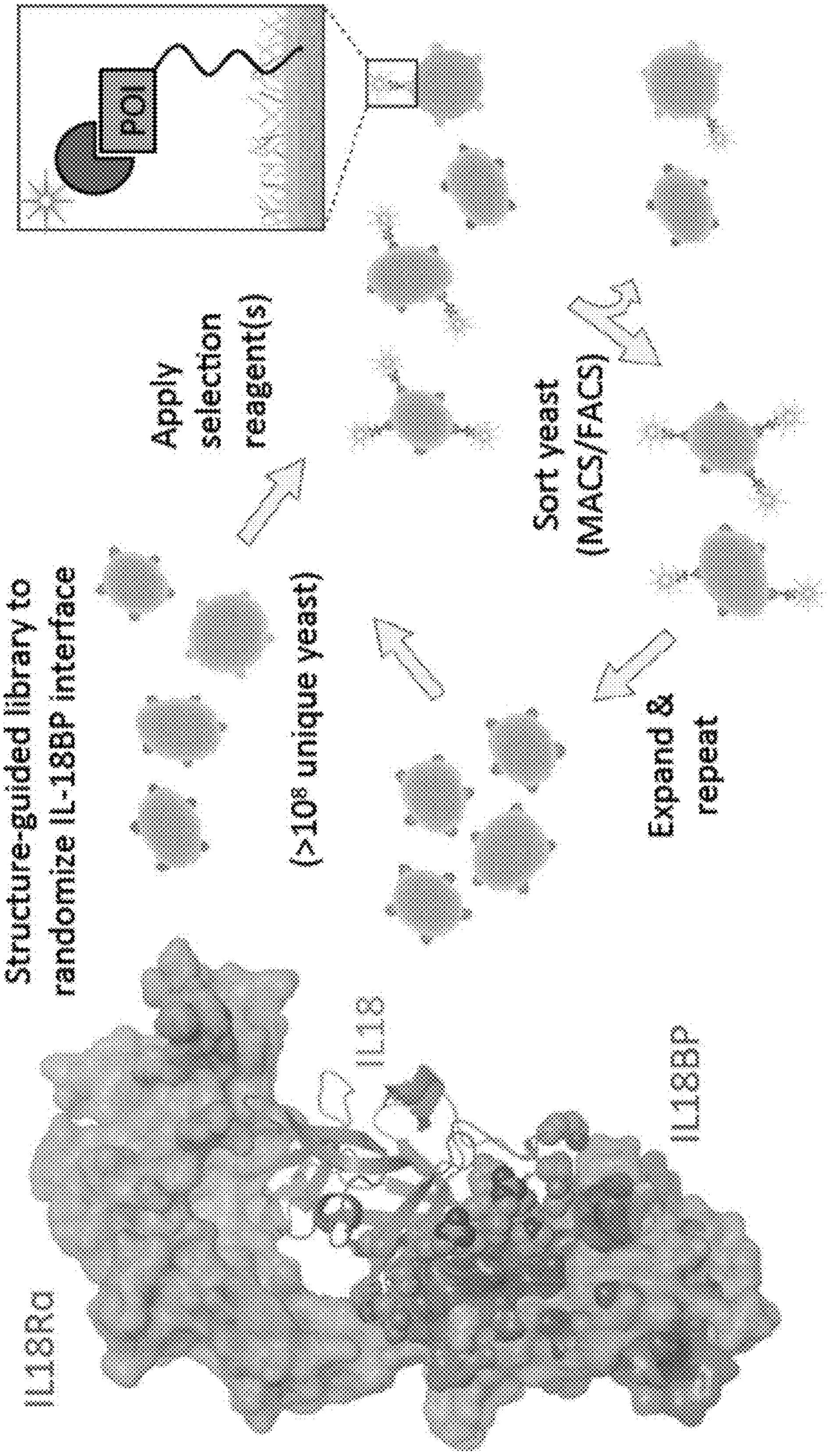
FIG. 3A through FIG. 3C depict results from example experiments, demonstrating engineering human IL-18 variants for independence to IL-18BP using yeast display.
Figure 3B:
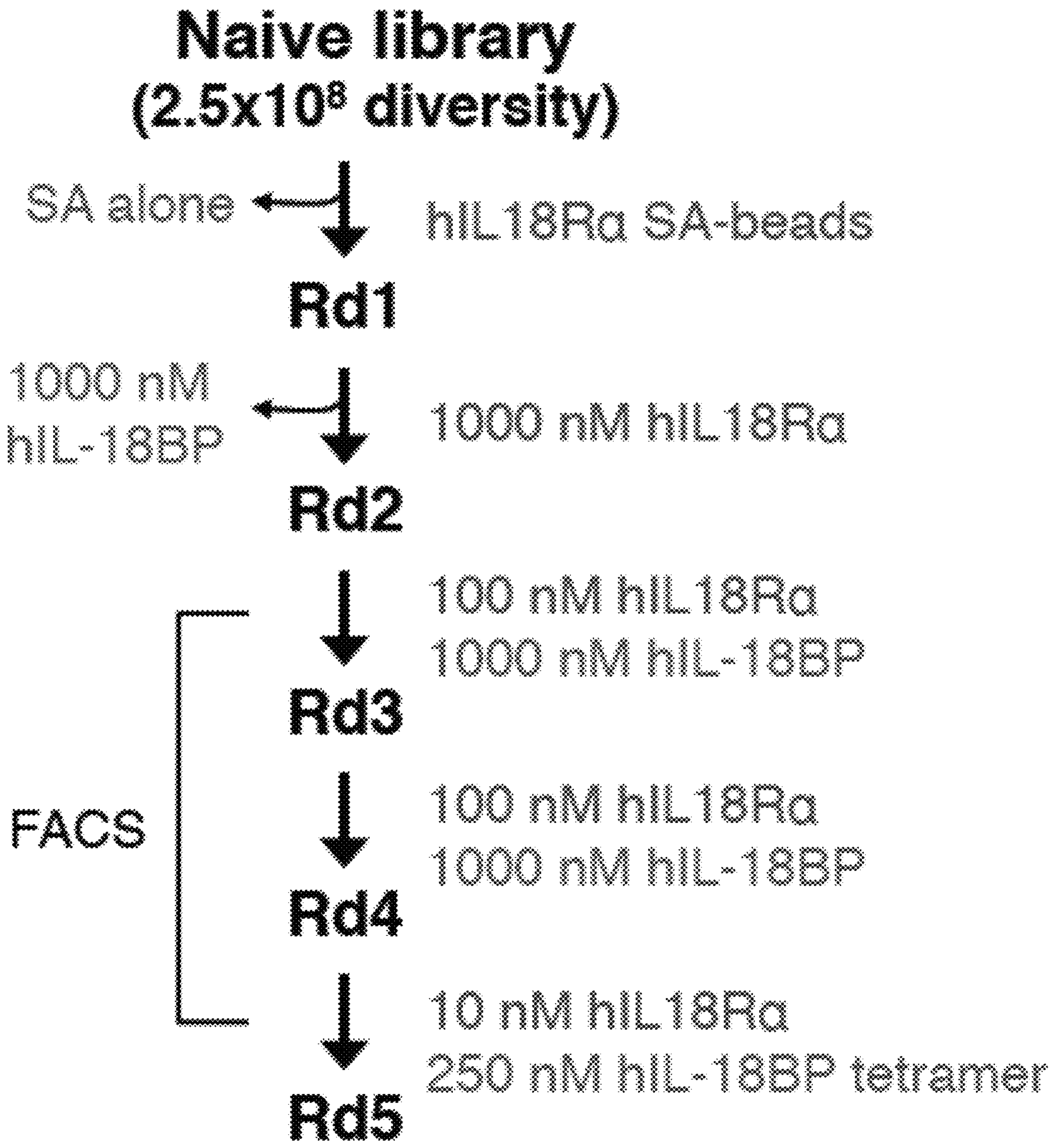

To obtain variants of IL-18 that can signal through IL-18Rα/IL-18Rβ, but are impervious to inhibition by IL-18BP, directed evolution with yeast surface display was utilized. The structure of the ternary signaling complex of human IL-18:IL-18Rα:IL-18Rβ (PDB=3OW4) was first analyzed, and residues of IL-18 that have a shared interface with the signaling complex and IL-18BP were identified (FIG. 3A). As the structure of hIL-18:hIL-18BP has not been determined, a related complex between IL-18 and a viral (ectromelia virus) orthologue of IL-18BP was utilized (PDB=3F62). A combinatorial library randomizing this set of residues to a defined set of alternatives (see Table 1) was created using degenerate oligonucleotide primers and assembly PCR. This library was electroporated into yeast together with the N-terminal yeast display vector pYAL to obtain a library with $2.5\times10^8$ transformants. Using this library, directed evolution was performed by conducting successive rounds of selection using magnetic and fluorescent cell sorting (FACS) with recombinant hIL-18Rα and counterselection with hIL-18BP, as summarized in FIG. 3B.

Figure 3C:
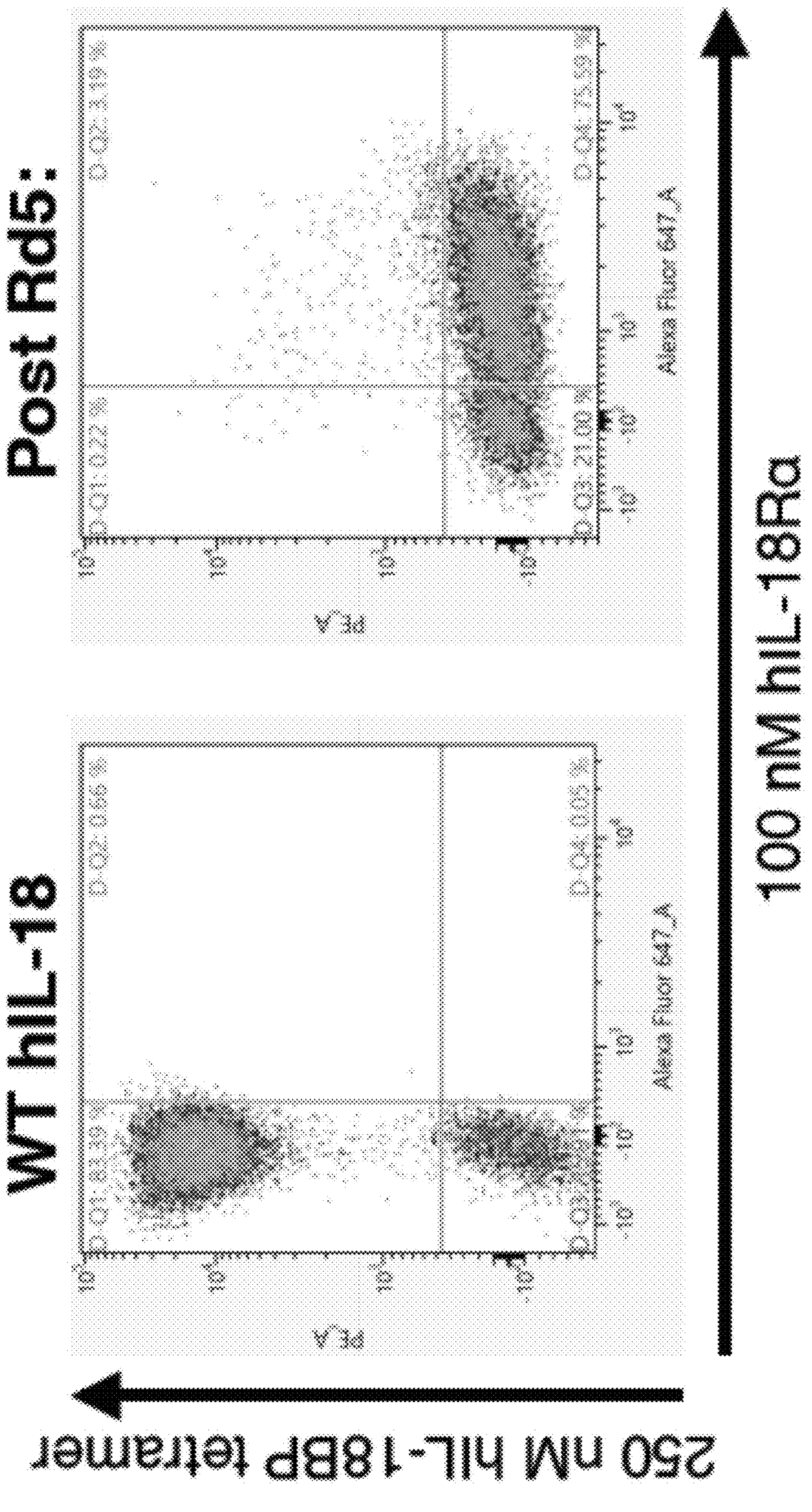

After five rounds of selection, the clear majority of the library clones had completely swapped their relative preference for hIL-18BP and hIL-18Rα as compared to WT hIL-18 (FIG. 3C). These clones were designated as "DR-hIL-18" variants, where "DR" stands for "decoy-resistant."

Figure 5A:
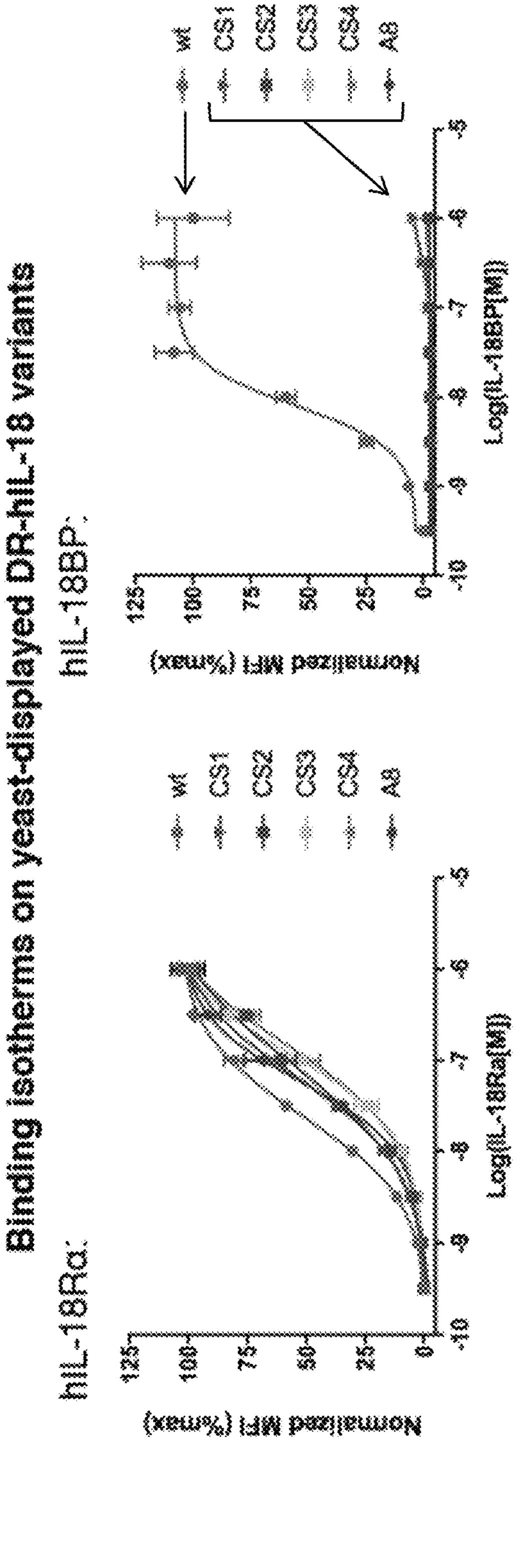
FIG. 5A and FIG. 5B depict results from example experiments, demonstrating biophysical characterization of human DR-IL-18 variants.
Figure 5B:
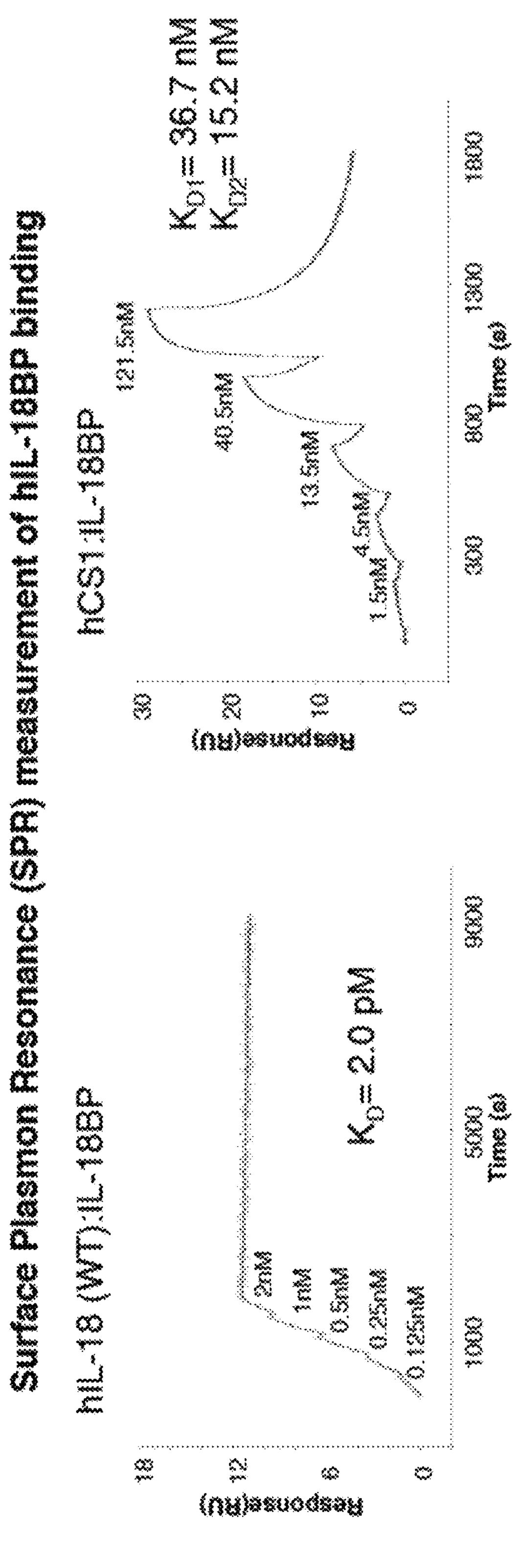

Sequencing of 96 clones from the post-round five pool revealed 21 unique sequences, which were analyzed to create four "consensus sequences", hCS1-4 (FIG. 4). To estimate the binding affinities of these variants for hIL-18Rα and hIL-18BP, binding isotherms were established for hIL-18Rα and IL-18BP binding using yeast-displayed cytokine variants and flow cytometry. As seen in FIG. 5A, the DR-hIL-18 variants bound hIL-18Rα with comparable affinity to WT IL-18, but showed severely attenuated binding to hIL-18BP, with apparent binding $EC_{50}$ values significantly greater than 1 μM. To additionally characterize the receptor binding activities of the DR-IL-18 variants, the cytokines were expressed recombinantly and surface plasmon resonance for IL-18Rα and IL-18BP was performed (see FIG. 5B for representative traces). These results are summarized in Tables 6 and 7 and demonstrate that the DR-hIL-18 variants have a dramatically decreased preference for IL-18BP compared to IL-18Rα, by several orders of magnitude.

TABLE 6

IL-18Rα and IL-18BP binding affinities of human IL-18 variants by on-yeast binding isotherms.

| IL-18 Variant | $K_D$ IL-18Rα (M) | $K_D$ IL-18BP (M) | $K_D$ ratio: IL-18BP/IL-18Rα | Dissociation Constant Ratio normalized to WT IL-18 |
|---|---|---|---|---|
| hIL-18 WT | 2.40E−08 | 7.08E−09 | 2.95E−01 | 1 |
| hA8 | 5.77E−08 | NBD | >3.47E+02 | >1.17E+03 |
| hH3 | 8.38E−08 | NBD | >2.39E+02 | >8.09E+02 |
| hB9 | 1.27E−07 | NBD | >1.57E+02 | >5.34E+02 |
| hCS1 | 6.44E−08 | 1.93E−05 | 3.00E+02 | 1.02E+03 |
| hCS2 | 9.15E−08 | NBD | >2.19E+02 | >7.41E+02 |
| hCS3 | 1.13E−07 | 1.16E−05 | 1.03E+02 | 3.48E+02 |
| hCS4 | 1.60E−07 | NBD | >1.25E+02 | >4.24E+02 |
| 6-31 | 4.1E−08 | NBD | 4.9E+02 | >7.2E+03 |
| 6-20 | N.D. | 3.4E−07 | — | — |
| 6-12 | 1.7E−08 | NBD | 1.2E+03 | >1.7E+04 |
| 6-27 | 4.2E−08 | NBD | 4.8E+02 | >7.0E+03 |
| 6-29 | 3.7E−08 | NBD | 5.4E+02 | >8.0E+03 |

NBD, no binding detected (20 μM used for ratio calculations)
—, value not determined

TABLE 7

IL-18Rα and IL-18BP binding affinities of human IL-18 variants by SPR

| IL-18 Variant | $K_D$ IL-18Rα (M) | $K_D$ IL-18BP (M) | $K_D$ ratio: IL-18BP/TL-18Rα | Dissociation Constant Ratio normalized to WT IL-18 |
|---|---|---|---|---|
| hIL-18 WT | 2.93E−09 | 1.90E−12 | 6.48E−04 | 1 |
| hA8 | — | — | — | — |
| hH3 | — | — | — | — |
| hB9 | — | — | — | — |
| hCS1 | 8.05E−09 | 1.94E−08 | 2.41E+00 | 3.72E+03 |
| hCS2 | 1.31E−08 | — | — | — |
| hCS3 | 8.18E−09 | 1.86E−08 | 2.27E+00 | 3.50E+03 |
| hCS4 | 4.38E−09 | 1.83E−07 | 4.18E+01 | 6.45E+04 |

—, value not determined

Functional Characterization of Human DR-IL-18 Variants

Figure 6A:
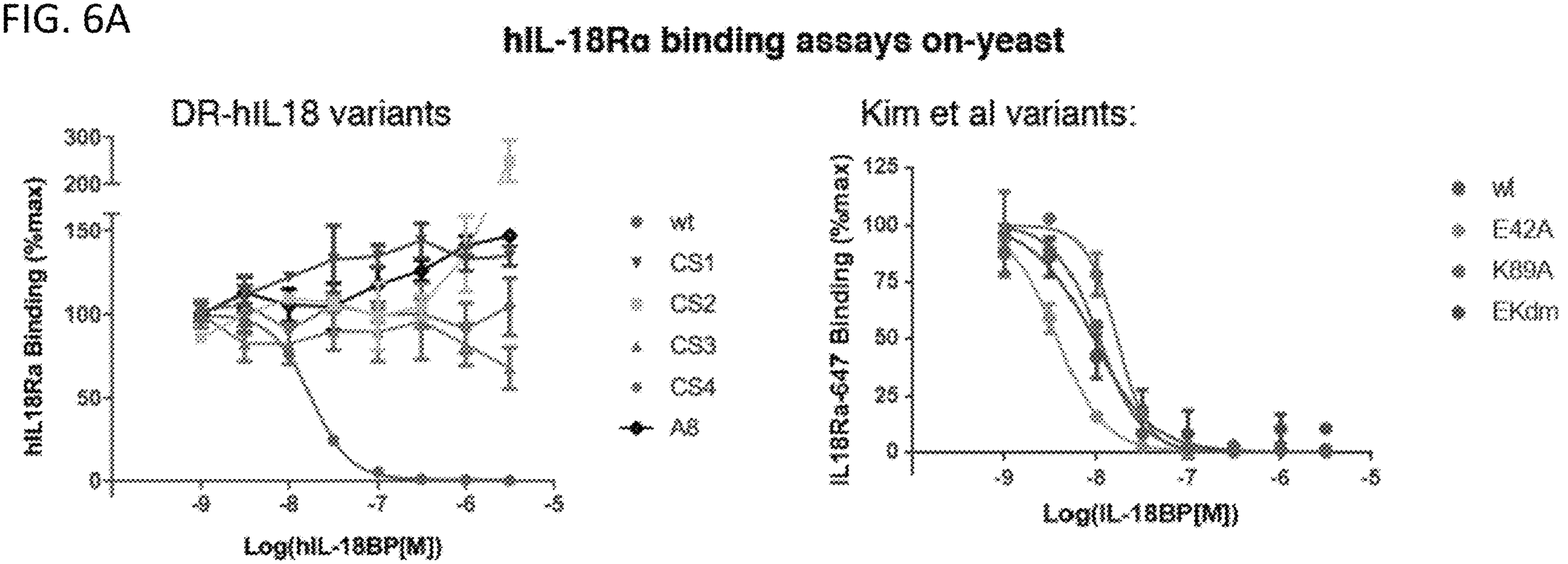
FIG. 6A and FIG. 6B depict results from example experiments, demonstrating human DR-IL-18 variants are not inhibited by IL-18BP.

A previous report from Kim et al (Kim et al., 2001, Proc Natl Acad Sci USA, 98(6):3304-9) described 3 hIL-18 variants with enhanced activity and purportedly decreased inhibition by IL-18BP: E42A, K89A, and E42A/K89A. These cytokine variants were displayed on yeast and IL-18BP inhibition of IL-18Rα binding was assessed by flow cytometry. As seen in FIG. 6A, while the DR-hIL-18 variants were impervious to inhibition of hIL-18Rα binding by hIL-18BP, the Kim et al variants showed roughly equivalent hIL-18BP neutralization as compared to WT hIL-18. These results indicate that the DR-hIL-18 variants are IL-18BP independent, whereas the Kim et al variants are highly sensitive to IL-18BP inhibition, similar to WT hIL-18.

Figure 6B:
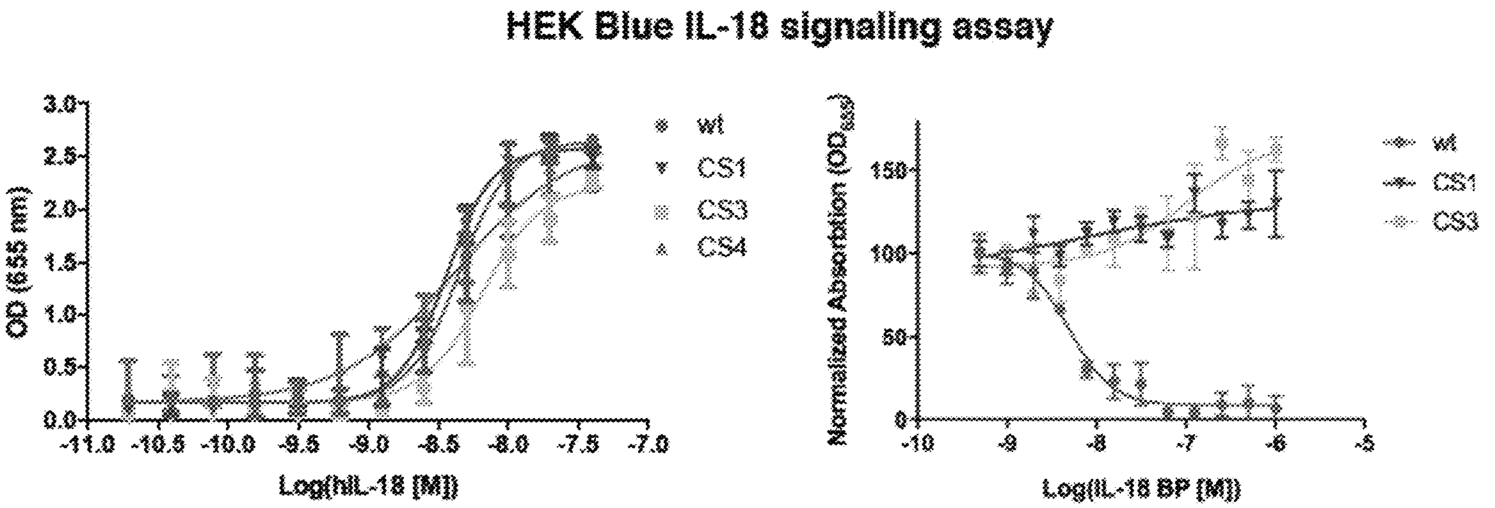

To confirm that the DR-hIL-18 could yield productive signaling through the IL-18 receptor in a cellular context, concentration-response experiments were performed using the HEK-blue IL-18 reporter cell line. In this system, IL-18R signaling is read-out by expression of secreted alkaline phosphatase (SEAP) downstream of a NFκb/API promotor. In the absence of IL-18BP, DR-hIL-18 variants yielded signaling EC50 values commensurate with WT hIL-18. However, the DR-hIL-18 variants demonstrated virtually no inhibition by hIL-18BP, with no detectable inhibition at 1 μM IL-18BP (FIG. 6B). Taken together, these studies establish that the DR-hIL-18 variants are biologically active and impervious to IL-18BP neutralization in a cell signaling context.

Engineering and Characterization of Second-Generation Human IL-18 Variants that are Resistant to IL-18BP Inhibition (Human v2.0 DR-IL-18 Variants)

Figure 7C:
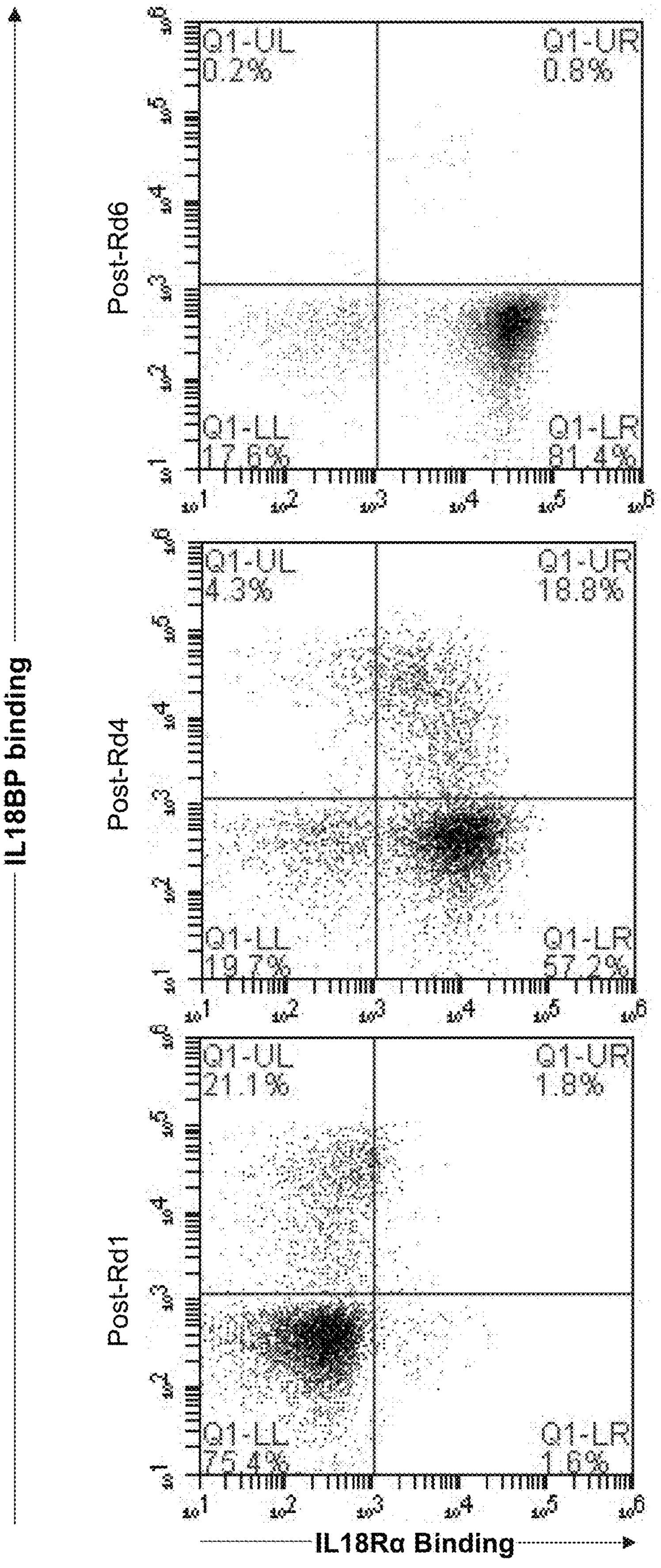

To obtain additional, potentially enhanced human DR-IL-18 variants, a second library of human IL-18 randomized at 11 positions (FIG. 7A) was designed and yeast was transformed as described above. The resulting library of $6\times10^8$ transformants was selected as outlined in (FIG. 7B), yielding a robust preference for IL-18Rα compared to IL-18BP with successive selection steps (FIG. 7C). 17 unique sequences were recovered after 5-6 rounds of selection (FIG. 8). (FIG. 9A) Compared to WT IL-18, clones 6-12, 6-27, 6-29, and 6-31 had equal or somewhat stronger binding to IL18Rα as measured by yeast-binding isotherms with biotinylated IL18Rα. (FIG. 9B) However, these clones did not show any appreciable binding to IL-18BP. (FIG. 9C) Measurement of thermal stability by applying a range of temperatures to the yeast-displayed clones showed that they were more thermal stable than WT IL-18 by 7-13° C. These results are summarized in (FIG. 9D).

Figure 10B:
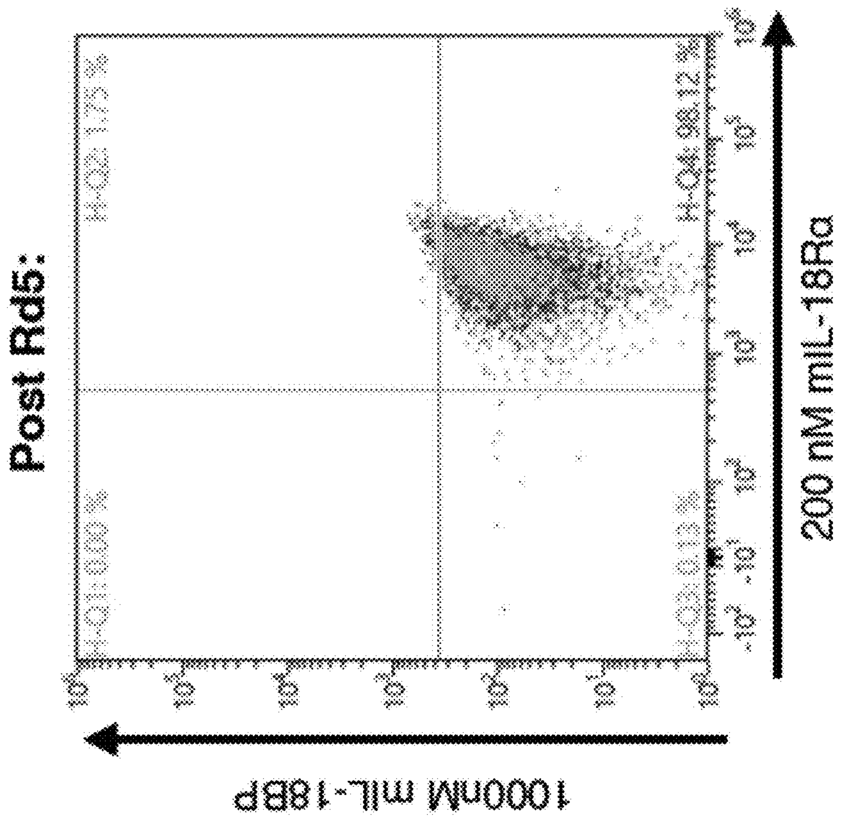
Figure 10A:
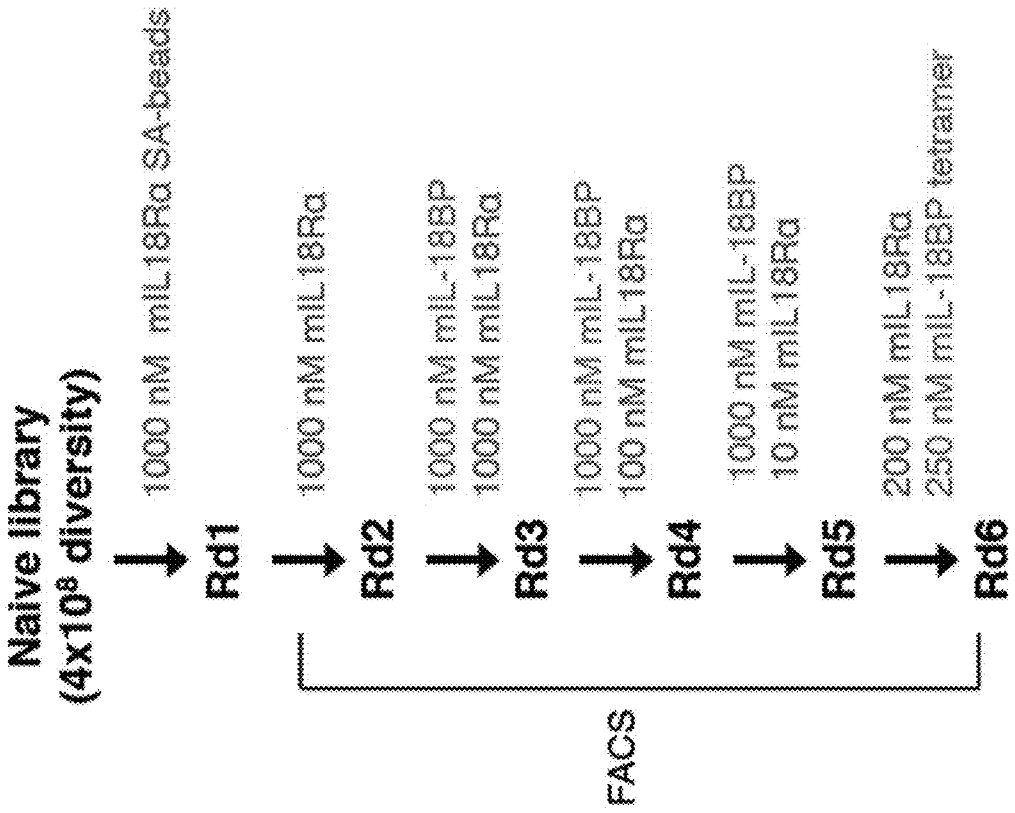
Figure 11A:
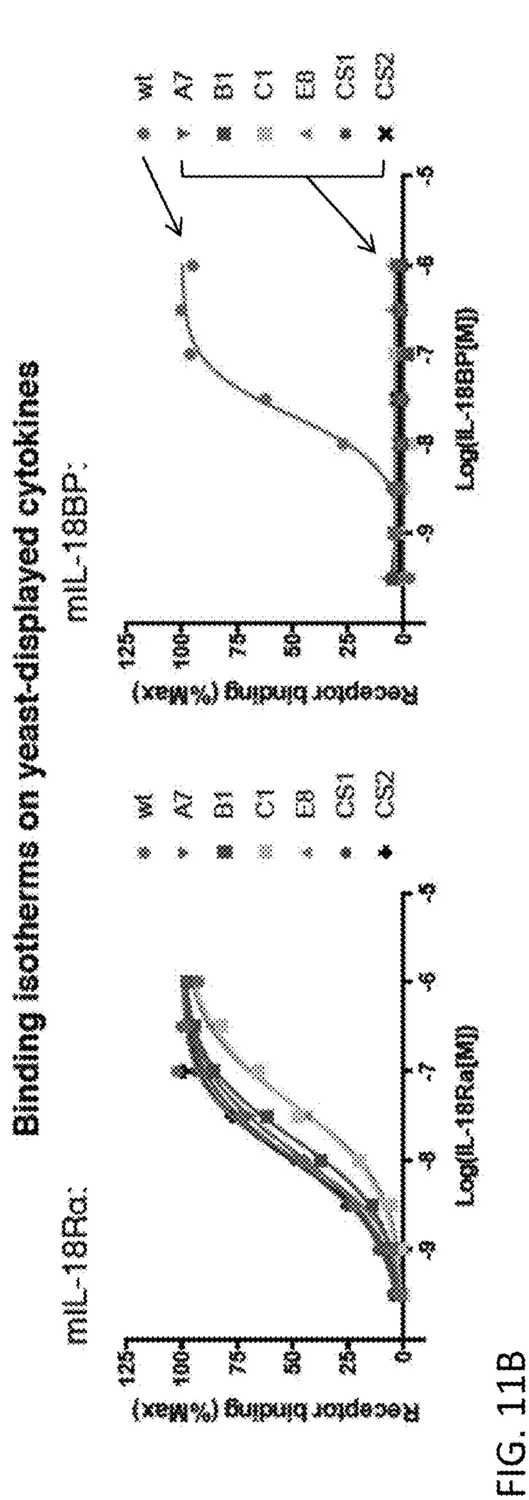
FIG. 11A and FIG. 11B depict results from example experiments, demonstrating biophysical characterization of murine DR-IL-18 variants.
Figure 11B:
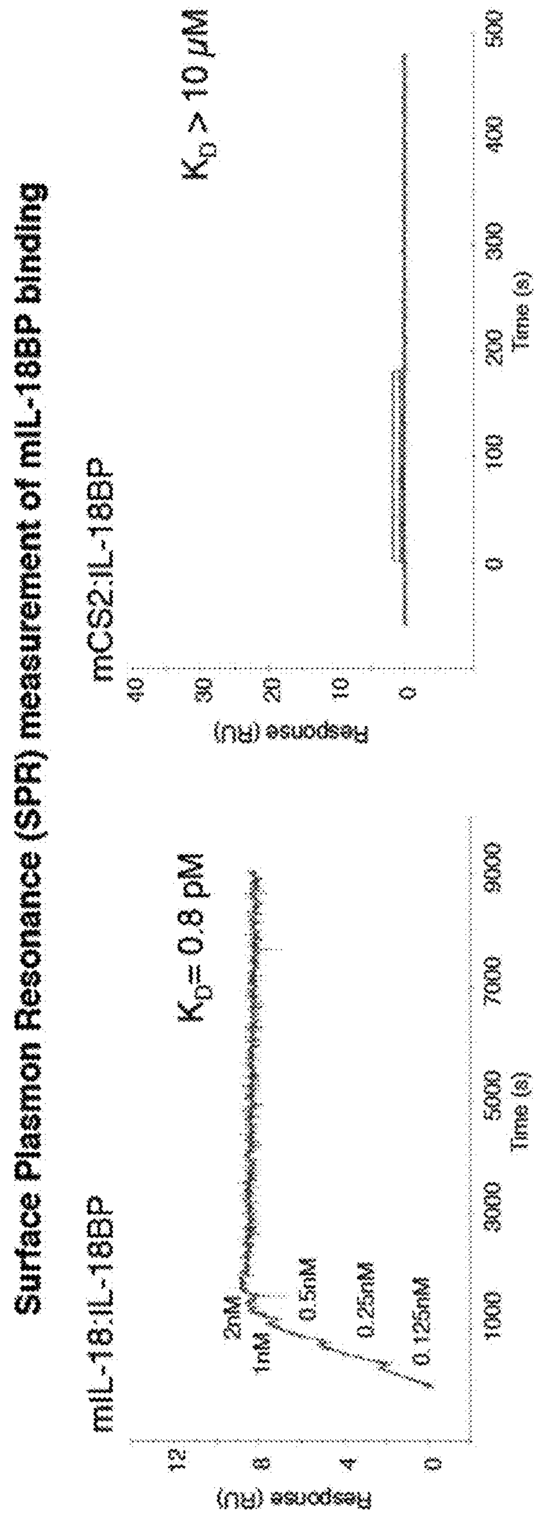

Engineering IL-18 variants that are resistant to IL-18BP inhibition (murine DR-IL-18 variants) As the human and mouse interspecies cross-reactivity of IL-18 for IL-18Rα is poor, murine equivalents of the DR-IL-18 variants that could be used for studies in mice were created. Similar to the approach taken for hIL-18 above, a combinatorial library of mIL-18 variants randomizing a similar set of mIL-18Rα/mIL-18BP contact residues (Table 3) was created, yielding a library of $4\times10^8$ transformants. Directed evolution was performed on this library similar to how it was performed with the human IL-18 library; the selection strategy is summarized in FIG. 10A. After the completion of six rounds of selection, the remaining clones had a near-complete preference for mIL-18Rα over mIL-18BP (FIG. 10B). Analysis of 96 clones revealed 11 unique sequences, from which were derived two consensus sequences mCS1 and mCS2 (FIG. 10C). Yeast binding isotherms and surface plasmon resonance experiments confirmed these DR-IL-18 clones had an even greater independence for IL-18BP than the human IL-18 variants described herein, with the mIL- 18BP binding KD's being well above 1 μM, with mIL-18Rα binding remaining roughly equal to WT mIL-18 (FIG. 11A, FIG. 11B, Tables 8 and 9).

TABLE 8

IL-18Rα and IL-18BP binding affinities of mouse IL-18 variants by on-yeast binding isotherms

| IL-18 Variant | $K_D$ IL-18Rα (M) | $K_D$ IL-18BP (M) | $K_D$ ratio: IL-18BP/IL-18Rα | Dissociation Constant Ratio normalized to WT IL-18 |
|---|---|---|---|---|
| mIL-18 WT | 1.13E−08 | 2.13E−09 | 1.88E−01 | 1 |
| mA7 | 1.35E−08 | NBD | >7.41E+02 | >3.93E+03 |
| mB1 | 1.79E−08 | NBD | >5.59E+02 | >2.96E+03 |
| mE8 | 4.20E−08 | NBD | >2.38E+02 | >1.26E+03 |
| mC1 | 4.30E−08 | NBD | >2.33E+02 | >1.23E+03 |
| mCS1 | 1.07E−08 | NBD | >9.35E+02 | >4.96E+03 |
| mCS2 | 1.13E−08 | NBD | >8.85E+02 | >4.69E+03 |

NBD, no binding detected (10 μM used for ratio calculations)

TABLE 9

IL-18Rα and IL-18BP binding affinities of mouse IL-18 variants by SPR

| IL-18 Variant | $K_D$ IL-18Rα (M) | $K_D$ IL-18BP (M) | $K_D$ ratio: IL-18BP/IL-18Rα | Dissociation Constant Ratio normalized to WT IL-18 |
|---|---|---|---|---|
| mIL-18 WT | 6.00E−10 | 1.10E−12 | 1.83E−03 | 1 |
| mA7 | 2.20E−10 | 1.39E−05 | 6.32E+04 | 3.45E+07 |
| mB1 | 7.00E−10 | 1.47E−05 | 2.10E+04 | 1.15E+07 |
| mE8 | 1.69E−09 | NBD | >1.78E+04 | >9.68E+06 |
| mC1 | 1.09E−09 | 2.87E−05 | 2.63E+04 | 1.44E+07 |
| mCS1 | 5.40E−10 | 3.80E−06 | 7.04E+03 | 3.84E+06 |
| mCS2 | 7.90E−11 | 1.05E−05 | 1.33E+05 | 7.25E+07 |

NBD, no binding detected (30 μM used for ratio calculations)

In Vivo Pharmacodynamic Studies of DR-IL-18 Variants

Figure 12A:
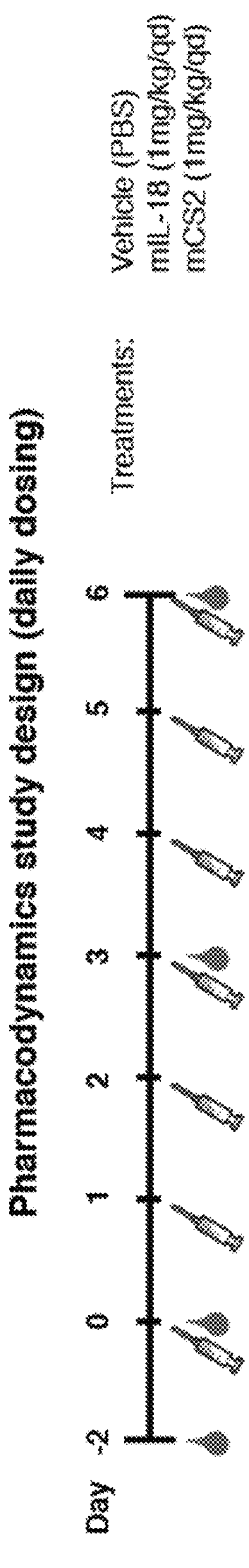
FIG. 12A through FIG. 12D depict results from example experiments, demonstrating pharmacodynamics of DR-IL-18 administered to mice.
Figure 12B:
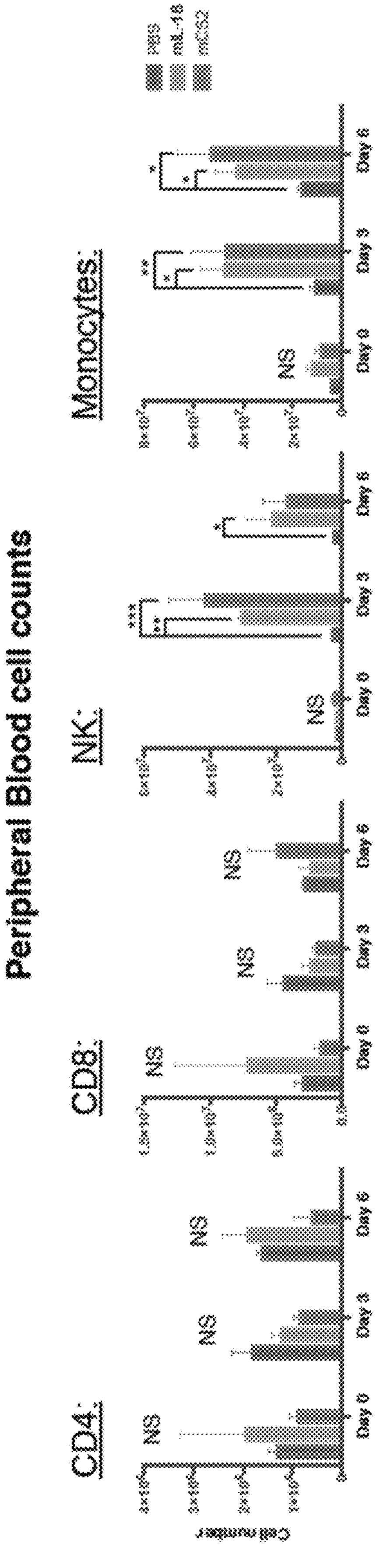
Figures 12C, 12D:
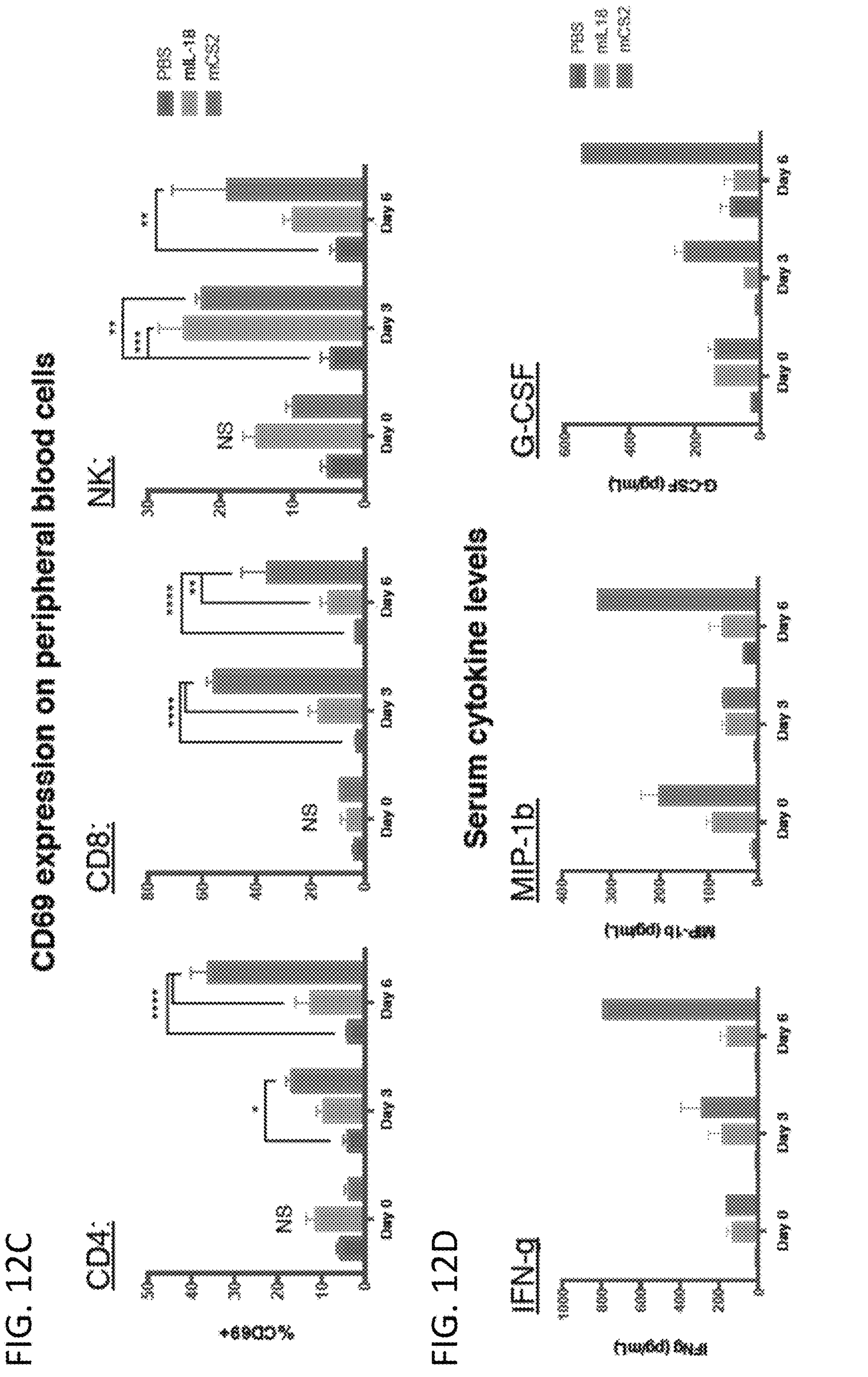

To assess the biologic effects of administration of the DR-IL-18 variants in vivo, pharmacodynamics studies were performed in mice, comparing WT mIL-18 to mCS2. In the first study, mice were treated with vehicle (PBS), mIL-18 (1 mg/kg/day), or mCS2 (1 mg/kg/day) for a total of seven injections (FIG. 12A). Analysis of peripheral blood phenotypes by flow cytometry showed that both WT mIL-18 and mCS2 increased peripheral NK cell numbers by over ten-fold, and peripheral monocyte counts by over five-fold compared to vehicle treatment; total CD4 and CD8 cell counts were not significantly affected (FIG. 12B). Examination of cellular activation status by CD69 induction revealed that mCS2 treatment dramatically increased CD69 levels on CD4 and CD8 cells compared to mIL-18 or vehicle treatment; reaching over 30% and over 50% positivity for CD4 and CD8 subsets, respectively (FIG. 12C). While both mIL-18 and mCS2 stimulated CD69 expression on peripheral NK cells to over 20% positive by day 3, the CD69 levels decreased to non-significant levels for mIL-18 by day 6, but remained significantly elevated with mCS2 treatment (FIG. 12C). Peripheral cytokine levels were also measured with a multiplexed Luminex® panel. As seen in FIG. 12D, both mIL-18 and mCS2 increased serum IFN-g, MIP1b, and G-CSF compared to vehicle treatment, but mCS2 achieved much higher levels than mIL-18 by day 6 for each of these cytokines, as mIL-18 exhibited tachyphylaxis with plateaued or decreasing induced cytokine levels with subsequent administration.

Effect of mCS2 on Body Fat Composition

Figure 13:
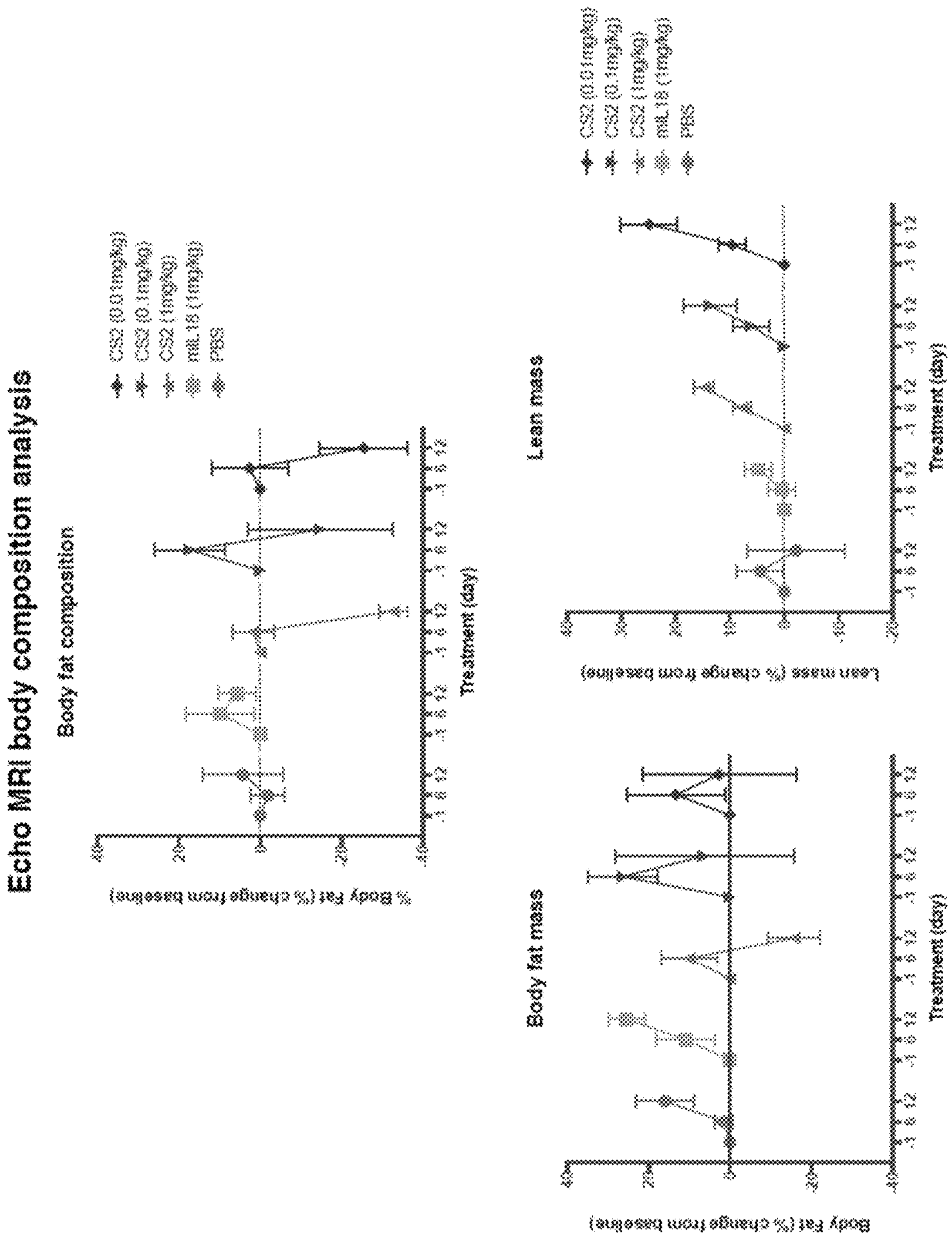
FIG. 13 depicts results from example experiments, demonstrating DR-IL-18 treatment decreases body fat composition in mice. Body fat and lean mass composition were measured in mice treated with 0.01, 0.1, or 1 mg/kg of the DR-IL-18 variant mCS2 or 1 mg/kg WT mIL-18 every three days. mCS2 treatment produced a significant decrease in body fat as a total percentage of body mass (top panel). This was manifested by decreases or stable fat mass (left panel), with concordant increases in lean mass (right panel). Vehicle treated and mIL-18 treated mice showed increases in body fat mass and stable lean mass over the same treatment period.

To assess the effect of the DR-IL-18 variants on body fat composition, we administered WT IL-18 at 1 mg/kg or 0.01, 0.1, or 1 mg/kg mCS2 by intraperitoneal injection to C57BL/6 mice every three days. Body fat and lean mass composition were monitored by echoMRI. All tested doses of mCS2 (1 mg/kg, 0.1 mg/kg, and 0.01 mg/kg) resulted in striking decreases in the overall percentage of body fat by day 12, while vehicle and mIL-18 treated mice did not have a significant change in total body fat composition (FIG. 13, top). Specifically, mCS2-treated mice had either reduced or stable levels of total fat mass during the experiment (FIG. 13, bottom left), but substantially increased their total lean mass (FIG. 13, bottom right). These results indicate that mCS2, and other variants disclosed herein, could be used to therapeutically decrease body fat composition (e.g., for treatment of obesity, diabetes, and/or metabolic syndrome).

Anti-Tumor Efficacy of DR-IL-18 Variants

Figure 14A:
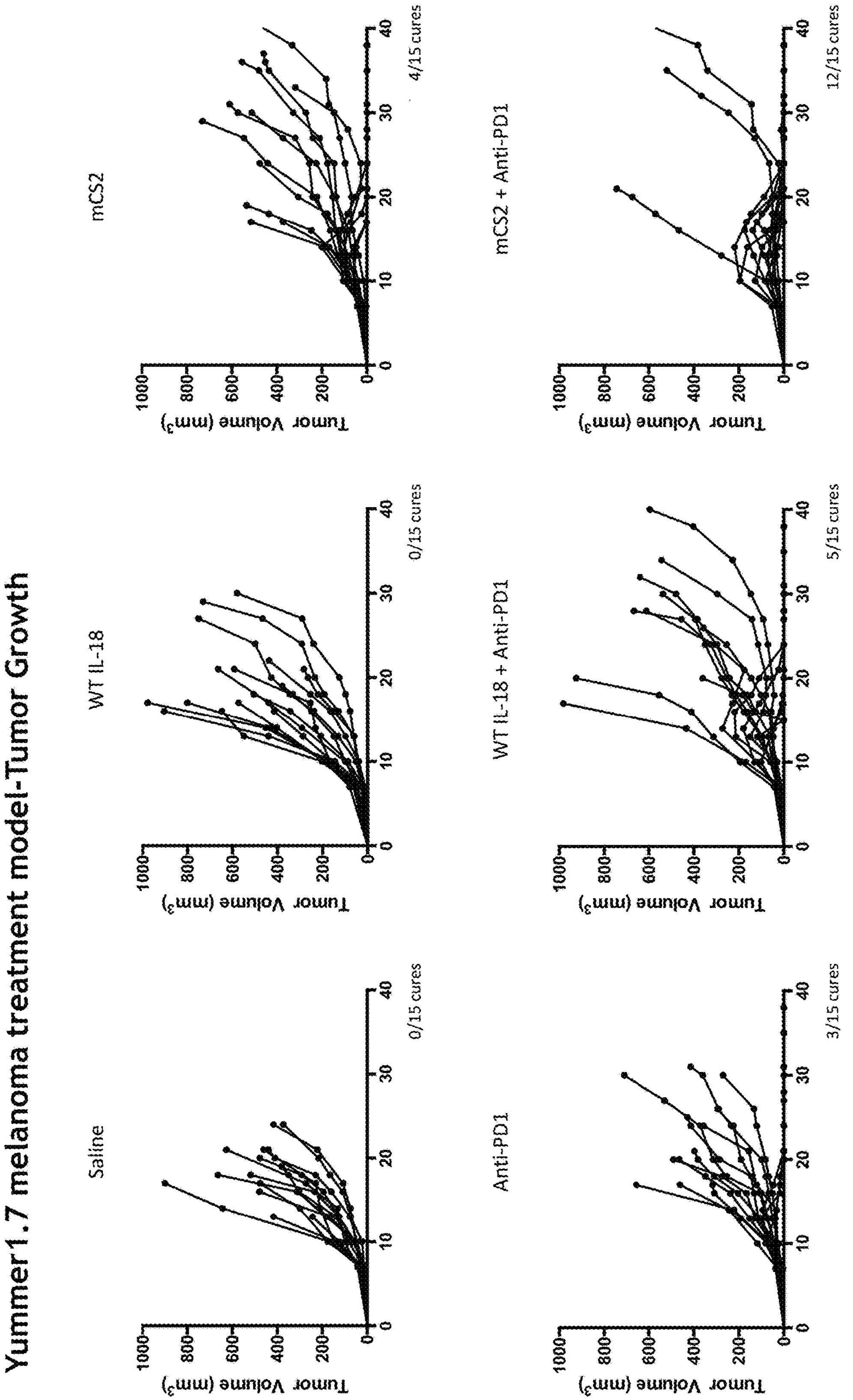
FIG. 14A through 14B depict results from example experiments, demonstrating DR-IL-18 is an effective immunotherapeutic in a melanoma model.
Figure 14B:
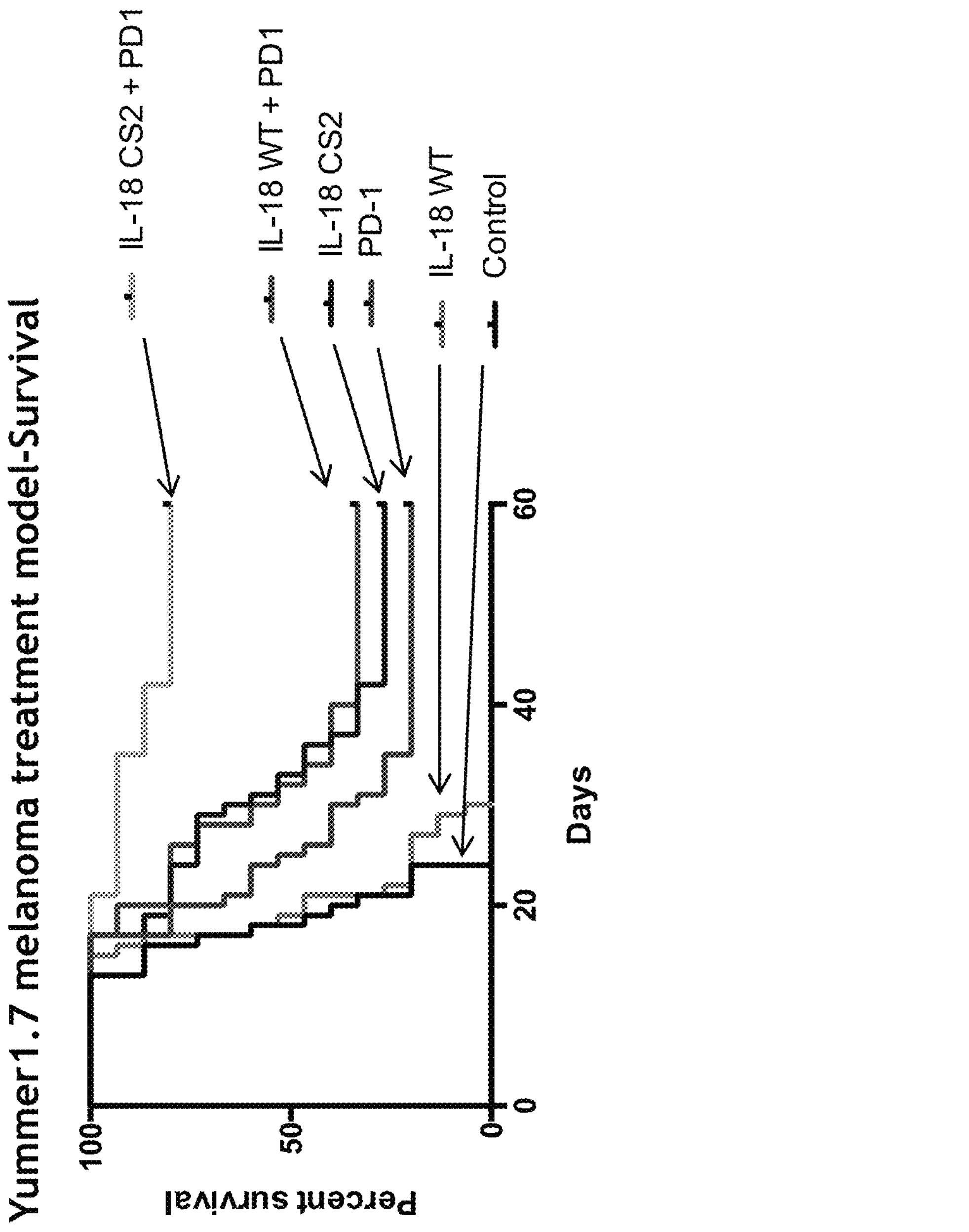

The anti-tumor efficacy of DR-IL-18 (mCS2) was assessed using the transplantable, syngenic YUMMER1.7 malignant melanoma tumor model. WT mIL-18 and mCS2 were administered to mice bearing YUMMER1.7 tumors biweekly at a dose of 0.32 mg/kg, with or without co-administration of anti-PD1 antibodies (8 mg/kg/q3d). Consistent with previous reports on its use in mice and humans, WT IL-18 did not affect tumor growth or survival compared to vehicle (saline), and only marginally improved the efficacy anti-PD1 when administered in combination. However, mCS2 cured 27% of treated mice as a monotherapy and produced a partial response in another 27%, an effect commensurate with anti-PD1 treatment. The combination of mCS2 with anti-PD1 cured 80% of treated mice (FIG. 14A and FIG. 14B).

Figure 15A:
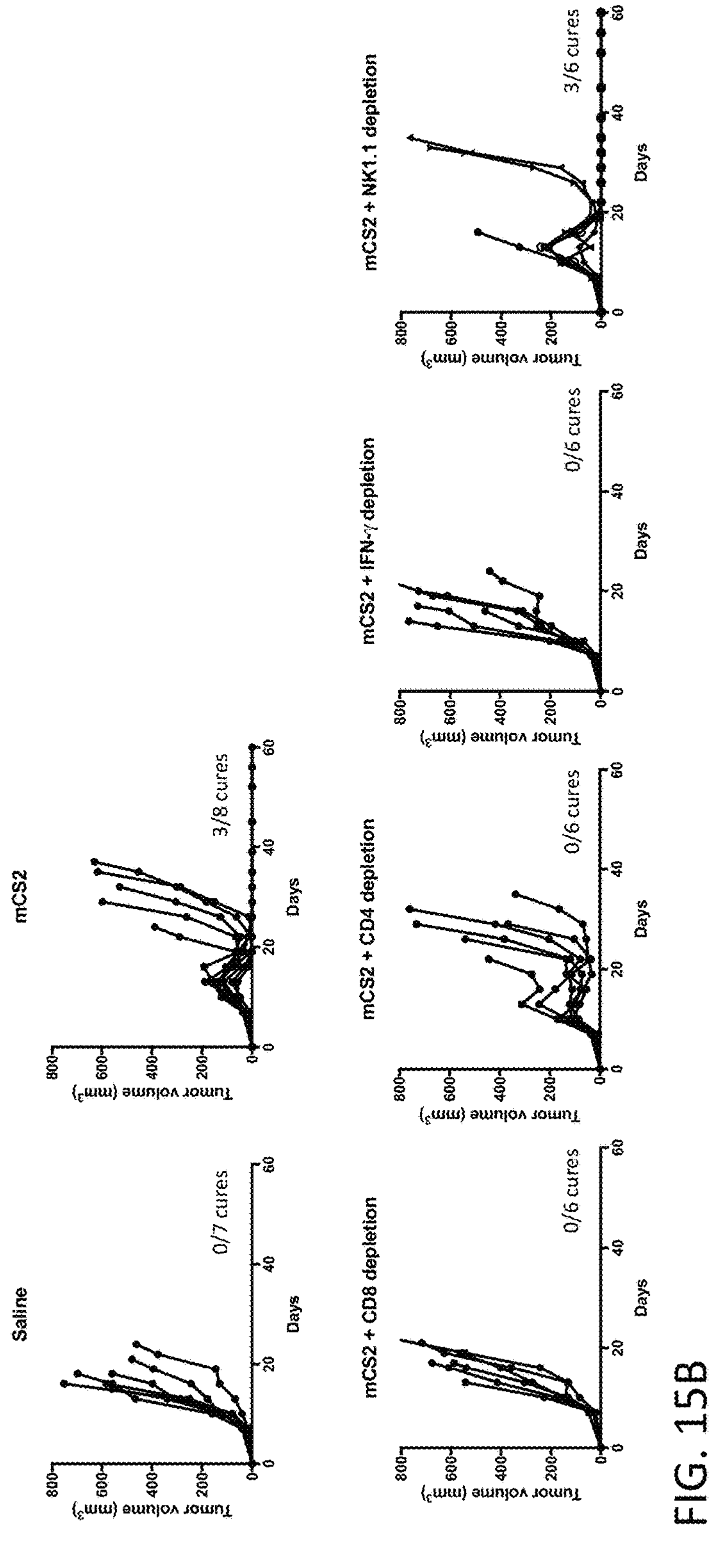
FIG. 15A and FIG. 15B depict results from example experiments that demonstrate that the effectiveness of DR-IL-18 in the melanoma model of FIG. 14 is dependent on CD4 and CD8 lymphocytes and interferon gamma.
Figure 15B:
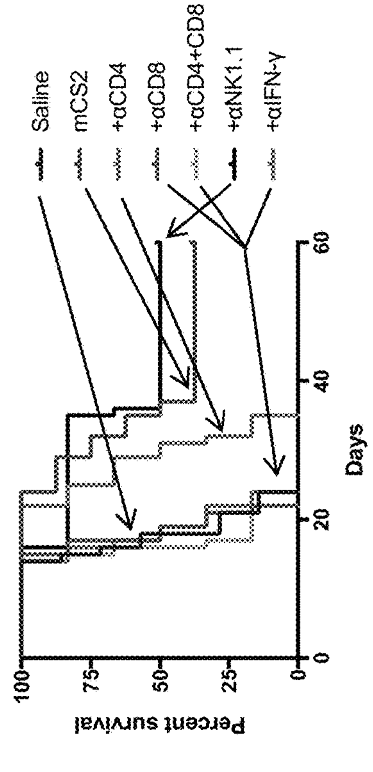

To establish the mechanism of action of DR-IL-18 on YUMMER1.7 tumors, cell depletion studies were performed using antibodies against CD8, CD4, NK1.1, and Interferon-gamma. As seen in FIG. 15A and FIG. 15B, depletion of CD8 cells or neutralization of Interferon-gamma completely abrogated the effectiveness of DR-IL-18. Depletion of CD4 cells did not affect the initial activity of DR-IL-18 in terms of tumor growth, however, in CD4 treated mice, therapeutic responses are not sustained, suggesting a role of CD4 cells in supporting and sustaining anti-tumor immunity. Depletion of NK cells did not affect tumor growth or survival in YUMMER1.7 cells.

Figure 16:
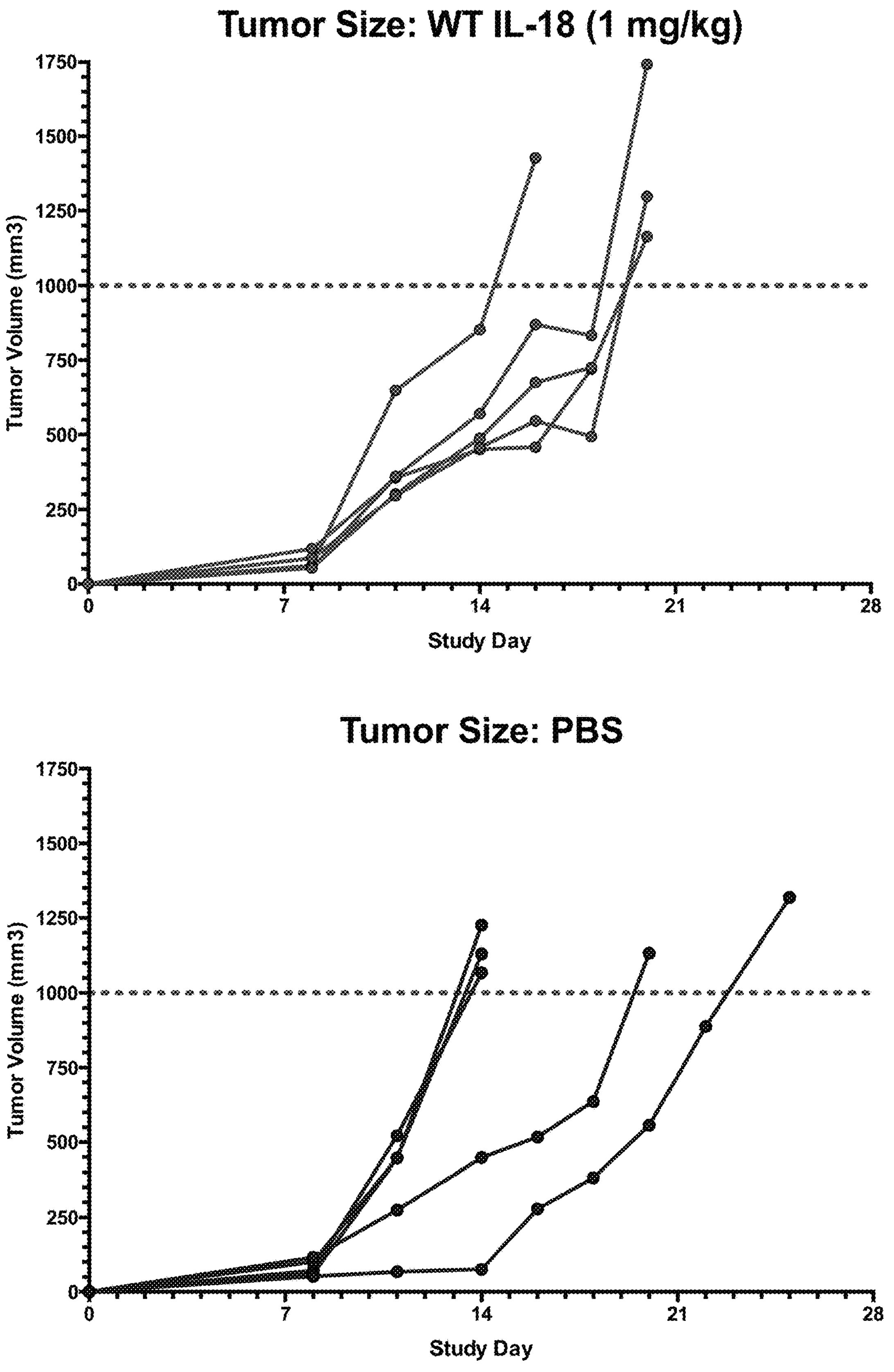
FIG. 16 depicts results from example experiments, demonstrating dose-dependent efficacy of DR-IL-18 in the MC38 tumor model. Tumor growth spider plots from mice bearing MC38 colon cancer tumors treated with PBS (control), 1.0 mg/kg WT IL-18, 1.0 mg/kg mCS2, 0.1 mg/kg mCS2, or 0.01 mg/kg mCS2 every three days. WT IL-18 was not efficacious at 1 mg/kg, whereas mCS2 showed partial efficacy at 0.1 mg/kg and maximal efficacy at 1.0 mg/kg.
Figure 16:
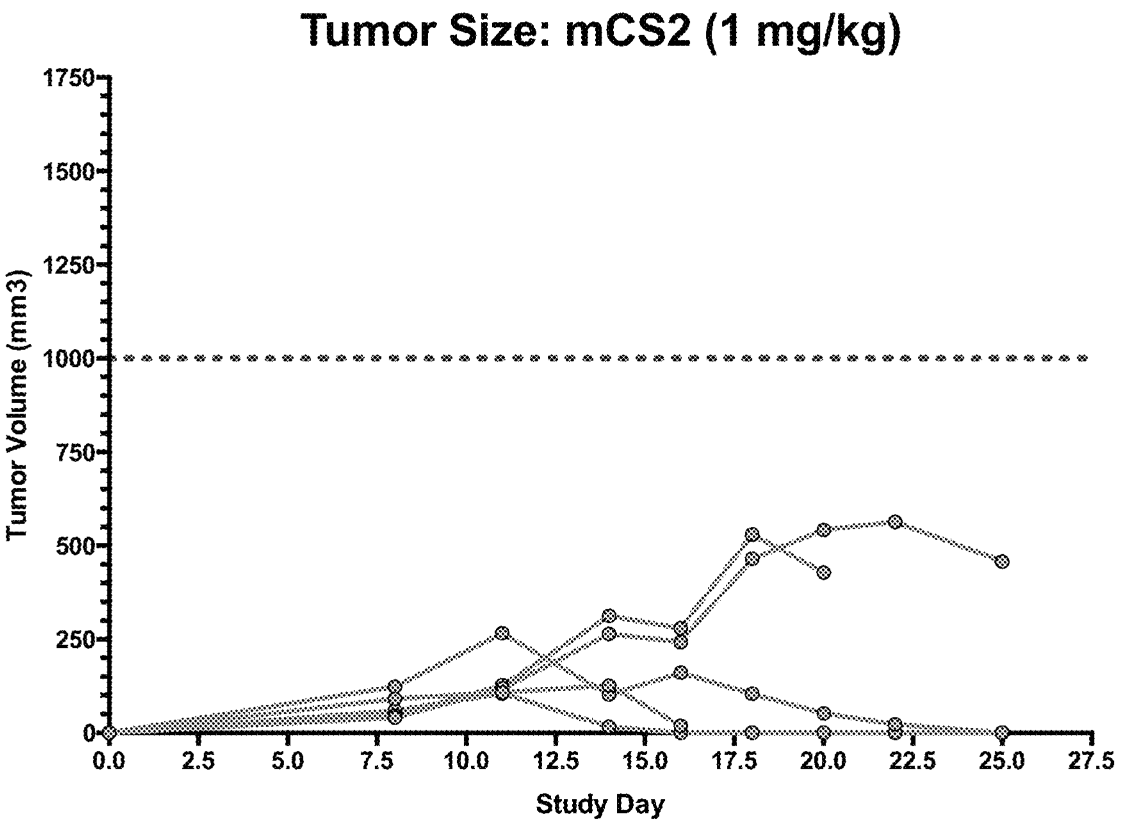
Figure 17:
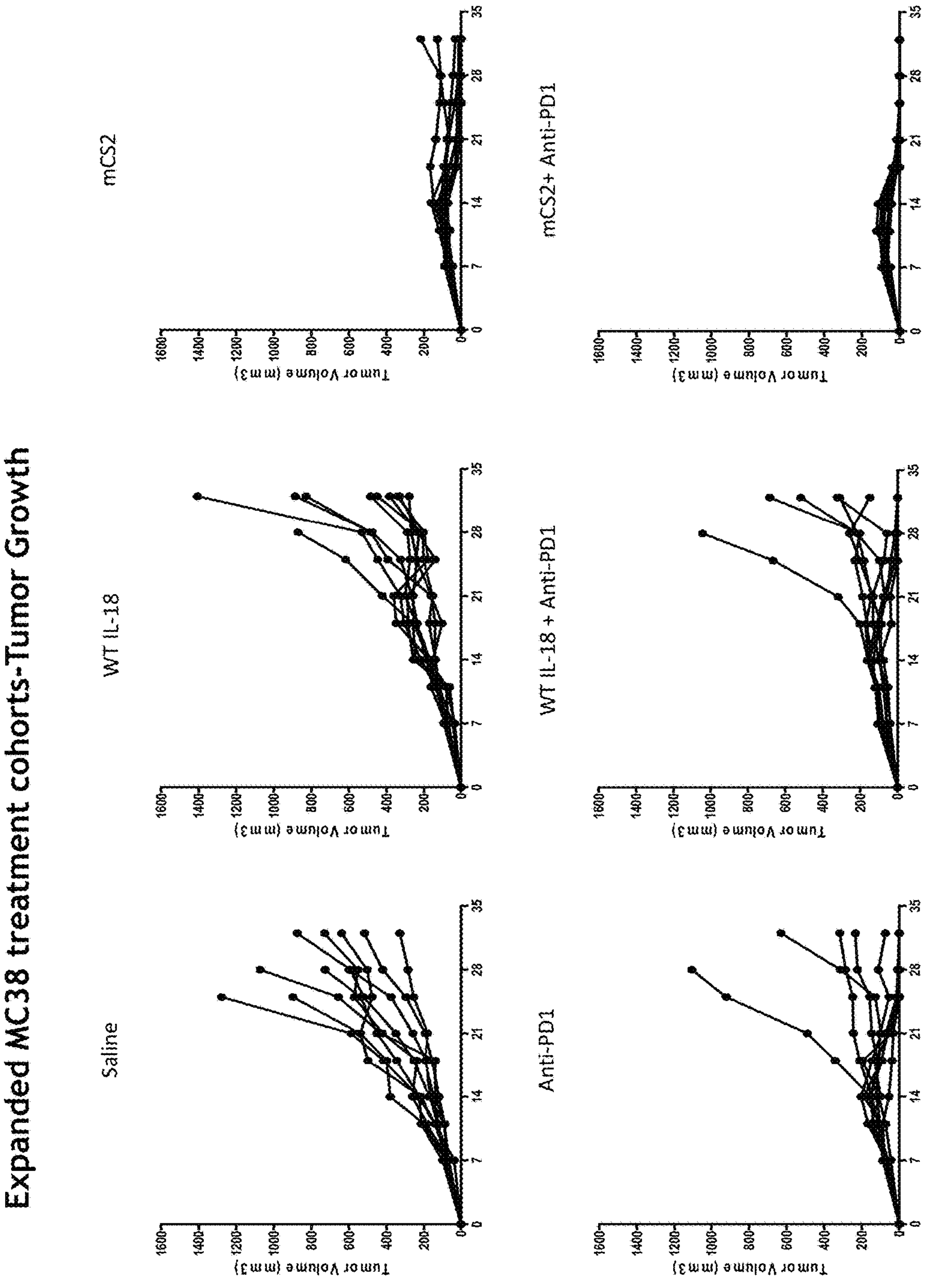
FIG. 17 depicts results from example experiments demonstrating the efficacy of DR-IL-18 alone in combination with the immune checkpoint inhibitor anti-PD1 in the MC38 tumor model. Tumor growth spider plots are shown from mice bearing MC38 colon cancer tumors treated with PBS (control), 0.32 mg/kg WT IL-18, 0.32 mg/kg of the DR-IL-18 variant mCS2, 5 mg/kg anti-PD1, the combinations of anti-PD1 with WT IL-18, or the combination of anti-PD1 with mCS2. All agents were dosed intraperitoneally twice per week for up to 6 total doses.

The activity of DR-IL-18 was additionally assessed in the immunogenic MC38 colorectal tumor model. A dose-finding study was first performed, administering saline, WT IL-18 (1 mg/kg twice weekly), or a range of DR-IL-18 doses from 0.01 mg/kg, 0.1 mg/kg, or 1 mg/kg twice weekly. As seen in FIG. 16, WT IL-18 had no effect on tumor growth, whereas DR-IL-18 (mCS2) showed dose-dependent efficacy, slowing tumor growth at 0.1 mg/kg and producing tumor regression at 1 mg/kg. The cohorts were then expanded and potential synergism with immune checkpoint inhibition was assessed. Again, WT IL-18 had no effect as a monotherapy and showed no enhancement of anti-PD1 efficacy. By contrast, DR-IL-18 showed robust monotherapeutic activity commensurate with or superior to anti-PD1, and the two therapies given together showed exceptional synergism, producing complete regression in all treated mice (FIG. 17).

Figure 18A:
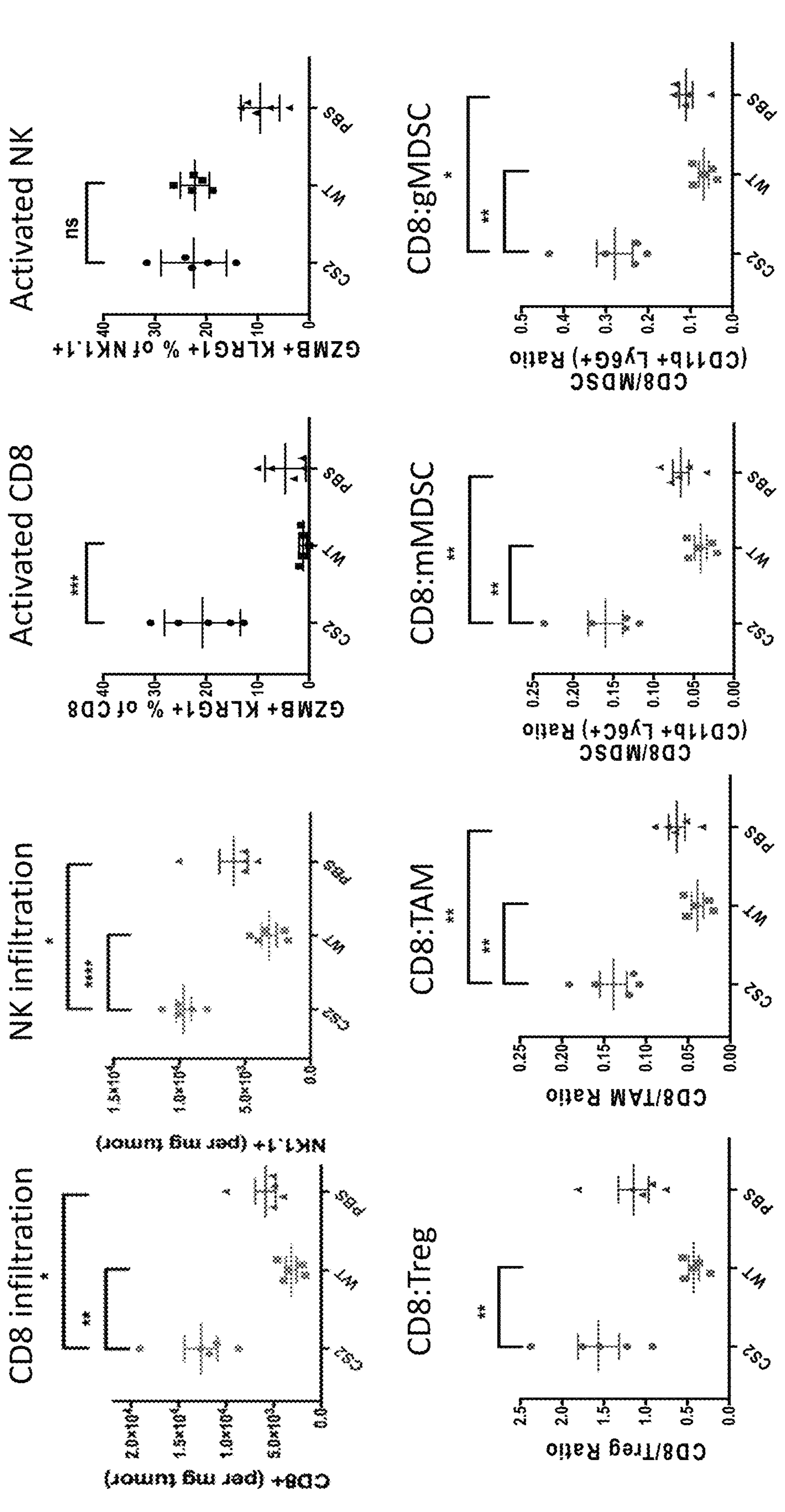
FIG. 18A and FIG. 18B depict results from example experiments that investigate the anti-tumor mechanism of DR-IL-18 in mice bearing MC38 tumors.
Figure 18B:
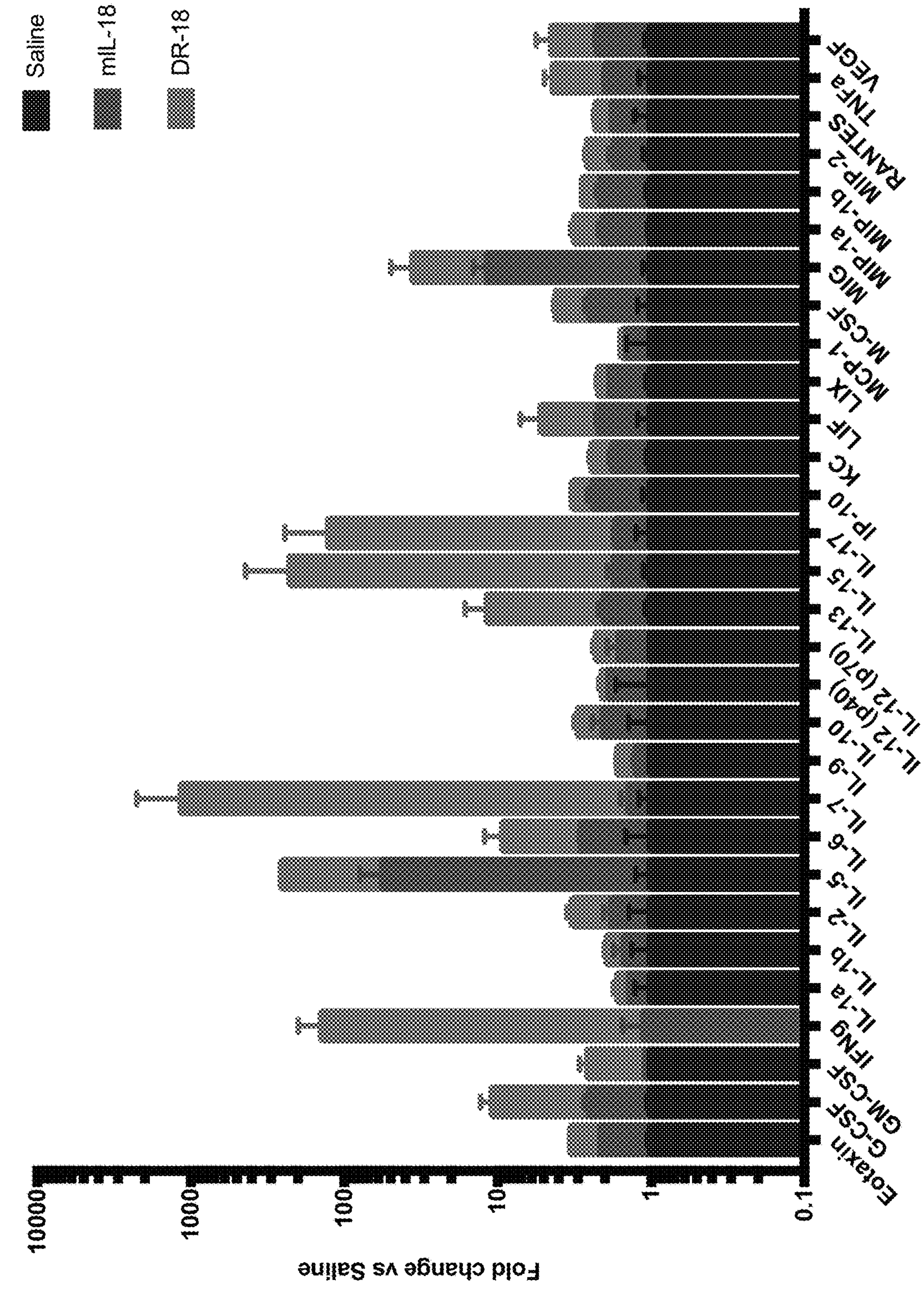

To further characterize the mechanism of DR-IL-18, flow cytometric studies were performed on the immune infiltrate of MC38 tumors from mice treated with saline, WT IL-18, or DR-IL-18 (mCS2). Relative to saline or WT IL-18, DR-IL-18 treatment increased CD8 and NK cell infiltration per mg of tumor and additionally resulting in upregulation of activation markers of effector cells such as granzyme B and KLRG1 (FIG. 18A, top row). Unlike other cytokine therapies such as IL-2 or IL-15, DR-IL-18 does not increase the CD8:Treg ratio within tumors compared to saline treatment. However, DR-IL-18 treatment leads to a more favorable tumor immune microenvironment, by increasing the ratio of CD8 cells to tumor associated macrophages (TAMs), and monocytic and granulocytic myeloids derived suppressor cells (MDSCs). The secondary cytokine release profile was also measured from serum of the same mice using a Luminex® assay. As seen in FIG. 18B, DR-IL-18 treatment increased systemic levels of Interferon-gamma, IL-7, and IL-15 by over 100-fold relative to WT IL-18 treatment. Taken in aggregate, these results indicate that DR-IL-18 produces anti-tumor efficacy through a unique mechanism of action distinct from IL-2, IL-15, or WT IL-18 treatment.

Some of the secondary cytokines induced by DR-IL-18 therapy would be predicted to potentially contribute to toxicity and/or decreased effectiveness. For instance, IL-17 which is upregulated >100-fold by DR-IL-18 contributes to colitis and psoriasis and additionally stimulates granulocytes that can become immunosuppressive myeloid derived suppressor cells. IL-5 and IL-13 are type 2 cytokines also upregulated by DR-IL-18 and could contribute to allergy, exacerbation of asthma, or analphylaxis. Th2 T cells do not contribute to immunotherapeutics responses and may promote immunosuppressive Treg development. As such, in certain instances the effectiveness and safety of DR-IL-18 could be enhanced by selective inhibition of undesired secondary cytokines such as IL-17, IL-5, and IL-13, for instance by a neutralizing antibody.

Figure 19A:
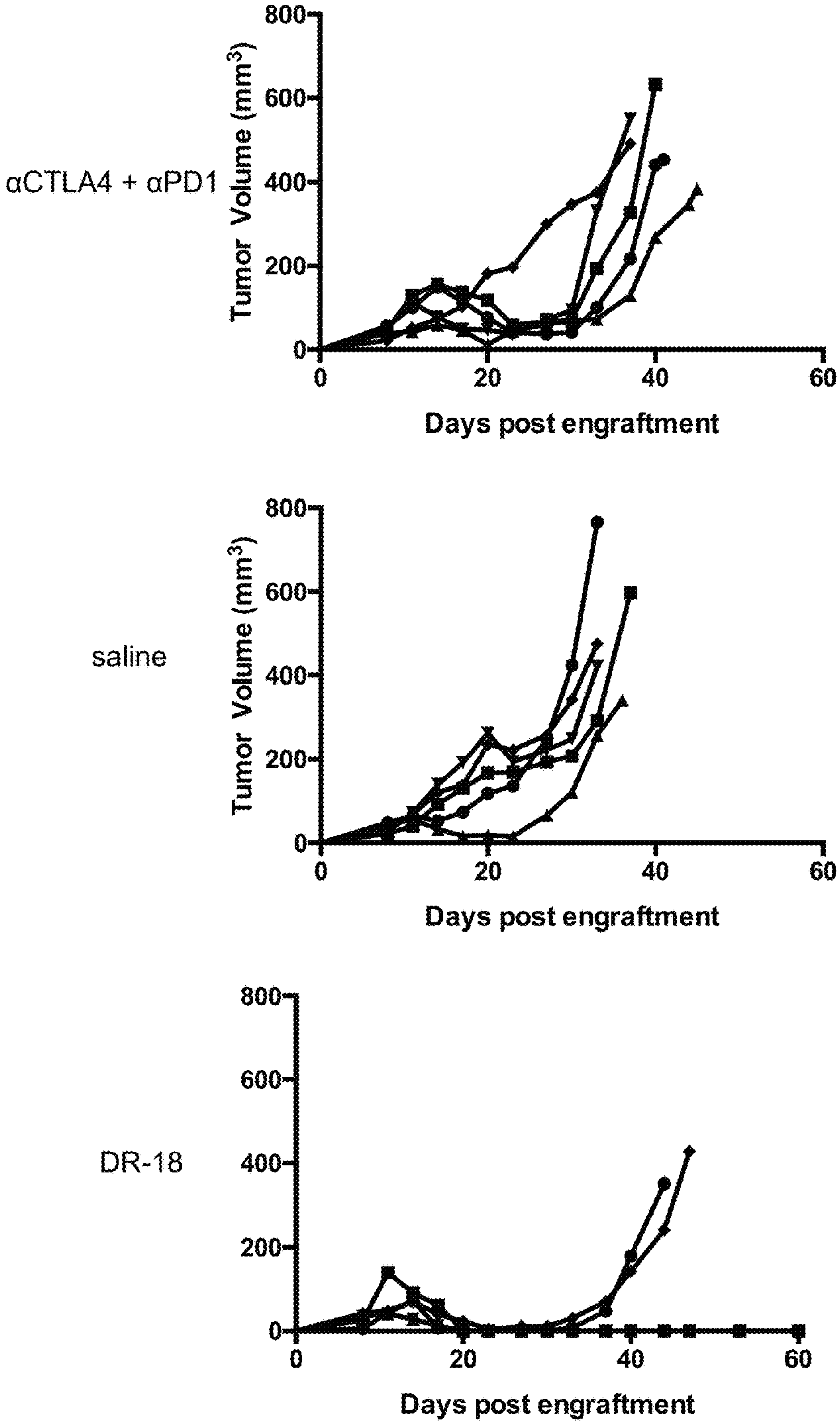
FIG. 19A through FIG. 19C depicts results from example experiments demonstrating the capability of DR-IL-18 to effectively treat tumors that are refractory to immune checkpoint inhibitors through loss of surface MHC class I expression.
Figure 19B:
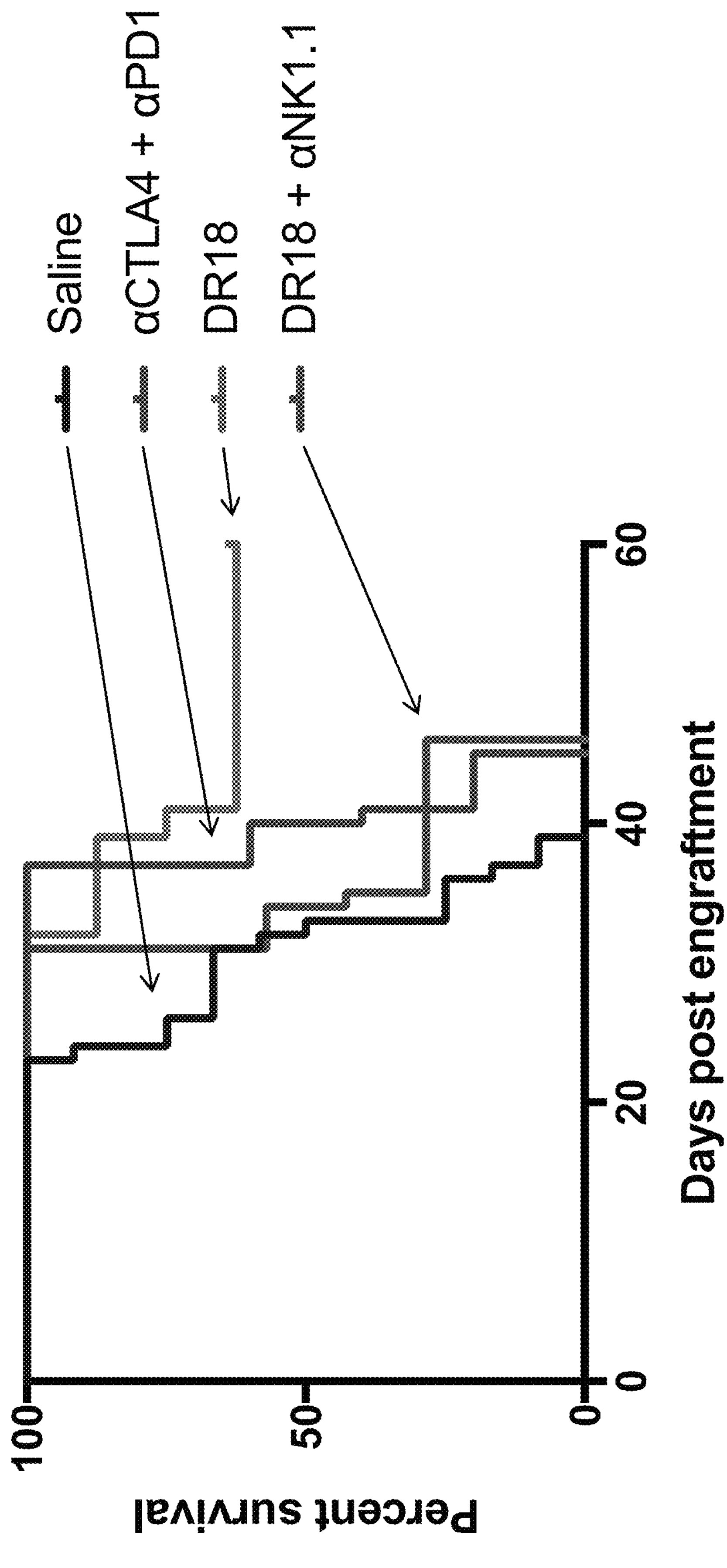
Figure 19C:
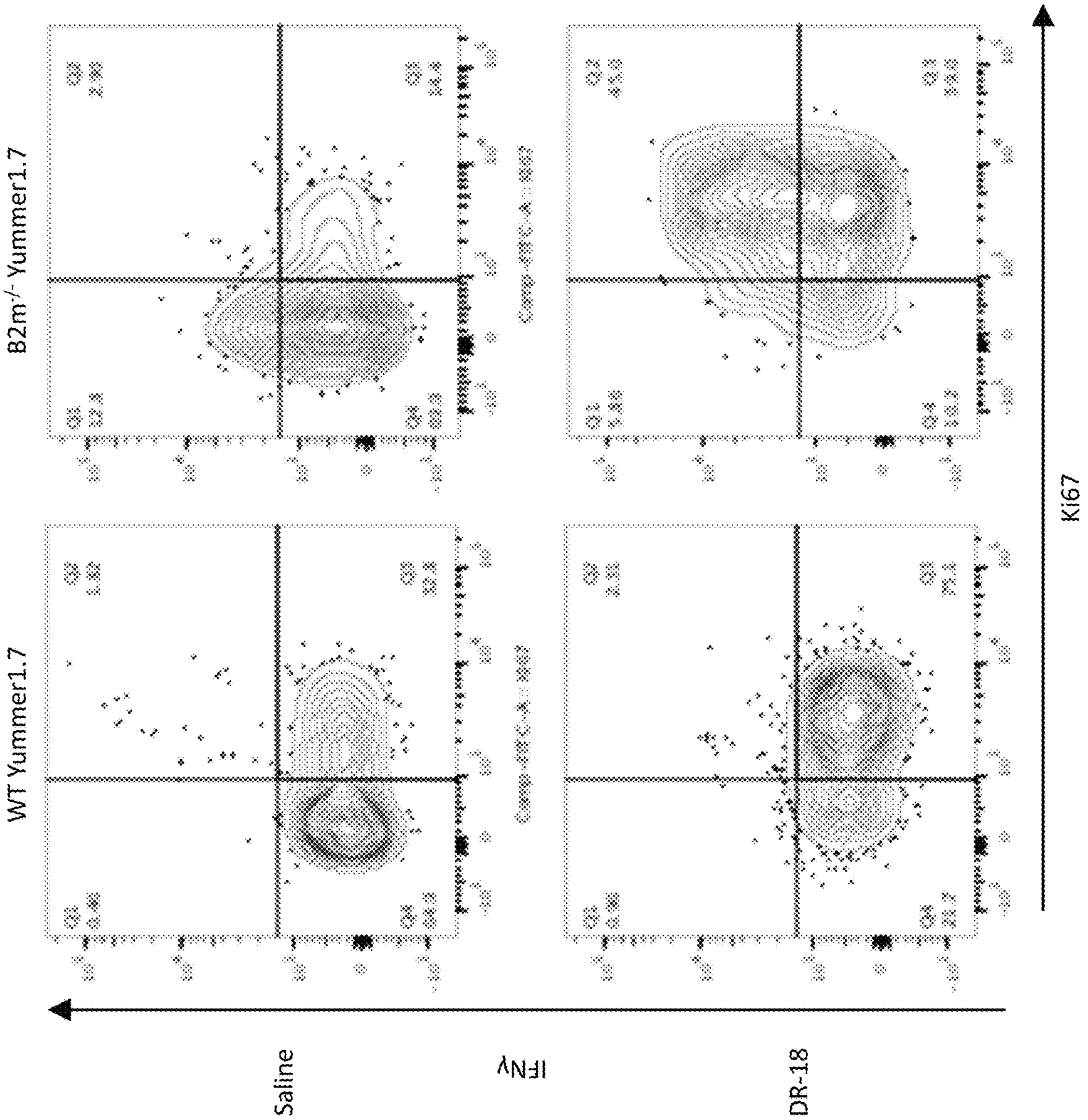

Many tumors are resistant to immune checkpoint inhibition, either at initial presentation (primary resistance) or after an initial response to treatment (secondary resistance). The most prevalent cause of resistance of checkpoint inhibitors is loss of antigen presentation through MHC class I. Loss of surface MHC class I is classically associated with NK-cell mediated cytolysis, however, NK cells can become exhausted within MHC I deficient tumors. As NK cells express the IL-18R and our previous results in MC38 indicated that NK cells are expanded and activated by DR-IL-18, we thus tested whether DR-IL-18 could stimulate NK cell attack against MHC I deficient tumors. We used CRISPR/cas9 to knockout B2m in the Yummer1.7 cell line and found that implanted B2m-deficient YUMMER1.7 tumors were refractory to even combined treatment with both anti-CTLA4 and anti-PD1 (FIG. 19A and FIG. 19B), a combination that routinely cures close to 100% of parental Yummer1.7 tumors. However, single-agent treatment with DR-IL-18 (mCS2) cured 60% of B2m-deficient Yummer1.7 tumors in an NK-cell dependent fashion, as depletion with anti-NK1.1 abrogated the effect (FIG. 19A and FIG. 19B). Experiments were conducted to understand the effect that DR-IL-18 had on intratumoral NK cells in the setting of an MHC class I deficient tumor. Immunophenotyping studies were performed with flow cytometry on B2m-deficient Yummer0.17 tumors from mice treated with saline or DR-IL-18. 24 hours after the 3rd dose of treatment, the mice were sacrificed, tumors were dissociated, and the cell suspension was treated with PMA/ionomycin for four hours. The proliferative index and functional capacity of the NK cells were then analyzed by intracellular flow cytometry with Ki67 and Interferon-gamma. As seen in FIG. 19C, NK cells from saline-treated B2m-deficient Yummer1.7 tumors had scant Interferon-gamma production and Ki67 levels, indicating an exhausted phenotype. By contrast, NK cells from tumors treated with DR-IL-18 had robust Interferon-gamma production and Ki67 levels, with the majority of NK cells being positive for both markers. These results thus establish that DR-IL-18 is effective in the treatment of MHC class I deficient tumors that are refractory to immune checkpoint blockade in an NK cell-dependent manner.

These results establish DR-IL-18 as a highly promising tumor immunotherapeutic, and provide strong evidence that IL-18BP greatly limits the effectiveness of IL-18 therapy, given the greatly improved activity of the mCS2 DR-IL-18 variant. From these results, it is predicted that other strategies, such as blocking IL-18BP with an antibody, small protein, and/or small molecule could augment IL-18 therapy and other immunotherapeutic regimens.

Efforts were undertaken to engineer an IL-18BP antagonist by creating a "decoy-to-the-decoy" (D2D), or IL-18 variants that specifically bind IL-18BP, but do not bind IL-18Rα and thus do not signal. The potential advantage of such an agent is that it would serve to neutralize IL-18BP and enhance the activity of endogenous IL-18, as opposed to driving IL-18R signaling systemically. IL-18 was thus randomized at contact positions for IL-18Rα (FIG. 20A) and a yeast-displayed library was prepared as described previously for human and mouse DR-IL-18. The resulting library of $3.9\times10^8$ transformants was selected for 3 rounds as indicated in (FIG. 20B), selecting for retained IL-18BP binding, while counterselecting against IL-18Rα. As seen in (FIG. 20C), each round of selection conferred enrichment for binding to IL-18BP (human and mouse), but without acquisition of IL-18Rα binding. 96 clones were sequenced, yielding 31 unique sequences, from which three consensus sequences hD2D-CS1, hD2D-CS2, and hD2D-CS3 were derived (FIG. 21). Biophysical characterization of the resulting clones indicated that they showed similar binding isotherms to IL-18BP as WT IL-18 (FIG. 22A), but with greatly decreased/absent binding to IL-18Rα (FIG. 22B). These data are summarized in (FIG. 22C). An identical selection process was performed for murine IL-18, creating a library of $2.0\times10^8$ transformants, which we selected to obtain 51 unique sequences (summarized in FIG. 23).

Example 2: Binding Affinity Measurements of Second Generation Variants

Figure 24:
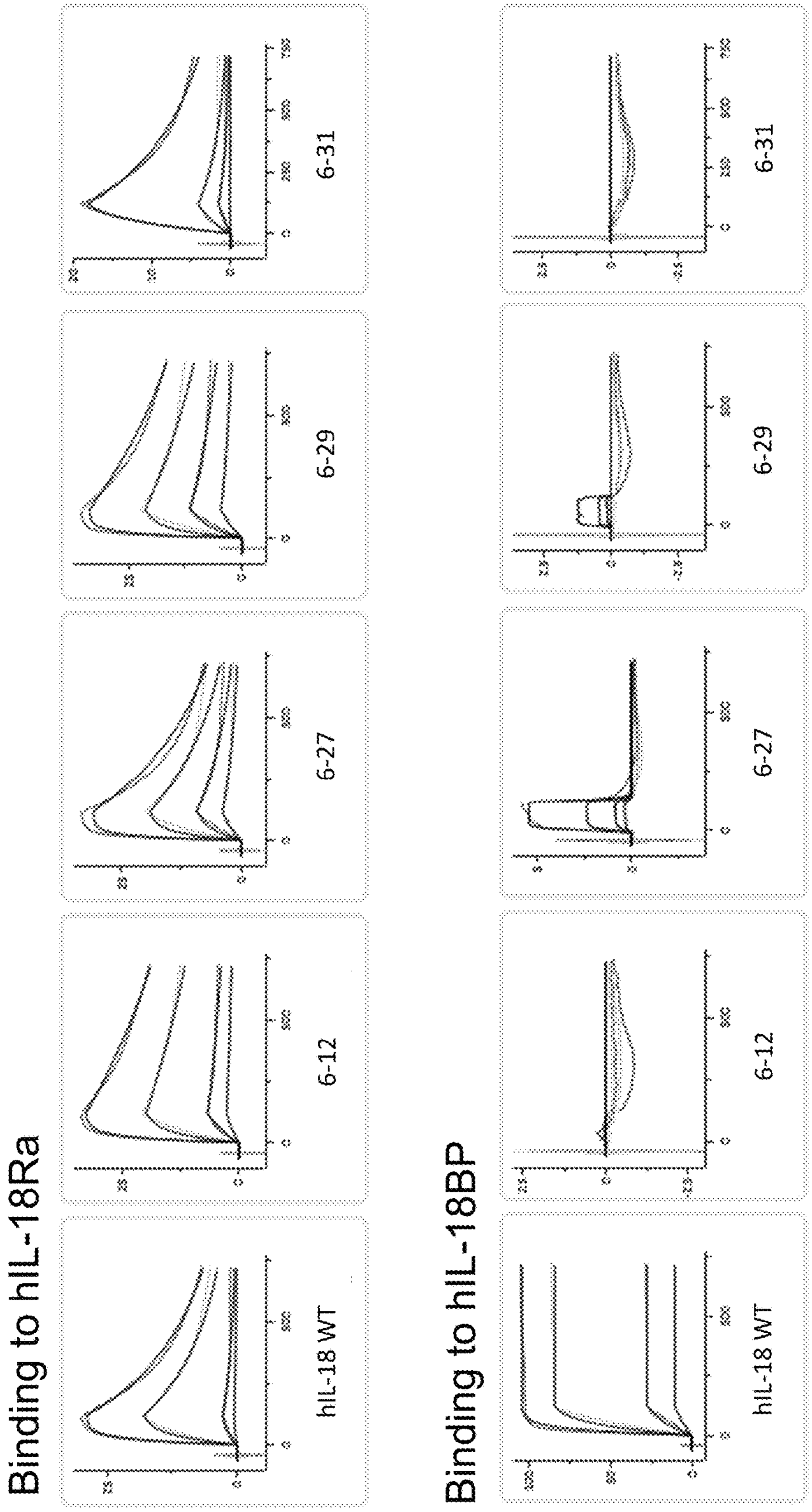
FIG. 24 depicts results from biophysical affinity measurements (sensograms) of the second-generation DR-IL-18 variants for binding to IL-18Rα and IL-18BP using Surface Plasmon Resonance (SPR). Top row: representative sensograms of the indicated IL-18 variants (soluble analytes) for hIL-18Rα (immobilized ligand). Bottom row: representative sensograms of the indicated IL-18 variants for human (hIL-18BP). The x axis is time in seconds and the y axis is Response Units (RU). The curves are the observed data over time for different concentrations (2-fold dilutions starting at InM), superimposed with curves of best fit assuming a 1:1 langmuir binding model.

Surface Plasmon Resonance (SPR) was used to perform biophysical affinity measurements of second generation DR-IL-18 variants (binding to IL-18R vs IL-18BP). See FIG. 24 for the generated sensograms. Table 10 is a summary of the measured kinetics, Table 11 is a summary of the affinity measurements, and Table 12 is a general summary, including results for the dissociation constant ratios of the second generation DR-IL-18 variants.

TABLE 10

Summary of SPR data for second generation hDR-IL-18 variants (kinetics)

| Surface Ligand | Analyte | ka (1/Ms) | kd (1/s) | KD (M) Exp 2 | KD (M) Exp 1 | % Rmax |
|---|---|---|---|---|---|---|
| hIL-18Ra | hIL-18 | 5.55E+05 | 2.97E−03 | 5.36E-09 | 5.35E-09 | 32 |
| hIL-18Ra | 6-12 | 4.95E+05 | 9.10E−04 | 1.84E-09 | 2.24E-09 | 35 |
| hIL-18Ra | 6-27 | 6.31E+05 | 2.43E−03 | 3.85E-09 | 3.48E-09 | 35 |
| hIL-18Ra | 6-29 | 5.75E+05 | 1.19E−03 | 2.07E-09 | 2.65E-09 | 36 |
| hIL-18Ra | 6-31 | 2.18E+05 | 3.32E−03 | 1.52E-08 | 1.94E-08 | 19 |
| hIL-18BP | hIL-18 | 5.18E+05 | 2.23E−07 | 4.30E-13 | 6.94E-13 | 48 |
| hIL-18BP | 6-12 | | Too weak to measure | | | −1 |
| hIL-18BP | 6-27 | | Too weak to measure | | | 2 |
| hIL-18BP | 6-29 | | Too weak to measure | | | 0 |
| hIL-18BP | 6-31 | | Too weak to measure | | | −1 |

TABLE 11

Summary of SPR data for second generation hDR-IL-18 variants (affinity)

| Sample | $KB_{apparent}$ hIL-18Ra (nM) | $KD_{apparent}$ hIL-18BP (nM) |
|---|---|---|
| hIL-18 | 5.4, 5.4 | <0.1 |
| 6-12 | 1.8. 2.2 | too weak |
| 6-27 | 3.9, 3.5 | too weak |
| 6-29 | 2.1, 2.7 | too weak |
| 6-31 | 15.2, 19.4 | too weak |

TABLE 12

Summary of SPR affinity measurements. Summary of the SPR affinity measurements of second generation hDR-IL-18 variants for IL-18Ra and IL-18BP. The IL-18 BP:Ra Dissociation Constant Ratio is the ratio of the KD for IL-18BP to the KD for IL-18Ra normalized to the same ratio of WT IL-18. A higher number for this ratio indicates that the IL-18 variant has an enhanced preference for binding IL-18Ra over IL-18BP compared to WT IL-18.

| Protein | SPR: $K_D$ Ra (nM) | SPR: $K_D$ BP (nM) | IL-18 BP:Ra Dissociation Constant Ratio |
|---|---|---|---|
| WT hIL-18 | 4.1* | 0.002 | 1 |
| hCS1 | 8.0* | 11.8* | 3,024 |
| hCS3 | 9.1* | 19.3* | 4,348 |
| hCS4 | 7.7* | 121* | 32,215 |
| 6-12 | 2.2 | >10,000 | >9,318,275 |
| 6-27 | 3.5 | >10,000 | >5,857,201 |
| 6-29 | 2.7 | >10,000 | >7,592,669 |
| 6-31 | 19.4 | >10,000 | >1,056,712 |
| WT mIL-18 | 0.60 | 0.0011 | 1 |
| mCS2 | 0.08 | 11,000 | >75,000,136 |
| A7, B1, C1, E8 | 0.22-1.7 | 14k-29k | 9.3m-35m |

*Average of 2 studies, k is a multiple of 1,000. m is a multiple of 1,000,000.

Example 3: Efficacy for Cancer Treatment

Efficacy of DR-IL-18 variants was tested using multiple different cancer models, including models of colorectal tumors, breast cancer, melanoma, and MHC class I deficient tumors that are resistant to immune checkpoint inhibitors. The results show that DR-IL-18 variants with a bias to bind IL-18R and not IL-18BP can be used to treat a broad range of cancers (not limited to just those that were tested).

Figure 25A:
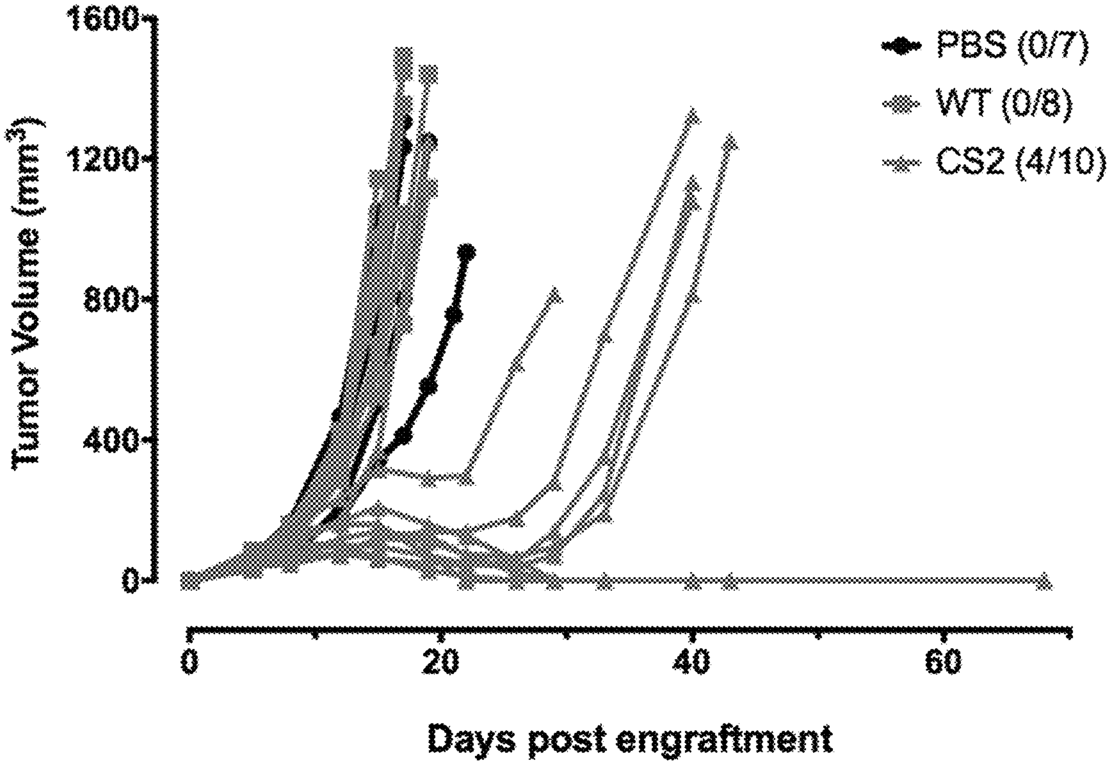
FIGS. 25A and 25B depict data demonstrating efficacy of DR-IL-18 on the CT26 colorectal tumor model. 250,000 CT26 cells were implanted subcutaneously and treatment initiated at day 7 once tumors were ~60 mm3 on average. WT IL-18 and mCS2 were dosed at 0.32 mg/kg twice weekly for a total of 5 doses. Anti-PD1 was given at 10 mg/kg at the same schedule. (A) Overlay of spider plots showing tumor growth of saline (PBS) treated animals in black lines (circles), WT IL-18 in blue lines (squares), and DR-IL-18 (mCS2) in pink (triangles). Only treatment with DR-IL-18, but not WT IL-18, resulted in tumor growth inhibition and tumor clearance in a subset of animals. (B) Survival curves for mice treated with anti-PD-1, WT IL-18, and DR-IL-18 (mCS2). Numbers of complete responses are indicated in parentheses. DR-IL-18, but not WT IL-18 resulted in prolonged survival and tumor clearance in 40% of mice, an improvement over the checkpoint inhibitor anti-PD-1.
Figure 25B:
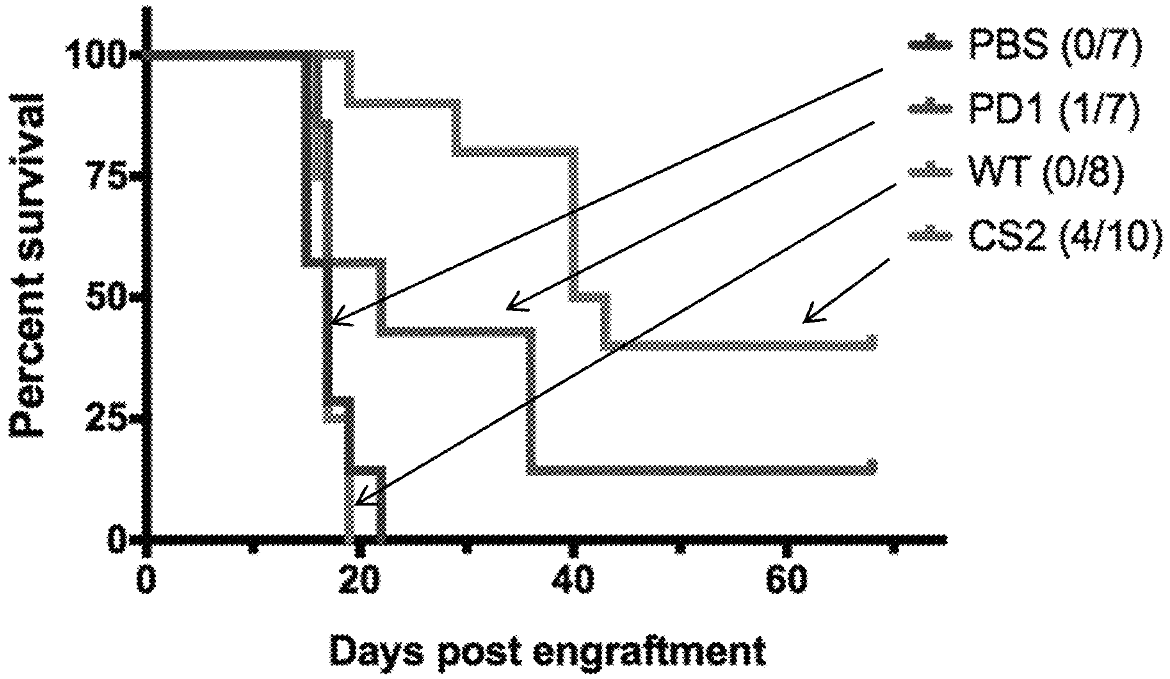

FIGS. 25A and 25B: data demonstrating efficacy of DR-IL-18 on the CT26 colorectal tumor model. 250,000 CT26 cells were implanted subcutaneously and treatment initiated at day 7 once tumors were ~60 mm3 on average. WT IL-18 and mCS2 were dosed at 0.32 mg/kg twice weekly for a total of 5 doses. Anti-PD1 was given at 10 mg/kg at the same schedule. (A) Overlay of spider plots showing tumor growth of saline (PBS) treated animals in black lines (circles), WT IL-18 in blue lines (squares), and DR-IL-18 (mCS2) in pink (triangles). Only treatment with DR-IL-18, but not WT IL-18, resulted in tumor growth inhibition and tumor clearance in a subset of animals. (B) Survival curves for mice treated with anti-PD-1, WT IL-18, and DR-IL-18 (mCS2). Numbers of complete responses are indicated in parentheses. DR-IL-18, but not WT IL-18 resulted in prolonged survival and tumor clearance in 40% of mice, an improvement over the checkpoint inhibitor anti-PD-1.

Figure 26A:
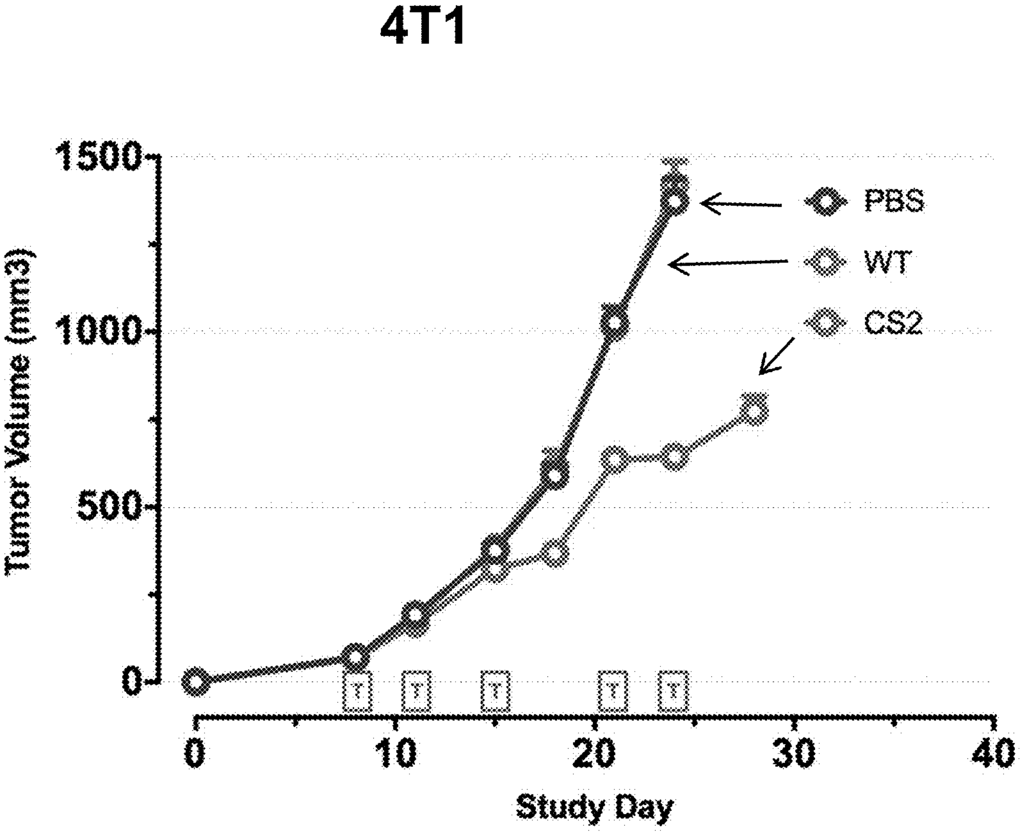
FIGS. 26A and 26B depict data demonstrating efficacy of DR-IL-18 in the 4T1 breast cancer model and B16-F10 melanoma model. (A) Tumor growth curves of 4T1 tumors engrafted into BALB/C mice after treatment with saline (PBS; black), WT IL-18 (blue), or the DR-IL-18 variant CS2 (pink). (B) Tumor growth curves of B16-F10 tumors engrafted into C57BL/6 mice after treatment with saline (PBS; black), WT IL-18 (blue), or the DR-IL-18 variant CS2 (pink). In both models, only DR-IL-18, but not WT IL-18 resulted in tumor growth inhibition. Treatments were administered after tumors exceeded an average volume 50 $mm^3$ as indicated by the boxes marked with "t".
Figure 26B:
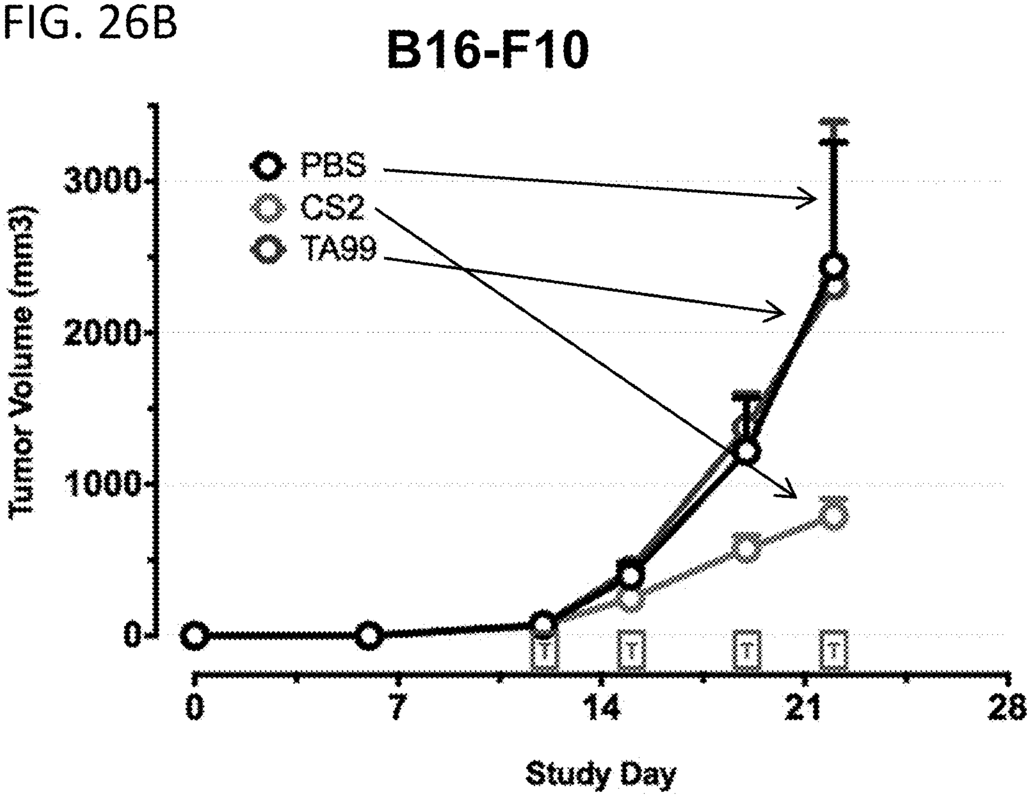

FIGS. 26A and 26B: data demonstrating efficacy of DR-IL-18 in the 4T1 breast cancer model and B16-F10 melanoma model. (A) Tumor growth curves of 4T1 tumors engrafted into BALB/C mice after treatment with saline (PBS; black), WT IL-18 (blue), or the DR-IL-18 variant CS2 (pink). (B) Tumor growth curves of B16-F10 tumors engrafted into C57BL/6 mice after treatment with saline (PBS; black), WT IL-18 (blue), or the DR-IL-18 variant CS2 (pink). In both models, only DR-IL-18, but not WT IL-18 resulted in tumor growth inhibition. Treatments were administered after tumors exceeded an average volume 50 $mm^3$ as indicated by the boxes marked with "t".

Figure 27A:
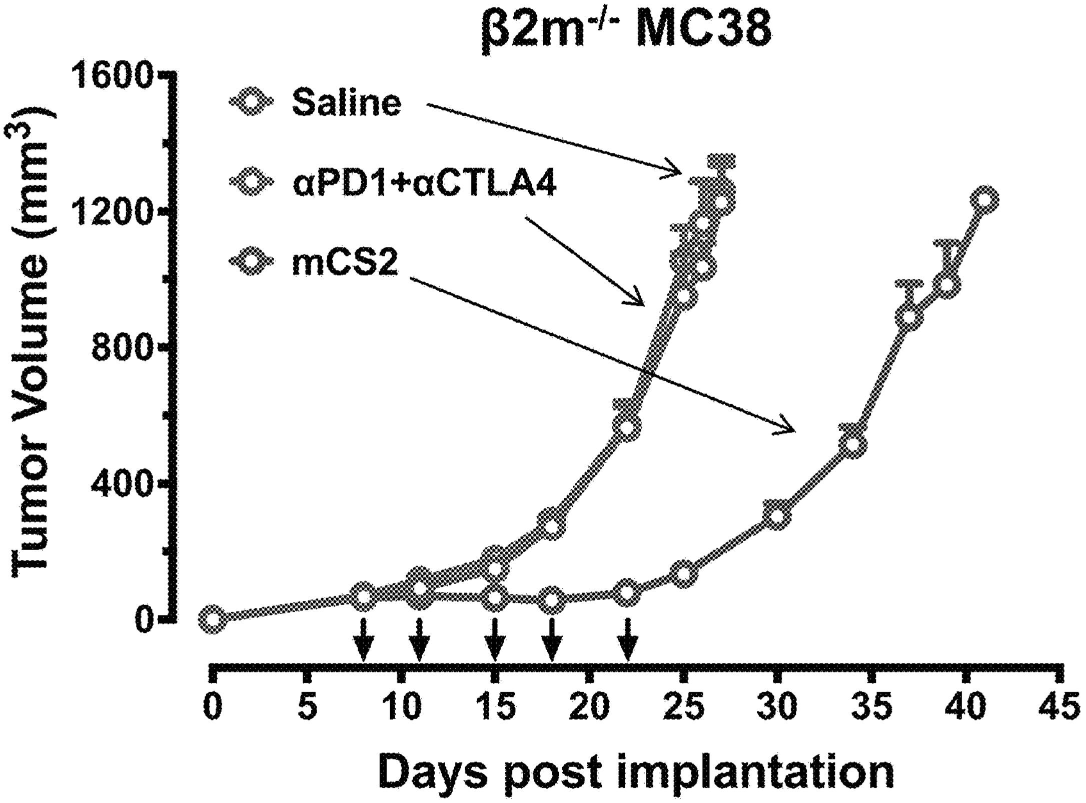
FIGS. 27A and 27B depict data that extend the data of FIG. 19A through 19C. Depicted is data demonstrating efficacy of DR-IL-18 in the treatment of additional MHC class I deficient tumor models that are resistant to immune checkpoint inhibitors. (A) B2m deficient MC38 cells were prepared using CRISPR/Cas9 mediated deletion as described for B2m deficient YUMMER cells. B2m−/− MC38 cells were implanted subcutaneously and treatment initiated at day 7 once tumors were ~65 mm3 on average. mCS2 was dosed at 0.32 mg/kg twice weekly for 5 doses. Anti-PD1 and anti-CTLA4 were given at 8 mg/kg at the same schedule. (B) RMA/S is a variant of the RMA lymphoma line that contains a spontaneous mutation in Tapasin. The result is a defect in antigen loading and therefore decreased MHC class I surface expression. It is congenic to C57BL/6 and refractory to immune checkpoint inhibitors. Mice were implanted with 1,000,000 RMA/S cells subcutaneously and treatment initiated at day 7. mCS2 was dosed at 0.32 mg/kg twice weekly. Anti-PD1 was given at 8 mg/kg at the same schedule. In both studies, only treatment with the DR-18 variant mCS2 exhibited anti-tumor efficacy in the form of tumor growth inhibition ($B2m^{-/-}$ MC38) or tumor clearance (RMA/S).
Figure 27B:
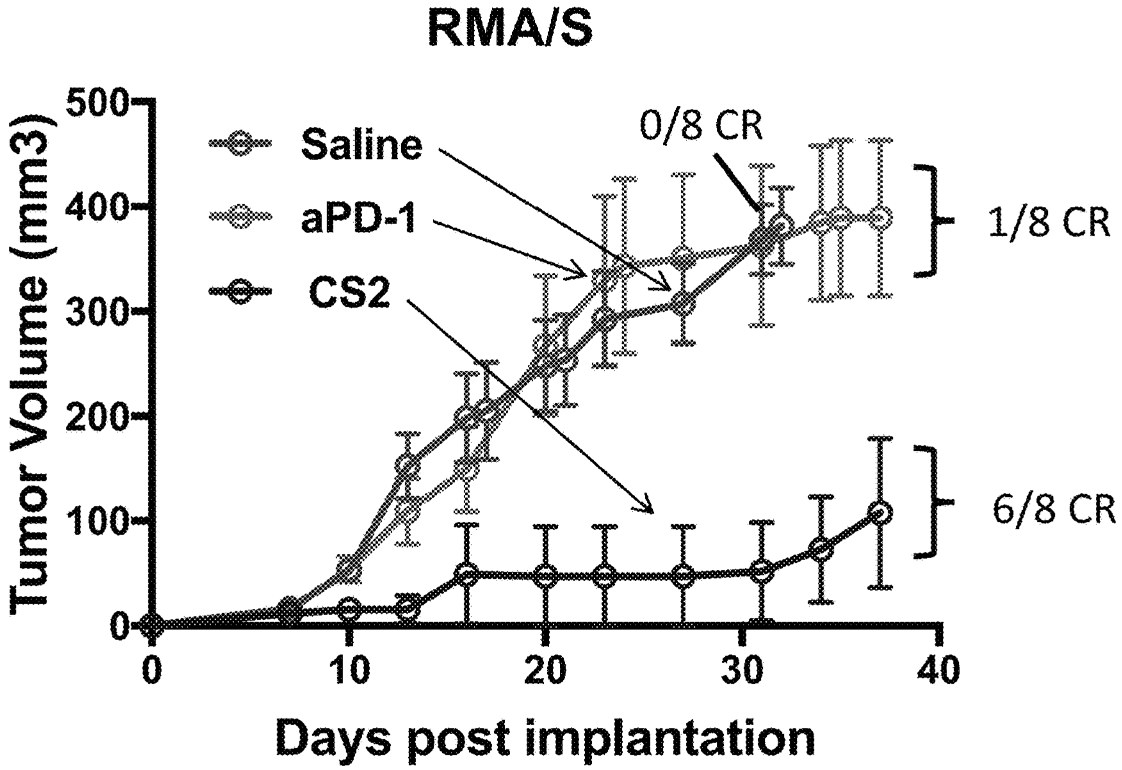

FIGS. 27A and 27B: These data extend those of FIG. 19A through 19C. Depicted is data demonstrating efficacy of DR-IL-18 in the treatment of additional MHC class I deficient tumor models that are resistant to immune checkpoint inhibitors. (A) B2m deficient MC38 cells were prepared using CRISPR/Cas9 mediated deletion as described for B2m deficient YUMMER cells. $B2m^{-/-}$ MC38 cells were implanted subcutaneously and treatment initiated at day 7 once tumors were ~65 mm3 on average. mCS2 was dosed at 0.32 mg/kg twice weekly for 5 doses. Anti-PD1 and anti-CTLA4 were given at 8 mg/kg at the same schedule. (B) RMA/S is a variant of the RMA lymphoma line that contains a spontaneous mutation in Tapasin. The result is a defect in antigen loading and therefore decreased MHC class I surface expression. It is congenic to C57BL/6 and refractory to immune checkpoint inhibitors. Mice were implanted with 1,000,000 RMA/S cells subcutaneously and treatment initiated at day 7. mCS2 was dosed at 0.32 mg/kg twice weekly. Anti-PD1 was given at 8 mg/kg at the same schedule.

Example 4: Combination Therapy

Figure 28:
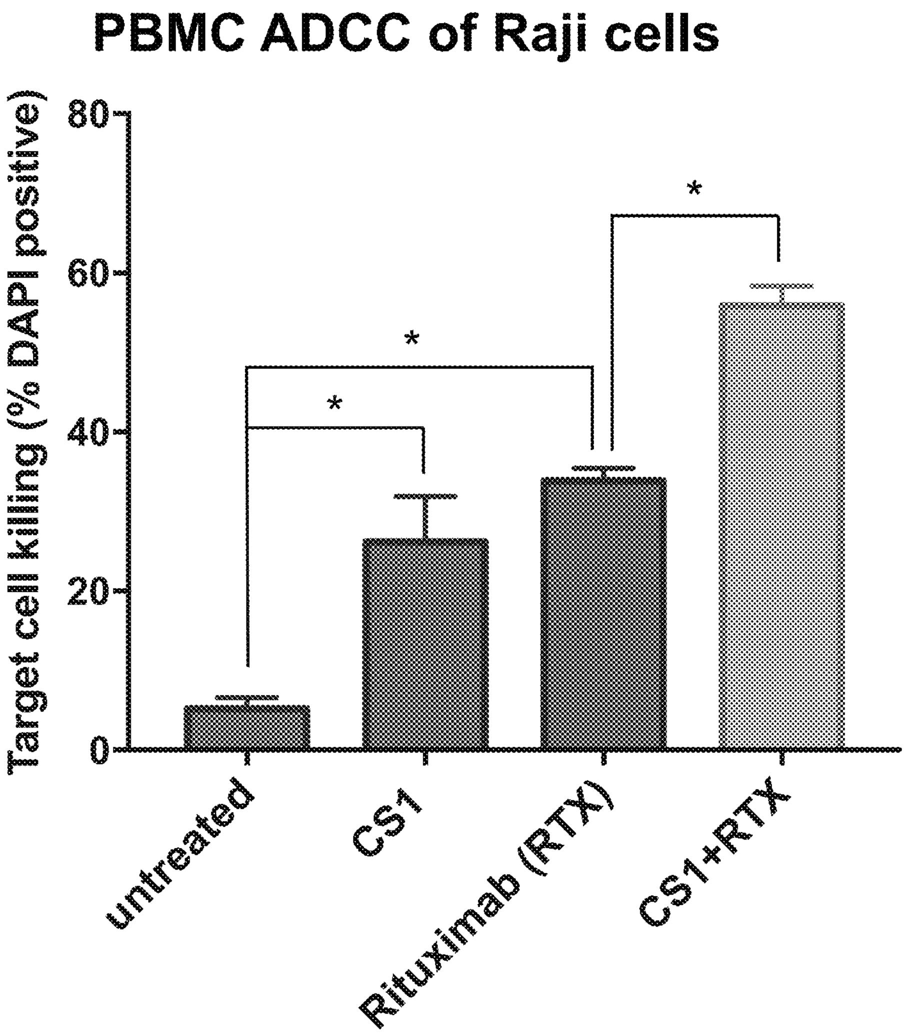
FIG. 28 depicts data demonstrating efficacy of DR-IL-18 to enhance anti-tumor antibody-dependent cell mediated cytotoxicity (ADCC). Ex vivo cytotoxicity studies used CFSE labeled Raji (B cell lymphoma) cells and isolated human peripheral blood mononuclear cells (PBMCs). PBMCs and labeled Raji cells were incubated together at an effector:target (E:T) ratio of 1:10 for 25 hours. The human DR-IL-18 variant hCS-1 (1 uM), rituximab (10 ug/mL), or the combination of both agents were applied to the samples as indicated. Cytotoxicity was measured by flow cytometry and calculated as the fraction of CFSE cells that became DAPI positive. DR-18 stimulated significant tumor cell killing as a single agent and significantly enhanced the killing by the therapeutic antibody rituximab. *$p<0.05$ by two-way ANOVA with Tukey's correction for multiple comparisons.

FIG. 28: data demonstrating efficacy of DR-IL-18 variants to enhance anti-tumor antibody-dependent cell mediated cytotoxicity (ADCC) (supporting combination therapy with opsonizing agents such as tumor-targeting antibodies).

Ex vivo cytotoxicity studies used CFSE labeled Raji (B cell lymphoma) cells and isolated human peripheral blood mononuclear cells (PBMCs). PBMCs and labeled Raji cells were incubated together at an effector:target (E:T) ratio of 1:10 for 25 hours. The human DR-IL-18 variant hCS-1 (1 uM), rituximab (10 ug/mL), or the combination of both agents were applied to the samples as indicated. Cytotoxicity was measured by flow cytometry and calculated as the fraction of CFSE cells that became DAPI positive. *p<0.05 by two-way ANOVA with Tukey's correction for multiple comparisons.

Example 5: Efficacy Against Viral Infections

Figure 29A:
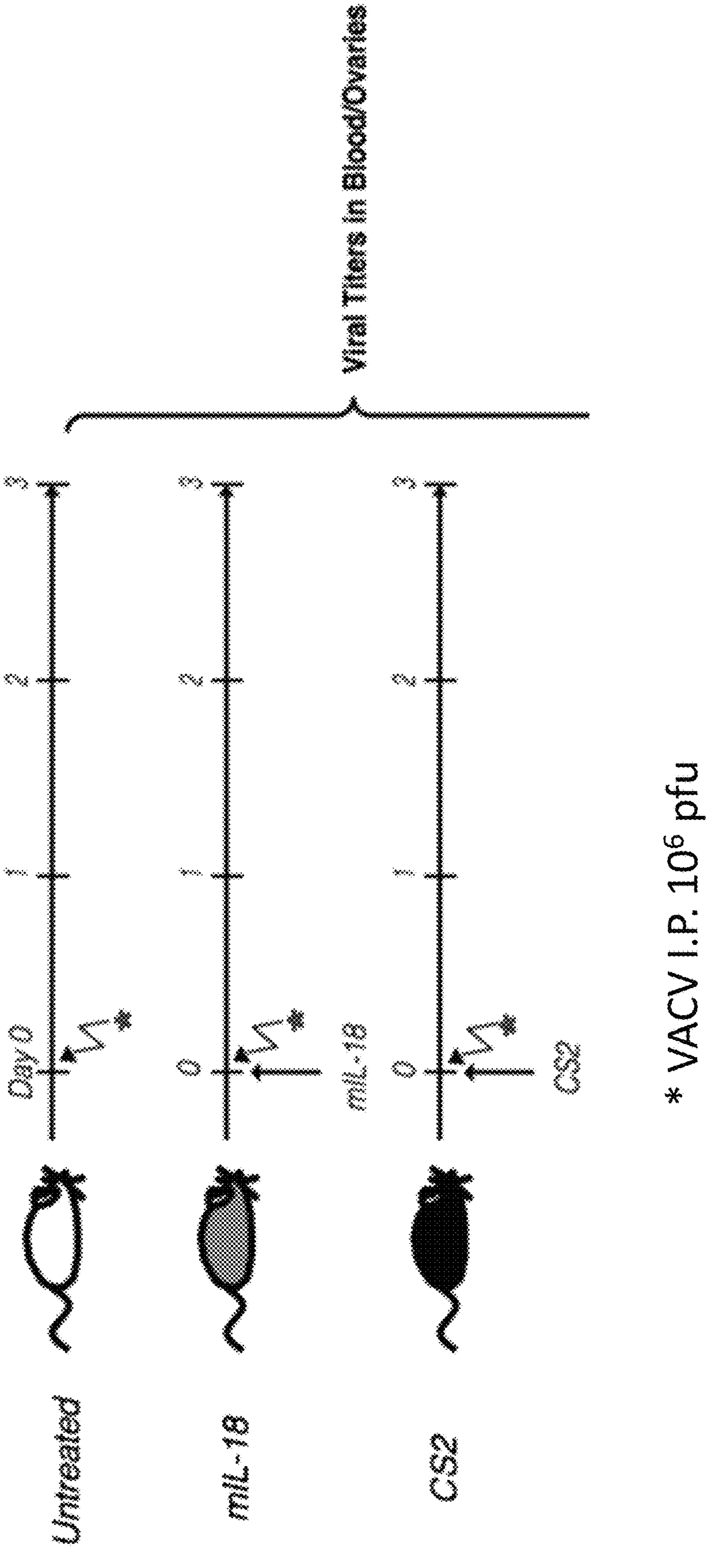
FIGS. 29A and 29B depict data demonstrating anti-viral efficacy of DR-18 variant mCS2 for the treatment viral infections (e.g., in this case in the treatment of systemic vaccinia virus infection). (A) Experimental design scheme. C57BL/6 mice were infected with 106 PFU of Vaccinia virus (VACV) intraperitoneally (IP) and administered 1 mg/kg WT mIL-18 or mCS2 IP. Mice were sacrificed and viral titers were measured in the blood and ovaries by RT-PCR on day 3 post-infection. (B) Quantification of VACV viral copies in ovaries and blood of treated mice at day 3 post infection. Treatment with CS2 showed a significant reduction of viral titers, whereas WT IL-18 was not effective. *$p<0.05$,$p<0.01$, *$p<0.001$.
Figure 29B:
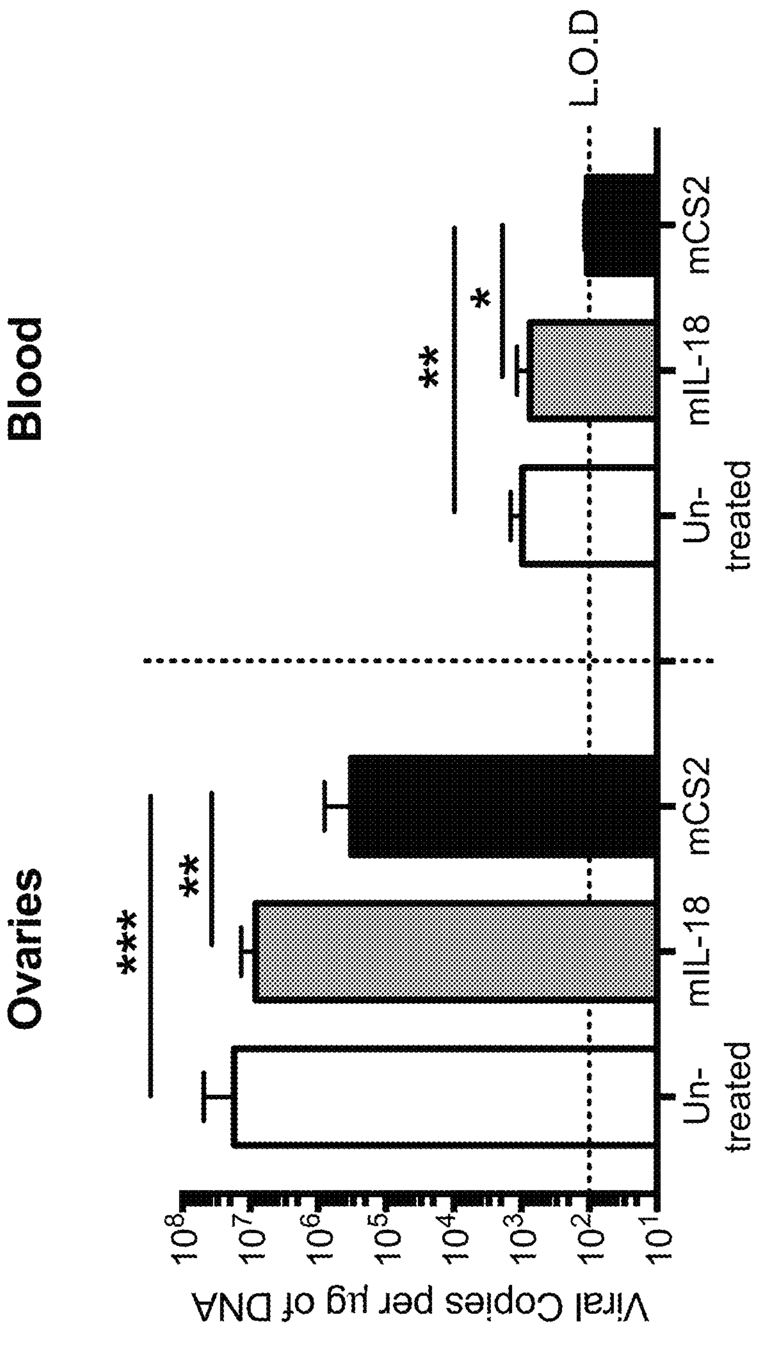

FIGS. 29A and 29B: data demonstrating anti-viral efficacy of DR-18 variants for the treatment of infection disease (e.g., for viral infections, e.g., in this illustrative example, mCS2 was used for treatment of systemic vaccinia virus infection). (A) Experimental design scheme. C57BL/6 mice were infected with $10^6$ PFU of Vaccinia virus (VACV) intraperitoneally (IP) and administered 1 mg/kg WT mIL-18 or mCS2 IP. Mice were sacrificed and viral titers were measured in the blood and ovaries by RT-PCR on day 3 post-infection. (B) Quantification of VACV viral copies in ovaries and blood of treated mice at day 3 post infection. Treatment with CS2 showed a significant reduction of viral titers, whereas WT IL-18 was not effective. *p<0.05, p<0.01, *p<0.001.

Example 6: Second Generation Human DR-IL-18 Variants

Figure 30A:
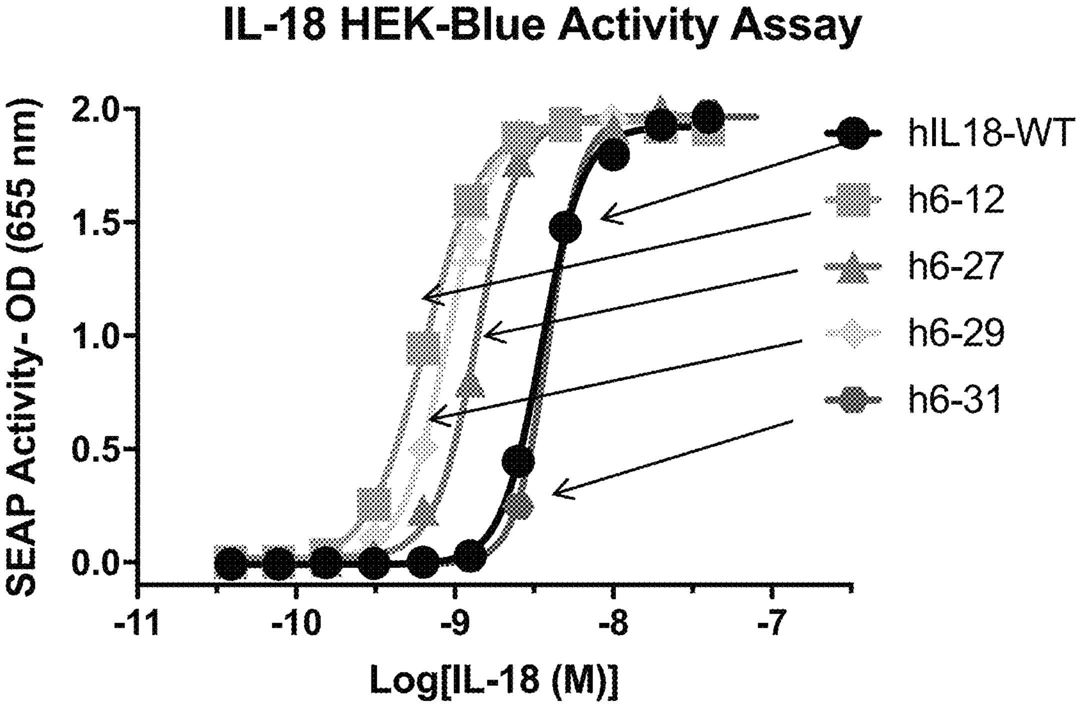
FIG. 30A depicts data demonstrating that the second generation human DR-IL-18 variants are active.

FIG. 30A depicts data demonstrating that the second generation human DR-IL-18 variants are active. (FIG. 30A) WT IL-18 and h6-12, h6-27, h6-29, and h6-31 stimulate IL-18 HEK-Blue reporter cells. h6-12, h6-27, and h6-29 show enhanced potency compared to WT hIL-18, whereas h6-31 has equivalent potency as WT hIL-18. The data demonstrate, therefore, that all tested second generation human DR-IL-18 variants actively signal through IL-18R.

Wild-Type IL-18 Amino Acid Sequences

HUMAN Interleukin-18 (mature form)
YFGKLESKLSVIRNLNDQVLFIDQGNRPLFEDMTDSDCRDNAPRTIFIISM
YKDSQPRGMAVTISVKCEKISTLSCENKIISFKEMNPPDNIKDTKSDIIFF
QRSVPGHDNKMQFESSSYEGYFLACEKERDLFKLILKKEDELGDRSIMFTV
QNED (SEQ ID NO: 30)

MOUSE Interleukin-18 (mature form)
NFGRLHCTTAVIRNINDQVLFVDKRQPVFEDMTDIDQSASEPQTRLIIYMY
KDSEVRGLAVTLSVKDSKMSTLSCKNKIISFEEMDPPENIDDIQSDLIFFQ
KRVPGHNKMEFESSLYEGHFLACQKEDDAFKLILKKKDENGDKSVMFTLTN
LHQS (SEQ ID NO: 31)

Q14116|IL18_HUMAN Interleukin-18
(uncleaved precursor)
MAAEPVEDNCINFVAMKFIDNTLYFIAEDDENLESDYFGKLESKLSVIRNL
NDQVLFIDQGNRPLFEDMTDSDCRDNAPRTIFIISMYKDSQPRGMAVTISV
KCEKISTLSCENKIISFKEMNPPDNIKDTKSDIIFFQRSVPGHDNKMQFES
SSYEGYFLACEKERDLFKLILKKEDELGDRSIMFTVQNED (SEQ ID
NO: 32)

P70380|IL18_MOUSE Interleukin-18 (uncleaved
precursor)
MAAMSEDSCVNFKEMMFIDNTLYFIPEENGDLESDNFGRLHCTTAVIRNIN
DQVLFVDKRQPVFEDMTDIDQSASEPQTRLIIYMYKDSEVRGLAVTLSVKD
SKMSTLSCKNKIISFEEMDPPENIDDIQSDLIFFQKRVPGHNKMEFESSLY
EGHFLACQKEDDAFKLILKKKDENGDKSVMFTLTNLHQS (SEQ ID
NO: 33)

| | |
|---|---|
| hCS1 | YFGKLESKLSVIRNLNDQVLFIDQGNRPLFEDMTDSDCRDNAPRTIFIIS<br>TYKDSQPRGKAVTISVKCEKISTLSCENKIISFKEMNPPDNIKDTKSDIIF<br>FQRDVPGHKHKMQFESSSYEGYFLACEKERDLFKLILKKEDELGDRSI<br>MFTVQNED (SEQ ID NO: 34) |
| hCS2 | YFGKLESKLSVIRNLNDQVLFIDQGNRPLFEDMTDSDCRDNAPRTIFIIS<br>TYKDKQPRAKAVTISVKCEKISTLSCENKIISFKEMNPPDNIKDTKSDIIF<br>FQRDVPGHKHKMQFESSSYEGYFLACEKERDLFKLILKKEDELGDRSI<br>MFTIQNED (SEQ ID NO: 35) |
| hCS3 | RFGKLESKLSVIRNLNDQVLFIDQGNRPLFEDMTDSDCRDNAPRTIFIIS<br>TYKDSQPRGKAVTISVKCEKISTLSCENKIISFKEMNPPDNIKDTKSDIIF<br>FQRDVPGHKHKMQFESSSYEGYFLACEKERDLFKLILKKEDELGDRSI<br>MFTVQNED (SEQ ID NO: 36) |
| hCS4 | RFGKLESKLSVIRNLNDQVLFIDQGNRPLFEDMTDSDCRDNAPRTIFIIS<br>TYRDSQPRGKAVTISVKCEKISTLSCENKIISFKEMNPPDNIKDTKSDIIF<br>FQRNVPGHKYKMQFESSSYEGYFLACEKERDLFKLILKKEDELGDRSI<br>MFTVQNED (SEQ ID NO: 37) |
| hC4 | YFGKLESQLSVIRNLNDQVLFIDQGNRPLFEDMTDSDCRDNAPRTIFIIS<br>TYKDKQPRTKAVTISVKCEKISTLSCENKIISFKEMNPPDNIKDTKSDIIF<br>FQRRVPGHHNKMQFESSSYEGYFLACEKERDLFKLILKKEDELGDRSI<br>MFTVQKED (SEQ ID NO: 38) |
| hA8 | YFGKLESRLSVIRNLNDQVLFIDQGNRPLFEDMTDSDCRDNAPRTIFIIS<br>KYKDKQPRAQAVTISVKCEKISTLSCENKIISFKEMNPPDNIKDTKSDIIF<br>FQRDVPGHKHKMQFESSSYEGYFLACEKERDLFKLILKKEDELGDRSI<br>MFTIQNED (SEQ ID NO: 39) |

-continued hD6 YFGKLESRLSVIRNLNDQVLFIDQGNRPLFEDMTDSDCRDNAPRTIFIIS
DYKDKQPRAXAVTISVKCEKISTLSCENKIISFKEMNPPDNIKDTKSDIIF
FQRDVPGHKHKMQFESSSYEGYFLACEKERDLFKLILKKEDELGDRSI
MFTIQNED (SEQ ID NO: 40)

hH12 YFGKHESKLSVIRNLNDQVLFIDQGNRPLFEDMTDSDCRDNAPRTIFIIS
TYRDSQPRGKAVTISVKCEKISTLSCENKIISFKEMNPPDNIKDTKSDIIF
FQRDVPGHNNKMQFESSSYEGYFLACEKERDLFKLILKKEDELGDRSI
MFTTQNED (SEQ ID NO: 41)

hB11 YFGKIESKLSVIRNLNDQVLFIDQGNRPLFEDMTDSDCRDNAPRTIFIIS
KYKDKQPRAQAVTISVKCEKISTLSCENKIISFKEMNPPDNIKDTKSDIIF
FQRKVPGHQHKMQFESSSYEGYFLACEKERDLFKLILKKEDELGDRSI
MFTVQKED (SEQ ID NO: 42)

hC3 YFGKIESKLSVIRNLNDQVLFIDQGNRPLFEDMTDSDCRDNAPRTIFIIST
YKDRQPRGKAVTISVKCEKISTLSCENKIISFKEMNPPDNIKDTKSDIIFF
ERDVPGHHHKMQFESSSYEGYFLACEKERDLFKLILKKEDELGDRSIM
FTIQNED (SEQ ID NO: 43)

hC2 YFGKIESKLSVIRNLNDQVLFIDQGNRPLFEDMTDSDCRDNAPRTIFIIST
YKDKQPRGKAVTISVKCEKISTLSCENKIISFKEMNPPDNIKDTKSDIIFF
QRDVPGHKHKMQFESSSYEGYFLACEKERDLFKLILKKEDELGDRSIM
FTTQHED (SEQ ID NO: 44)

hG10 YFGKIESKLSVIRNLNDQVLFIDQGNRPLFEDMTDSDCRDNAPRTIFIIST
YKDKQPRAKAVTISVKCEKISTLSCENKIISFKEMNPPDNIKDTKSDIIFF
QRRVPGHHHKMQFESSSYEGYFLACEKERDLFKLILKKEDELGDRSIM
FTIQKED (SEQ ID NO: 45)

hG1 YFGKIESRLSVIRNLNDQVLFIDQGNRPLFEDMTDSDCRDNAPRTIFIIST
YKDKQPRGKAVTISVKCEKISTLSCENKIISFKEMNPPDNIKDTKSDIIFF
QRDVPGHDYKMQFESSSYEGYFLACEKERDLFKLILKKEDELGDRSIM
FTIQKED (SEQ ID NO: 46)

hF1 YFGKYESRLSVIRNLNDQVLFIDQGNRPLFEDMTDSDCRDNAPRTIFIIS
TYRDSQPRGKAVTISVKCEKISTLSCENKIISFKEMNPPDNIKDTKSDIIF
FQRDVPGHEHKMQFESSSYEGYFLACEKERDLFKLILKKEDELGDRSI
MFTVQKED (SEQ ID NO: 47)

hD2 HFGKYESKLSVIRNLNDQVLFIDQGNRPLFEDMTDSDCRDNAPRTIFIIS
TYRDSQPRGKAVTISVKCEKISTLSCENKIISFKEMNPPDNIKDTKSDIIF
FQRDVPGHHNKMQFESSSYEGYFLACEKERDLFKLILKKEDELGDRSI
MFTVQKED (SEQ ID NO: 48)

hA1 RFGKLESKLSVIRNLNDQVLFIDQGNRPLFEDMTDSDCRDNAPRTIFIIS
TYRDSQPRAKAVTISVKCEKISTLSCENKIISFKEMNPPDNIKDTKSDIIF
FQRDVPGHQHKMQFESSSYEGYFLACEKERDLFKLILKKEDELGDRSI
MFTAQKED (SEQ ID NO: 49)

hB3 RFGKLESRLSVIRNLNDQVLFIDQGNRPLFEDMTDSDCRDNAPRTIFIIS
DYRDSQPRGRAVTISVKCEKISTLSCENKIISFKEMNPPDNIKDTKSDIIF
FKRNVPGHKYKMQFESSSYEGYFLACEKERDLFKLILKKEDELGDRSI
MFTVQHED (SEQ ID NO: 50)

hB4 RFGKLESRLSVIRNLNDQVLFIDQGNRPLFEDMTDSDCRDNAPRTIFIIS
NYRDSQPRGQAVTISVKCEKISTLSCENKIISFKEMNPPDNIKDTKSDIIF
FKRRVPGHNHKMQFESSSYEGYFLACEKERDLFKLILKKEDELGDRSI
MFTVQKED (SEQ ID NO: 51)

hH3 RFGKLESRLSVIRNLNDQVLFIDQGNRPLFEDMTDSDCRDNAPRTIFIIS
TYKDSQPRGKAVTISVKCEKISTLSCENKIISFKEMNPPDNIKDTKSDIIF
FQRDVPGHKHKMQFESSSYEGYFLACEKERDLFKLILKKEDELGDRSI
MFTVQNED (SEQ ID NO: 52)

hH5 RFGKHESKLSVIRNLNDQVLFIDQGNRPLFEDMTDSDCRDNAPRTIFIIS
TYRDSQPRGKAVTISVKCEKISTLSCENKIISFKEMNPPDNIKDTKSDIIF
FERNVPGHKYKMQFESSSYEGYFLACEKERDLFKLILKKEDELGDRSI
MFTVQNED (SEQ ID NO: 53)

hH4 RFGKLESRLSVIRNLNDQVLFIDQGNRPLFEDMTDSDCRDNAPRTIFIIS
TYRDSQPRAKAVTISVKCEKISTLSCENKIISFKEMNPPDNIKDTKSDIIF
FERDVPGHQHKMQFESSSYEGYFLACEKERDLFKLILKKEDELGDRSI
MFTIQXED (SEQ ID NO: 54)

-continued

| | |
|---|---|
| hE1 | RFGKLESRLSVIRNLNDQVLFIDQGNRPLFEDMTDSDCRDNAPRTIFIIS<br>TYRDSQPRTKAVTISVKCEKISTLSCENKIISFKEMNPPDNIKDTKSDIIF<br>FQRNVPGHHDKMQFESSSYEGYFLACEKERDLFKLILKKEDELGDRSI<br>MFTVQHED (SEQ ID NO: 55) |
| hG2 | RFGKLESRLSVIRNLNDQVLFIDQGNRPLFEDMTDSDCRDNAPRTIFIIS<br>TYKDSQPRAKAVTISVKCEKISTLSCENKIISFKEMNPPDNIKDTKSDIIF<br>FERDVPGHQHKMQFESSSYEGYFLACEKERDLFKLILKKEDELGDRSI<br>MFTIQKED (SEQ ID NO: 56) |
| hB9 | RFGKHESKLSVIRNLNDQVLFIDQGNRPLFEDMTDSDCRDNAPRTIFIIS<br>TYRDSQPRGKAVTISVKCEKISTLSCENKIISFKEMNPPDNIKDTKSDIIF<br>FERNVPGHKYKMQFESSSYEGYFLACEKERDLFKLILKKEDELGDRSI<br>MFTVQNED (SEQ ID NO: 57) |
| hE12 | RFGKYESKLSVIRNLNDQVLFIDQGNRPLFEDMTDSDCRDNAPRTIFIIS<br>TYKDSQPRTKAVTISVKCEKISTLSCDNKIISFKEMNPPDNIKDTKSDIIF<br>FQRDVPGHKHKMQFESSSYEGYFLACEKERDLFKLILKKEDELGDRSI<br>MFTVQNED (SEQ ID NO: 58) |
| hC5 | RFGKLESRLSVIRNLNDQVLFIDQGNRPLFEDMTDSDCRDNAPRTIFIIS<br>TYRDSQPRTKAVTISVKCEKISTLSCENKIISFKEMNPPDNIKDTKSDIIF<br>FQRKVPGHNHKMQFESSSYEGYFLACEKERDLFKLILKKEDELGDRSI<br>MFTVQKED (SEQ ID NO: 59) |

Generation 2 Human Interleukin-18 Decoy-Resistant Variants Amino Sequences

| | |
|---|---|
| 5-18 | YFGKLESKLSVIRNLNDQVLFIDQGNRPLFEDMTDSDCRDNAPRTIFIIS<br>EYKDSELRGRAVTISVKCEKISTLSCENKIISFKEMNPPDNIKDTKSDIIF<br>FPRAVPGHNRKVQFESSSYEGYFLACEKERDLFKLILKKEDELGDRSIM<br>FTVQNED (SEQ ID NO: 73) |
| 5-29 | YFGKLESKLSVIRNLNDQVLFIDQGNRPLFEDMTDSDCRDNAPRTIFIIS<br>KYKDSAGRGLAVTISVKCEKISTLSCENKIISFKEMNPPDNIKDTKSDIIF<br>FERDVPGHSNKVQFESSSYEGYFLACEKERDLFKLILKKEDELGDRSIM<br>FTVQNED (SEQ ID NO: 74) |
| 5-8 | YFGKLESKLSVIRNLNDQVLFIDQGNRPLFEDMTDSDCRDNAPRTIFIIS<br>KYGDSAARGLAVTISVKCEKISTLSCENKIISFKEMNPPDNIKDTKSDIIF<br>FQRSVPGHKRKMQFESSSYEGYFLACEKERDLFKLILKKEDELGDRSI<br>MFTVQNED (SEQ ID NO: 75) |
| 5-6 | YFGKLESKLSVIRNLNDQVLFIDQGNRPLFEDMTDSDCRDNAPRTIFIIS<br>KYGDSRGRGLAVTISVKCEKISTLSCENKIISFKEMNPPDNIKDTKSDIIF<br>FERDVPGHNSKRQFESSSYEGYFLACEKERDLFKLILKKEDELGDRSIM<br>FTVQNED (SEQ ID NO: 76) |
| 5-27 | YFGKLESKLSVIRNLNDQVLFIDQGNRPLFEDMTDSDCRDNAPRTIFIIS<br>KYGDSVPRGLAVTISVKCEKISTLSCENKIISFKEMNPPDNIKDTKSDIIF<br>FARAVPGHSRKTQFESSSYEGYFLACEKERDLFKLILKKEDELGDRSIM<br>FTVQNED (SEQ ID NO: 77) |
| 5-20 | YFGKLESKLSVIRNLNDQVLFIDQGNRPLFEDMTDSDCRDNAPRTIFIIS<br>KYSDSGARGLAVTISVKCEKISTLSCENKIISFKEMNPPDNIKDTKSDIIF<br>FARAVPGHGRKTQFESSSYEGYFLACEKERDLFKLILKKEDELGDRSIM<br>FTVQNED (SEQ ID NO: 78) |
| 5-2 | YFGKLESKLSVIRNLNDQVLFIDQGNRPLFEDMTDSDCRDNAPRTIFIIS<br>KYSDSKARGMAVTISVKCEKISTLSCENKIISFKEMNPPDNIKDTKSDIIF<br>FARDVPGHSSKRQFESSSYEGYFLACEKERDLFKLILKKEDELGDRSIM<br>FTVQNED (SEQ ID NO: 79) |
| 5-9 | YFGKLESKLSVIRNLNDQVLFIDQGNRPLFEDMTDSDCRDNAPRTIFIIS<br>KYSDSLARGLAVTISVKCEKISTLSCENKIISFKEMNPPDNIKDTKSDIIF<br>FQRDVPGHSRKMQFESSSYEGYFLACEKERDLFKLILKKEDELGDRSI<br>MFTVQNED (SEQ ID NO: 80) |
| 5-42 | YFGKLESKLSVIRNLNDQVLFIDQGNRPLFEDMTDSDCRDNAPRTIFIIS<br>KYSDSRARGLAVTISVKCEKISTLSCENKIISFKEMNPPDNIKDTKSDIIF<br>FQRNVPGHGRKMQFESS SYEGYFLACEKERDLFKLILKKEDELGDRSI<br>MFTVQNED (SEQ ID NO: 81) |

-continued

| | |
|---|---|
| 5-13 | YFGKLESKLSVIRNLNDQVLFIDQGNRPLFEDMTDSDCRDNAPRTIFIIS KYSDSRARGLAVTISVKCEKISTLSCENKIISFKEMNPPDNIKDTKSDIIF FARSVPGHGRKTQFESSSYEGYFLACEKERDLFKLILKKEDELGDRSIM FTVQNED (SEQ ID NO: 82) |
| 5-12 | YFGKLESKLSVIRNLNDQVLFIDQGNRPLFEDMTDSDCRDNAPRTIFIIS KYSDSRARGLAVTISVKCEKISTLSCENKIISFKEMNPPDNIKDTKSDIIF FARDVPGHSGKRQFESSSYEGYFLACEKERDLFKLILKKEDELGDRSIM FTVQNED (SEQ ID NO: 83) |
| 5-1 | YFGKLESKLSVIRNLNDQVLFIDQGNRPLFEDMTDSDCRDNAPRTIFIIS KYTDSRPRGLAVTISVKCEKISTLSCENKIISFKEMNPPDNIKDTKSDIIF FERDVPGHSSKKQFESSSYEGYFLACEKERDLFKLILKKEDELGDRSIM FTVQNED (SEQ ID NO: 84) |
| 5-33 | YFGKLESKLSVIRNLNDQVLFIDQGNRPLFEDMTDSDCRDNAPRTIFIIS KYTDSRARGMAVTISVKCEKISTLSCENKIISFKEMNPPDNIKDTKSDIIF FERDVPGHNDKRQFESSSYEGYFLACEKERDLFKLILKKEDELGDRSIM FTVQNED (SEQ ID NO: 85) |
| 5-21 | YFGKLESKLSVIRNLNDQVLFIDQGNRPLFEDMTDSDCRDNAPRTIFIIS RYKDSGKRGLAVTISVKCEKISTLSCENKIISFKEMNPPDNIKDTKSDIIF FRRSVPGHSRKVQFESSSYEGYFLACEKERDLFKLILKKEDELGDRSIM FTVQNED (SEQ ID NO: 86) |
| 6-31 | YFGKLESKLSVIRNLNDQVLFIDQGNRPLFEDMTDSDCRDNAPRTIFIIS KYGDSGARGLAVTISVKCEKISTLSCENKIISFKEMNPPDNIKDTKSDIIF FERDVPGHSGKVQFESSSYEGYFLACEKERDLFKLILKKEDELGDRSIM FTVQNED (SEQ ID NO: 87) |
| 6-20 | YFGKLESKLSVIRNLNDQVLFIDQGNRPLFEDMTDSDCRDNAPRTIFIIS KYGDSRPRGMAVTISVKCEKISTLSCENKIISFKEMNPPDNIKDTKSDIIF FQRAVPGHNRKMQFESSSYEGYFLACEKERDLFKLILKKEDELGDRSI MFTVQNED (SEQ ID NO: 88) |
| 6-12 | YFGKLESKLSVIRNLNDQVLFIDQGNRPLFEDMTDSDCRDNAPRTIFIIS KYSDSLARGLAVTISVKCEKISTLSCENKIISFKEMNPPDNIKDTKSDIIF FQRDVPGHSRKMQFESSSYEGYFLACEKERDLFKLILKKEDELGDRSI MFTVQNED (SEQ ID NO: 89) |
| 6-27 | YFGKLESKLSVIRNLNDQVLFIDQGNRPLFEDMTDSDCRDNAPRTIFIIS KYSDSRARGLAVTISVKCEKISTLSCENKIISFKEMNPPDNIKDTKSDIIF FARSVPGHGRKTQFESSSYEGYFLACEKERDLFKLILKKEDELGDRSIM FTVQNED (SEQ ID NO: 90) |
| 6-29 | YFGKLESKLSVIRNLNDQVLFIDQGNRPLFEDMTDSDCRDNAPRTIFIIS KYSDSRARGLAVTISVKCEKISTLSCENKIISFKEMNPPDNIKDTKSDIIF FQRNVPGHGRKMQFESS SYEGYFLACEKERDLFKLILKKEDELGDRSI MFTVQNED (SEQ ID NO: 91) |
| 5-26 | YFGKLESKLSVIRNLNDQVLFIDQGNRPLFEDMTDSDCRDNAPRTIFIIS KYGDSVPRGLAVTISVKCEKISTLSCENKIISFKEMNPPDNIKDTKSDIIF FARAVPGHSRKTQFESSSYEGYFLACEKERDLFKLILKKEDELGDRSIM FTVQNED (SEQ ID NO: 191) |
| 5-17 | YFGKLESKLSVIRNLNDQVLFIDQGNRPLFEDMTDSDCRDNAPRTIFIIS KYSDSRARGLAVTISVKCEKISTLSCENKIISFKEMNPPDNIKDTKSDIIF FARSVPGHGRKTQFESSSYEGYFLACEKERDLFKLILKKEDELGDRSIM FTVQNED (SEQ ID NO: 192) |
| 5-41 | YFGKLESKLSVIRNLNDQVLFIDQGNRPLFEDMTDSDCRDNAPRTIFIIS KYSDSRARGLAVTISVKCEKISTLSCENKIISFKEMNPPDNIKDTKSDIIF F ARDVPGHSGKRQFESSSYEGYFLACEKERDLFKLILKKEDELGDRSIM FTVQNED (SEQ ID NO: 193) |

Mouse Interleukin-18 Decoy-Resistant Variants Amino Acid Sequences

| | |
|---|---|
| mCS1 | NFGRLHCTTAVIRNINDQVLFVDKRQPVFEDMTDIDQSASEPQTRLIIY GYADSRVRGKAVTLSVKDSKMSTLSCKNKIISFEEMDPPENIDDIQSDL IFFQKRVPGHNKMEFESSLYEGHFLACQKEDDAFKLILKKKDENGDKS VMFTLTNLHQS (SEQ ID NO: 60) |
| mCS2 | HFGRLHCTTAVIRNINDQVLFVDKRQPVFEDMTDIDQSASEPQTRLIIY AYGDSRARGKAVTLSVKDSKMSTLSCKNKIISFEEMDPPENIDDIQSDL |

-continued

| | |
|---|---|
| | IFFQKRVPGHNKMEFESSLYEGHFLACQKEDDAFKLILKKKDENGDKS<br>VMFTLTNLHQS (SEQ ID NO: 61) |
| mC1 | NFGRLHCTTAVIRNINDQVLFVDKRQPVFEDMTDIDQSASEPQTRLIIY<br>AYVDRRLRGKAVTLSVKDSKMSTLSCKNKIISFEEMDPPENIDDIQSDL<br>IFFQKKVPGHNKMEFESSLYEGHFLACQKEDDAFKLILKKKDENGDKS<br>VMFTLTNLHQS (SEQ ID NO: 62) |
| mA12 | NFGRLHCTTAVIRNINDQVLFVDKRQPVFEDMTDIDQSASEPQTRLIIYS<br>YSDKHMRGKAVTLSVKDSKMSTLSCKNKIISFEEMDPPENIDDIQSDLI<br>FFQKLVPGHNKMEFESSLYEGHFLACQKEDDAFKLILKKKDENGDKS<br>VMFTLTNLHQS (SEQ ID NO: 63) |
| mE8 | NFGRLHCTTAVIRNINDQVLFVDKRQPVFEDMTDIDQSASEPQTRLIIY<br>VYTDGRRRGKAVTLSVKDSKMSTLSCKNKIISFEEMDPPENIDDIQSDL<br>IFFQKKVPGHDKMEFESSLYEGHFLACQKEDDAFKLILKKKDENGDKS<br>VMFTLTNLHQS (SEQ ID NO: 64) |
| mC10 | HFGRLHCTTAVIRNINDQVLFVDKRQPVFEDMTDIDQSASEPQTRLIIY<br>AYGDSHMRGKAVTLSVKDSKMSTLSCKNKIISFEEMDPPENIDDIQSDL<br>IFFQKQVPGHNKMEFESSLYEGHFLACQKEDDAFKLILKKKDENGDKS<br>VMFTVTNLHQS (SEQ ID NO: 65) |
| mB7 | HFGRLHCTTAVIRNINDQVLFVDKRQPVFEDMTDIDQSASEPQTRLIIY<br>AYGDSNAGGRAVTLSVKDSKMSTLSCKNKIISFEEMDPPENIDDIQSDL<br>IFFQKKVPGHNKMEFESSLYEGHFLACQKEDDAFKLILKKKDENGDKS<br>VMFTLTNLHQS (SEQ ID NO: 66) |
| mB1 | HFGRLHCTTAVIRNINDQVLFVDKRQPVFEDMTDIDQSASEPQTRLIIY<br>GYADSDARAKAVTLSVKDSKMSTLSCKNKIISFEEMDPPENIDDIQSDL<br>IFFQKSVPGHNKMEFESSLYEGHFLACQKEDDAFKLILKKKDENGDKS<br>VMFTVTNLHQS (SEQ ID NO: 67) |
| mD1 | HFGRLHCTTAVIRNINDQVLFVDKRQPVFEDMTDIDQSASEPQTRLIIY<br>GYSDRGSKGKAVTLSVKDSKMSTLSCKNKIISFEEMDPPENIDDIQSDLI<br>FFQKQVPGHNKMEFESSLYEGHFLACQKEDDAFKLILKKKDENGDKS<br>VMFTLTNLHQS (SEQ ID NO: 68) |
| mH7 | YFGRLHCTTAVIRNINDQVLFVDKRQPVFEDMTDIDQSASEPQTRLIIY<br>MYADRRARGKAVTLSVKDSKMSTLSCKNKIISFEEMDPPENIDDIQSD<br>LIFFQKKVPGHDKMEFESSLYEGHFLACQKEDDAFKLILKKKDENGDK<br>SVMFTVTNLHQS (SEQ ID NO: 69) |
| mA7 | YFGRLHCTTAVIRNINDQVLFVDKRQPVFEDMTDIDQSASEPQTRLIIY<br>AYGDNRVRGKAVTLSVKDSKMSTLSCKNKIISFEEMDPPENIDDIQSDL<br>IFFQKRVPGHNKMEFESSLYEGHFLACQKEDDAFKLILKKKDENGDKS<br>VMFTLTNLHQS (SEQ ID NO: 70) |
| mE1 | YFGRLHCTTAVIRNINDQVLFVDKRQPVFEDMTDIDQSASEPQTRLIIY<br>GYGDSERGGRAVTLSVKDSKMSTLSCKNKIISFEEMDPPENIDDIQSDLI<br>FFQKRVPGHDKMEFESSLYEGHFLACQKEDDAFKLILKKKDENGDKS<br>VMFTLTNLHQS (SEQ ID NO: 71) |
| mH3 | YFGRLHCTTAVIRNINDQVLFVDKRQPVFEDMTDIDQSASEPQTRLIIY<br>TRTDGGQKGVAVTLSVKDSKMSTLSCKNKIISFEEMDPPENIDDIQSDL<br>IFFQKRVPGHDKMEFESSLYEGHFLACQKEDDAFKLILKKKDENGDKS<br>VMFTLTNLHQS (SEQ ID NO: 72) |

Human Decoy-to-the-Decoy (D2D) Variants Amino Acid Sequences

| | |
|---|---|
| hD2D-5F12 | HFGKLESKLSVIRNLNGQVLFIDQGNRPLFKDMTASDCRANAPR<br>TIFIISFYKDSQPRGMAVTISVKCEKISTLSCENKIISFKEMNPPDNI<br>KDTKSDIIFFIRSVPGADNKFQFESSSYEGYFLACEKERDLFKLIL<br>KKEDELGDRSIMFTVQNED (SEQ ID NO: 92) |
| hD2D-5F11 | DFGKLESKLSVIRNLNDQVLFIDQGNRPLFADMTDNPCRSNAPR<br>TIFIISFYKDSQPRGIAVTISVKCEKISTLSCENKIISFKEMNPPDNIK<br>DTKSDIIFFLRSVPGPDNKMQFESSSYEGYFLACEKERDLFKLILK<br>KEDELGDRSIMFTVQNED (SEQ ID NO: 93) |
| hD2D-5F10 | HFGKLESKLSVIRNLNGQVLFIDQGNRPLFADMEASPCRDNAPR<br>TIFIISFYKDSQPRGLAVTISVKCEKISTLSCENKIISFKEMNPPDNI<br>KDTKSDIIFFLRSVPGHDNKMQFESSSYEGYFLACEKERDLFKLIL<br>KKEDELGDRSIMFTVQNED (SEQ ID NO: 94) |

-continued

| | |
|---|---|
| hD2D-5F08 | LFGKLESKLSVIRNLNGQVLFIDQGNRPLFADMTSSPCRSRAPRTI<br>FIISFYKDSQPRGFAVTISVKCEKISTLSCENKIISFKEMNPPDNIKD<br>TKSDIIFFIRSVPGHDNKIQFESSSYEGYFLACEKERDLFKLILKKE<br>DELGDRSIMFTVQNED (SEQ ID NO: 95) |
| hD2D-5F06 | HFGKLESKLSVIRNLNDQVLFIDQGNRPLFTDMESKPCRDSAPRT<br>IFIISMYKDSQPRGIAVTISVKCEKISTLSCENKIISFKEMNPPDNIK<br>DTKSDIIFFIRSVPGHDNKFQFESSSYEGYFLACEKERDLFKLILK<br>KEDELGDRSIMFTVQNED (SEQ ID NO: 96) |
| hD2D-5F04 | YFGKLESKLSVIRNLNRQVLFIDQGNRPLFTDMTYKDCRDNAPR<br>TIFIISFYKDSQPRGFAVTISVKCEKISTLSCENKIISFKEMNPPDNI<br>KDTKSDIIFFIRSVPGADNKIQFESSSYEGYFLACEKERDLFKLILK<br>KEDELGDRSIMFTVQNED (SEQ ID NO: 97) |
| hD2D-5F02 | HFGKLESKLSVIRNLNGQVLFIDQGNRPLFGDMEASPCRDNAPR<br>TIFIISFYKDSQPRGMAVTISVKCEKISTLSCENKIISFKEMNPPDNI<br>KDTKSDIIFFIRSVPGADNKLQFESSSYEGYFLACEKERDLFKLIL<br>KKEDELGDRSIMFTVQNED (SEQ ID NO: 98) |
| hD2D-5F01 | HFGKLESKLSVIRNLNGQVLFIDQGNRPLFTDMTSSDCRDKAPRT<br>IFIISFYKDSQPRGLAVTISVKCEKISTLSCENKIISFKEMNPPDNIK<br>DTKSDIIFFLRSVPGPDNKFQFESSSYEGYFLACEKERDLFKLILK<br>KEDELGDRSIMFTVQNED (SEQ ID NO: 99) |
| hD2D-5E10 | HFGKLESKLSVIRNLNGQVLFIDQGNRPLFADMESNRCRDSAPRT<br>IFIISMYKDSQPRGFAVTISVKCEKISTLSCENKIISFKEMNPPDNIK<br>DTKSDIIFFLRSVPGHDNKIQFESSSYEGYFLACEKERDLFKLILK<br>KEDELGDRSIMFTVQNED (SEQ ID NO: 100) |
| hD2D-5E08 | YFGKLESKLSVIRNLNGQVLFIDQGNRPLFTDMTASPCRDNAPRT<br>IFIISFYKDSQPRGLAVTISVKCEKISTLSCENKIISFKEMNPPDNIK<br>DTKSDIIFFLRSVPGHDNKIQFESSSYEGYFLACEKERSLFKLILKK<br>EDELGDRSIMFTVQNED (SEQ ID NO: 101) |
| hD2D-5E03 | DFGKLESKLSVIRNLNDQVLFIDQGNRPLFADMKSNVCRANAPR<br>TIFIISMYKDSQPRGMAVTISVKCEKISTLSCENKIISFKEMNPPDN<br>IKDTKSDIIFFIRSVPGPDNKLQFESSSYEGYFLACEKERDLFKLIL<br>KKEDELGDRSIMFTVQNED (SEQ ID NO: 102) |
| hD2D-5E02 | HFGKLESKLSVIRNLNGQVLFIDQGNRPLFGDMEASPCRAKAPR<br>TIFIISIYKDSQPRGFAVTISVKCEKISTLSCENKIISFKEMNPPDNIK<br>DTKSDIIFFLRSVPGHDNKFQFESSSYEGYFLACEKERSLFKLILK<br>KEDELGDRSIMFTVQNED (SEQ ID NO: 103) |
| hD2D-5D10 | HFGKLESKLSVIRNLNGQVLFIDQGNRPLFADMASNRCRANAPR<br>TIFIISMYKDSQPRGFAVTISVKCEKISTLSCENKIISFKEMNPPDNI<br>KDTKSDIIFFIRSVPGPDNKFQFESSSYEGYFLACEKERDLFKLILK<br>KEDELGDRSIMFTVQNED (SEQ ID NO: 104) |
| hD2D-5D08 | YFGKLESKLSVIRNLNDQVLFIDQGNRPLFADMKAKACRSNAPR<br>TIFIISFYKDSQPRGFAVTISVKCEKISTLSCENKIISFKEMNPPDNI<br>KDTKSDIIFFLRSVPGADNKIQFESSSYEGYFLACEKERDLFKLIL<br>KKEDELGDRSIMFTVQNED (SEQ ID NO: 105) |
| hD2D-5D06 | HFGKLESKLSVIRNLNHQVLFIDQGNRPLFTDMADNACRDNAPR<br>TIFIISFYKDSQPRGLAVTISVKCEKISTLSCENKIISFKEMNPPDNI<br>KDTKSDIIFFIRSVPGDDNKMQFESSSYEGYFLACEKERDLFKLIL<br>KKEDELGDRSIMFTVQNED (SEQ ID NO: 106) |
| hD2D-5D05 | YFGKLESKLSVIRNLNGQVLFIDQGNRPLFTDMKSNLCRSNAPRT<br>IFIISFYKDSQPRGIAVTISVKCEKISTLSCENKIISFKEMNPPDNIK<br>DTKSDIIFFIRSVPGDDNKIQFESSSYEGYFLACEKERDLFKLILKK<br>EDELGDRSIMFTVQNED (SEQ ID NO: 107) |
| hD2D-5D03 | HFGKLESKLSVIRNLNGQVLFIDQGNRPLFRDMAASHCRDSAPR<br>TIFIISIYKDSQPRGFAVTISVKCEKISTLSCENKIISFKEMNPPDNIK<br>DTKSDIIFFLRSVPGHDNKIQFESSSYEGYFLACEKERDLFKLILK<br>KEDELGDRSIMFTVQNED (SEQ ID NO: 108) |
| hD2D-5D02 | YFGI<LESI<LSVIRNLNDQVLFIDQGNRPLFADMASNPCRYI<APR<br>TIFIISMYKDSQPRGLAVTISVKCEKISTLSCENKIISFKEMNPPDNI<br>KDTKSDIIFFLRSVPGADNKLQFESSSYEGYFLACEKERDLFKLIL<br>KKEDELGDRSIMFTVQNED (SEQ ID NO: 109) |
| hD2D-5C10 | HFGKLESKLSVIRNLNGQVLFIDQGNRPLFTDMASNHCRYNAPR<br>TIFIISMYKDSQPRGLAVTISVKCEKISTLSCENKIISFKEMNPPDNI<br>KDTKSDIIFFLRSVPGADNKIQFESSSYEGYFLACEKERDLFKLIL<br>KKEDELGDRSIMFTVQNED (SEQ ID NO: 110) |

-continued

| | |
|---|---|
| hD2D-5C09 | HFGKLESKLSVIRNLNGQVLFIDQGNRPLFADMTDNPCRSRAPRT<br>IFIISFYKDSQPRGMAVTISVKCEKISTLSCENKIISFKEMNPPDNIK<br>DTKSDIIFFIRSVPGHDNKFQFESSSYEGYFLACEKERDLFKLILK<br>KEDELGDRSIMFTVQNED (SEQ ID NO: 111) |
| hD2D-5C08 | YFGKLESKLSVIRNLNGQVLFIDQGNRPLFTDMTASHCRSSAPRT<br>IFIISLYKDSQPRGMAVTISVKCEKISTLSCENKIISFKEMNPPDNIK<br>DTKSDIIFFLRSVPGHDNKFQFESSSYEGYFLACEKERDLFKLILK<br>KEDELGDRSIMFTVQNED (SEQ ID NO: 112) |
| hD2D-5C05 | YFGKLESKLSVIRNLNGQVLFIDQGNRPLFTDMEYRLCRANAPR<br>TIFIISFYKDSHPRGLAVTISVKCEKISTLSCENKIISFKEMNPPDNI<br>KDTKSDIIFFLRSVPGDDNKLQFESSSYEGYFLACEKERDLFKLIL<br>KKEDELGDRSIMFTVQNED (SEQ ID NO: 113) |
| hD2D-5C04 | YFGKLESKLSVIRNLNGQVLFIDQGNRPLFTDMESSLCRDNAPRT<br>IFIISLYKDSQPRGMAVTISVKCEKISTLSCENKIISFKEMNPPDNIK<br>DTKSDIIFFLRSVPGADNKFQFESSSYEGYFLACEKERSLFKLILK<br>KEDELGDRSIMFTVQNED (SEQ ID NO: 114) |
| hD2D-5C03 | YFGKLESKLSVIRNLNGQVLFIDQGNRPLFKDMEANDCRSSAPR<br>TIFIISIYKDSQPRGLAVTISVKCEKISTLSCENKIISFKEMNPPDNIK<br>DTKSDIIFFIRSVPGADNKMQFESSSYEGYFLACEKERDLFKLILK<br>KEDELGDRSIMFTVQNED (SEQ ID NO: 115) |
| hD2D-5B11 | DFGKLESKLSVIRNLNDQVLFIDQGNRPLFADMKASACRANAPR<br>TIFIISMYKDSQPRGLAVTISVKCEKISTLSCENKIISFKEMNPPDNI<br>KDTKSDIIFFLRSVPGHDNKFQFESSSYEGYFLACEKERDLFKLIL<br>KKEDELGDRSIMFTVQNED (SEQ ID NO: 116) |
| hD2D-5B10 | YFGKLESKLSVIRNLNGQVLFIDQGNRPLFGDMTAKHCRARAPR<br>TIFIISFYKDSQPRGMAVTISVKCEKISTLSCENKIISFKEMNPPDNI<br>KDTKSDIIFFIRSVPGADNKFQFESSSYEGYFLACEKERDLFKLIL<br>KKEDELGDRSIMFTVQNED (SEQ ID NO: 117) |
| hD2D-5B06 | FFGKFESKLSVIRNLNGQVLFIDQGNRPLFTDMESKDCRDRAPRT<br>IFIISFYKDSQPRGLAVTISVKCEKISTLSCENKIISFKEMNPPDNIK<br>DTKSDIIFFLRSVPGHDNKLQFESSSYEGYFLACEKERDLFKLILK<br>KEDELGDRSIMFTVQNED (SEQ ID NO: 118) |
| hD2D-5B05 | FFGKLESKLSVIRNLNGQVLFIDQGNRPLFADMASNHCRANAPR<br>TIFIISLYKDSQPRGLAVTISVKCEKISTLSCENKIISFKEMNPPDNI<br>KDTKSDIIFFIRSVPGHDNKMQFESSSYEGYFLACEKERDLFKLIL<br>KKEDELGDRSIMFTVQNED (SEQ ID NO: 119) |
| hD2D-5B02 | YFGKLESKLSVIRNLNGQVLFIDQGNRPLFADMTSKRCRDNAPR<br>TIFIISLYKDSQPRGFAVTISVKCEKISTLSCENKIISFKEMNPPDNI<br>KDTKSDIIFFIRSVPGHDNKIQFESSSYEGYFLACEKERDLFKLILK<br>KEDELGDRSIMFTVQNED (SEQ ID NO: 120) |
| hD2D-5A09 | LFGKHESKLSVIRNLNGQVLFIDQGNRPLFGDMESSPCRYNAPRT<br>IFIISFYKDSQPRGLAVTISVKCEKISTLSCENKIISFKEMNPPDNIK<br>DTKSDIIFFIRSVPGHDNKMQFESSSYEGYFLACEKERDLFKLILK<br>KEDELGDRSIMFTVQNED (SEQ ID NO: 121) |
| hD2D-5A02 | YFGKLESKLSVIRNLNAQVLFIDQGNRPLFTDMTASPCRSSAPRTI<br>FIISLYKDSQPRGLAVTISVKCEKISTLSCENKIISFKEMNPPDNIK<br>DTKSDIIFFLRSVPGPDNKIQFESSSYEGYFLACEKERDLFKLILKK<br>EDELGDRSIMFTVQNED (SEQ ID NO: 122) |
| hD2D-CS1 | YFGKLESKLSVIRNLNGQVLFIDQGNRPLFADMTDSDCRDNAPR<br>TIFIISMYKDSQPRGMAVTISVKCEKISTLSCENKIISFKEMNPPDN<br>IKDTKSDIIFFLRSVPGHDNKMQFESSSYEGYFLACEKERDLFKLI<br>LKKEDELGDRSIMFTVQNED (SEQ ID NO: 123) |
| hD2D-CS2 | YFGKLESKLSVIRNLNGQVLFIDQGNRPLFADMTSSDCRDNAPR<br>TIFIISFYKDSQPRGMAVTISVKCEKISTLSCENKIISFKEMNPPDNI<br>KDTKSDIIFFLRSVPGHDNKMQFESSSYEGYFLACEKERDLFKLIL<br>KKEDELGDRSIMFTVQNED (SEQ ID NO: 124) |
| hD2D-CS3 | YFGKLESKLSVIRNLNGQVLFIDQGNRPLFADMESSDCRDNAPR<br>TIFIISFYKDSQPRGLAVTISVKCEKISTLSCENKIISFKEMNPPDNI<br>KDTKSDIIFFLRSVPGHDNKMQFESSSYEGYFLACEKERDLFKLIL<br>KKEDELGDRSIMFTVQNED (SEQ ID NO: 125) |

Mouse Decoy-to-the-Decoy (D2D) Variants Amino Acid Sequences

| | |
|---|---|
| mD2D-A5 | YFGRYHCTTAVIRNINQQVLFVDKRQPVFADMGYTVQSASEPQT<br>RLIIYMYKDSEVRGLAVTLSVKDSKMSTLSCKNKIISFEEMDPPE<br>NIDDIQSDLIFFLKEVPGHRKLEFESSLYEGHFLACQKEDEAFKLI<br>LKKKDENGDKSVMFTLTNLHQS (SEQ ID NO: 126) |
| mD2D-A6 | DFGRLHCTTAVIRNINDQVLFVDKRQPVFADMGSIAQSASEPQT<br>RLIIYFYKDSEVRGLAVTLSVKDSKMYTLSCKNKIISFEEMDPPE<br>NIDDIQSDLIFFLKAVPGDNKIEFESSLYEGHFLACQKEATAFKLI<br>LKKKDENGDKSVMFTLTNLHQS (SEQ ID NO: 127) |
| mD2D-A7 | YFGRLHCTTAVIRNINGQVLFVDKRQPVFRDMADTVQSASEPQT<br>RLIIYFYKDSEVRGLAVTLSVKDSKMSTLSCKNKIISFEEMDPPEN<br>IDDIQSDLIFFIKPVPGASKMEFESSLYEGHFLACQKEAGAFKLIL<br>KKKDENGDKSVMFTLTNLHQS (SEQ ID NO: 128) |
| mD2D-A8 | HFGRLHCTTAVIRNINDQVLFVDKRQPVFKDMEYTVQSASEPQT<br>RLIIYMYKDSEVRGLAVTLSVKDSKMSTLSCKNKIISFEEMDPPE<br>NIDDIQSDLIFFIKAVPGDRKIEFESSLYEGHFLACQKEDNAFKLIL<br>KKKDENGDKSVMFTLTNLHQS (SEQ ID NO: 129) |
| mD2D-A9 | YFGRLHCTTAVIRNINAQVLFVDKRQPVFADMADKGQSASEPQT<br>RLIIYMYKDSEVRGLAVTLSVKDSKMSTLSCKNKIISFEEMDPPE<br>NIDDIQSDLIFFLKPVPGDTKMEFESSLYEGHFLACQKEFGAFKLI<br>LKKKDENGDKSVMFTLTNLHQS (SEQ ID NO: 130) |
| mD2D-A11 | YFGRLHCTTAVIRNINEQVLFVDKRQPVFADMGDRHQSASEPQT<br>RLIIYMYKDSEVRGLAVTLSVKDSKMSTLSCKNKIISFEEMDPPE<br>NIDDIQSDLIFFIKPVPGASKLEFESSLYEGHFLACQKEDDAFKLIL<br>KKKDENGDKSVMFTLTNLHQS (SEQ ID NO: 131) |
| mD2D-A12 | HFGRLHCTTAVIRNINDQVLFVDKRQPVFRDMGAIGQSASEPQT<br>RLIIYFYKDSEVRGLAVTLSVKDSKMSTLSCKNKIISFEEMDPPEN<br>IDDIQSDLIFFIKPVPGDSKLEFESSLYEGHFLACQKEVDAFKLILK<br>KKDENGDKSVMFTLTNLHQS (SEQ ID NO: 132) |
| mD2D-B4 | HFGRLHCTTAVIRNINSQVLFVDKRQPVFTDMGSIVQSASEPQTR<br>LIIYMYKDSEVRGLAVTLSVKDSKMSTLSCKNKIISFEEMDPPENI<br>DDIQSDLIFFIKGVPGDNKIEFESSLYEGHFLACQKEDRAFKLILK<br>KKDENGDKSVMFTLTNLHQS (SEQ ID NO: 133) |
| mD2D-B7 | YFGRLHCTTAVIRNINSQVLFVDKRQPVFRDMEDTPQSASEPQTR<br>LIIYFYKDSEVRGLAVTLSVKDSKMSTLSCKNKIISFEEMDPPENI<br>DDIQSDLIFFIKRVPGDSKLEFESSLYEGHFLACQKEFEAFKLILK<br>KKDENGDKSVMFTLTNLHQS (SEQ ID NO: 134) |
| mD2D-B11 | HFGRLHCTTAVIRNINAQVLFVDKRQPVFGDMTATVQSASEPQT<br>RLIIYFYKDSEVRGLAVTLSVKDSKMSTLSCKNKIISFEEMDPPEN<br>IDDIQSDLIFFIKPVPGDSKLEFESSLYEGHFLACQKEDNAFKLILK<br>KKDENGDKSVMFTLTNLHQS (SEQ ID NO: 135) |
| mD2D-B12 | NFGRLHCTTAVIRNINNQVLFVDKRQPVFKDMEYTLQSASEPQT<br>RLIIYFYKDSEVRGLAVTLSVKDSKMSTLSCKNKIISFEEMDPPEN<br>IDDIQSDLIFFIKPVPGDNKLEFESSLYEGHFLACQKEYEAFKLILK<br>KKDENGDKSVMFTLTNLHQS (SEQ ID NO: 136) |
| mD2D-C1 | YFGRLHCTTAVIRNINGQVLFVDKRQPVFADMEATRQSASEPQT<br>RLIIYFYKDSEVRGLAVTLSVKDSKMSTLSCKNKIISFEEMDPPEN<br>IDDIQSDLIFFIKGVPGANKMEFESSLYEGHFLACQKEDGAFKLIL<br>KKKDENGDNSVMFTLTNLHQS (SEQ ID NO: 137) |
| mD2D-C3 | NFGRLHCTTAVIRNINGQVLFVDKRQPVFADMRAILQSASEPQT<br>RLIIYFYKDSEVRGLAVTLSVKDSKMSTLSCKNKIISFEEMDPPEN<br>IDDIQSDLIFFLKGVPGDNKLEFESSLYEGHFLACQKEDRAFKLIL<br>KKKDENGDKSVMFTLTNLHQS (SEQ ID NO: 138) |
| mD2D-C5 | YFGRLHCTTAVIRNINAQVLFVDKRQPVFADMEATAQSASEPQT<br>RLIIYFYKDSEVRGLAVTLSVKDSKMSTLSCKNKIISFEEMDPPEN<br>IDDIQSDLIFFIKGVPGASKMEFESSLYEGHFLACQKEDGAFKLIL<br>KKKDENGDKSVMFTLTNLHQS (SEQ ID NO: 139) |
| mD2D-C6 | LFGRLHCTTAVIRNINGQVLFVDKRQPVFADMGATLQSASEPQT<br>RLIIYMYKDSEVRGLAVTLSVKDSKMSTLSCKNKIISFEEMDPPE<br>NIDDIQSDLIFFLKPVPGDTKMEFESSLYEGHFLACQKEASAFKLI<br>LKKKDENGDKSVMFTLTNLHQS (SEQ ID NO: 140) |

-continued mD2D-C9
NFGRLHCTTAVIRNINGQVLFVDKRQPVFEDMAYTVQSASEPQT
RLIIYFYKDSEVRGLAVTLSVKDSKMSTLSCKNKIISFEEMDPPEN
IDDIQSDLIFFIKGVPGDSKMEFESSLYEGHFLACQKEYDAFKLIL
KKKDENGDKSVMFTLTNLHQS (SEQ ID NO: 141)

mD2D-C10
DFGRLHCTTAVIRNINDQVLFVDKRQPVFKDMESKPQSASEPQT
RLIIYFYKDSEVRGLAVTLSVKDSKMSTLSCKNKIISFEEMDPPEN
IDDIQSDLIFFLKAVPGASKLEFESSLYEGHFLACQKEANAFKLIL
KKKDENGDKSVMFTLTNLHQS (SEQ ID NO: 142)

mD2D-C11
LFGRLHCTTAVIRNINGQVLFVDKRQPVFADMGDKVQSASEPQT
RLIIYMYKDSEVRGLAVTLSVKDSKMSTLSCKNKIISFEEMDPPE
NIDDIQSDLIFFIKPVPGDNKLEFESSLYEGHFLACQKEDEAFKLIL
KTKDENGDKSVMFTLTNLHQS(SEQIDNO: 143)

mD2D-D1
YFGRHHCTTAVIRNINQQVLFVDKRQPVFRDMAATRQSASEPQT
RLIIYMYKDSEVRGLAVTLSVKDSKMSTLSCKNKIISFEEMDPPE
NIDDIQSDLIFFLKGVPGDNKMEFESSLYEGHFLACQKEDDAFKL
ILKKKDENGDKSVMFTLTNLHQS (SEQ ID NO: 144)

mD2D-D9
NFGRLHCTTAVIRNINQQVLFVDKRQPVFTDMESIGQSASEPQTR
LIIYFYKDSEVRGLAVTLSVKDSKMSTLSCKNKIISFEEMDPPENI
DDIQSDLIFFLKAVPGANKLEFESSLYEGHFLACQKEDSAFKLILK
KKDENGDKSVMFTLTNLHQS (SEQ ID NO: 145)

mD2D-D12
FFGRHHCTTAVIRNINGQVLFVDKRQPVFGDMGDRVQSASEPQT
RLIIYMYKDSEVRGLAVTLSVKDSKMSTLSCKNKIISFEEMDPPE
NIDDIQSDLIFFIKAVPGDSKIEFESSLYEGHFLACQKEDGAFKLIL
KKKDENGDKSVMFTLTNLHQS (SEQ ID NO: 146)

mD2D-E3
VFGRHHCTTAVIRNINGQVLFVDKRQPVFKDMTYIDQSASEPQT
RLIIYMYKDSEVRGLAVTLSVKDSKMSTLSCKNKIISFEEMDPPE
NIDDIQSDLIFFLKAVPGDTKMEFESSLYEGHFLACQKEAQAFKLI
LKKKDEIGDKSVMFTLTNLHQS (SEQ ID NO: 147)

mD2D-E4
NFGRLHCTTAVIRNINGQVLFVDKRQPVFADMTATRQSASEPQT
RLIIYMYKDSEVRGLAVTLSVKDSKMSTLSCKNKIISFEEMDPPE
NIDDIQSDLIFFIKQVPGANKIEFESSLYEGHFLACQKEFRAFKLIL
KKKDENGDKSVMFTLTNLHQS (SEQ ID NO: 148)

mD2D-E5
DFGRLHCTTAVIRNINGQVLFVDKRQPVFGDMAYIGQSASEPQT
RLIIYFYKDSEVRGLAVTLSVKDSKMSTLSCKNKIISFEEMDPPEN
IDDIQSDLIFFIKAVPGHSKIEFESSLYEGHFLACQKESGAFKLILK
KKDENGDKSVMFTLTNLHQS (SEQ ID NO: 149)

mD2D-E7
YFGRLHCTTAVIRNINDQVLFVDKRQPVFRDMGSIAQSASEPQTR
LIIYMYKDSEVRGLAVTLSVKDSKMSTLSCKNKIISFEEMDPPENI
DDIQSDLIFFIKPVPGATKLEFESSLYEGHFLACQKEDGAFKLILK
KKDENGDNSVMFTLTNLHQS (SEQ ID NO: 150)

mD2D-E8
YFGRLHCTTAVIRNINEQVLFVDKRQPVFTDMEAIGQSASEPQTR
LIIYFYKDSEVRGLAVTLSVKDSKMSTLSCKNKIISFEEMDPPENI
DDIQSDLIFFIKGVPGDRKMEFESSLYEGHFLACQKEDGAFKLIL
KKKDENGDKSVMFTLTNLHQS (SEQ ID NO: 151)

mD2D-E9
FFGRLHCTTAVIRNINNQVLFVDKRQPVFEDMEYRLQSASEPQT
RLIIYMYKDSEVRGLAVTLSVKDSKMSTLSCKNKIISFEEMDPPE
NIDDIQSDLIFFLKPVPGASKLEFESSLYEGHFLACQKESDAFKLIL
KKKDENGDKSVMFTLTNLHQS (SEQ ID NO: 152)

mD2D-E10
NFGRLHCTTAVIRNINNQVLFVDKRQPVFADMEDRLQSASEPQT
RLIIYMYKDSEVRGLAVTLSVKDSKMSTLSCKNKIISFEEMDPPE
NIDDIQSDLIFFLKGVPGDNKMEFESSLYEGHFLACQKEDHAFKL
ILKKKDENGDKSVMFTLTNLHQS (SEQ ID NO: 153)

mD2D-E11
YFGRLHCTTAVIRNINAQVLFVDKRQPVFRDMGYILQSASEPQT
RLIIYLYKDSEVRGLAVTLSVKESKMSTLSCKNKIISFEEMDPPEN
IDDIQSDLIFFLKPVPGDTKIEFESSLYEGHFLACQKEDNAFKLILK
KKDENGDKSVMFTLTNLHQS (SEQ ID NO: 154)

mD2D-E12
YFGRLHCTTAVIRNINDQVLFVDKRQPVFGDMADTAQSASEPQT
RLIIYFYKDSEVRGLAVTLSVKDSKMSTLSCKNKIISFEEMDPPEN
IDDIQSDLIFFIKPVPGDSKMEFESSLYEGHFLACQKEADAFKLIL
KKKDENGDKSVMFTLTNLHQS (SEQ ID NO: 155)

-continued mD2D-F3 DFGRLHCTTAVIRNINGQVLFVDKRQPVFEDMAYIAQSASEPQT
RLIIYFYKDSEVRGLAVTLSVKDSKMSTLSCKNKIISFEEMDPPEN
IDDIQSDLIFFIKPVPGDSKIEFESSLYEGHFLACQKEADAFKLILK
KKDENGDKSVMFTLTNLHQS (SEQ ID NO: 156)

mD2D-F4 NFGRLHCTTAVIRNINEQVLSVDKRQPVFRDMKYILQSASEPQTR
LIIYFYKDSEVRGLAVTLSVKDSKMSTLSCKNKIISFEEMDPPENI
DDIQSDLIFFLKGVPGDNKMEFESSLYEGHFLACQKEYGAFKLIL
KKKDENGDKSVMFTLTNLHQS (SEQ ID NO: 157)

mD2D-F5 DFGRLHCTTAVIRNINEQVLFVDKRQPVFTDMAYILQSASEPQTR
LIIYFYKDSEVRGLAVTLSVKESKMSTLSCKNKIISFEEMDPPENI
DDIQSDLIFFIKAVPGDSKLEFESSLYEGHFLACQKEDTAFKLILK
KKDENGDKSVMFTLTNLHQS (SEQ ID NO: 158)

mD2D-F7 DFGRLHCTTAVIRNINNQVLFVDKRQPVFKDMESTAQSASEPQT
RLIIYMYKDSEVRGLAVTLSVKDSKMSTLSCKNKIISFEEMDPPE
NIDDIQSDLIFFLKGVPGASKLEFESSLYEGHFLACQKEAGAFKLI
LKKKDENGDKSVMFTLTNLHQS (SEQ ID NO: 159)

mD2D-F8 HFGRLHCTTAVIRNINEQVLFVDKRQPVFADMEAIGQSASEPQTR
LIIYFYKDSEVRGLAVTLSVKESKMSTLSCKNKIISFEEMDPPENI
DDIQSDLIFFIKGVPGDTKLEFESSLYAGHFLACQKEDGAFKLILK
KKDENGDKSVMFTLTNLHQS (SEQ ID NO: 160)

mD2D-F9 IFGRLHCTTAVIRNINEQVLFVDKRQPVFKDMRYIVQSASEPQTR
LIIYFYKDSEVRGLAVTLSVKDSKMSTLSCKNKIISFEEMDPPENI
DDIQSDLIFFIKEVPGASKLEFESSLYEGHFLACQKEDEAFKLILK
KKDENGDKSVMFTLTNLHQS (SEQIDNO: 161)

mD2D-Gl YFGRLHCTTAVIRNINAQVLFVDKRQPVFTDMGYTLQSASEPQT
RLIIYLYKDSEVRGLAVTLSVKDSKMSTLSCKNKIISFEEMDPPEN
IDDIQSDLIFFIKPVPGHNKIEFESSLYEGHFLACQKEDRAFKLILK
KKDENGDKSVMFTLTNLHQS (SEQ ID NO: 162)

mD2D-G7 NFGRLHCTTAVIRNINNQVLFVDKRQPVFRDMASTAQSASEPQT
RLIIYMYKDSEVRGLAVTLSVKDSKMSTLSCKNKIISFEEMDPPE
NIDDIQSDLIFFIKGVPGANKIEFESSLYEGHFLACQKEDDAFKLIL
KKKDENGDKSVMFTLTNLHQS (SEQ ID NO: 163)

mD2D-G9 DFGRLHCTTAVIRNINGQVLFVDKRQPVFEDMKDRAQSASEPQT
RLIIYFYKDSEVRGLAVTLSVKDSKMSTLSCKNKIISFEEMDPPEN
IDDIQSDLIFFLKAVPGHSKMEFESSLYEGHFLACQKEDEAFKLIL
KKKDENGDKSVMFTLTNLHQS (SEQ ID NO: 164)

mD2D-H7 NFGRLHCTTAVIRNINEQVLFVDKRQPVFADMTDIAQSASEPQTR
LIIYMYKDSEVRGLAVTLSVKESKMSTLSCKNKIISFEEMDPPENI
DDIQSDLIFFLKPVPGDIKMEFESSLYEGHFLACQKEYGAFKLILK
KKDENGDNSVMFTLTNLHQS (SEQ ID NO: 165)

mD2D-E1 YFGRLHCTTAVIRNINEQVLFVDKRQPVFADMTDTLQSASEPQT
RLIIYFYKDSEVRGLAVTLSVKDSKMSTLSCKNKIISFEEMDPPEN
IDDIQSDLIFFLKGVPGDNKMEFESSLYEGHFLACQKEDTAFKLIL
KKKDENGDKSVMFTLTNLHQS (SEQ ID NO: 166)

mD2D-G8 YFGRLHCTTAVIRNINEQVLFVDKRQPVFADMTDTLQSASEPQT
RLIIYFYKDSEVRGLAVTLSVKDSKMSTLSCKNKIISFEEMDPPEN
IDDIQSDLIFFLKGVPGDNKMEFESSLYEGHFLACQKEDTAFKLIL
KKKDENGDKSVMFTLTNLHQS (SEQ ID NO: 167)

mD2D-H3 YFGRLHCTTAVIRNINEQVLFVDKRQPVFADMTDTLQSASEPQT
RLIIYFYKDSEVRGLAVTLSVKDSKMSTLSCKNKIISFEEMDPPEN
IDDIQSDLIFFLKGVPGDNKMEFESSLYEGHFLACQKEDTAFKLIL
KKKDENGDKSVMFTLTNLHQS (SEQ ID NO: 168)

mD2D-A10 HFGRLHCTTAVIRNINGQVLFVDKRQPVFKDMKYIVQSASEPQT
RLIIYMYKDSEVRGLAVTLSVKDSKMSTLSCKNKIISFEEMDPPE
NIDDIQSDLIFFLKAVPGHSKIEFESSLYEGHFLACQKEDSAFKLIL
KKKDENGDKSVMFTLTNLHQS (SEQ ID NO: 169)

mD2D-H1 HFGRLHCTTAVIRNINGQVLFVDKRQPVFKDMKYIVQSASEPQT
RLIIYMYKDSEVRGLAVTLSVKDSKMSTLSCKNKIISFEEMDPPE
NIDDIQSDLIFFLKAVPGHSKIEFESSLYEGHFLACQKEDSAFKLIL
KKKDENGDKSVMFTLTNLHQS (SEQ ID NO: 170)

mD2D-F12 YFGRLHCTTAVIRNINGQVLFVDKRQPVFEDMKAKAQSASEPQT
RLIIYFYKDSEVRGLAVTLSVKDSKMSTLSCKNKIISFEEMDPPEN

-continued

| | |
|---|---|
| | IDDIQSDLIFFIKPVPGASKMEFESSLYEGHFLACQKEDGAFKLIL<br>KKKDENGDKSVMFTLTNLHQS (SEQ ID NO: 171) |
| mD2D-G10 | YFGRLHCTTAVIRNINGQVLFVDKRQPVFEDMKAKAQSASEPQT<br>RLIIYFYKDSEVRGLAVTLSVKDSKMSTLSCKNKIISFEEMDPPEN<br>IDDIQSDLIFFIKPVPGASKMEFESSLYEGHFLACQKEDGAFKLIL<br>KKKDENGDKSVMFTLTNLHQS (SEQ ID NO: 172) |
| mD2D-G12 | YFGRLHCTTAVIRNINGQVLFVDKRQPVFEDMKAKAQSASEPQT<br>RLIIYFYKDSEVRGLAVTLSVKDSKMSTLSCKNKIISFEEMDPPEN<br>IDDIQSDLIFFIKPVPGASKMEFESSLYEGHFLACQKEDGAFKLIL<br>KKKDENGDKSVMFTLTNLHQS (SEQ ID NO: 173) |
| mD2D-E2 | LFGRLHCTTAVIRNINGQVLFVDKRQPVFGDMGSIPQSASEPQTR<br>LIIYFYKDSEVRGLAVTLSVKDSKMSTLSCKNKIISFEEMDPPENI<br>DDIQSDLIFFIKHVPGATKMEFESSLYEGHFLACQKEDNAFKLILK<br>KKDENGDKSVMFTLTNLHQS (SEQ ID NO: 174) |
| mD2D-G11 | LFGRLHCTTAVIRNINGQVLFVDKRQPVFGDMGSIPQSASEPQTR<br>LIIYFYKDSEVRGLAVTLSVKDSKMSTLSCKNKIISFEEMDPPENI<br>DDIQSDLIFFIKHVPGATKMEFESSLYEGHFLACQKEDNAFKLILK<br>KKDENGDKSVMFTLTNLHQS (SEQ ID NO: 175) |
| mD2D-C4 | YFGRLHCTTAVIRNINSQVLFVDKRQPVFTDMAYTVQSASEPQT<br>RLIIYFYKDSEVRGLAVTLSVKDSKMSTLSCKNKIISFEEMDPPEN<br>IDDIQSDLIFFIKAVPGDSKLEFESSLYEGHFLACQKEDNAFKLILK<br>KKDENGDKSVMFTLTNLHQS (SEQ ID NO: 176) |
| mD2D-F11 | YFGRLHCTTAVIRNINSQVLFVDKRQPVFTDMAYTVQSASEPQT<br>RLIIYFYKDSEVRGLAVTLSVKDSKMSTLSCKNKIISFEEMDPPEN<br>IDDIQSDLIFFIKAVPGDSKLEFESSLYEGHFLACQKEDNAFKLILK<br>KKDENGDKSVMFTLTNLHQS (SEQ ID NO: 177) |
| mD2D-C2 | YFGRLHCTTAVIRNINGQVLFVDKRQPVFTDMGARVQSASEPQT<br>RLIIYFYKDSEVRGLAVTLSVKDSKMYTLSCKNKIISFEEMDPPE<br>NIDDIQSDLIFFLKPVPGDNKLEFESSLYEGHFLACQKESGAFKLI<br>LKKKDENGDKSVMFTLTNLHQS (SEQ ID NO: 178) |
| mD2D-F10 | YFGRLHCTTAVIRNINGQVLFVDKRQPVFTDMGARVQSASEPQT<br>RLIIYFYKDSEVRGLAVTLSVKDSKMYTLSCKNKIISFEEMDPPE<br>NIDDIQSDLIFFLKPVPGDNKLEFESSLYEGHFLACQKESGAFKLI<br>LKKKDENGDKSVMFTLTNLHQS (SEQ ID NO: 179) |
| mD2D-A2 | DFGRLHCTTAVIRNINGQVLFVDKRQPVFGDMKATGQSASEPQT<br>RLIIYFYKDSEVRGLAVTLSVKDSKMSTLSCKNKIISFEEMDPPEN<br>IDDIQSDLIFFIKAVPGANKLEFESSLYEGHFLACQKEAGAFKLIL<br>KKKDENGDKSVMFTLTNLHQS (SEQ ID NO: 180) |
| mD2D-F6 | DFGRLHCTTAVIRNINGQVLFVDKRQPVFGDMKATGQSASEPQT<br>RLIIYFYKDSEVRGLAVTLSVKDSKMSTLSCKNKIISFEEMDPPEN<br>IDDIQSDLIFFIKAVPGANKLEFESSLYEGHFLACQKEAGAFKLIL<br>KKKDENGDKSVMFTLTNLHQS (SEQ ID NO: 181) |
| mD2D-A1 | DFGRLHCTTAVIRNINSQVLFVDKRQPVFRDMGSIHQSASEPQTR<br>LIIYFYKDSEVRGLAVTLSVKDSKMSTLSCKNKIISFEEMDPPENI<br>DDIQSDLIFFLKAVPGANKLEFESSLYEGHFLACQKEDGAFKLIL<br>KKKDENGDKSVMFTLTNLHQS (SEQ ID NO: 182) |
| mD2D-E6 | DFGRLHCTTAVIRNINSQVLFVDKRQPVFRDMGSIHQSASEPQTR<br>LIIYFYKDSEVRGLAVTLSVKDSKMSTLSCKNKIISFEEMDPPENI<br>DDIQSDLIFFLKAVPGANKLEFESSLYEGHFLACQKEDGAFKLIL<br>KKKDENGDKSVMFTLTNLHQS (SEQ ID NO: 183) |
| mD2D-D4 | YFGRLHCTTAVIRNINEQVLFVDKRQPVFKDMKDKLQSASEPQT<br>RLIIYFYKDSEVRGLAVTLSVKDSKMSTLSCKNKIISFEEMDPPEN<br>IDDIQSDLIFFLKGVPGDNKLEFESSLYEGHFLACQKEFGAFKLIL<br>KKKDENGDKSVMFTLTNLHQS (SEQ ID NO: 184) |
| mD2D-D6 | YFGRLHCTTAVIRNINEQVLFVDKRQPVFKDMKDKLQSASEPQT<br>RLIIYFYKDSEVRGLAVTLSVKDSKMSTLSCKNKIISFEEMDPPEN<br>IDDIQSDLIFFLKGVPGDNKLEFESSLYEGHFLACQKEFGAFKLIL<br>KKKDENGDKSVMFTLTNLHQS (SEQ ID NO: 185) |
| mD2D-A3 | YFGRLHCTTAVIRNINGQVLFVDKRQPVFADMASTHQSASEPQT<br>RLIIYFYKDSEVRGLAVTLSVKDSKMSTLSCKNKIISFEEMDPPEN<br>IDDIQSDLIFFLKGVPGANKIEFESSLYEGHFLACQKEDDAFKLIL<br>KKKDENGDKSVMFTLTNLHQS (SEQ ID NO: 186) |

-continued

| | |
|---|---|
| mD2D-A4 | YFGRLHCTTAVIRNINGQVLFVDKRQPVFADMASTHQSASEPQT RLIIYFYKDSEVRGLAVTLSVKDSKMSTLSCKNKIISFEEMDPPEN IDDIQSDLIFFLKGVPGANKIEFESSLYEGHFLACQKEDDAFKLIL KKKDENGDKSVMFTLTNLHQS (SEQ ID NO: 187) |
| mD2D-B10 | YFGRLHCTTAVIRNINGQVLFVDKRQPVFADMASTHQSASEPQT RLIIYFYKDSEVRGLAVTLSVKDSKMSTLSCKNKIISFEEMDPPEN IDDIQSDLIFFLKGVPGANKIEFESSLYEGHFLACQKEDDAFKLIL KKKDENGDKSVMFTLTNLHQS (SEQ ID NO: 188) |
| mD2D-B8 | YFGRLHCTTAVIRNINSQVLFVDKRQPVFGDMKYIVQSASEPQT RLIIYFYKDSEVRGLAVTLSVKDSKMSTLSCKNKIISFEEMDPPEN IDDIQSDLIFFLKGVPGDTKMEFESSLYEGHFLACQKESGAFKLIL KKKDENGDKSVMFTLTNLHQS (SEQ ID NO: 189) |
| mD2D-B9 | YFGRLHCTTAVIRNINSQVLFVDKRQPVFGDMKYIVQSASEPQT RLIIYFYKDSEVRGLAVTLSVKDSKMSTLSCKNKIISFEEMDPPEN IDDIQSDLIFFLKGVPGDTKMEFESSLYEGHFLACQKESGAFKLIL KKKDENGDKSVMFTLTNLHQS (SEQ ID NO: 190) |

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below in SET A and SET B. As will be apparent to those of ordinary skill in the art upon reading this disclosure, each of the individually numbered aspects may be used or combined with any of the preceding or following individually numbered aspects. This is intended to provide support for all such combinations of aspects and is not limited to combinations of aspects explicitly provided below. It will be apparent to one of ordinary skill in the art that various changes and modifications can be made without departing from the spirit or scope of the invention.

SET A

1. A composition comprising an IL-18 variant polypeptide, wherein the IL-18 variant polypeptide specifically binds to IL-18 receptor (IL-18R) and wherein the IL-18 variant polypeptide exhibits substantially reduced binding to IL-18 binding protein (IL-18BP).

2. The composition of 1, wherein the IL-18 variant polypeptide comprises at least one mutation relative to wild-type (WT) IL-18.

3. The composition of 2, wherein the WT IL-18 is human IL-18 comprising the amino acid sequence of SEQ ID NO: 30.

4. The composition of 2, wherein the WT IL-18 is murine IL-18 comprising the amino acid sequence of SEQ ID NO: 31.

5. The composition of 3, wherein the IL-18 variant polypeptide comprises at least one mutation selected from the group consisting of Y1X, L5X, K8X, M51X, K53X, S55X, Q56X, P57X, G59X, M60X, E77X, Q103X, S105X, D110X, N111X, M113X, V153X, and N155X, relative to SEQ ID NO: 30.

6. The composition of 3, wherein the IL-18 variant polypeptide comprises at least one mutation selected from the group consisting of Y1H, Y1R, L5H, L51, L5Y, K8Q, K8R, M51T, M51K, M51D, M51N, M51E, M51R, K53R, K53G, K53S, K53T, S55K, S55R, Q56E, Q56A, Q56R, Q56V, Q56G, Q56K, Q56L, P57L, P57G, P57A, P57K, G59T, G59A, M60K, M60Q, M60R, M60L, E77D, Q103E, Q103K, Q103P, Q103A, Q103R, S105R, S105D, S105K, S105N, S105A, D110H, D110K, D110N, D110Q, D110E, D110S, D110G, N111H, N111Y, N111D, N111R, N111S, N111G, M113V, M113R, M113T, M113K, V153I, V153T, V153A, N155K, and N155H, relative to SEQ ID NO: 30.

7. The composition of 2, wherein the IL-18 variant polypeptide comprises at least one IL-18 variant polypeptide selected from the group consisting of SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, or a fragment thereof.

8. The composition of 4, wherein the IL-18 variant polypeptide comprises at least one mutation selected from the group consisting of N1X, M50X, Y51X, K52X, S54X, E55X, V56X, R57X, G58X, L59X, R104X, N109X, and L151X, relative to SEQ ID NO: 31.

9. The composition of 4, wherein the IL-18 variant polypeptide comprises at least one mutation selected from the group consisting of N1H, N1Y, M50A, M50S, M50V, M50G, M50T, Y51R, K52V, K52S, K52T, K52G, K52A, S54R, S54K, S54G, S54N, E55R, E55H, E55N, E55D, E55G, V56L, V56M, V56R, V56A, V56S, V56Q, R57G, R57K, G58A, L59K, L59R, L59V, R104K, R104L, R104Q, R104S, N109D, and L151V, relative to SEQ ID NO: 31.

10. The composition of 2, wherein the IL-18 variant polypeptide comprises at least one IL-18 variant polypeptide selected from the group consisting of SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, or a fragment thereof.

11. A composition comprising a nucleic acid encoding at least one of the IL-18 variant polypeptides of 1-10.

12. A method of treating or preventing a disease or disorder in a subject in need thereof, comprising administering to the subject at least one composition of 1-11.

13. The method of 12, wherein the disease or disorder is cancer.

14. The method of 13, wherein the cancer is a cancer that is resistant to immune checkpoint inhibitors (ICIs).

15. The method of 13, wherein the cancer is associated with a tumor that has lost expression of MHC class I.

16. The method of 12, wherein the disease or disorder is a metabolic disease or disorder.

17. The method of 12, wherein the disease or disorder is an infectious disease.

18. The method of 12, further comprising administering to the subject at least one other agent.

19. The method of 18, wherein the at least one other agent comprises an inhibitor of one or more secondary cytokines.

20. The method of 19, wherein the one or more secondary cytokines are at least one selected from the group consisting of IL-17, IL-5, and IL-13.

21. The method of 19, wherein the inhibitor of one or more secondary cytokines comprises at least one selected from the group consisting of: a chemical compound, a polypeptide, a peptide, a peptidomimetic, an antibody, a ribozyme, a small molecule chemical compound, and an antisense nucleic acid molecule.

22. A composition comprising an IL-18BP inhibitor or IL-18BP antagonist, wherein the inhibitor or antagonist inhibits the ability of IL18BP to neutralize endogenous IL-18.

23. The composition of 22, wherein the inhibitor or antagonist comprises at least one selected from the group consisting of: a chemical compound, a polypeptide, a peptide, a peptidomimetic, an antibody, a ribozyme, a small molecule chemical compound, and an antisense nucleic acid molecule.

24. The composition of 22 comprising an IL-18 variant polypeptide, wherein the IL-18 variant polypeptide specifically binds to IL-18 binding protein (IL-18BP) and wherein the IL-18 variant polypeptide exhibits substantially reduced binding to IL-18 receptor (IL-18R).

25. The composition of 24, wherein the IL-18 variant polypeptide comprises at least one mutation relative to wild-type (WT) IL-18.

26. The composition of 24, wherein the WT IL-18 is human IL-18 comprising the amino acid sequence of SEQ ID NO: 30.

27. The composition of 24, wherein the WT IL-18 is murine IL-18 comprising the amino acid sequence of SEQ ID NO: 31.

28. The composition of 26, wherein the IL-18 variant polypeptide comprises at least one mutation selected from the group consisting of Y1X, L5X, D17X, E31X, T34X, D35X, S36X, D37X, D40X, N41X, M51X, Q56X, M60X, Q103X, H109X, M113X, and R131X, relative to SEQ ID NO: 30.

29. The composition of 26, wherein the IL-18 variant polypeptide comprises at least one mutation selected from the group consisting of Y1D, Y1F, Y1H, Y1L, L5F, L5H, D17A, D17G, D17R, D17H, E31A, E31T, E31G, E31K, E31R, T34A, T34K T34E, D35S, D35A, D35Y, S36N, S36K, S36R, D37P, D37A, D37R, D37H, D37L, D37V, D40Y D40S, D40A, N41K, N41S, N41R, M51F, M51L, M511, Q56H, M60L, M60F, M601, Q103L, Q1031, H109A, H109P, H109D, M113L, M1131, M113F, and R131S, relative to SEQ ID NO: 30.

30. The composition of 24, wherein the IL-18 variant polypeptide comprises at least one IL-18 variant polypeptide selected from the group consisting of SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, or a fragment thereof.

31. The composition of 27, wherein the IL-18 variant polypeptide comprises at least one mutation selected from the group consisting of NIX, L5X, D17X, E30X, T33X, D34X, I35X, D36X, M50X, Q102X, R104, H108X, N109X, M111X, D129X, and D130X, relative to SEQ ID NO: 31.

32. The composition of 4, wherein the IL-18 variant polypeptide comprises at least one mutation selected from the group consisting of N1Y, N1D, N1H, N1L, N1F, N1V, N1I, L5Y, L5H, D17Q, D17G, D17A, D17E, D17S, D17N, E30A, E30R, E30K, E30T, E30G, T33G, T33A, T33E, T33R, T33K, D34Y, D34S, D34A, 135T, 135K, I35R, D36V, D36A, D36G, D36H, D36P, D36R, D36L, M50F, M50L, Q102L, Q102I, R104E, R104A, R104P, R104G, R104Q, R104H, H108D, H108A, N109R, N109S, N109T, N109I, M111L, M111I, D129A, D129F, D129V, D129Y, D129S, D130E, D130T, D130G, D130N, D130R, D130S, D130Q, and D130H, relative to SEQ ID NO: 31.

33. The composition of 2, wherein the IL-18 variant polypeptide comprises at least one IL-18 variant polypeptide selected from the group consisting of SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, or a fragment thereof.

34. A composition comprising a nucleic acid encoding at least one of the IL-18 variant polypeptides of 24-33.

35. A method of treating or preventing a disease or disorder in a subject in need thereof, comprising administering to the subject at least one composition of 22-34.

36. The method of 35, wherein the disease or disorder is cancer.

37. The method of 36, wherein the cancer is a cancer that is resistant to immune checkpoint inhibitors (ICIs).

38. The method of 36, wherein the cancer is associated with a tumor that has lost expression of MHC class I.

39. The method of 35, wherein the disease or disorder is a metabolic disease or disorder.

40. The method of 35, wherein the disease or disorder is an infectious disease.

41. The method of 35, further comprising administering to the subject at least one other agent.

42. The method of 41, wherein the at least one other agent comprises an inhibitor of one or more secondary cytokines.

43. The method of 42, wherein the one or more secondary cytokines are at least one selected from the group consisting of IL-17, IL-5, and IL-13.

44. The method of 42, wherein the inhibitor of one or more secondary cytokines comprises at least one selected from the group consisting of: a chemical compound, a polypeptide, a peptide, a peptidomimetic, an antibody, a ribozyme, a small molecule chemical compound, and an antisense nucleic acid molecule.

SET B

1. A composition comprising an IL-18 variant polypeptide, wherein the IL-18 variant polypeptide specifically binds to IL-18 receptor (IL-18R) and wherein the IL-18 variant polypeptide exhibits substantially reduced binding to IL-18 binding protein (IL-18BP).

2. The composition of 1, wherein the IL-18 variant polypeptide comprises at least one mutation relative to wild-type (WT) IL-18.

3. The composition of 2, wherein the WT IL-18 is human IL-18 comprising the amino acid sequence of SEQ ID NO: 30.

4. The composition of 2, wherein the WT IL-18 is murine IL-18 comprising the amino acid sequence of SEQ ID NO: 31.

5. The composition of 3, wherein the IL-18 variant polypeptide comprises at least one mutation selected from the group consisting of Y1X, L5X, K8X, M51X, K53X, S55X, Q56X, P57X, G59X, M60X, E77X, Q103X, S105X, D110X, N111X, M113X, V153X, and N155X, relative to SEQ ID NO: 30.

6. The composition of 3, wherein the IL-18 variant polypeptide comprises at least one mutation selected from the group consisting of Y1H, Y1R, L5H, L5I, L5Y, K8Q, K8R, M51T, M51K, M51D, M51N, M51E, M51R, K53R, K53G, K53S, K53T, S55K, S55R, Q56E, Q56A, Q56R, Q56V, Q56G, Q56K, Q56L, P57L, P57G, P57A, P57K, G59T, G59A, M60K, M60Q, M60R, M60L, E77D, Q103E, Q103K, Q103P, Q103A, Q103R, S105R, S105D, S105K, S105N, S105A, D110H, D110K, D110N, D110Q, D11E, D110S, D110G, N111H, N111Y, N111D, N111R, N111S, N111G, M113V, M113R, M113T, M113K, V153I, V153T, V153A, N155K, and N155H, relative to SEQ ID NO: 30.

7. The composition of 3, wherein the IL-18 variant polypeptide comprises the mutations M51X, M60X, S105X, D110X, and N111X, relative to SEQ ID NO: 30.

8. The composition of 3, wherein the IL-18 variant polypeptide comprises the mutations M51X, K53X, Q56X, S105X, and N111X, relative to SEQ ID NO: 30.

9. The composition of 2, wherein the IL-18 variant polypeptide comprises the amino acid sequence set forth in any one of SEQ ID NOs.: 34-59, 73-91, and 191-193, or a fragment thereof.

10. The composition of 4, wherein the IL-18 variant polypeptide comprises at least one mutation selected from the group consisting of NIX, M50X, Y51X, K52X, S54X, E55X, V56X, R57X, G58X, L59X, R104X, N109X, and L151X, relative to SEQ ID NO: 31.

11. The composition of 4, wherein the IL-18 variant polypeptide comprises at least one mutation selected from the group consisting of N1H, N1Y, M50A, M50S, M50V, M50G, M50T, Y51R, K52V, K52S, K52T, K52G, K52A, S54R, S54K, S54G, S54N, E55R, E55H, E55N, E55D, E55G, V56L, V56M, V56R, V56A, V56S, V56Q, R57G, R57K, G58A, L59K, L59R, L59V, R104K, R104L, R104Q, R104S, N109D, and L151V, relative to SEQ ID NO: 31.

12. The composition of 2, wherein the IL-18 variant polypeptide comprises the amino acid sequence set forth in any one of SEQ ID NOs.: 60-72, or a fragment thereof.

13. A composition comprising a nucleic acid encoding the IL-18 variant polypeptide of the composition of any one of 1-12.

14. The composition of any one of 1-13, further comprising one or more agents selected from: (i) an immune checkpoint inhibitor; (ii) an agent that inhibits one or more proteins selected from PD-L1, PD1, CTLA4, TIM3, TIGIT, LAG3, B7H3, B7H4, VISTA, ICOS, GITR, 41BB, OX40, and CD40; (iii) a cancer cell opsonizing agent; and (iv) an agent that targets one or more antigens selected from: CD19, CD20, CD22, CD24, CD25, CD30, CD33, CD37, CD38, CD44, CD45, CD47, CD51, CD52, CD56, CD62L, CD70, CD74, CD79, CD80, CD96, CD97, CD99, CD123, CD134, CD138, CD152 (CTLA-4), CD200, CD213A2, CD221, CD248, CD276 (B7-H3), B7-H4, CD279 (PD-1), CD274 (PD-L1), CD319, EGFR, EPCAM, 17-1A, HER1, HER2, HER3, CD117, C-Met, HGFR, PDGFRA, AXL, TWEAKR, PTHR2, HAVCR2 (TIM3), GD2 ganglioside, MUC1, mucin CanAg, mesothelin, endoglin, Lewis-Y antigen, CEA, CEACAM1, CEACAM5, CA-125, PSMA, BAFF, FGFR2, TAG-72, gelatinase B, glypican 3, nectin-4, BCMA, CSF1R, SLAMF7, integrin $\alpha_v\beta_3$, TYRP1, GPNMB, CLDN18.2, FOLR1, CCR4, CXCR4, MICA, C242 antigen, D113, D114, EGFL7, vimentin, fibronectin extra domain-B, TROP-2, LRRC15, FAP, SLITRK6, NOTCH2, NOTCH3, Tenascin-3, STEAP1, and NRP1.

15. A method of treating or preventing a disease or disorder in a subject in need thereof, comprising administering to the subject the composition of any one of 1-14.

16. The method of 15, wherein the disease or disorder is cancer.

17. The method of 16, wherein the cancer is a cancer that is resistant to immune checkpoint inhibitors (ICIs).

18. The method of 16, wherein the cancer is associated with a tumor that has lost expression of MHC class I.

19. The method of 15, wherein the disease or disorder is a metabolic disease or disorder.

20. The method of 15, wherein the disease or disorder is an infectious disease.

21. The method of any one of 15-20, wherein the method comprises administering to the subject the IL-18 variant polypeptide and at least one other agent.

22. The method of 21, wherein the at least one other agent comprises an immune checkpoint inhibitor.

23. The method of 22, wherein the immune checkpoint inhibitor is an agent that inhibits PD-L1, PD1, CTLA4, TIM3, TIGIT, LAG3, B7H3, B7H4, VISTA, ICOS, GITR, 41BB, OX40, or CD40, or any combination thereof.

24. The method of 21, wherein the at least one other agent comprises a cancer cell opsonizing agent.

25. The method of 24, wherein the at least one other agent targets one or more antigens selected from: CD19, CD20, CD22, CD24, CD25, CD30, CD33, CD37, CD38, CD44, CD45, CD47, CD51, CD52, CD56, CD62L, CD70, CD74, CD79, CD80, CD96, CD97, CD99, CD123, CD134, CD138, CD152 (CTLA-4), CD200, CD213A2, CD221, CD248, CD276 (B7-H3), B7-H4, CD279 (PD-1), CD274 (PD-L1), CD319, EGFR, EPCAM, 17-1A, HER1, HER2, HER3, CD117, C-Met, HGFR, PDGFRA, AXL, TWEAKR, PTHR2, HAVCR2 (TIM3), GD2 ganglioside, MUC1, mucin CanAg, mesothelin, endoglin, Lewis-Y antigen, CEA, CEACAM1, CEACAM5, CA-125, PSMA, BAFF, FGFR2, TAG-72, gelatinase B, glypican 3, nectin-4, BCMA, CSF1R, SLAMF7, integrin $\alpha_v\beta_3$, TYRP1, GPNMB, CLDN18.2, FOLR1, CCR4, CXCR4, MICA, C242 antigen, D113, D114, EGFL7, vimentin, fibronectin extra domain-B, TROP-2, LRRC15, FAP, SLITRK6, NOTCH2, NOTCH3, Tenascin-3, STEAP1, and NRP1.

26. The method of any one of 21-25, wherein the at least one other agent is conjugated to the IL-18 variant polypeptide.

27. The method of 21, wherein the at least one other agent is an altered T-cell or NK cell.

28. The method of 21, wherein the at least one other agent is an oncolytic virus.

29. A composition comprising an IL-18BP inhibitor or IL-18BP antagonist, wherein the inhibitor or antagonist inhibits the ability of IL18BP to neutralize endogenous IL-18.

30. The composition of 29, wherein the inhibitor or antagonist comprises at least one selected from the group consisting of: a chemical compound, a polypeptide, a peptide, a peptidomimetic, an antibody, a ribozyme, a small molecule chemical compound, and an antisense nucleic acid molecule.

31. The composition of 30, comprising an IL-18 variant polypeptide, wherein the IL-18 variant polypeptide specifically binds to IL-18 binding protein (IL-18BP) and wherein the IL-18 variant polypeptide exhibits substantially reduced binding to IL-18 receptor (IL-18R).

32. The composition of 31, wherein the IL-18 variant polypeptide comprises at least one mutation relative to wild-type (WT) IL-18.

33. The composition of 32, wherein the WT IL-18 is human IL-18 comprising the amino acid sequence of SEQ ID NO: 30.

34. The composition of 32, wherein the WT IL-18 is murine IL-18 comprising the amino acid sequence of SEQ ID NO: 31.

35. The composition of 33, wherein the IL-18 variant polypeptide comprises at least one mutation selected from the group consisting of Y1X, L5X, D17X, E31X, T34X, D35X, S36X, D37X, D40X, N41X, M51X, Q56X, M60X, Q103X, H109X, M113X, and R131X, relative to SEQ ID NO: 30.

36. The composition of 33, wherein the IL-18 variant polypeptide comprises at least one mutation selected from the group consisting of Y1D, Y1F, Y1H, Y1L, L5F, L5H, D17A, D17G, D17R, D17H, E31A, E31T, E31G, E31K, E31R, T34A, T34K T34E, D35S, D35A, D35Y, S36N, S36K, S36R, D37P, D37A, D37R, D37H, D37L, D37V, D40Y D40S, D40A, N41K, N41S, N41R, M51F, M51L, M51I, Q56H, M60L, M60F, M601, Q103L, Q1031, H109A, H109P, H109D, M113L, M1131, M113F, and R131S, relative to SEQ ID NO: 30.

37. The composition of 33, wherein the IL-18 variant polypeptide comprises the amino acid sequence set forth in any one of SEQ ID NOs.: 92-125, or a fragment thereof.

38. The composition of 33, wherein the IL-18 variant polypeptide comprises the mutations D17X, E30X, and Q103X, relative to SEQ ID NO: 30.

39. The composition of 33, wherein the IL-18 variant polypeptide comprises the mutations D17X, E30X, D35X, M51X, and Q103X, relative to SEQ ID NO: 30.

40. The composition of 34, wherein the IL-18 variant polypeptide comprises at least one mutation selected from the group consisting of N1X, L5X, D17X, E30X, T33X, D34X, I35X, D36X, M50X, Q102X, R104, H108X, N109X, M111X, D129X, and D130X, relative to SEQ ID NO: 31.

41. The composition of 34, wherein the IL-18 variant polypeptide comprises at least one mutation selected from the group consisting of N1Y, N1D, N1H, NIL, N1F, N1V, N1I, L5Y, L5H, D17Q, D17G, D17A, D17E, D17S, D17N, E30A, E30R, E30K, E30T, E30G, T33G, T33A, T33E, T33R, T33K, D34Y, D34S, D34A, I35T, 135K, I35R, D36V, D36A, D36G, D36H, D36P, D36R, D36L, M50F, M50L, Q102L, Q1021, R104E, R104A, R104P, R104G, R104Q, R104H, H108D, H108A, N109R, N109S, N109T, N109I, M111L, M111I, D129A, D129F, D129V, D129Y, D129S, D130E, D130T, D130G, D130N, D130R, D130S, D130Q, and D130H, relative to SEQ ID NO: 31.

42. The composition of 34, wherein the IL-18 variant polypeptide comprises the amino acid sequence set forth in any one of SEQ ID NOs.: 126-190, or a fragment thereof.

43. A composition comprising a nucleic acid encoding the IL-18 variant polypeptide of the composition of any one of 31-42.

44. The composition of any one of 19-43, further comprising one or more agents selected from: (i) an immune checkpoint inhibitor; (ii) an agent that inhibits one or more proteins selected from PD-L1, PD1, CTLA4, TIM3, TIGIT, LAG3, B7H3, B7H4, VISTA, ICOS, GITR, 41BB, OX40, and CD40; (iii) a cancer cell opsonizing agent; and (iv) an agent that targets one or more antigens selected from: CD19, CD20, CD22, CD24, CD25, CD30, CD33, CD37, CD38, CD44, CD45, CD47, CD51, CD52, CD56, CD62L, CD70, CD74, CD79, CD80, CD96, CD97, CD99, CD123, CD134, CD138, CD152 (CTLA-4), CD200, CD213A2, CD221, CD248, CD276 (B7-H3), B7-H4, CD279 (PD-1), CD274 (PD-L1), CD319, EGFR, EPCAM, 17-1A, HER1, HER2, HER3, CD117, C-Met, HGFR, PDGFRA, AXL, TWEAKR, PTHR2, HAVCR2 (TIM3), GD2 ganglioside, MUC1, mucin CanAg, mesothelin, endoglin, Lewis-Y antigen, CEA, CEACAM1, CEACAM5, CA-125, PSMA, BAFF, FGFR2, TAG-72, gelatinase B, glypican 3, nectin-4, BCMA, CSF1R, SLAMF7, integrin $\alpha_v\beta_3$, TYRP1, GPNMB, CLDN18.2, FOLR1, CCR4, CXCR4, MICA, C242 antigen, D113, D114, EGFL7, vimentin, fibronectin extra domain-B, TROP-2, LRRC15, FAP, SLITRK6, NOTCH2, NOTCH3, Tenascin-3, STEAP1, and NRP1.

45. A method of treating or preventing a disease or disorder in a subject in need thereof, comprising administering to the subject the composition of any one of 29-44.

46. The method of 45, wherein the disease or disorder is cancer.

47. The method of 46, wherein the cancer is a cancer that is resistant to immune checkpoint inhibitors (ICIs).

48. The method of 46, wherein the cancer is associated with a tumor that has lost expression of MHC class I.

49. The method of 45, wherein the disease or disorder is a metabolic disease or disorder.

50. The method of 45, wherein the disease or disorder is an infectious disease.

51. The method of any one of 45-50, wherein the method comprises administering to the subject the IL-18 variant polypeptide and at least one other agent.

52. The method of 51, wherein the at least one other agent comprises an immune checkpoint inhibitor.

53. The method of 52, wherein the immune checkpoint inhibitor is an agent that inhibits PD-L1, PD1, CTLA4, TIM3, TIGIT, LAG3, B7H3, B7H4, VISTA, ICOS, GITR, 41BB, OX40, or CD40, or any combination thereof.

54. The method of 51, wherein the at least one other agent comprises a cancer cell opsonizing agent.

55. The method of 51, wherein the at least one other agent targets one or more antigens selected from: CD19, CD20, CD22, CD24, CD25, CD30, CD33, CD37, CD38, CD44, CD45, CD47, CD51, CD52, CD56, CD62L, CD70, CD74, CD79, CD80, CD96, CD97, CD99, CD123, CD134, CD138, CD152 (CTLA-4), CD200, CD213A2, CD221, CD248, CD276 (B7-H3), B7-H4, CD279 (PD-1), CD274 (PD-L1), CD319, EGFR, EPCAM, 17-1A, HER1, HER2, HER3, CD117, C-Met, HGFR, PDGFRA, AXL, TWEAKR, PTHR2, HAVCR2 (TIM3), GD2 ganglioside, MUC1, mucin CanAg, mesothelin, endoglin, Lewis-Y antigen, CEA, CEACAM1, CEACAM5, CA-125, PSMA, BAFF, FGFR2, TAG-72, gelatinase B, glypican 3, nectin-4, BCMA, CSF1R, SLAMF7, integrin avp$_3$, TYRP1, GPNMB, CLDN18.2, FOLR1, CCR4, CXCR4, MICA, C242 antigen, D113, D114, EGFL7, vimentin, fibronectin extra domain-B, TROP-2, LRRC15, FAP, SLITRK6, NOTCH2, NOTCH3, Tenascin-3, STEAP1, and NRP1.

56. The method of any one of 51-55, wherein the at least one other agent is conjugated to the IL-18 variant polypeptide.

57. The method of 51, wherein the at least one other agent is an altered T-cell or NK cell.

58. The method of 51, wherein the at least one other agent is an oncolytic virus.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of promoting interleukin-18 (IL-18) signaling activity in a subject in need thereof, comprising administering to the subject a composition comprising a nucleic acid encoding a modified IL-18 polypeptide that specifically binds to the IL-18 receptor (IL-18R) and exhibits reduced binding to the IL-18 binding protein (IL-18BP) as compared to wild type (WT) IL-18 as set forth in SEQ ID NO: 30, wherein the modified IL-18 polypeptide comprises 90% or more sequence identity with WT IL-18 as set forth in SEQ ID NO:30 and at least four amino acid substitutions, relative to WT IL-18 as set forth in SEQ ID NO:30, at positions selected from: Methionine-51, Glutamine-56, Proline-57, Methionine-60, Glutamine-103, Serine-105, Aspartic acid-110, Asparagine-111, and Methionine-113.

2. The method of claim 1, wherein the modified IL-18 polypeptide comprises substitutions relative to SEQ ID NO: 30 at five or more of the following positions: Tyrosine-1, Leucine-5, Lysine-8, Methionine-51, Lysine-53, Serine-55, Glutamine-56, Proline-57, Glycine-59, Methionine-60, Glutamic acid-77, Glutamine-103, Serine-105, Aspartic acid-110, Asparagine-111, Methionine-113, Valine-153, and Asparagine-155.

3. The method of claim 1, wherein the at least four amino acid substitutions, relative to SEQ ID NO: 30, are selected from the group consisting of:

(1) Methionine-51 to threonine, Methionine-51 to lysine, Methionine-51 to aspartic acid, Methionine-51 to asparagine, Methionine-51 to glutamic acid, or Methionine-51 to arginine, (2) Glutamine-56 to glutamic acid, Glutamine-56 to alanine, Glutamine-56 to arginine, Glutamine-56 to valine, Glutamine-56 to glycine, Glutamine-56 to lysine, or Glutamine-56 to leucine, (3) Proline-57 to leucine, Proline-57 to glycine, Proline-P57 to alanine, or Proline-57 to lysine, (4) Methionine-60 to lysine, Methionine-60 to glutamine, Methionine-60 to arginine, or Methionine-60 to leucine, (5) Glutamine-103 to glutamic acid, Glutamine-103 to lysine, Glutamine-103 to proline, Glutamine-103 to alanine, or Glutamine-103 to arginine, (6) Serine-105 to arginine, Serine-105 to aspartic acid, Serine-105 to lysine, Serine-105 to asparagine, or Serine-105 to alanine, (7) Aspartic acid-110 to histidine, Aspartic acid-110 to lysine, Aspartic acid-110 to asparagine, Aspartic acid- 110 to glutamine, Aspartic acid-110 to glutamic acid, Aspartic acid-110 to serine, or Aspartic acid-110 to glycine, (8) Asparagine-111 to histidine, Asparagine-111 to tyrosine, Asparagine-111 to aspartic acid, Asparagine-111 to arginine, Asparagine-111 to serine, or Asparagine-111 to glycine, and (9) Methionine-113 to valine, Methionine-113 to arginine, Methionine-113 to threonine, or Methionine-113 to lysine.

4. The method of claim 3, wherein the modified IL-18 polypeptide comprises five or more substitutions, relative to SEQ ID NO: 30, selected from the group consisting of:

(1) Methionine-51 to threonine, Methionine-51 to lysine, Methionine-51 to aspartic acid, Methionine-51 to asparagine, Methionine-51 to glutamic acid, or Methionine-51 to arginine, (2) Lysine-53 to arginine, Lysine-53 to glycine, Lysine-53 to serine, or Lysine-53 to threonine, (3) Glutamine-56 to glutamic acid, Glutamine-56 to alanine, Glutamine-56 to arginine, Glutamine-56 to valine, Glutamine-56 to glycine, Glutamine-56 to lysine, or Glutamine-56 to leucine, (4) Proline-57 to leucine, Proline-57 to glycine, Proline-P57 to alanine, or Proline-57 to lysine, (5) Methionine-60 to lysine, Methionine-60 to glutamine, Methionine-60 to arginine, or Methionine-60 to leucine, (6) Glutamine-103 to glutamic acid, Glutamine-103 to lysine, Glutamine-103 to proline, Glutamine-103 to alanine, or Glutamine-103 to arginine, (7) Serine-105 to arginine, Serine-105 to aspartic acid, Serine-105 to lysine, Serine-105 to asparagine, or Serine-105 to alanine, (8) Aspartic acid-110 to histidine, Aspartic acid-110 to lysine, Aspartic acid-110 to asparagine, Aspartic acid-110 to glutamine, Aspartic acid-110 to glutamic acid, Aspartic acid-110 to serine, or Aspartic acid-110 to glycine, (9) Asparagine-111 to histidine, Asparagine-111 to tyrosine, Asparagine-111 to aspartic acid, Asparagine-111 to arginine, Asparagine-111 to serine, or Asparagine-111 to glycine, and

(10) Methionine-113 to valine, Methionine-113 to arginine, Methionine-113 to threonine, or Methionine-113 to lysine.

5. The method of claim 1, wherein the modified IL-18 polypeptide comprises 95% or more sequence identity with any one of the amino acid sequences as set forth in SEQ ID NOs: 34-59, 73-91, and 191-193.

* * * * *